US006908919B2

(12) United States Patent
South et al.

(10) Patent No.: US 6,908,919 B2
(45) Date of Patent: Jun. 21, 2005

(54) SUBSTITUTED POLYCYCLIC ARYL AND HETEROARYL PYRAZINONES USEFUL FOR SELECTIVE INHIBITION OF THE COAGULATION CASCADE

(75) Inventors: Michael S. South, St. Louis, MO (US); Brenda L. Case, St. Louis, MO (US); Thomas A. Dice, St. Charles, MO (US); Ricky L. Fenton, Collinsville, IL (US); Gary W. Franklin, Godfrey, IL (US); Michael J. Hayes, St. Louis, MO (US); Horng-Chih Huang, Chesterfield, MO (US); Wei Huang, Wildwood, MO (US); Darin E. Jones, Ballwin, MO (US); Carrie L. Kusturin, Edwardsville, IL (US); Richard J. Lindmark, St. Louis, MO (US); Scott A. Long, Ballwin, MO (US); William L. Neumann, St. Louis, MO (US); David B. Reitz, Chesterfield, MO (US); John I. Trujillo, St. Louis, MO (US); Ching-Cheng Wang, Wildwood, MO (US); Rhonda Wood, Maryland Heights, MO (US); Qingping Zeng, Ballwin, MO (US); Matthew W. Mahoney, St. Peters, MO (US); John J. Parlow, Arnold, MO (US); Melvin L. Rueppel, St. Louis, MO (US)

(73) Assignee: Pharmacia Corporation, Chicago, IL (US)

( * ) Notice: Subject to any disclaimer, the term of this patent is extended or adjusted under 35 U.S.C. 154(b) by 46 days.

(21) Appl. No.: 10/195,573
(22) Filed: Jul. 15, 2002

(65) Prior Publication Data

US 2004/0006230 A1 Jan. 8, 2004

Related U.S. Application Data

(60) Division of application No. 09/716,961, filed on Nov. 20, 2000, which is a continuation-in-part of application No. 09/574,752, filed on May 18, 2000.
(60) Provisional application No. 60/134,958, filed on May 19, 1999.

(51) Int. Cl.$^7$ .................... C07D 241/20; C07D 417/12; C07D 401/12; A61K 31/495; A61P 7/02
(52) U.S. Cl. ............................... 514/235.8; 514/255.05; 514/248; 544/405; 544/237; 544/295; 544/120
(58) Field of Search ......................... 514/235.8, 255.05, 514/248; 544/405, 237, 295, 120

(56) References Cited

FOREIGN PATENT DOCUMENTS

| WO | WO 9809987 A1 * | 3/1998 | ............ C07K/5/078 |
|---|---|---|---|
| WO | WO 9959591 A1 * | 11/1999 | ......... A61K/31/535 |

* cited by examiner

Primary Examiner—Richard L. Raymond
Assistant Examiner—Hong Liu

(57) ABSTRACT

The invention relates to substituted polycyclic aryl and heteroaryl pyrazinone compounds useful as inhibitors of serine proteases of the coagulation cascade and compounds, compositions and methods for anticoagulant therapy for the treatment and prevention of a variety of thrombotic conditions including coronary artery and cerebrovascular diseases.

27 Claims, No Drawings

SUBSTITUTED POLYCYCLIC ARYL AND HETEROARYL PYRAZINONES USEFUL FOR SELECTIVE INHIBITION OF THE COAGULATION CASCADE

This application is a divisional of application Ser. No. 09/716,961, filed Nov. 20, 2000, which is a continuation-in-part of application Ser. No. 09/574,752, filed May 18, 2000 claiming priority from provisional application Ser. No. 60/134,958 filed May 19, 1999.

FIELD OF THE INVENTION

This invention is in the field of anticoagulant therapy, and specifically relates to compounds, compositions and methods for preventing and treating thrombotic conditions such as coronary artery and cerebrovascular disease. More particularly, the invention relates to substituted polycyclic aryl and heteroaryl pyrazinone compounds that inhibit serine proteases of the coagulation cascade.

BACKGROUND OF THE INVENTION

Physiological systems control the fluidity of blood in mammals [Majerus, P. W. et al: Anticoagulant, Thrombolytic, and Antipiplatelet Drugs. In Hardman, J. G. and Limbird, L. E., editors: Goodman & Gilman's The Pharmacological Basis of Therapeutics. 9th edition. New York, McGraw-Hill Book Co., 1996, pp. 1341–1343]. Blood must remain fluid within the vascular systems and yet be able to undergo hemostasis, cessation of blood loss from a damaged vessel, quickly. Hemostasis or clotting begins when platelets first adhere to macromolecules in subendothelian regions of an injured and/or damaged vessels. These platelets aggregate to form the primary hemostatic plug and stimulate local activation of plasma coagulation factors leading to generation of a fibrin clot that reinforces the aggregated platelets.

Plasma coagulation factors include factors II, V, VII, VIII, IX, X, XI, and XII; these are also called protease zymogens. These coagulation factors or protease zymogens are activated by serine proteases leading to coagulation in a so called "coagulation cascade" or chain reaction [Handin, R. I.: Bleeding and Thrombosis. In Wilson, J., et al. editors: Harrison's Principles of Internal Medicine. 12th Edition, New York, McGraw-Hill Book Co., 1991, p.350]. Coagulation or clotting occurs in two ways through different pathways. An intrinsic or contact pathway leads from XII to XIIa to XIa to IXa and to the conversion of X to Xa. Xa with factor Va converts prothrombin (II) to thrombin (IIa) leading to conversion of fibrinogen to fibrin. Polymerization of fibrin leads to a fibrin clot. An extrinsic pathway is initiated by the conversion of coagulation factor VII to VIIa by Xa. The presence of Tissue Factor and VIIa accelerates formation of Xa in the presence of calcium ion and phospholipids. Formation of Xa leads to thrombin, fibrin, and a fibrin clot as described above. The presence of one or more of these many different coagulation factors and two distinct pathways of clotting could enable the efficacious, selective control and better understanding of parts of the coagulation or clotting process.

While clotting as a result of an injury to a blood vessel is a critical physiological process for mammals such as man, clotting can also lead to disease states. A pathological process called thrombosis results when platelet aggregation and/or a fibrin clot blocks (i.e., occludes) a blood vessel. Arterial thrombosis may result in ischemic necrosis of the tissue supplied by the artery. When the thrombosis occurs in a coronary artery, a myocardial infarction or heart attack can result. A thrombosis occurring in a vein may cause tissues drained by the vein to become edematous and inflamed. Thrombosis of a deep vein may be complicated by a pulmonary embolism. Preventing or treating clots in a blood vessel may be therapeutically useful by inhibiting formation of blood platelet aggregates, inhibiting formation of fibrin, inhibiting thrombus formation, inhibiting embolus formation, and for treating or preventing unstable angina, refractory angina, myocardial infarction, transient ischermic attacks, atrial fibrillation, thrombotic stroke, embolic stroke, deep vein thrombosis, disseminated intravascular coagulation, ocular build up of fibrin, and reocclusion or restenosis of recanalized vessels.

There have been several reports of non-peptidic and peptidic compounds that act as an inhibitor of a coagulation factor present in the coagulation cascade or clotting process. In PCT Patent Application WO 97/40024, Sanderson et al. describe alkyl, cycloalkyl, and trifluoromethyl substituted pyrazinones reported to inhibit thrombin activity. In PCF Patent Application WO 98/08840, Duggan et al. describe 2-heterocyclylacetyl derivatives of β-alanine esters reported to inhibit αvβ3 and αvβ5 receptors and possess utility in atheriosclerosis. In PCT Patent Application WO 98/09949, Suzuki et al. describe 2-heterocyclylacetamido derivatives of 1,2-diketones and report that they inhibit proteases, especially chymase inhibitors. In PCT Patent Application WO 98/42342, Isaacs et al. describe additional alkyl, cycloalkyl, and trifluoromethyl substituted pyrazinones reported to inhibit human thrombin. In PCT Patent Application WO 99/61442, Sanderson and Naylor-Olsen describe 1-(5-methylenecarboxamidomethyleneimidazo-[1,2-a]pyridinyl)pyrazinones without substitution in the imidazolyl portion and reported that the compounds inhibit thrombin activity. In PCT Patent Application WO 99/59591, Sanderson et al. describe 1-((N-substitutedaminopyridyl and N-substitutedphenyl)amidocarbonylmethylene)pyrazinones reported to inhibit thrombin. In PCT Patent Application WO 99/64446, Lu et al. describe 1-((N-amidinoaminooxyalkylene and N-amidinohydrazinoalkylene)amidocarbonylmethylene) pyrazinones reported to inhibit trypsin-like serine proteases and thrombin. In Japanese Patent Application 99/229491, Black et al. describe thrombin inhibiting halo and alkyl substituted pyrazinone acetamides in which the amide nitrogen is substituted by a group containing a benzimidazole or indole ring.

SUMMARY OF THE INVENTION

It is an object of the present invention to provide compounds that are beneficial in anticoagulant therapy and that have a general structure:

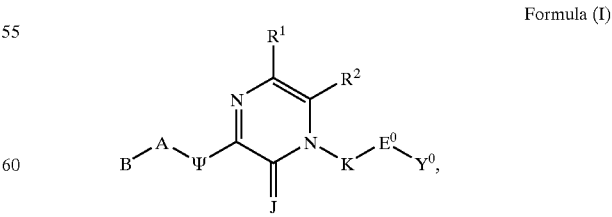

Formula (I)

It is another object of the present invention to provide methods for preventing and treating thrombotic conditions, such as coronary artery disease, cerebrovascular disease, and other coagulation related disorders. Such thrombotic conditions are prevented and treated by administering to a patient in need thereof an effective amount of a compound of Formula (I).

Various other objects and advantages of the present invention will become apparent from the following description of the invention.

DESCRIPTION OF THE INVENTION

The present invention relates to a class of compounds comprising Substituted Polycyclic Aryl and Heteroaryl Pyrazinones, which are beneficial in anticoagulant therapy for the treatment and prevention of a variety of thrombotic conditions including coronary artery and cerebrovascular disease, as given in Formula (I):

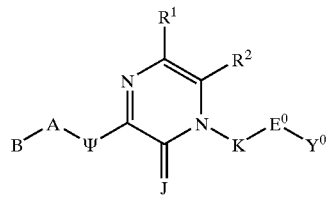

(I)

or a pharmaceutically acceptable salt thereof, wherein;

J is selected from the group consisting of O and S;

J is optionally selected from the group consisting of CH—$R^6$ and N—$R^6$ wherein $R^6$ is a linear spacer moiety having a chain length of 1 to 4 atoms linked to the point of bonding of a substituent selected from the group consisting of $R^{4a}$, $R^{4b}$, $R^{39}$, $R^{40}$, $R^5$, $R^{14}$, and $R^{15}$ to form a heterocyclyl ring having 5 through 8 members;

J is optionally selected from the group consisting of CH—$R^6$ and N—$R^6$ wherein $R^6$ is a linear spacer moiety having a chain length of 1 to 4 atoms linked to the points of bonding of both $R^{4a}$ and $R^{4b}$ to form a heterocyclyl ring having 5 through 8 members;

J is optionally selected from the group consisting of CH—$R^6$ and N—$R^6$ wherein $R^6$ is a linear spacer moiety having a chain length of 1 to 4 atoms linked to the points of bonding of both $R^{39}$ and $R^{40}$ to form a heterocyclyl ring having 5 through 8 members;

B is formula (V):

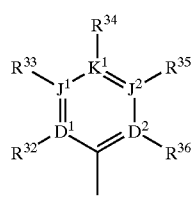

(V)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the provisos that $D^1$, $D^2$, $J^1$, $J^2$ and $K^1$ are selected to maintain an aromatic ring system and that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of heterocyclylalkoxy, N-alkyl-N-arylamino, heterocyclylamino, heterocyclylalkylamino, hydrido, acetamido, haloacetamido, amidino, guanidino, dialkylsulfonium, trialkylphosphonium, dialkylsulfoniumalkyl, carboxy, heteroaralkylthio, haloalkylthio, alkanoyloxy, alkoxy, alkoxyalkyl, haloalkoxyalkyl, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyll halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{36}$ are independently optionally $Q^b$;

$R^{32}$ and $R^{33}$, $R^{33}$ and $R^{34}$, $R^{34}$ and $R^{35}$, and $R^{35}$ and $R^{36}$ are independently optionally selected to form a spacer pair wherein a spacer pair is taken together to form a linear moiety having from 3 through 6 atoms connecting the points of bonding of said spacer pair members to form a ring selected from the group consisting of a cycloalkenyl ring having 5 through 8 members, a partially saturated heterocyclyl ring having 5 through 8 members, a heteroaryl ring having 5 through 6 members, and an aryl with the proviso that no more than one of the group consisting of spacer pairs $R^{32}$ and $R^{33}$, $R^{33}$, and $R^{34}$, $R^{34}$ and $R^{35}$, and $R^{35}$ and $R^{36}$ are used at the same time;

$R^9$ and $R^{10}$, $R^{10}$ and $R^{11}$, $R^{11}$ and $R^{12}$, and $R^{12}$ and $R^{13}$ are independently optionally selected to form a spacer pair wherein a spacer pair is taken together to form a linear moiety having from 3 through 6 atoms connecting the points of bonding of said spacer pair members to form a ring selected from the group consisting of a cycloalkenyl ring having 5 through 8 members, a partially saturated heterocyclyl ring having 5 through 8 members, a heteroaryl ring having 5 through 6 members, and an aryl with the proviso that no more than one of the group consisting of spacer pairs $R^9$ and $R^{10}$, $R^{10}$ and $R^{11}$, $R^{11}$ and $R^{12}$, and $R^{12}$ and $R^{13}$ are used at the same time;

B is optionally formula (VI):

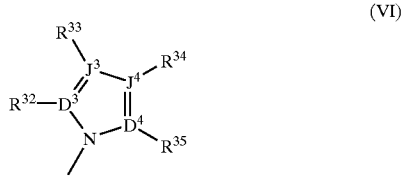

(VI)

wherein $D^3$, $D^4$, $J^3$, and $J^4$ are independently selected from the group consisting of C, N, O, and S, no more than one of $D^3$, $D^4$, $J^3$, and $J^4$ is O, no more than one of $D^3$, $D^4$, $J^3$, and $J^4$ is S, and no more than three of $D^1$, $D^2$, $J^1$, and $J^2$ are N, with the provisos that $D^3$, $D^4$, $J^3$, and $J^4$ are selected to maintain an aromatic ring system and that $R^{32}$, $R^{33}$, $R^{34}$, and $R^{35}$, and $R^{36}$ are each independently selected to maintain the tetravalent nature of carbon, trivalent nature of nitrogen, the divalent nature of sulfur, and the divalent nature of oxygen;

B is optionally selected from the group consisting of hydrido, trialkylsilyl, C2–C8 alkyl, C3–C8 alkenyl, C3–C8 alkylenyl, C3–C8 alkynyl, C2–C8 haloalkyl, and C3–C8 haloalkenyl wherein each member of group B is optionally substituted at any carbon up to and including 6 atoms from the point of attachment of B to A with one or more of the group consisting of $R_{32}$, $R_{33}$, $R_{34}$, $R_{35}$, and $R_{36}$;

B is optionally selected from the group consisting of C3–C15 cycloalkyl, C5–C10 cycloalkenyl, C4–C12 saturated heterocyclyl, and C4–C9 partially saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $^{R9}$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(S), C(O)S, C(S)O, C(O)N($R^7$), C(S)N($R^7$), ($R^7$)NC(O), ($R^7$)NC(S), S(O), S(O)$_2$, S(O)$_2$N($R^7$), ($R^7$)NS(O)$_2$, Se(O), Se(O)$_2$, Se(O)$_2$N($R^7$), ($R^7$)NSe(O)$_2$, P(O)($R^8$), N($R^7$)P(O)($R^8$), P(O)($R^8$)N($R^7$), C(N$R^7$)N($R^7$), ($R^7$)NC(N$R^7$), ($R^7$)NC(N$R^7$)N$R^7$, and N($R^7$) with the proviso that no more than one of the group consisting of rr and pa is 0 at the same time;

$R^7$ and $R^8$ are independently selected from the group consisting of hydrido, hydroxy, alkyl, alkenyl, aryl, aralkyl, aryloxy, alkoxy, alkenyloxy, alkylthio, alkylamino, arylthio, arylamino, acyl aroyl, heteroaroyl, aralkoxyalkyl, heteroaralkoxyalkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, heteroaryl, heteroaryloxy, heteroarylamino, heteroaralkyl, heteroaralkyloxy, heteroaralkylamino, and heteroaryloxyalkyl;

$R^{14}$, $R^{15}$, $R^{37}$, $R^{38}$, $R^{39}$, $R^{40,}$ $^{R41}$ and $R^{42}$ are independently selected from the group consisting of amidino, hydroxyamino, hydrido, hydroxy, halo, cyano, aryloxy, amino, alkylamino, dialkylamino, hydroxyalkyl, aminoalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamido, carboxamidoalkyl, carboaralkoxy, trialkylsilyl, dialkoxyphosphono, diaralkoxyphosphono, dialkoxyphosphonoalkyl, and diaralkoxyphosphonoalkyl with the proviso that $R^{37}$ and $R^{38}$ are independently selected from other than formyl and 2-oxoacyl and $R^{38}$ is optionally substituted at from one through three of the ring carbons with a substituent selected from the group consisting of $R^{16}$, $R^{17}$, $R^{18}$, and $R^{19}$;

$R^{14}$ and $R^{14}$, when bonded to different carbons, are optionally taken together to form a group selected from the group consisting of covalent bond, alkylene, haloalkylene, and a linear moiety spacer selected to form a ring selected from the group consisting of cycloalkyl ring having from 5 through 8 members, cycloalkenyl ring having from 5 through 8 members, and a heterocyclyl having from 5 through 8 members;

$R^{14}$ and $R^{15}$, when bonded to different carbons, are optionally taken together to form a group selected from the group consisting of covalent bond, alkylene, haloalkylene, and a linear moiety spacer selected to form a ring selected from the group consisting of a cycloalkyl ring having from 5 through 8 members, a cycloalkenyl ring having from 5 through 8 members, and a heterocyclyl having from 5 through 8 members;

$R^{15}$ and $R^{15}$, when bonded to different carbons, are optionally taken together to form a group selected from the group consisting of covalent bond, alkylene, haloalkylene, and a linear moiety spacer selected to form a ring selected from the group consisting of cycloalkyl ring having from 5 through 8 members, cycloalkenyl ring having from 5 through 8 members, and a heterocyclyl having from 5 through 8 members;

$\Psi$ is selected from the group consisting of $NR^5$, O, C(O), C(S), S, S(O), S(O)$_2$, ON($R^5$), P(O)($R^8$), and $CR^{39}R^{40}$;

$R^5$ is selected from the group consisting of hydrido, hydroxy, amino, alkyl, alkenyl, alkynyl, aryl, aralkyl, aryloxy, aralkoxy, alkoxy, alkenyloxy, alkylthio, arylthio, aralkoxyalkyl, heteroaralkoxyalkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, and dialkoxyphosphonoalkyl;

$R^{39}$ and $R^{40}$, when bonded to the same carbon, are optionally taken together to form a group selected from a group consisting of oxo, thiono, $R^5$—N, alkylene, haloalkylene, and a linear moiety spacer having from 2 through 7 atoms to form a ring selected from the group consisting of a cycloalkyl ring having from 3 through 8 members, a cycloalkenyl ring having from 3 through 8 members, and a heterocyclyl ring having from 3 through 8 members;

$R^2$ and $R^1$ are independently selected from the group consisting of $Z^0$—Q, hydrido, alkyl, alkenyl, and halo with the provisos that $R^2$ is selected from other than the group consisting of hydrido, alkyl, cycloalkyl, and trifluoromethyl and $R^1$ is selected from other than the group consisting of hydrido and halo unless $E^1$ is other than C(O)NH, or unless $E^0$ is selected from the group consisting of $E^2$ and $E^3$, or unless K is other than $(CR^{4a}R^{4b})_n$ wherein n is 1 unless one of $R^{4a}$ and $R^{4b}$ are independently selected from other than hydrido, or unless $\Psi$ is selected from other than $NR^5$, or unless $R^5$ is selected from other than hydrido, or unless $Y^0$ is selected from other than wherein $Q^s$ is $C_{1-4}$ alkyl, $C_{3-4}$ alkenyl or $C_{3-4}$ alkynyl where the $C_{1-4}$ alkyl, $C_{3-4}$ alkenyl or $C_{3-4}$ alkynyl group is bonded concurrently to $E^1$ wherein $E^1$ is C(O)NH and to the 4-position of an imidazole, the 4-position of a thiazole or the 5-position of a thiazole, or unless a spacer pair is present selected from the group of spacer pairs consisting of $R^2$ and $R^{4a}$, $R^2$ and $R^{4b}$, $R^2$ together with both $R^{4a}$ and $R^{4b}$, $R^2$ and $R^{14}$, $R^2$ and $R^{15}$, and $R^6$ with another group selected from the group consisting of $R^{4a}$, $R^{4b}$, $R^{4a}$ and $R^{4b}$ together, $R^{39}$, $R^{40}$, $R^{39}$ and $R^{40}$ together, $R^{14}$, $R^{15}$, and $R^5$, that $R^2$ is selected from other than the group consisting of alkyl, aryl, and heteroaryl and $R^1$ is selected from other than the group consisting of hydrido unless $E^1$ is other than C(O)NH, or unless $E^0$ is selected from the group consisting of $E^2$ and $E^3$, or unless K is other than $(CR^{4a}R^{4b})_n$ wherein n is 1 unless one of $R^{4a}$ and $R^{4b}$ are independently selected from other than hydrido, or unless $\Psi$ is selected from other than $NR^5$, or unless $R^5$ is selected from other than hydrido, or unless $R^{37}$ and $R^{38}$ are independently selected from other than formyl and 2-oxoacyl, that $R^2$ is selected from other than the group consisting of hydroxymethyl, methyl, methoxymethyl, methylthiomethyl, phenylthiomethyl, methylsulfinyl, methylthio, alkoxy, cycloalkoxy, alkylthio, alkylsulfinyl, alkysulfonyl, cycloalkylthio, cycloalkylsulfinyl, and cycloalkysulfonyl, when $Y^0$ is other than phenyl, mono-substituted phenyl, di-substituted phenyl, 5-(2-amino)pyridindyl, or 4-(2-amino)pyridindyl, and that $R^2$ is selected from other than the group consisting of hydrido, halo, alkyl, cycloalkyl when $Y^0$ is methyleneimidazo(1,2-a)pyridinyl, 4,5-benzimidazol-5-yl, or indol-5-yl unless $R^1$ is selected from other than the group consisting of hydrido or halo, or unless $E^1$ is other than C(O)NH, or unless $E^0$ is selected from the group consisting of $E^2$ and $E^3$, or unless K is other than $(CR^{4a}R^{4b})_n$ wherein n is 1 unless one of $R^{4a}$ and $R^{4b}$ are independently selected from other than hydrido, or unless $\Psi$ is selected from other than $NR^5$ wherein $R^5$ is hydrido;

$R^1$ is optionally selected from the group consisting of amino, aminoalkyl, alkylamino, amidino, guanidino, hydroxy, hydroxyamino, alkoxy, hydroxyalkyl, alkoxyamino, thiol, alkylthio, dialkylsulfonium, trialkylphosphonium, dialkylsulfoniumalkyl, heteroarylamino, nitro, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$R^2$ is optionally selected from the group consisting of amidino guanidino, dialkylsulfonium, trialkylphosphonium, dialkylsulfoniumalkyl, heteroarylamino, amino, nitro, alkylamino, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$R^2$ and $R^1$ are optionally taken together to form a spacer pair wherein the spacer pair forms a linear moiety having from 3 through 6 atoms connecting the points of bonding of said spacer pair members to form a ring selected from the group consisting of a cycloalkenyl ring having from 5 through 8 members and a partially saturated heterocyclyl ring having from 5 through 8 members;

$R^2$ and $R^1$ spacer pairs are optionally selected to be —W=X—Y=Z— forming a ring selected from the group consisting of a heteroaryl ring having from 5 through 6 members and an aryl, wherein W, X, Y, and Z are independently selected from the group consisting of $C(R^9)$, N, $N(R^{10})$, O, S and a covalent bond with the provisos that one of W, X, Y, and Z is independently selected to be a covalent bond when one of W, X, Y, and Z is selected from the group consisting of O and S, no more than one of W, X, Y, and Z is selected from the group consisting of O and S, no more than three of W, X, Y, and Z are selected from the group consisting of N and $N(R^{10})$, and $C(R^9)$, N, $N(R^{10})$, O, and S are independently selected to maintain the tetravalent nature of carbon, trivalent nature of nitrogen, the divalent nature of sulfur, the divalent nature of oxygen, and the aromaticity of the ring;

$R^2$ and $R^{4a}$, $R^2$ and $R^{4b}$, $R^2$ and $R^{14}$, and $R^2$ and $R^{15}$ are optionally independently selected to form spacer pairs wherein a spacer pair is taken together to form a linear moiety having from 2 through 5 atoms connecting the points of bonding of said spacer pair members to form a heterocyclyl ring having from 5 through 8 members with the proviso that no more than one of the group of spacer pairs consisting of $R^2$ and $R^{4a}$, $R^2$ and $R^{4b}$, $R^2$ and $R^{14}$, and $R^2$ and $R^{15}$ is used at the same time;

$R^2$ is optionally independently selected to form a linear moiety having from 2 through 5 atoms linked to the points of bonding of both $R^{4a}$ and $R^{4b}$ to form a heterocyclyl ring having from 5 through 8 members;

$Z^0$ is selected from the group consisting of covalent single bond, $(CR^{41}R^{42})_q$ wherein q is an integer selected from 1 through 6, $(CH(R^{41}))_g$—$W^0$—$(CH(R^{42}))_p$ wherein g and p are integers independently selected from 0 through 3 and $W^0$ is selected from the group consisting of O, S, C(O), C(S), C(O)O, C(S)O, C(O)S, C(S)S, $C(O)N(R^{41})$, $(R^{41})NC(O)$, $C(S)N(R^{41})$, $(R^{41})NC(S)$, $OC(O)N(R^{41})$, $(R^{41})NC(O)O$, $SC(S)N(R^{41})$, $(R^{41})NC(S)S$, $SC(O)N(R^{41})$, $(R^{41})NC(O)S$, $OC(S)N(R^{41})$, $(R^{41})NC(S)O$, $N(R^{42})C(O)N(R^{41})$, $(R^{41})NC(O)N(R^{42})$, $N(R^{42})C(S)N(R^{41})$, $(R^{41})NC(S)N(R^{42})$, S(O), $S(O)_2$, $S(O)_2N(R^{41})$, $N(R^{41})S(O)_2$, Se, Se(O), $Se(O)_2$, $Se(O)_2N(R^{41})$, $N(R^{41})Se(O)_2$, $P(O)(R^8)$, $N(R^7)P(O)(R^8)$, $P(O)(R^8)N(R^7)$, $N(R^{41})$, $ON(R^{41})$, and $SiR^{28}R^{29}$ and $(CH(R^{41}))_e$—$W^{22}$—$(CH(R^{42}))_h$ wherein e and h are integers independently selected from 0 through 2 and $W^{22}$ is selected from the group consisting, of $CR^{41}$=$CR^{42}$, $CR^{41}R^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{41}$ and $R^{42}$ are selected from other than halo and cyano when directly bonded to N, $Z^0$ is directly bonded to the pyrazinone ring, and $W^{22}$ is optionally substituted with one or more substituents selected from the group consisting of $R^9$, $R^{10}$, $R^{11}$, $R^{12}$, and $R^{13}$;

$R^{28}$ and $R^{29}$ are independently selected from the group consisting of hydrido, hydroxyalkyl, alkyl, alkenyl, alkynyl, aryl, aralkyl, aryloxyalkyl, acyl, aroyl, aralkanoyl, heteroaroyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, arylsulfinylalkyl, arylsulfonylalkyl, aralkylsulfinyl, cycloalkylsulfinylalkyl, cycloalkylsufonylalkyl, heteroarylsulfonylalkyl, heteroarylsulfinylalkyl, aralkylsulfinylalkyl, aralkylsulfonylalkyl, carboxy, dialkoxyphosphono, diaralkoxyphosphono, dialkoxyphosphonoalkyl and diaralkoxyphosphonoalkyl;

$R^{28}$ and $R^{29}$ are optionally taken together to form a linear moiety spacer having from 2 through 7 atoms and forming a ring selected from the group consisting of a cycloalkyl ring having from 3 through 8 members, a cycloalkenyl ring having from 3 through 8 members, and a heterocyclyl ring having from 3 through 8 members;

Q is formula (II):

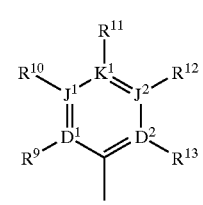

(II)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ can be N, with the provisos that $D^1$, $D^2$, $J^1$, $J^2$ and $K^1$ are selected to maintain an aromatic ring system and that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

Q is optionally selected from formula (III):

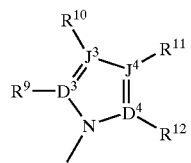

(III)

wherein $D^3$, $D^4$, $J^3$, and $J^4$ are independently selected from the group consisting of C, N, O, and S, no more than one of $D^3$, $D^4$, $J^3$, and $J^4$ is O, no more than one of $D^3$, $D^4$, $J^3$ and $J^4$ is S, and no more than three of $D^3$, $D^4$, $J^3$, and $J^4$ are N, with the provisos that $D^3$, $D^4$, $J^3$, and $J^4$ are selected to maintain an aromatic ring system and that $R^9$, $R^{10}$, $R^{11}$, and $R^{12}$ are each independently selected to maintain the tetravalent nature of carbon, trivalent nature of nitrogen, the divalent nature of sulfur, and the divalent nature of oxygen;

Q is optionally selected from the group consisting of hydrido, alkyl, alkoxy, alkylamino, alkylthio, haloalkylthio, alkenyl, alkynyl, saturated heterocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that $Z^0$ is selected from other than a single covalent bond when Q is hydrido;

K is $(CR^{4a}R^{4b})_n$ wherein n is an integer selected from 1 through 4;

$R^{4a}$ and $R^{4b}$ are independently selected from the group consisting of halo, hydrido, hydroxy, cyano, hydroxyalkyl, alkyl, alkenyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, haloalkyl, haloalkenyl, heteroaryl, heteroarylalkyl, heteroarylthioalkyl, heteroaralkylthioalkyl, cyanoalkyl, alkylsulfinylalkyl, alkylsulfonylalkyl, haloalkylsulfinyl, arylsulfinylalkyl, arylsulfonylalkyl, heteroarylsulfonylalkyl, heteroarylsulfinylalkyl, aralkylsulfinylalkyl, and aralkylsulfonylalkyl with the provisos that halo, hydroxy, and cyano are bonded to different carbons when simultaneously present and that $R^{4a}$ and $R^{4b}$ are other than hydroxy or cyano when bonded to the carbon directly bonded to the pyrazinone nitrogen;

$R^{4a}$ and $R^{4b}$, when bonded to the same carbon, are optionally taken together to form a group selected from the group consisting of oxo, thiono, and a linear spacer moiety having from 2 through 7 atoms connected to form a ring selected from the group consisting of a cycloalkyl ring having 3 through 8 members, a cycloalkenyl ring having 5 through 8 members, and a heterocyclyl ring having 5 through 8 members with the proviso that $R^{4a}$ and $R^{4b}$ taken together is other than oxo or thiono when the common carbon is directly bonded to the pyrazinone nitrogen;

$E^0$ is $E^1$, when K is $(CR^{4a}R^{4b})_n$, wherein $E^1$ is selected from the group consisting of a covalent single bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N($R^7$)C(O), C(O)N($R^7$)S(O)$_2$, Se, Se(O), Se(O)$_2$, Se(O)$_2$N($R^7$), N($R^7$)Se(O)$_2$, P(O)($R^8$), N($R^7$)P(O)($R^8$), P(O)($R^8$)N($R^7$), N($R^7$), ON($R^7$), Si$R^{28}R^{29}$, $CR^{4a}$=$CR^{4b}$, ethynylidene (C≡C; 1,2-ethynyl), and C=$CR^{4a}R^{4b}$;

K is optionally selected to be $(CH(R^{14}))_j$—T wherein j is selected from a integer from 0 through 3 and T is selected from the group consisting of single covalent bond, O, S, and N($R^7$) with the provisos that $R^{14}$ is other than hydroxy, cyano, halo, amino, alkylamino, dialkylamino, and sulfhydryl when j is 1 and that $(CH(R^{14}))_j$ is bonded to the pyrazinone ring;

$E^0$ is optionally $E^2$, when K is $(CH(R^{14}))_j$—T, wherein $E^2$ is selected from the group consisting of a covalent single bond, C(O), C(S), C(O)O, C(S)O, C(O)S, C(S)S, C(O)N($R^7$), ($R^7$)NC(O), C(S)N($R^7$), ($R^7$)NC(S), ($R^7$) NC(O)O, ($R^7$)NC(S)S, ($R^7$)NC(O)S, ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S (O)$_2$, S(O)$_2$N(H)C(O), C(O)N(H)S(O)$_2$, Se(O), Se(O)$_2$, Se(O)$_2$N($R^7$), N($R^7$)Se(O)$_2$, P(O)($R^8$), N($R^7$)P(O)($R^8$), P(O)($R^8$)N($R^7$), and N($R^7$);

K is optionally selected to be G—$(CH(R^{15}))_k$ wherein k is selected from an integer from 1 through 3 and G is selected from the group consisting of O, S, and N($R^7$) with the proviso that $R^{15}$ is other than hydroxy, cyano, halo, amino, alkylamino, dialkylamino, and sulfhydryl when k is 1;

$E^0$ is optionally $E^3$ when K is G—$(CH(R^{15}))_k$ wherein $E^3$ is selected from the group consisting of a covalent single bond, O, S, C(O), C(S), C(O)O, C(S)O, C(O)S, C(S)S, C(O)N($R^7$), ($R^7$)NC(O), C(S)N($R^7$), ($R^7$)NC (S), OC(O)N($R^7$), ($R^7$)NC(O)O, SC(S)N($R^7$), ($R^7$)NC (S)S, SC(O)N($R^7$), ($R^7$)NC(O)S, OC(S)N($R^7$), ($R^7$)NC (S)O, N($R^8$)C(O)N($R^7$), ($R^7$)NC(O)N($R^8$), N($R^8$)C(S) N($R^7$), ($R^7$)NC(S)N($R^8$), S(O), S(O)$_2$, S(O)$_2$N($R^7$), N($R^7$)S(O)$_2$, Se, Se(O), Se(O)$_2$, Se(O)$_2$N($R^7$), N($R^7$) Se(O)$_2$, P(O)($R^8$), N($R^7$)P(O)($R^8$), P(O)($R^8$)N($R^7$), N($R^7$), ON($R^7$), Si$R^{28}R^{29}$, $CR^{4a}$=$CR^{4b}$, ethynylidene (C≡C; 1,2-ethynyl), and C=$CR^{4a}R^{4b}$;

$Y^0$ is formula (IV):

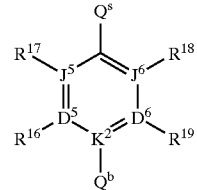

(IV)

wherein $D^5$, $D^6$, $J^5$, and $J^6$ are independently selected from the group consisting of C, N, O, S and a covalent bond with the provisos that no more than one is a covalent bond, $K^2$ is independently selected from the group consisting of C and $N^+$, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, no more than three of $D^5$, $D^6$, $J^5$, and $J^6$ are N when $K^2$ is $N^+$, and no more than four of $D^5$, $D^6$, $J^5$, and $J^6$ are N when $K^2$ is carbon, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen and that $D^5$, $D^6$, $J^5$, and $J^6$ are selected to maintain an aromatic ring system;

$R^{16}$ and $R^{17}$ are independently optionally taken together to form a linear moiety spacer having from 3 through 6 atoms connected to form a ring selected from the group consisting of a cycloalkenyl ring having from 5 through 8 members, a partially saturated heterocyclyl ring having from 5 through 8 members, a heteroaryl having from 5 through 6 members, and an aryl;

$R^{18}$ and $R^{19}$ are independently optionally taken together to form a linear moiety spacer having from 3 through 6 atoms connected to form a ring selected from the group consisting of a cycloalkenyl ring having from 5 through 8 members, a partially saturated heterocyclyl ring having from 5 through 8 members, a heteroaryl having from 5 through 6 members, and an aryl;

$Q^b$ is selected from the group consisting of $NR^{20}R^{21}$, $^+NR^{20}R^{21}R^{22}$, oxy, alkyl, aminoalkyl, alkylamino, dialkylamino, dialkylsulfoniumalkyl, acylamino and hydrido, wherein $R^{20}$, $R^{21}$, and $R^{22}$ are independently selected from the group consisting of hydrido, amino, alkyl, hydroxy, alkoxy, aminoalkylalkylamino, dialkylamino, and hydroxyalkyl with the provisos that no more than one of $R^{20}$, $R^{21}$, and $R^{22}$ is hydroxy, alkoxy, alkylamino, amino, and dialkylamino at the same time and that $R^{20}$, $R^{21}$, and $R^{22}$ must be other than be hydroxy, alkoxy, alkylamino, amino, and dialkylamino when $K^2$ is $N^+$;

$R^{20}$ and $R^{21}$, $R^{20}$ and $R^{22}$, and $R^{21}$ and $R^{22}$ are independently optionally selected to form a spacer pair wherein a spacer pair is taken together to form a linear moiety having from 4 through 7 atoms connecting the points of bonding of said spacer pair members to form a heterocyclyl ring having 5 through 8 members with the proviso that no more than one of the group consisting of spacer pairs $R^{20}$ and $R^{21}$, $R^{20}$ and $R^{22}$, and $R^{21}$ and $R^{22}$ is used at the same time;

$Q^b$ is optionally selected from the group consisting of $N(R^{26})SO_2N(R^{23})(R^{24})$, $N(R^{26})C(O)OR^5$, $N(R^{26})C(O)SR^5$, $N(R^{26})C(S)OR^5$ and $N(R^{26})C(S)SR^5$ with the proviso that no more than one of $R^{23}$, $R^{24}$, and $R^{26}$ can be hydroxy, alkoxy, aminoalkyl, alkylamino, amino, or dialkylamino when two of the group consisting of $R^{23}$, $R^{24}$, and $R^{26}$ are bonded to the same atom;

$Q^b$ is optionally selected from the group consisting of dialkylsulfonium, trialkylphosphonium, $C(NR^{25})NR^{23}R^{24}$, $N(R^{26})C(NR^{25})N(R^{23})(R^{24})$, $N(R^{26})C(O)N(R^{23})(R^{24})$, $N(R^{26})C(S)N(R^{23})(R^{24})$, $C(NR^{25})OR^5$, $C(O)N(R^{26})C(NR^{25})N(R^{23})(R^{24})$ $C(S)N(R^{26})C(NR^{25})N(R^{23})(R^{24})$, $N(R^{26})N(R^{26})C(NR^{25})N(R^{23})(R^{24})$, $ON(R^{26})C(NR^{25})N(R^{23})(R^{24})$, $N(R^{26})N(R^{26})SO_2N(R^{23})(R^{24})$, $C(NR^{25})SR^5$, $C(O)NR^{23}R^{24}$, and $C(O)NR^{23}R^{24}$ with the provisos that no more than one of $R^{23}$, $R^{24}$, and $R^{26}$ can be hydroxy, alkoxy, alkylamino, amino, or dialkylamino when any two of the group consisting of $R^{23}$, $R^{24}$, and $R^{26}$ are bonded to the same atom and that said $Q^b$ group is bonded directly to a carbon atom;

$R^{23}$, $R^{24}$, $R^{25}$, and $R^{26}$ are independently selected from the group consisting of hydrido, alkyl, hydroxy, alkoxy, alkylenylamino, amino, alkylamino, dialkylamino, and hydroxyalkyl;

$R^{23}$ and $R^{24}$ are optionally taken together to form a linear spacer moiety having from 4 through 7 atoms connecting the points of bonding to form a heterocyclyl ring having 5 through 8 members;

$R^{23}$ and $R^{25}$, $R^{24}$ and $R^{25}$, $R^{25}$ and $R^{26}$, $R^{24}$ and $R^{26}$, and $R^{23}$ and $R^{26}$ are independently optionally selected to form a spacer pair wherein a spacer pair is taken together from the points of bonding of selected spacer pair members to form the group L—U—V wherein L, U, and V are independently selected from the group consisting of O, S, C(O), C(S), $C(J_H)_2$, S(O), $SO_2$, $OP(OR^{31})R^{30}$, $P(O)R^{30}$, $P(S)R^{30}$, $C(R^{30})R^{31}$, C=C$(R^{30})R^{31}$, $(O)_2POP(O)_2$, $R^{30}(O)POP(O)R^{30}$, $Si(R^{29})R^{28}$, $Si(R^{29})R^{28}Si(R^{29})R^{28}$, $Si(R^{29})R^{28}OSi(R^{29})R^{28}$, $(R^{28})R^{29}COC(R^{28})R^{29}$, $(R^{28})R^{29}CSC(R^{28})R^{29}$, $C(O)C(R^{30})=C(R^{31})$, $C(S)C(R^{30})=C(R^{31})$, $S(O)C(R^{30})=C(R^{31})$, $SO_2C(R^{30})=C(R^{31})$, $PR^{30}C(R^{30})=C(R^{31})$, $P(O)R^{30}C(R^{30})=C(R^{31})$, $P(S)R^{30}C(R^{30})=C(R^{31})$, $DC(R^{30})(R^{31})D$, $OP(OR^{31})R^{30}$, $P(O)R^{30}$ $P(S)R^{30}$, $Si(R^{28})R^{29}$ and $N(R^{30})$, and a covalent bond with the proviso that no more than any two of L, U and V are simultaneously covalent bonds and the heterocyclyl comprised of by L, U, and V has from 5 through 10 member;

D is selected from the group consisting of oxygen, C=O, C=S, $S(O)_m$ wherein m is an integer selected from 0 through 2;

$J_H$ is independently selected from the group consisting of $OR^{27}$, $SR^{27}$ and $N(R^{20})R^{21}$;

$R^{27}$ is selected from the group consisting of hydrido, alkyl, alkenyl, alkynyl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryloxyalkyl, heteroaryl, heteroarylalkyl, heteroarylthioalkyl, heteroaralkylthioalkyl, arylsulfinylalkyl, arylsulfonylalkyl, cycloalkylsulfinylalkyl, cycloalkylsufonylalkyl, heteroarylsulfonylalkyl, heteroarylsulfinylalkyl, aralkylsulfinylalkyl and aralkylsulfonylalkyl;

$R^{30}$ and $R^{31}$ are independently selected from the group consisting of hydrido, hydroxy, thiol, aryloxy, amino, alkylamino, dialkylamino, hydroxyalkyl, heteroaryloxyalkyl, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, haloaralkylsulfinylalkyl, aralkylsulfonylalkyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, sulfonylalkyl, alkoxysulfonylalkyl, aralkoxysulfonylalkyl, alkoxysulfonylalkoxy, aralkoxysulfonylalkoxy, sulfonylalkoxy, alkoxysulfonylalkylamino, aralkoxysulfonylalkylamino, and sulfonylalkylamino;

$R^{30}$ and $R^{31}$ are optionally taken to form a linear moiety spacer group having from 2 through 7 atoms to form a ring selected from the group consisting of a cycloalkyl ring having from 3 through 8 members, a cycloalkenyl ring having from 3 through 8 members, and a heterocyclyl ring having from 3 through 8 members;

$R^{23}$ and $R^{25}$, $R^{24}$ and $R^{25}$, $R^{25}$ and $R^{26}$, $R^{24}$ and $R^{26}$, and $R^{23}$ and $R^{26}$ are independently optionally selected to form a spacer pair wherein a spacer pair is taken together from the points of bonding of selected spacer pair members to form the group L—U—V wherein L, U, and V are independently selected from the group of 1,2-disubstituted radicals consisting of a cycloalkyl radical, a cycloalkenyl radical wherein cycloalkyl and cycloalkenyl radicals are substituted with one or more groups selected from $R^{30}$ and $R^{31}$, an aryl radical, an heteroaryl radical, a saturated heterocyclic radical and a partially saturated heterocyclic radical wherein said 1,2-substitutents are independently selected from C=O, C=S, C($R^{28}$)$R^{32}$, S(O), S(O)$_2$, OP(O$R^{31}$)$R^{30}$, P(O)$R^{30}$, P(S)$R^{30}$ and Si($R^{28}$)$R^{29}$;

$R^{23}$ and $R^{25}$, $R^{24}$ and $R^{25}$, $R^{25}$ and $R^{26}$, $R^{24}$ and $R^{26}$, and $R^{23}$ and $R^{26}$ are independently optionally selected to form a spacer pair wherein a spacer pair is taken together from the points of bonding of selected spacer pair members to form the group L—U—V wherein L, U, and V are independently selected from the group of radicals consisting of 1,2-disubstituted alkylene radicals and 1,2-disubstituted alkenylene radical wherein said 1,2-substitutents are independently selected from C=O, C=S, C($R^{28}$)$R^{29}$, S(O), S(O)$_2$, OP(O$R^{31}$)$R^{30}$, P(O)$R^{30}$, P(S)$R^{30}$, and Si($R^{28}$)$R^{29}$ and said alkylene and alkenylene radical are substituted with one or more $R^{30}$ or $R^{31}$ substituents;

$Q^s$ is selected from the group consisting of a single covalent bond, $(CR^{37}R^{38})_b$—$(W^0)_{az}$ wherein az is an integer selected from 0 through 1, b is an integer selected from 1 through 4, and $W^0$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), SC(S)N($R^{14}$), SC(O)N($R^{14}$), OC(S)N($R^{14}$), N($R^{15}$)C(O)N($R^{14}$), ($R^{14}$)NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, Se, Se(O), Se(O)$_2$, Se(O)$_2$N($R^{14}$), N($R^{14}$)Se(O)$_2$, P(O)($R^8$), N($R^7$)P(O) ($R^8$), P(O)($R^8$)N($R^7$), N($R^{14}$), ON($R^{14}$), and Si$R^{28}R^{29}$, $(CH(R^{14}))_c$—$W^1$—$(CH(R^{15}))_d$ wherein c and d are integers independently selected from 1 through 4, and $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N ($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{15}$), N($R^{15}$)C(S)N ($R^{14}$), ($R^{14}$)NC(S)N($R^{15}$), S(O), S(O)$_2$, S(O)$_2$N($R^{14}$), N($R^{14}$)S(O)$_2$, Se, Se(O), Se(O)$_2$, Se(O)$_2$N($R^{14}$), N($R^{14}$)Se(O)$_2$, P(O)($R^8$), N($R^7$)P(O)($R^8$), P(O)($R^8$)N ($R^7$), N($R^{14}$), ON($R^{14}$), Si$R^{28}R^{29}$, and $(CH(R^{14}))_e$—$W^{22}$—$(CH(R^{15}))_h$ wherein e and h are integers independently selected from 0 through 2 and $W^{22}$ is selected from the group consisting of $CR^{41}$=$CR^{42}$, $CR^{41}R^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{14}$ and $R^{15}$ are selected from other than halo and cyano when directly bonded to N and that $(CR^{37}R^{38})_b$, $(CH(R^{14}))_c$, $(CH(R^{14}))_e$ and are bonded to $E^0$;

$R^{37}$ and $R^{37}$, when bonded to different carbons, are optionally taken together to form a linear moiety spacer having from 1 through 7 atoms to form a ring selected from the group consisting of a cycloalkyl ring having from 3 through 8 members, a cycloalkenyl ring having from 3 through 8 members, and a heterocyclyl ring having from 3 through 8 members;

$R^{37}$ and $R^{38}$, when bonded to different carbons, are taken together to form a linear moiety spacer having from 1 through 7 atoms to form a ring selected from the group consisting of a cycloalkyl ring having from 3 through 8 members, a cycloalkenyl ring having from 3 through 8 members, and a heterocyclyl ring having from 3 through 8 members;

$R^{38}$ and $R^{38}$, when bonded to different carbons, are taken together to form a linear moiety spacer having from 1 through 7 atoms to form a ring selected from the group consisting of a cycloalkyl ring having from 3 through 8 members, a cycloalkenyl ring having from 3 through 8 members, and a heterocyclyl ring having from 3 through 8 members;

$R^{37}$ and $R^{38}$, when bonded to the same carbon, are taken together to form a group selected from a group consisting of oxo, thiono, alkylene, haloalkylene, and a linear moiety spacer having from 2 through 7 atoms to form a ring selected from the group consisting of a cycloalkyl ring having from 3 through 8 members, a cycloalkenyl ring having from 3 through 8 members, and a heterocyclyl ring having from 3 through 8 members;

$Y^0$ is optionally $Y^{AT}$ wherein $Q^b$—$Q^s$;

$Y^0$ is optionally $Q^b$—$Q^{ss}$ wherein $Q^{ss}$ is selected from the group consisting of $(CR^{37}R^{38})_f$ wherein f is an integer selected from 1 through 6, $(CH(R^{14}))_c$—$W^1$—$(CH(R^{15}))_d$ wherein c and d are integers independently selected from 1 through 4, and $W^1$ is selected from the group consisting of $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N ($R^{14}$), ($R^{14}$)NC(S)O, N($R^{15}$)C(O)N($R^{14}$), ($R^{14}$)NC(O)N ($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, Se, Se(O), Se(O)$_2$, Se(O)$_2$N($R^{14}$), N($R^{14}$)Se(O)$_2$, P(O)($R^8$), N($R^7$)P(O) ($R^8$), P(O)($R^8$)N($R^7$), N($R^{14}$), ON($R^{14}$), Si$R^{28}R^{29}$, and $(CH(R^{14}))_e$—$W^2$—$(CH(R^{15}))_h$ wherein e and h are integers independently selected from 0 through 2 and $W^2$ is selected from the group consisting of $CR^{4a}$=$CR^{4b}$, ethynylidene (C≡C; 1,2-ethynyl), and C=$CR^{4a}R^{4b}$ with the provisos that $R^{14}$ and $R^{15}$ are selected from other than halo and cyano when directly bonded to N, that $(CR^{37}R^{38})_p$, $(CH(R^{15}))_e$, and $(CH(R^{15}))_e$ are bonded to $E^0$, and $Q^b$ is selected from other than $N(R^{26})N(R^{26})C(NR^{25})N(R^{23})(R^{24})$ or $ON(R^{26})C(NR^{25})N(R^{23})(R^{24})$ when $Q^{ss}$ is $(CR^{37}R^{38})_f$ wherein f is other than the integer 1;

$Y^0$ is optionally $Q^b$—$Q^{sss}$ wherein $Q^{sss}$ is $(CH(R^{38}))_r$—$W^3$, r is an integer selected from 1 through 3, $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^3$ other than the points of attachment is optionally substituted with one or more of the group consisting of $R^9$, $R^{10}$, $R^{11}$, and $R^{12}$, with the proviso that $(CH(R^{38}))_r$ is bonded to $E^0$ and $Q^b$ is bonded to lowest numbered substituent position of each $W^3$;

$Y^0$ is optionally $Q^b$—$Q^{sssr}$ wherein $Q^{sssr}$ is $(CH(R^{38}))_r$—$W^4$, r is an integer selected from 1 through 3, $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^4$ other than the points of attachment is optionally substituted with one or more of the group consisting of $R^9$, $R^{10}$, $R^{11}$, and $R^{12}$, with the provisos that $(CH(R^{38}))_r$ is bonded to $E^0$ and $Q^b$ is bonded to highest number substituent position of each $W^4$;

$Y^0$ is optionally $Q^b$—$Q^{ssss}$ wherein $Q^{ssss}$ is $(CH(R^{38}))_r$—$W^5$, r is an integer selected from 1 through 3, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-imidazo(1,2-a)pyridinyl, 2,5-imidazo(1,2-a)pyridinyl, 2,6-imidazo(1,2-a)pyridinyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^0$;

$Y^0$ is optionally $Q^b$—$Q^{ssssr}$ wherein $Q^{ssssr}$ is $(CH(R^{38}))_r$—$W^6$, r is an integer selected from 1 through 3, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-imidazo(1,2-a)pyridinyl, 2,5-imidazo(1,2-a)pyridinyl, 2,6-imidazo(1,2-a)pyridinyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In an embodiment of a compound of Formula I or a pharmaceutically acceptable salt thereof, J is selected from the group consisting of O and S;

J is optionally selected from the group consisting of CH—$R^6$ and N—$R^6$ wherein $R^6$ is a linear spacer moiety having a chain length of 1 to 4 atoms linked to the point of bonding of a substituent selected from the group consisting of $R^{4a}$, $R^{4b}$, $R^{39}$, $R^{40}$, $R^5$, $R^{14}$, and $R^{15}$ to form a heterocyclyl ring having 5 through 8 members;

B is formula (V):

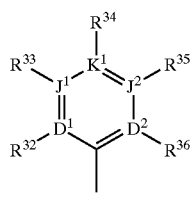

(V)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J_2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the provisos that $D^1$, $D^2$, $J^1$, $J^2$ and $K^1$ are selected to maintain an aromatic ring system and that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of heterocyclylalkoxy, N-alkyl-N-arylamino, heterocyclylamino, heterocyclylalkylamino, hydrido, acetamido, haloacetamido, amidino, guanidino, dialkylsulfonium, trialkylphosphonium, dialkylsulfoniumalkyl, carboxy, heteroaralkylthio, haloalkylthio, alkanoyloxy, alkoxy, alkoxyalkyl, haloalkoxylalkyl, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy; heteroaryloxyalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{36}$ are independently optionally $Q^b$;

$R^{32}$ and $R^{33}$, $R^{33}$ and $R^{34}$, $R^{34}$ and $R^{35}$, and $R^{35}$ and $R^{36}$ are independently optionally selected to form a spacer pair wherein a spacer pair is taken together to form a linear moiety having from 3 through 6 atoms connecting the points of bonding of said spacer pair members to form a ring selected from the group consisting of a cycloalkenyl ring having 5 through 8 members, a partially saturated heterocyclyl ring having 5 through 8 members, a heteroaryl ring having 5 through 6 members, and an aryl with the proviso that no more than one of the group consisting of spacer pairs $R^{32}$ and $R^{33}$, $R^{33}$ and $R^{34}$, $R^{34}$ and $R^{35}$, and $R^{35}$ and $R^{36}$ can be used at the same time;

$R^9$ and $R^{10}$, $R^{10}$ and $R^{11}$, $R^{11}$ and $R^{12}$, and $R^{12}$ and $R^{13}$ are independently optionally selected to form a spacer pair wherein a spacer pair is taken together to form a linear moiety having from 3 through 6 atoms connecting the points of bonding of said spacer pair members to form a ring selected from the group consisting of a cycloalkenyl ring having 5 through 8 members, a partially saturated heterocyclyl ring having 5 through 8 members, a heteroaryl ring having 5 through 6 members, and an aryl with the proviso that no more than one of the group consisting of spacer pairs $R^9$ and $R^{10}$, $R^{10}$ and $R^{11}$, $R^{11}$ and $R^{12}$, and $R^{12}$ and $R^{13}$ can be used at the same time;

B is optionally selected from the group consisting of hydrido, trialkylsilyl, C2–C8 alkyl, C3–C8 alkylenyl, C3–C8 alkenyl, C3–C8 alkynyl, C2–C8 haloalkyl, and C3–C8 haloalkenyl wherein each member of group B may be optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C15 cycloalkyl, C5–C10 cycloalkenyl, C4–C12 saturated heterocyclyl, and C4–C9 partially saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(S), C(O)S, C(S)O, C(O)N($R^7$), C(S)N($R^7$), ($R^7$)NC(O), ($R^7$)NC(S), S(O), S(O)$_2$, S(O)$_2$N($R^7$), ($R^7$)NS(O)$_2$, P(O)($R^8$), N($R^7$)P(O)($R^8$), P(O)($R^8$)N($R^7$), C(NR$^7$)N ($R^7$), ($R^7$)NC(NR$^7$), ($R^7$)NC(NR$^7$)NR$^7$, and N($R^7$) with the proviso that no more than one of the group consisting of rr and pa can be 0 at the same time;

$R^7$ and $R^8$ are independently selected from the group consisting of hydrido, hydroxy, alkyl, acyl, aroyl, heteroaroyl, and alkoxyalkyl;

$R^{14}$, $R^{15}$, $R^{37}$, and $R^{38}$ are independently selected from the group consisting of hydrido, hydroxy, halo, cyano, hydroxyalkyl, alkoxy, alkyl, alkoxyalkyl, cycloalkyl, cycloalkylalkyl, cycloalkenyl, cycloalkenylalkyl, haloalkyl, haloalkenyl, haloalkoxy, haloalkoxyalkyl, haloalkenyloxyalkyl, halocycloalkoxy, halocycloalkoxyalkyl, halocycloalkenyloxyalkyl, carboxy, carboxyalkyl, carboalkoxy, carboxamido, and carboxamidoalkyl, wherein $R^{38}$ is optionally substituted at from one through three of the ring carbons with a substituent selected from the group consisting of $R^{16}$, $R^{17}$, $R^{18}$, and $R^{19}$;

$R^{14}$ and $R^{38}$ can be independently selected from the group consisting of acyl, aroyl, and heteroaroyl with the proviso that acyl is selected from other than formyl and 2-oxoacyl and $R^{38}$ is optionally substituted at from one through three of the ring carbons with a substituent selected from the group consisting of $R^{16}$, $R^{17}$, $R^{18}$, and $R^{19}$;

Ψ is selected from the group consisting of NR$^5$, O, C(O), C(S), S, S(O), S(O)$_2$, ON($R^5$), P(O)($R^8$), and CR$^{39}$R$^{40}$;

$R^5$ is selected from the group consisting of hydrido, hydroxy, amino, alkyl, alkoxy, alkoxyalkyl, haloalkyl, acyl, aroyl, and heteroaroyl;

$R^{39}$ and $R^{40}$ are independently selected from the group consisting of hydrido, hydroxy, halo, cyano, hydroxyalkyl, acyl, aroyl, heteroaroyl, acylamido, alkoxy, alkyl, alkoxyalkyl, haloalkyl, haloalkoxy, haloalkoxyalkyl, alkylsulfonyl, haloalkylsulfonyl, carboxy, carboxyalkyl, carboalkoxy, carboxamido, and carboxamidoalkyl;

$R^2$ and $R^1$ are independently selected from the group consisting of $Z^0$—Q, hydrido, alkyl, alkenyl, and halo with the provisos that $R^2$ is selected from other than the group consisting of hydrido, alkyl, cycloalkyl, and trifluoromethyl and $R^1$ is selected from other than the group consisting of hydrido and halo unless $E^1$ is other than C(O)NH, or unless $E^0$ is selected from the group consisting of $E^2$ and $E^3$, or unless K is other than $(CR^{4a}R^{4b})_n$ wherein n is 1 unless one of $R^{4a}$ and $R^{4b}$ are independently selected from other than hydrido, or unless Ψ is selected from other than NR$^5$, or unless $R^5$ is selected from other than hydrido, or unless $Y^0$ is selected from other than wherein $Q^s$ is $C_{1-4}$ alkyl, $C_{3-4}$ alkenyl or $C_{3-4}$ alkynyl where the $C_{1-4}$ alkyl, $C_{3-4}$ alkenyl or $C_{3-4}$ alkynyl group is bonded concurrently to $E^1$ wherein $E^1$ is C(O)NH and to the 4-position of an imidazole, the 4-position of a thiazole or the 5-position of a thiazole, or unless a spacer pair is present selected from the group of spacer pairs consisting of $R^2$ and $R^{4a}$, $R^2$ and $R^{4b}$, $R^2$ together with both $R^{4a}$ and $R^{4b}$, $R^2$ and $R^{14}$, $R^2$ and $R^{15}$, and $R^6$ with another group selected from the group consisting of $R^{4a}$, $R^{4b}$, $R^{4a}$ and $R^{4b}$ together, $R^{39}$, $R^{40}$, $R^{39}$ and $R^{40}$ together, $R^{14}$, $R^{15}$, and $R^5$, that $R^2$ is selected from other than the group consisting of hydroxymethyl, methyl, methoxymethyl, methylthiomethyl, phenylthiomethyl, methylsulfinyl, methylthio, alkoxy, cycloalkoxy, alkylthio, alkylsulfinyl, alkysulfonyl, cycloalkylthio, cycloalkylsulfinyl, and cycloalkysulfonyl, when $Y^0$ is other than phenyl, mono-substituted phenyl, and di-substituted phenyl 5-(2-amino)pyridindyl, or 4-(2-amino)pyridindyl, and that $R^2$ is selected from other than the group consisting of hydrido, halo, alkyl, cycloalkyl when $Y^0$ is methyleneimidazo(1,2-a) pyridinyl, 4,5-benzimidazol-5-yl, or indol-5-yl unless $R^1$ is selected from other than the group consisting of hydrido or halo, or unless $E^1$ is other than C(O)NH, or unless $E^0$ is selected from the group consisting of $E^2$ and $E^3$, or unless K is other than $(CR^{4a}R^{4b})_n$ wherein n is 1 unless one of $R^{4a}$ and $R^{4b}$ are independently selected from other than hydrido, or unless Ψ is selected from other than NR$^5$ wherein $R^5$ is hydrido;

23

R¹ is optionally selected from the group consisting of amino, aminoalkyl, alkylamino, amidino, guanidino, hydroxy, hydroxyamino, alkoxy, hydroxyalkyl, alkoxyamino, thiol, alkylthio, dialkylsulfonium, trialkylphosphonium, dialkylsulfoniumalkyl, heteroarylamino, nitro, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

Z⁰ is selected from the group consisting of covalent single bond, $(CR^{41}R^{42})_q$ wherein q is an integer selected from 1 through 6, $(CH(R^{41}))_g—W^0—(CH(R^{42}))_p$ wherein g and p are integers independently selected from 0 through 3 and $W^0$ is selected from the group consisting of O, S, C(O), C(S), C(O)O, C(S)O, C(O)S, C(S)S, C(O)N(R⁴¹), (R⁴¹)NC(O), C(S)N(R⁴¹), (R⁴¹)NC(S), OC(O)N(R⁴¹), (R⁴¹)NC(O)O, SC(S)N(R⁴¹), (R⁴¹)NC(S)S, SC(O)N(R⁴¹), (R⁴¹)NC(O)S, OC(S)N(R⁴¹), (R⁴¹)NC(S)O, N(R⁴²)C(O)N(R⁴¹), (R⁴¹)NC(O)N(R⁴²), N(R⁴²)C(S)N(R⁴¹), (R⁴¹)NC(S)N(R⁴²), S(O), S(O)₂, S(O)₂N(R⁴¹), N(R⁴¹)S(O)₂, Se, Se(O), Se(O)₂, Se(O)₂N(R⁴¹), N(R⁴¹)Se(O)₂, P(O)(R⁸), N(R⁷)P(O)(R⁸), P(O)(R⁸)N(R⁷), N(R⁴¹), ON(R⁴¹), and SiR²⁸R²⁹, and $(CH(R^{41}))_e—W^{22}—(CH(R^{42}))_h$ wherein e and h are integers independently selected from 0 through 2 and $W^{22}$ is selected from the group consisting of CR⁴¹=CR⁴², CR⁴¹R⁴²=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that R⁴¹ and R⁴² are selected from other than halo and cyano when directly bonded to N, Z⁰ is directly bonded to the pyrazinone ring, and $W^{22}$ is optionally substituted with one or more substituents selected from the group consisting of R⁹, R¹⁰, R¹¹, R¹², and R¹³;

R⁴¹ and R⁴² are independently selected from the group consisting of amidino, hydroxyamino, hydrido, hydroxy, amino, halo, cyano, aryloxy, hydroxyalkyl, acyl, aroyl, heteroaroyl, heteroaryloxyalkyl, alkoxy, alkyl, aryl, aralkyl, aryloxyalkyl, aralkoxyalkylalkoxy, alkoxyalkyl, heteroaryloxyalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroaralkyl, heteroarylthioalkyl, heteroaralkylthioalkyl, alkylsulfonyl, haloalkylsulfonyl, arylsulfonyl, arylsulfonylalkyl, aralkylsulfonyl, cycloalkylsulfonyl, cycloalkylsufonylalkyl, heteroarylsulfonylalkyl, heteroarylsulfonyl, and aralkylsulfonylalkyl;

24

Q is formula (II):

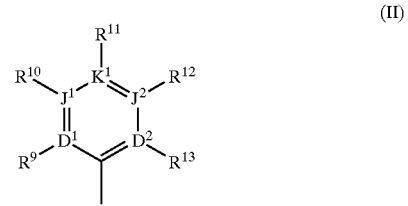

wherein D¹, D², J¹, J² and K¹ are independently selected from the group consisting of C, N, O, S and a covalent bond with the provisos that no more than one is a covalent bond, no more than one of D¹, D², J¹, J² and K¹ is O, no more than one of D¹, D², J¹, J² and K¹ is S, one of D¹, D², J¹, J² and K¹ must be a covalent bond when two of D¹, D², J¹, J² and K¹ are O and S, and no more than four of D¹, D², J¹, J² and K¹ are N, with the proviso that R⁹, R¹⁰, R¹¹, R¹², and R¹³ are each independently selected to maintain the tetravalent nature of carbon, trivalent nature of nitrogen, the divalent nature of sulfur, and the divalent nature of oxygen and that D¹, D², J¹, J² and K¹ are selected to maintain an aromatic ring system;

Q is optionally selected from formula (III):

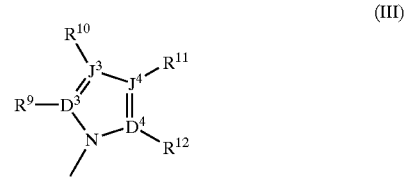

wherein D³, D⁴, J³, and J⁴ are independently selected from the group consisting of C, N, O and S, no more than one of D³, D⁴, J³, and J⁴ is O, no more than one of D³, D⁴, J³ and J⁴ is S, and no more than three of D¹, D², J¹, and J² are N, with the provisos that R⁹, R¹⁰, R¹¹, and R¹² are each independently selected to maintain the tetravalent nature of carbon, trivalent nature of nitrogen, the divalent nature of sulfur, and the divalent nature of oxygen and that D³, D⁴, J³, and J⁴ are selected to maintain an aromatic ring system;

Q is optionally selected from the group consisting of hydrido, alkyl, alkoxy, alkylamino, alkylthio, haloalkylthio, alkenyl, alkynyl, saturated heterocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that Z⁰ is selected from other than a single covalent bond when Q is hydrido;

K is $(CR^{4a}R^{4b})_n$ wherein n is an integer selected from 1 through 2;

R⁴ᵃ and R⁴ᵇ are independently selected from the group consisting of halo, hydrido, hydroxy, cyano, hydroxyalkyl, alkyl, alkenyl, alkoxyalkyl, aralkyl, heteroaralkyl, alkylthioalkyl, haloalkyl, haloalkenyl, and cyanoalkyl;

E⁰ is E¹, when K is $(CR^{4a}R^{4b})_n$, wherein E¹ is selected from the group consisting of a covalent single bond, O, S, C(O), C(S), C(O)O, C(S)O, C(O)S, C(S)S, C(O)N(R$^7$), (R$^7$)NC(O), C(S)N(R$^7$), (R$^7$)NC(S), OC(O)N(R$^7$), (R$^7$)NC(O)O, SC(S)N(R$^7$), (R$^7$)NC(S)S, SC(O)N(R$^7$), (R$^7$)NC(O)S, OC(S)N(R$^7$), (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N(R$^7$), N(R$^7$)S(O)$_2$, S(O)$_2$N(R$^7$)C(O), C(O)N(R$^7$)S(O)$_2$, P(O)(R$^8$), N(R$^7$)P(O)(R$^8$), P(O)(R$^8$)N(R$^7$), N(R$^7$), ON(R$^7$), CR$^{4a}$=CR$^{4b}$, ethynylidene (C≡C; 1,2-ethynyl), and C=CR$^{4a}$R$^{4b}$;

K is optionally (CH(R$^{14}$))$_j$—T wherein j is selected from a integer from 0 through 2 and T is selected from the group consisting of single covalent bond, O, S, and N(R$^7$) with the proviso that (CH(R$^{14}$))$_j$ is bonded to the pyrazinone ring;

E$^0$ is optionally E$^2$, when K is (CH(R$^{14}$))$_j$—T, wherein E$^2$ is selected from the group consisting of a covalent single bond, C(O), C(S), C(O)O, C(S)O, C(O)S, C(S)S, C(O)N(R$^7$), (R$^7$)NC(O), C(S)N(R$^7$), (R$^7$)NC(S), (R$^7$)NC(O)O, (R$^7$)NC(S)S, (R$^7$)NC(O)S, (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O), S(O)$_2$N(R$^7$), N(R$^7$)S(O)$_2$, S(O)$_2$N(H)C(O), C(O)N(H)S(O)$_2$, P(O)(R$^8$), N(R$^7$)P(O)(R$^8$), P(O)(R$^8$)N(R$^7$), and N(R$^7$));

K is optionally G—(CH(R$^{15}$))$_k$ wherein k is selected from an integer from 1 through 2 and G is selected from the group consisting of O, S, and N(R$^7$) with the proviso that R$^{15}$ is other than hydroxy, cyano, halo, amino, alkylamino, dialkylamino, and sulfhydryl when k is 1;

E$^0$ is optionally E$^3$ when K is G—(CH(R$^{15}$))$_k$, wherein E$^3$ is selected from the group consisting of a covalent single bond, O, S, C(O), C(S), C(O)O, C(S)O, C(O)S, C(S)S, C(O)N(R$^7$), (R$^7$)NC(O), C(S)N(R$^7$), (R$^7$)NC(S), OC(O)N(R$^7$), (R$^7$)NC(O)O, SC(S)N(R$^7$), (R$^7$)NC(S)S, SC(O)N(R$^7$), (R$^7$)NC(O)S, OC(S)N(R$^7$), (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N(R$^7$), N(R$^7$)S(O)$_2$, P(O)(R$^8$), N(R$^7$)P(O)(R$^8$), P(O)(R$^8$)N(R$^7$), N(R$^7$), ON(R$^7$), CR$^{4a}$=CR$^{4b}$, ethynylidene (C≡C; 1,2-ethynyl), and C=CR$^{4a}$R$^{4b}$;

Y$^0$ is formula (IV):

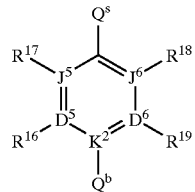

(IV)

wherein D$^5$, D$^6$, J$^5$, and J$^6$ are independently selected from the group consisting of C, N, O, S and a covalent bond with the provisos that no more than one is a covalent bond, K$^2$ is independently selected from the group consisting of C and N$^+$, no more than one of D$^5$, D$^6$, J$^5$, and J$^6$ is O, no more than one of D$^5$, D$^6$, J$^5$, and J$^6$ is S, one of D$^5$, D$^6$, J$^5$, and J$^6$ must be a covalent bond when two of D$^5$, D$^6$, J$^5$, and J$^6$ are O and S, no more than three of D$^5$, D$^6$, J$^5$, and J$^6$ is N when K$^2$ is N$^+$, and no more than four of D$^5$, D$^6$, J$^5$, and J$^6$ are N when K$^2$ is carbon, with the provisos that R$^{16}$, R$^{17}$, R$^{18}$, and R$^{19}$ are each independently selected to maintain the tetravalent nature of carbon, trivalent nature of nitrogen, the divalent nature of sulfur, and the divalent nature of oxygen and that D$^5$, D$^6$, J$^5$, and J$^6$ are selected to maintain an aromatic ring system;

R$^{16}$ and R$^{17}$ are optionally independently taken together to form a linear moiety spacer having from 3 through 6 atoms connected to form a ring selected from the group consisting of a cycloalkenyl ring having from 5 through 8 members, a partially saturated heterocyclyl ring having from 5 through 8 members, a heteroaryl having from 5 through 6 members, and an aryl;

Q$^b$ is selected from the group consisting of NR$^{20}$R$^{21}$, $^+$NR$^{20}$R$^{21}$, R$^{22}$, oxy, alkyl, aminoalkyl, alkylamino, dialkylamino, dialkylsulfoniumalkyl, acylamino and hydrido, wherein R$^{20}$, R$^{21}$, and R$^{22}$ are independently selected from the group consisting of hydrido, amino, alkyl, hydroxy, alkoxy, aminoalkyl, alkylamino, dialkylamino, and hydroxyalkyl with the provisos that no more than one of R$^{20}$, R$^{21}$, and R$^{22}$ is hydroxy, alkoxy, alkylamino, amino, and dialkylamino at the same time and that R$^{20}$, R$^{21}$, and R$^{22}$ must be other than be hydroxy, alkoxy, alkylamino, amino, and dialkylamino when K$^2$ is N$^+$;

R$^{20}$ and R$^{21}$, R$^{20}$ and R$^{22}$, and R$^{21}$ and R$^{22}$ are independently optionally selected to form a spacer pair wherein a spacer pair is taken together to form a linear moiety having from 4 through 7 atoms connecting the points of bonding of said spacer pair members to form a heterocyclyl ring having 5 through 8 members with the proviso that no more than one of the group consisting of spacer pairs R$^{20}$ and R$^{21}$, R$^{20}$ and R$^{22}$, and R$^{21}$ and R$^{22}$ is used at the same time;

Q$^b$ is optionally selected from the group consisting of N(R$^{26}$)SO$_2$N(R$^{23}$)(R$^{24}$), N(R$^{26}$)C(O)OR$^5$, N(R$^{26}$)C(O)SR$^5$, N(R$^{26}$)C(S)OR$^5$ and N(R$^{26}$)C(S)SR$^5$ with the proviso that no more than one of R$^{23}$, R$^{24}$, and R$^{26}$ is hydroxy, alkoxy, alkylamino, amino, and dialkylamino when two of the group consisting of R$^{23}$, R$^{24}$, and R$^{26}$ are bonded to the same atom;

Q$^b$ is optionally selected from the group consisting of dialkylsulfonium, trialkylphosphonium, C(NR$^{25}$)NR$^{23}$R$^{24}$, N(R$^{26}$)C(NR$^{25}$)N(R$^{23}$)(R$^{24}$), N(R$^{26}$)C(O)N(R$^{23}$)(R$^{24}$), N(R$^{26}$)C(S)N(R$^{23}$)(R$^{24}$), C(NR$^{25}$)OR$^5$, C(O)N(R$^{26}$)C(NR$^{25}$)N(R$^{23}$)(R$^{24}$), C(S)N(R$^{26}$)C(NR$^{25}$)N(R$^{23}$)(R$^{24}$), N(R$^{26}$)N(R$^{26}$)C(NR$^{25}$)N(R$^{23}$)(R$^{24}$), ON(R$^{26}$)C(NR$^{25}$)N(R$^{23}$)(R$^{24}$), N(R$^{26}$)N(R$^{26}$)SO$_2$N(R$^{23}$)(R$^{24}$), C(NR$^{25}$)SR$^5$, C(O)NR$^{23}$R$^{24}$, and C(O)NR$^{23}$R$^{24}$ with the provisos that no more than one of R$^{23}$, R$^{24}$, and R$^{26}$ can be hydroxy, alkoxy, alkylaminol, amino, or dialkylamino when two of the group consisting of R$^{23}$, R$^{24}$ and R$^{26}$ are bonded to the same atom and that said Q$^b$ group is bonded directly to a carbon atom;

R$^{23}$, R$^{24}$, R$^{25}$, and R$^{26}$ are independently selected from the group consisting of hydrido, alkyl, hydroxy, alkoxy, aminoalkyl, alkylamino, dialkylamino, amino, and hydroxyalkyl;

R$^{23}$ and R$^{24}$ are optionally taken together to form a linear spacer moiety having from 4 through 7 atoms connecting the points of bonding to form a heterocyclyl ring having 5 through 8 members;

Q$^s$ is selected from the group consisting of a single covalent bond, (CR$^{37}$R$^{38}$)$_b$—(W$^0$)$_{az}$ wherein az is an integer selected from 0 through 1, b is an integer selected from 1 through 4, and W$^0$ is selected from the group consisting of O, S, C(O), C(S), C(O)O, C(S)O, C(O)S, C(S)S, C(O)N(R$^{14}$), (R$^{14}$)NC(O), C(S)N(R$^{14}$), (R$^{14}$)NC(S), OC(O)N(R$^{14}$), SC(S)N(R$^{14}$), SC(O)N(R$^{14}$), OC(S)N(R$^{14}$), N(R$^{15}$)C(O)N(R$^{14}$), (R$^{14}$)NC(O)N(R$^{15}$) N(R$^{15}$)C(S)N(R$^{14}$), (R$^{14}$)NC(S)N(R$^{15}$), S(O), S(O)$_2$, S(O)$_2$N(R$^{14}$), N(R$^{14}$)S(O)$_2$, P(O)(R$^8$), N(R$^7$)P(O)(R$^8$), P(O)(R$^8$)N(R$^7$), N(R$^{14}$), ON(R$^{14}$), (CH(R$^{14}$))$_c$—W$^1$—(CH(R$^{15}$))$_d$ wherein c and d are integers independently selected from 1 through 4, and W$^1$ is selected from the group consisting of O, S, C(O), C(S), C(O)O, C(S)O, C(O)S, C(S)S, C(O)N(R$^{14}$), (R$^{14}$)NC(O), C(S)N(R$^{14}$), (R$^{14}$)NC(S), OC(O)N(R$^{14}$), (R$^{14}$)NC(O)O, SC(S)N(R$^{14}$), (R$^{14}$)NC(S)S, SC(O)N(R$^{14}$), (R$^{14}$)NC(O)S, OC(S)N(R$^{14}$), (R$^{14}$)NC(S)O, N(R$^{15}$)C(O)N(R$^{14}$), (R$^{14}$)NC(O)N(R$^{15}$), N(R$^{15}$)C(S)N(R$^{14}$), (R$^{14}$)NC(S)N(R$^{15}$), S(O), S(O)$_2$, S(O)$_2$N(R$^{14}$), N(R$^{14}$)S(O)$_2$, P(O)(R$^8$), N(R$^7$)P(O)(R$^8$), P(O)(R$^8$)N(R$^7$), N(R$^{14}$), ON(R$^{14}$), and (CH(R$^{14}$))$_e$—W$^{22}$—(CH(R$^{15}$))$_h$ wherein e and h are integers independently selected from 0 through 2 and W$^{22}$ is selected from the group consisting of CR$^{41}$=CR$^{42}$, CR$^{41}$R$^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that R$^{14}$ and R$^{15}$ are selected from other than halo and cyano when directly bonded to N and that (CR$^{37}$R$^{38}$)$_b$, (CH(R$^{14}$))$_c$, (CH(R$^{14}$))$_e$ and are bonded to E$^0$;

Y$^0$ is optionally Y$^{AT}$ wherein Y$^{AT}$ is Q$^b$—Q$^s$;

Y$^0$ is optionally Q$^b$—Q$^{ss}$ wherein Q$^{ss}$ is selected from the group consisting of (CR$^{37}$R$^{38}$)$_f$ wherein f is an integer selected from 1 through 6, (CH(R$^{14}$))$_c$—W$^1$—(CH(R$^{15}$))$_d$ wherein c and d are integers independently selected from 1 through 4, and W$^1$ is selected from the group consisting of W$^1$ is selected from the group consisting of O, S, C(O), C(S), C(O)O, C(S)O, C(O)S, C(S)S, C(O)N(R$^{14}$), (R$^{14}$)NC(O), C(S)N(R$^{14}$), (R$^{14}$)NC(S), OC(O)N(R$^{14}$), (R$^{14}$)NC(O)O, SC(S)N(R$^{14}$), (R$^{14}$)NC(S)S, SC(O)N(R$^{14}$), (R$^{14}$)NC(O)S, OC(S)N(R$^{14}$), (R$^{14}$)NC(S)O, N(R$^{15}$)C(O)N(R$^{14}$), (R$^{14}$)NC(O)N(R$^{15}$), N(R$^{15}$)C(S)N(R$^{14}$), (R$^{14}$)NC(S)N(R$^{15}$), S(O), S(O)$_2$, S(O)$_2$N(R$^{14}$), N(R$^{14}$)S(O)$_2$, P(O)(R$^8$), N(R$^7$)P(O)(R$^8$), P(O)(R$^8$)N(R$^7$), N(R$^{14}$) ON(R$^{14}$), and (CH(R$^{14}$))$_e$—W$^2$—(CH(R$^{15}$))$_h$ wherein e and h are integers independently selected from 0 through 2 and W$^2$ is selected from the group consisting of CR$^{4a}$=CR$^{4b}$, ethynylidene (C≡C; 1,2-ethynyl), and C=CR$^{4a}$R$^{4b}$ with the provisos that R$^{14}$ and R$^{15}$ are selected from other than halo and cyano when directly bonded to N and that (CR$^{37}$R$^{38}$)$_f$, (CH(R$^{14}$))$_c$, and (CH(R$^{14}$))$_e$ are bonded to E$^0$;

Y$^0$ is optionally Q$^b$—Q$^{sss}$ wherein Q$^{sss}$ is (CH(R$^{38}$))$_r$—W$^3$, r is an integer selected from 1 through 3, W$^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the W$^3$ other than the points of attachment is optionally substituted with one or more of the group consisting of R$^9$, R$^{10}$, R$^{11}$, and R$^{12}$, with the proviso that (CH(R$^{38}$))$_r$ is bonded to E$^0$ and Q$^b$ is bonded to lowest numbered substituent position of each W$^3$;

Y$^0$ is optionally Q$^b$—Q$^{sssr}$ wherein Q$^{sssr}$ is (CH(R$^{38}$))$_r$—W$^4$, r is an integer selected from 1 through 3, W$^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hydrido containing nitrogen member of the ring of the W$^4$ other than the points of attachment is optionally substituted with one or more of the group consisting of R$^9$, R$^{10}$, R$^{11}$, and R$^{12}$, with the provisos that (CH(R$^{38}$))$_r$ is bonded to E$^0$ and Q$^b$ is bonded to highest number substituent position of each W$^4$;

Y$^0$ is optionally Q$^b$—Q$^{ssss}$ wherein Q$^{ssss}$ is (CH(R$^{38}$))$_r$—W$^5$, r is an integer selected from 1 through 3, W$^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3, benzisoxazolyl, 3,6- benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^0$;

$Y^0$ is optionally $Q^b$—$Q^{ssssr}$ wherein $Q^{ssssr}$ is $(CH(R^{38}))_r$—$W^6$, r is an integer selected from 1 through 3, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In another embodiment of a compound of Formula I or a pharmaceutically acceptable salt thereof, J is selected from the group consisting of O and S;

B is formula (V):

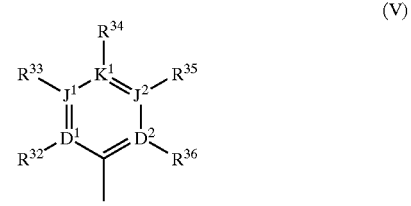

(V)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the provisos that $D^1$, $D^2$, $J^1$, $J^2$ and $K^1$ are selected to maintain an aromatic ring system and that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{32}$, $R^{18}$, $R^{19}$, $R^{33}$, $R^{34}$, $R^{35}$, and $R^{36}$ are independently selected from the group consisting of heterocyclylalkoxy, N-alkyl-N-arylamino, heterocyclylamino, heterocyclylalkylamino, hydrido, acetamido, haloacetamido, amidino, guanidino, dialkylsulfonium, trialkylphosphonium, dialkylsulfoniumalkyl, carboxy, heteroaralkylthio, haloalkylthio, alkanoyloxy, alkoxy, alkoxyalkyl, haloalkoxyalkyl, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{36}$ are independently optionally $Q^b$;

B is optionally selected from the group consisting of hydrido, trialkylsilyl, C2–C8 alkyl, C3–C8 alkylenyl, C3–C8 alkenyl, C3–C8 alkynyl, C2–C8 haloalkyl, and C3–C8 haloalkenyl wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C12 cycloalkyl, C5–C10 cycloalkenyl, and C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(O)N($R^7$), C(S)N($R^7$), ($R^7$)NC(O), ($R^7$)NC(S), and N($R^7$) with the proviso that no more than one of the group consisting of rr and pa can be 0 at the same time;

$R^7$ and $R^8$ are independently selected from the group consisting of hydrido, hydroxy, alkyl, and alkoxyalkyl;

$R^{14}$, $R^{15}$, $R^{37}$, and $R^{38}$ are independently selected from the group consisting of hydrido, hydroxy, halo, alkyl, alkoxyalkyl, haloalkyl, haloalkoxy, and haloalkoxyalkyl;

$R^{14}$ and $R^{38}$ can be independently selected from the group consisting of aroyl and heteroaroyl, wherein $R^{38}$ is optionally substituted at from one through three of the ring carbons with a substituent selected from the group consisting of $R^{16}$, $R^{17}$, $R^{18}$, and $R^{19}$;

Ψ is selected from the group consisting of $NR^5$, C(O), and S(O)$_2$;

$R^5$ is selected from the group consisting of hydrido, hydroxy, alkyl, and alkoxy;

$R^{39}$ and $R^{40}$ are independently selected from the group consisting of hydrido, hydroxy, halo, hydroxyalkyl, alkyl, alkoxyalkyl, haloalkyl, haloalkoxy, and haloalkoxyalkyl;

$R^1$ is selected from the group consisting of hydrido, alkyl, alkenyl, cyano, halo, haloalkyl, haloalkoxy, haloalkylthio, amino, aminoalkyl, alkylamino, amidino, guanidino, hydroxy, hydroxyamino, alkoxy, hydroxyalkyl, alkoxyamino, thiol, alkylthio, and phosphono;

$R^2$ is $Z^0$—Q;

$Z^0$ is selected from the group consisting of covalent single bond, $(CR^{41}R^{42})_q$ wherein q is an integer selected from 1 through 3, $(CH(R^{41}))_g$—$W^0$—$(CH(R^{42}))_p$ wherein g and p are integers independently selected from 0 through 3 and $W^0$ is selected from the group consisting of O, S, C(O), S(O), S(O)$_2$, N($R^{41}$), and ON($R^{41}$), and $(CH(R^{41}))_e$—$W^{22}$—$(CH(R^{42}))_h$ wherein e and h are integers independently selected from 0 through 2 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $Z^0$ is directly bonded to the pyrazinone ring and $W^{22}$ is optionally substituted with one or more substituents selected from the group consisting of $R^9$, $R^{10}$, $R^{11}$, $R^{12}$, and $R^{13}$;

$R^{41}$ and $R^{42}$ are independently selected from the group consisting of amidino, hydroxyamino, hydrido, hydroxy, amino, and alkyl;

Q is selected from the group consisting of hydrido, with the proviso that $Z^0$ is other than a covalent single bond, the formula (II):

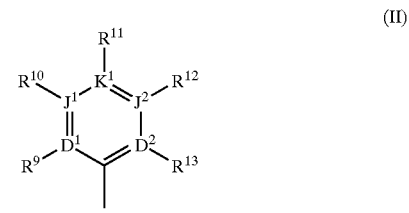

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ is N, with the provisos that $D^1$, $D^2$, $J^1$, $J^2$ and $K^1$ are selected to maintain an aromatic ring system and that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

K is $(CR^{4a}R^{4b})_n$ wherein n is 1 or 2;

$R^{4a}$ and $R^{4b}$ are independently selected from the group consisting of halo, hydrido, hydroxyalkyl, alkyl, alkoxyalkyl, alkylthioalkyl, and haloalkyl;

$E^o$ is selected from the group consisting of a covalent single bond, C(O), C(S), C(O)N($R^7$), ($R^7$)NC(O), S(O)$_2$, ($R^7$)NS(O)$_2$, and S(O)$_2$N($R^7$);

$Y^o$ is formula (IV):

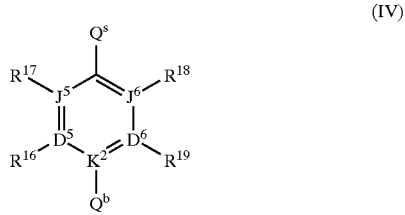

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N when $K^2$ is carbon, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen and that $D^5$, $D^6$, $J^5$, and $J^6$ are selected to maintain an aromatic ring system;

$Q^b$ is selected from the group consisting of $NR^{20}R^{21}$, $^+NR^{20}R^{21}R^{22}$, aminoalkyl, and hydrido, wherein $R^{20}$, $R^{21}$, and $R^{22}$ are independently selected from the group consisting of hydrido, alkyl, hydroxy, amino, aminoalkyl, dialkylamino, alkylamino, and hydroxyalkyl with the proviso that no more than one of $R^{20}$ and $R^{21}$ is selected from the groujp consisting of hydroxy, amino, alkylamino, and dialkylamino at the same time;

$Q^b$ is optionally selected from the group consisting of C($NR^{25}$)$NR^{23}R^{24}$, N($R^{26}$)C($NR^{25}$)N($R^{23}$)($R^{24}$), C(O)N($R^{26}$)C($NR^{25}$)N($R^{23}$)($R^{24}$), N($R^{26}$)N($R^{26}$)C($NR^{25}$)N($R^{23}$)($R^{24}$), and ON($R^{26}$)C($NR^{25}$)N($R^{23}$)($R^{24}$) with the provisos that no more than one of $R^{23}$, $R^{24}$, and $R^{26}$ is selected from the groujp consisting of hydroxy, amino, alkylamino, and dialkylamino when two of the group consisting of $R^{23}$, $R^{24}$, and $R^{26}$ are bonded to the same atom;

$R^{23}$, $R^{24}$, $R^{25}$, and $R^{26}$ are independently selected from the group consisting of hydrido, alkyl, hydroxy, amino, aminoalkyl, dialkylamino, alkylamino, and hydroxyalkyl;

$Q^s$ is selected from the group consisting of a single covalent bond, $(CR^{37}R^{38})_b$—$(W^o)_{az}$ wherein az is an integer selected from 0 through 1, b is an integer selected from 1 through 5, and $W^o$ is selected from the group consisting of O, C(O), S(O), S(O)$_2$, S(O)$_2$N($R^{14}$), N($R^{14}$)S(O)$_2$, and N($R^{14}$), (CH($R^{14}$))$_c$—$W^1$—(CH($R^{15}$))$_d$ wherein c and d are integers independently selected from 1 through 4 and $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, P(O)($R^8$), N($R^7$)P(O)($R^8$), P(O)($R^8$)N($R^7$), N($R^{14}$), ON($R^{14}$), and (CH($R^{14}$))$_e$—$W^{22}$—(CH($R^{15}$))$_h$ wherein e and h are integers independently selected from 0 through 2 and $W^{22}$ is selected from the group consisting of $CR^{41}$=$CR^{42}$, $CR^{41}R^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{14}$ and $R^{15}$ are selected from other than halo and cyano when directly bonded to N and that $(CR^{37}R^{38})_b$, $(CH(R^{14}))_c$, and $(CH(R^{14}))_e$ are bonded to $E^o$;

$Y^o$ is optionally $Y^{AT}$ wherein $Y^{AT}$ is $Q^b$—$Q^s$;

$Y^o$ is optionally $Q^b$—$Q^{ss}$ wherein $Q^{ss}$ is selected from the group consisting of $(CR^{37}R^{38})_f$ wherein f is an integer selected from 1 through 4, $(CH(R^{14}))_c$—$W^1$—(CH($R^{15}$))$_d$ wherein c and d are integers independently selected from 1 through 2, and $W^1$ is selected from the group consisting of $W^1$ is selected from the group consisting of O, S, C(O), C(O)N($R^{14}$), ($R^{14}$)NC(O), N($R^{15}$)C(O)N($R^{14}$), ($R^{14}$)NC(O)N($R^{15}$), N($R^{14}$), ON($R^{14}$), and (CH($R^{14}$))$_e$—$W^2$—(CH($R^{15}$))$_h$ wherein e and h are integers independently selected from 0 through 2 and $W^2$ is selected from the group consisting of $CR^{4a}$=$CR^{4b}$, ethynylidene (C≡C; 1,2-ethynyl), and C=$CR^{4a}R^{4b}$ with the provisos that $R^{14}$ and $R^{15}$ are selected from other than halo when directly bonded to N and that $(CR^{37}R^{38})_f$, $(CH(R^{14}))_c$, and $(CH(R^{14}))_e$ are bonded to $E^o$;

$Y^o$ is optionally $Q^b$—$Q^{sss}$ wherein $Q^{sss}$ is $(CH(R^{38}))_r$—$W^3$, r is an integer selected from 1 through 2, $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3- tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^3$ other than the points of attachment is optionally substituted with one or more of the group consisting of $R^9$, $R^{10}$, $R^{11}$, and $R^{12}$, with the proviso that $(CH(R^{38}))_r$ is bonded to $E^0$ and $Q^b$ is bonded to lowest numbered substituent position of each $W^3$;

$Y^0$ is optionally $Q^b$—$Q^{sssr}$ wherein $Q^{sssr}$ is $(CH(R^{38}))_r$—$W^4$, r is an integer selected from 1 through 2, $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^4$ other than the points of attachment is optionally substituted with one or more of the group consisting of $R^9$, $R^{10}$, $R^{11}$, and $R^{12}$, with the provisos that $(CH(R^{38}))_r$ is bonded to $E^0$ and $Q^b$ is bonded to highest number substituent position of each $W^4$;

$Y^0$ is optionally $Q^b$—$Q^{ssss}$ wherein $Q^{ssss}$ is $(CH(R^{38}))_r$—$W^5$, r is an integer selected from 1 through 2, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^0$;

$Y^0$ is optionally $Q^b$—$Q^{ssssr}$ wherein $Q^{ssssr}$ is $(CH(R^{38}))_r$—$W^6$, r is an integer selected from 1 through 2, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In a preferred embodiment of a compound of Formula I or a pharmaceutically acceptable salt thereof, J is O;

B is formula (V):

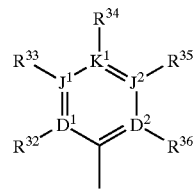

(V)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the proviso that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen and that $D^1$, $D^2$, $J^1$, $J^2$ and $K^1$ are selected to maintain an aromatic ring system;

$R^9$, $R^{10}$, $R^{11}$, $R^{12}$, $R^{13}$, $R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, alkoxyalkyl, haloalkoxyalkyl, hydroxy, amino, alkoxyamino, nitro, alkylamino, alkylthio, alkylthioalkyl, alkylsulfinyl, alkylsulfonyl, alkylsulfonylalkyl, aryl, aralkyl, cycloalkyl, cycloalkylalkyl, heteroaryl, heterocyclyl, alkylsulfonamido, alkylaminosulfonyl, amidosulfonyl, monoalkyl amidosulfonyl, dialkyl amidosulfonyl, alkanoyl, haloalkanoyl, alkyl, alkenyl, halo, haloalkyl, haloalkenyl, haloalkoxy, hydroxyhaloalkyl, hydroxyalkyl, aminoalkyl, haloalkoxyalkyl, carboxyalkyl, carboalkoxy, carboxy, carboxamido, carboxamidoalkyl, and cyano;

$R^{32}$, $R^{33}$, $R^{34}$, $R^{35}$, and $R^{36}$ are independently optionally $Q^b$;

B is optionally selected from the group consisting of hydrido, trialkylsilyl, C2–C8 alkyl, C3–C8 alkylenyl, $C_3$–C8 alkenyl, C3–C8 alkynyl, and C2–C8 haloalkyl, wherein each member of group B may be optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C12 cycloalkyl and C4–C9 saturated heterocyclyl, wherein each ring carbon may be optionally substituted with $R^{33}$, a ring carbon other than the ring carbon at the point of attachment of B to A may be optionally substituted with oxo provided that no more than one ring carbon is substituted by oxo at the same time, ring carbon and nitrogen atoms adjacent to the carbon atom at the point of attachment may be optionally substituted with $R^9$ or $R^{13}$, a ring carbon or nitrogen atom adjacent to the $R^9$ position and two atoms from the point of attachment may be substituted with $R^{10}$, a ring carbon or nitrogen atom adjacent to the $R^{13}$ position and two atoms from the point of attachment may be substituted with $R^{12}$, a ring carbon or nitrogen atom three atoms from the point of attachment and adjacent to the $R^{10}$ position may be substituted with $R^{11}$, a ring carbon or nitrogen atom three atoms from the point of attachment and adjacent to the $R^{12}$ position may be substituted with $R^{33}$, and a ring carbon or nitrogen atom four atoms from the point of attachment and adjacent to the $R^{11}$ and $R^{33}$ positions may be substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), $(R^7)NC(O)$, $(R^7)NC(S)$, and $N(R^7)$ with the proviso that no more than one of the group consisting of rr and pa is 0 at the same time;

$R^7$ is selected from the group consisting of hydrido, hydroxy, and alkyl;

$R^{15}$ is selected from the group consisting of hydrido, hydroxy, halo, alkyl, and haloalkyl;

Ψ is selected from the group consisting of NH and NOH;

$R^1$ is selected from the group consisting of hydrido, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of covalent single bond, $(CR^{41}R^{42})_q$ wherein q is an integer selected from 1 through 3, $(CH(R^{41}))_g$—$W^0$—$(CH(R^{42}))_p$ wherein g and p are integers independently selected from 0 through 3 and $W^0$ is selected from the group consisting of O, S, C(O), S(O), $N(R^{41})$, and $ON(R^{42})$, and $(CH(R^{41}))_e$—$W^{22}$—$(CH(R^{41}))_h$ wherein e and h are integers independently selected from 0 through 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the proviso that $Z^0$ is directly bonded to the pyrazinone ring;

$R^{41}$ and $R^{42}$ are independently selected from the group consisting of amidino, hydroxyamino, hydrido, hydroxy, amino, and alkyl;

Q is selected from the group consisting of hydrido, with the proviso that $Z^0$ is other than a covalent single bond, and the formula (II):

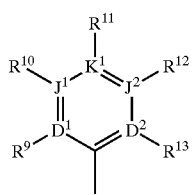

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen and that $D^1$, $D^2$, $J^1$, $J^2$ and $K^1$ are selected to maintain an aromatic ring system;

K is $(CR^{4a}R^{4b})_n$ wherein n is an integer selected from 1 through 2;

$R^{4a}$ and $R^{4b}$ are independently selected from the croup consisting of halo, hydrido, hydroxyalkyl, alkyl, alkoxyalkyl, alkylthioalkyl, and haloalkyl;

$E^0$ is $E^1$, when K is $(CR^{4a}R^{4b})_n$, wherein $E^1$ is selected from the group consisting of a covalent single bond, C(O), C(S), C(O)N($R^7$), ($R^7$)NC(O), S(O)$_2$, ($R^7$)NS(O)$_2$, and S(O)$_2$N($R^7$);

$Y^0$ is formula (IV):

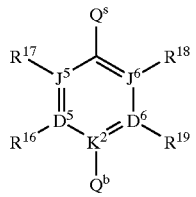

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, $J^5$ and $J^6$ is S, one of $D^5$, $D^6$, $J^6$, and $J^6$ mus be a covalent bond when two of $D^5$, $D^6$, $J^5$, and $J^6$ are O and S, and no more than four of $D^5$, $D^6$, $J^5$, and $J^6$ are N, with the proviso that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen and that $D^5$, $D^6$, $J^5$, and $J^6$ are selected to maintain an aromatic ring system;

$R^{16}$, $R^{17}$, $R^{18}$, and $R^{19}$ are independently selected from the group consisting of hydrido, amidino, guanidino, carboxy, haloalkylthio, alkoxy, hydroxy, amino, nitro, alkoxyamino, alkylamino, alkylthio, alkylsulfinyl, alkylsulfonyl, alkanoyl, haloalkanoyl, alkyl, alkenyl, halo, haloalkyl, haloalkoxy, hydroxyalkyl, alkylenylamino, haloalkoxyalkyl, carboalkoxy, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, aminoalkyl, hydrido, $N(R^{26})C(NR^{25})N(R^{23})(R^{24})$, and $C(NR^{25})NR^{23}R^{24}$, with the provisos that no more than one of $R^{20}$ and $R^{21}$ is selected from the group consisting of hydroxy, amino, alkylamino, and dialkylamino at the same time and that no more than one of $R^{23}$ and $R^{24}$ is selected from the group consisting of hydroxy, amino, alkylamino, and dialkylamino at the same time;

$R^{20}$, $R^{21}$, $R^{23}$, $R^{24}$, $R^{25}$, and $R^{26}$ are independently selected from the group consisting of hydrido, alkyl, hydroxy, aminoalkyl, amino, dialkylamino, alkylamino, and hydroxyalkyl;

$Q^s$ is selected from the group consisting of a single covalent bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, $S(O)$, $S(O)_2$, $S(O)_2N(R^{14})$, $N(R^{14})S(O)_2$, and $N(R^{14})$, with the provisos that $R^{14}$ is selected from other than halo when directly bonded to N and that $(CR^{37}R^{38})_b$, and $(CH(R^{14}))_c$ are bonded to $E^0$:

$R^{14}$ is selected from the group consisting of hydrido, halo, alkyl, and haloalkyl;

$R^{37}$ and $R^{38}$ are independently selected from the group consisting, of hydrido, alkyl, and haloalkyl;

$R^{38}$ is optionally selected from the group consisting of aroyl and heteroaroyl;

$Y^0$ is optionally $Q^b$—$Q^{ss}$ wherein $Q^{ss}$ is $(CH(R^{14}))_e$—$W^2$—$(CH(R^{15}))_h$, wherein e and h are integers independently selected from 1 through 2 and $W^2$ is $CR^{4a}$=$CR^{4b}$ with the proviso that $(CH(R^{14}))_e$ is bonded to $E^0$;

$Y^0$ is optionally selected from the group consisting of $Q^b$—$Q^{ssss}$ and $Q^b$—$Q^{ssssr}$ wherein $Q^{ssss}$ is $(CH(R^{38}))_r$—$W^5$ and $Q^{ssssr}$ is $(CH(R^{38}))_r$—$W^6$, r is an integer selected from 1 through 2, and $W^5$ and $W^6$ are independently selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a) pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6- quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^5$ and of the ring of the $W^6$, other than the points of attachment of $W^5$ and $W^6$, is optionally substituted with one or more of the group consisting of $R^9$, $R^{10}$, $R^{11}$, and $R^{12}$, with the provisos that $Q^b$ is bonded to lowest number substituent position of each $W^5$, $Q^b$ is bonded to highest number substituent position of each $W^6$, and $(CH(R^{38}))_r$ is bonded to $E^0$.

In a another preferred embodiment of a compound of Formula I, said compound is the Formula:

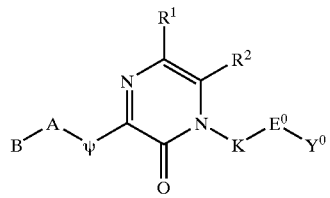

or a pharmaceutically acceptable salt thereof, wherein;

B is phenyl or a heteroaryl of 5 or 6 ring members, wherein a nitrogen with a removable hydrogen or a carbon adjacent to the carbon at the point of attachment is optionally substituted by $R^{32}$, a nitrogen with a removable hydrogen or a carbon at the other position adjacent to the point of attachment is optionally substituted by $R^{36}$, a nitrogen with a removable hydrogen or a carbon adjacent to $R^{32}$ and two atoms from the point of attachment is optionally substituted by $R^{33}$, a nitrogen with a removable hydrogen or a carbon adjacent to $R^{36}$ and two atoms from the point of attachment is optionally substituted by $R^{35}$, and a nitrogen with a removable hydrogen or a carbon adjacent to both $R^{33}$ and $R^{35}$ is optionally substituted by $R^{34}$;

$R^9$, $R^{10}$, $R^{11}$, $R^{12}$, $R^{13}$, $R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, cycloalkoxy, cycloalkylalkoxy, aralkoxy, aryloxy, heteroaryloxy, heteroaralkoxy, heterocyclyloxy, heterocyclylalkoxy, alkoxyalkyl, haloalkoxyalkyl, hydroxy, amino, alkoxyamino, nitro, alkylamino, N-alkyl-N-arylamino, arylamino, aralkylamino, heteroarylamino, heteroaralkylamino, heterocyclylamino, heterocyclylalkylamino, alkylthio, alkylthioalkyl, alkylsulfinyl, arylsulfinyl, aralkylsulfinyl, cycloalkylsulfinyl, heteroarylsulfinyl, alkylsulfonyl, arylsulfonyl, aralkylsulfonyl, cycloalkylsulfonyl, heteroarylsulfonyl, alkylsulfonylalkyl, aryl, aralkyl, cycloalkyl, cycloalkylalkyl, heteroaryl, heterocyclyl, alkylsulfonamido, amidosulfonyl, alkanoyl, haloalkanoyl, alkyl, alkenyl, halo, haloalkyl, haloalkenyl, haloalkoxy, hydroxyhaloalkyl, hydroxyalkyl, aminoalkyl, haloalkoxyalkyl, carboxyalkyl, carboalkoxy, carboxy, carboxamido, carboxamidoalkyl, and cyano;

$R^{32}$, $R^{33}$, $R^{34}$, $R^{35}$, and $R^{36}$ are independently optionally $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C12 cycloalkyl or C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen atom adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is 0 or 1, pa is an integer selected from 0 through 6, and $W^7$ is selected from the group consisting of O, S, C(O), $(R^7)NC(O)$, $(R^7)NC(S)$, and $N(R^7)$ with the proviso that no more than one of the group consisting of rr and pa is 0 at the same time;

$R^7$ is selected from the group consisting of hydrido, hydroxy, and alkyl;

$R^{15}$ is selected from the group consisting of hydrido, hydroxy, halo, alkyl, and haloalkyl;

Ψ is NH or NOH;

$R^1$ is selected from the group consisting of hydrido, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of covalent single bond, $(CR^{41}R^{42})_q$ wherein q is an integer selected from 1 through 3, $(CH(R^{41}))_g$—$W^0$—$(CH(R^{42}))_p$ wherein g and p are integers independently selected from 0 through 3 and $W^0$ is selected from the group consisting of O, S, C(O), S(O), $N(R^{41})$, and $ON(R^{41})$;

$Z^0$ is optionally $(CH(R^{41}))_e$—$W^{22}$—$(CH(R^{42}))_h$ wherein e and h are independently 0 or 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3- piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein $Z^O$ is directly bonded to the pyrazinone ring and $W^{22}$ is optionally substituted with one or more substituents selected from the group consisting of $R^9$, $R^{10}$, $R^{11}$, $R^{12}$, and $R^{13}$;

$R^{41}$ and $R^{42}$ are independently selected from the group consisting of amidino, hydroxyamino, hydrido, hydroxy, amino, and alkyl;

Q is phenyl or a heteroaryl of 5 or 6 ring members, wherein a nitrogen with a removable hydrogen or a carbon adjacent to the carbon at the point of attachment is optionally substituted by $R^9$, a nitrogen with a removable hydrogen or a carbon at the other position adjacent to the point of attachment is optionally substituted by $R^{13}$, a nitrogen with a removable hydrogen or a carbon adjacent to $R^9$ and two atoms from the point of attachment is optionally substituted by $R^{10}$, a nitrogen with a removable hydrogen or a carbon adjacent to $R^{13}$ and two atoms from the point of attachment is optionally substituted by $R^{12}$, and a nitrogen with a removable hydrogen or a carbon adjacent to both $R^{10}$ and $R^{12}$ is substituted by $R^{11}$;

Q is optionally hydrido with the proviso that $Z^O$ is selected from other than a covalent single bond or $(CR^{41}R^{42})_q$;

K is $(CR^{4a}R^{4b})_n$ wherein n is 1 or 2;

$R^{4a}$ and $R^{4b}$ are independently selected from the group consisting of halo, hydrido, hydroxyalkyl, alkyl, alkoxyalkyl, alkylthioalkyl, and haloalkyl;

$E^O$ is $E^1$, when K is $(CR^{4a}R^{4b})_n$, wherein $E^1$ is selected from the group consisting of a covalent single bond, C(O), C(S), C(O)N($R^7$), ($R^7$)NC(O), S(O)$_2$, ($R^7$)NS(O)$_2$, and S(O)$_2$N($R^7$);

$Y^O$ is phenyl or a heteroaryl of 5 or 6 ring members, wherein one carbon of said phenyl or said heteroaryl is substituted by $Q^s$, a carbon two or three atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, nitro, alkoxyamino, alkylamino, alkylthio, alkylsulfinyl, alkylsulfonyl, alkanoyl, haloalkanoyl, alkyl, alkenyl, halo, haloalkyl, haloalkoxy, hydroxyalkyl, aminoalkyl, haloalkoxyalkyl, carboalkoxy, and cyano, with the provisos that $R^{16}$ and $R^{19}$ are independently selected from other than the group consisting of hydrido, amino, aminoalkyl, hydroxyalkyl, and alkyl, wherein Q is hydrido, $Y^0$ is a thiazolyl or imidazolyl ring and $Z^o$ is $(CH(R^{41}))_e$—$W^{22}$—$(CH(R^{42}))_h$ wherein $W^{22}$ is a cycloalkyl and $R^{16}$ and $R^{19}$ are independently other than hydrido or amino wherein Q is hydrido, $Y^0$ is a pyridyl, and $Z^o$ is $(CH(R^{41}))_e$—$W^{22}$—$(CH(R^{42}))_h$ wherein $W^{22}$ is a cycloalkyl or $(CH(R^{41}))_g$—$W^0$—$(CH(R^{42}))_p$ wherein $W^0$ is O, S, or S(O);

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, aminoalkyl, hydrido, $N(R^{26})C(NR^{25})N(R^{23})(R^{24})$, and $C(NR^{25})NR^{23}R^{24}$, with the provisos that no more than one of $R^{20}$ and $R^{21}$ is selected from the group consisting of hydroxy, amino, alkylamino, and dialkylamino at the same time and that no more than one of $R^{23}$ and $R^{24}$ is selected from the group consisting of hydroxy, amino, alkylamino, and dialkylamino at the same time, that $Q^b$ is other than hydrido or amino wherein Q is hydrido, $Y^0$ is thiazolyl or imidazolyl and $Z^o$ is $(CH(R^{41}))_e$—$W^{22}$—$(CH(R^{42}))_h$ wherein $W^{22}$ is a cycloalkyl, and that $Q^b$ is other than hydrido or amino wherein Q is hydrido, $Y^0$ is pyridyl, and $Z^o$ is $(CH(R^{41}))_e$—$W^{22}$—$(CH(R^{42}))_h$ wherein $W^{22}$ is a cycloalkyl or $(CH(R^{41}))_g$—$W^o$—$(CH(R^{42}))_p$ wherein $W^0$ is O, S, or S(O);

$R^{20}$, $R^{21}$, $R^{23}$, $R^{24}$, $R^{25}$, and $R^{26}$ are independently selected from the group consisting of hydrido, alkyl, hydroxy, aminoalkyl, amino, dialkylamino, alkylamino, and hydroxyalkyl;

$Q^s$ is selected from the group consisting of a single covalent bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, $S(O)$, $S(O)_2$, $S(O)_2N(R^{14})$, $N(R^{14})S(O)_2$, and $N(R^{14})$, with the provisos that $R^{14}$ is selected from other than halo when directly bonded to N, $Q^s$ is selected from other than a single covalent bond when $Y^0$ is 2-$Q^b$-5-$Q^s$-6-$R^{17}$-4-$R^{18}$-3-$R^{19}$pyridine or 2-$Q^b$-4-$Q^s$-3-$R^{16}$-5-$R^{18}$-6-$R^{19}$-pyridine, and that $(CR^{37}R^{38})_b$ and $(CH(R^{14}))_c$ are bonded to $E^O$;

$R^{14}$ is selected from the group consisting of hydrido, halo, alkyl, and haloalkyl;

$R^{37}$ and $R^{38}$ are independently selected from the group consisting of hydrido, alkyl, and haloalkyl;

$R^{38}$ is optionally aroyl or heteroaroyl, wherein $R^{38}$ is optionally substituted at from one through three of the ring carbons with a substituent selected from the group consisting of $R^{16}$, $R^{17}$, $R^{18}$, and $R^{19}$;

$Y^0$ is optionally $Y^{AT}$ wherein $Y^{AT}$ is $Q^b$—$Q^s$;

$Y^0$ is optionally $Q^b$—$Q^{ss}$ wherein $Q^{ss}$ is $(CH(R^{14}))$—$W^2$—$(CH(R^{15}))_h$, wherein e and h are independently 1 or 2 and $W^2$ is $CR^{4a}$=$CR^{4b}$ with the proviso that $(CH(R^{14}))_e$ is bonded to $E^O$;

$Y^0$ is optionally selected from the group consisting of $Q^b$—$Q^{ssss}$ and $Q^b$—$Q^{ssssr}$ wherein $Q^{ssss}$ is $(CH(R^{38}))_r$—$W^5$ and $Q^{ssssr}$ is $(CH(R^{38}))_r$—$W^6$, r is 1 or 2, $W^5$ and $W^6$ are independently selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6- indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^5$ and of the ring of the $W^6$, other than the points of attachment of $W^5$ and $W^6$, is optionally substituted with one or more of the group consisting of $R^9$, $R^{10}$, $R^{11}$, and $R^{12}$, with the provisos that $Q^b$ is bonded to lowest number substituent position of each $W^5$, $Q^b$ is bonded to highest number substituent position of each $W^6$, $W^5$ and $W^6$ are selected from other than 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, and 3,7-benzisoxazolyl, when r is the integer one, and $(CH(R^{38}))_r$ is bonded to $E^0$.

In a more preferred embodiment of a compound of Formula I or a pharmaceutically acceptable salt thereof, J is O;

B is phenyl or heteroaryl of 5 or 6 ring members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, alkanoyl, haloalkanoyl, nitro, alkylamino, alkylthio, aryl, aralkyl, cycloalkyl, cycloalkylalkyl, heteroaryl, heterocyclyl, alkylsulfonamido, amidosulfonyl, monoalkyl amidosulfonyl, dialkyl amidosulfonyl, alkyl, alkenyl, halo, haloalkyl, haloalkenyl, haloalkoxy, hydroxyalkyl, alkylenylamino, carboalkoxy, carboxy, carboxamido, cyano, and $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of $C_3$–C12 cycloalkyl and C4–C9 saturated heterocyclyl, wherein each ring carbon is optionally optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

$R^9$, $R^{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, hydroxy, amino, alkylamino, alkylthio, alkylsulfinyl, alkylsulfonyl, alkylsulfonamido, amidosulfonyl, monoalkyl amidosulfonyl, dialkyl amidosulfonyl, alkyl, halo, haloalkyl, haloalkoxy, hydroxyalkyl, aminoalkyl, carboalkoxy, carboxyalkyl, carboxy, carboxamido, and cyano;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of O, S, C(O), $(R^7)NC(O)$, $(R^7)NC(S)$, and $N(R^7)$;

$R^7$ is selected from the group consisting of hydrido, hydroxy and alkyl;

$R^{15}$ is selected from the group consisting of hydrido, hydroxy, halo, alkyl, and haloalkyl;

Ψ is NH;

$R^1$ is selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of covalent single bond and $(CR^{41}R^{42})_q$ wherein q is an integer selected from 1 through 2, $(CH(R^{41}))_g$—$W^0$—$(CH(R^{42}))_p$ wherein g and p are integers independently selected from 0 through 3 and $W^0$ is selected from the group consisting of O, S, and $N(R^{41})$, and $(CH(R^{41}))_e$—$W^{22}$—$(CH(R^{42}))_h$ wherein e and h are integers independently selected from 0 through 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the proviso that $Z^0$ is directly bonded to the pyrazinone ring;

$R^{41}$ and $R^{42}$ are independently selected from the group consisting of hydrido, hydroxy, and amino;

Q is selected from the group consisting of hydrido, with the proviso that $Z^0$ is other than a covalent single bond, aryl, and heteroaryl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is $CHR^{4a}$ wherein $R^{4a}$ is selected from the group consisting of hydrido, hydroxyalkyl, alkyl, alkoxyalkyl, alkylthioalkyl, and haloalkyl;

$E^0$ is selected from the group consisting of a covalent single bond, C(O)N(H), (H)NC(O), $(R^7)NS(O)_2$, and $S(O)_2N(R^7)$;

$Y^0$ is formula (IV):

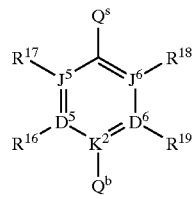

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen and that $D^5$, $D^6$, $J^5$, and $J^6$ are selected to maintain an aromatic ring system;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkoxyamino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $N(R^{26})C(NR^{25})N(R^{23})(R^{24})$, and $C(NR^{25})NR^{23}R^{24}$, with the provisos that no more than one of $R^{20}$ and $R^{21}$ is selected from the group consisting of hydroxy, amino, alkylamino, and dialkylamino at the same time and that no more than one of $R^{23}$ and $R^{24}$ is selected from the group consisting of hydroxy, amino, alkylamino, and dialkylamino at the same time;

$R^{20}$, $R^{21}$, $R^{23}$, $R^{24}$, $R^{25}$, and $R^{26}$ are independently selected from the group consisting of hydrido, alkyl, hydroxy, amino, alkylamino and dialkylamino;

$Q^s$ is selected from the group consisting of a single covalent bond, $(CR^{37}R^{38})_b$ wherein b is an integer selected from 1 through 4, and $(CH(R^{14}))_c$—$W^1$—$(CH(R^{15})_d$ wherein c and d are integers independently selected from 1 through 3 and $W^1$ is selected from the group consisting of $C(O)N(R^{14})$, $(R^{14})NC(O)$, $S(O)$, $S(O)_2$, $S(O)_2N(R^{14})$, $N(R^{14})S(O)_2$, and $N(R^{14})$, with the provisos that $R^{14}$ is selected from other than halo when directly bonded to N and that $(CR^{37}R^{38})_b$, and $(CH(R^{14})_c$ are bonded to $E^0$;

$R^{14}$ is selected from the group consisting of hydrido, halo, alkyl, and haloalkyl;

$R^{37}$ and $R^{38}$ are independently selected from the group consisting of hydrido, alkyl, and haloalkyl;

$R^{38}$ is optionally selected from the group consisting of aroyl and heteroaroyl;

$Y^0$ is optionally $Q^b$—$Q^{ss}$ wherein $Q^{ss}$ is $(CH(R^{14}))_e$—$W^2$—$(CH(R^{15}))_h$, wherein e and h are integers independently selected from 1 through 2 and $W^2$ is $CR^{4a}$=$CH$ with the proviso that $(CH(R^{14}))_e$ is bonded to $E^0$.

In a another preferred embodiment of a compound of Formula I, said compound is the Formula:

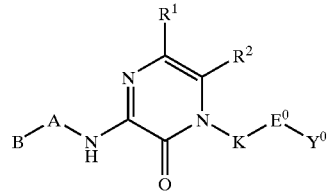

or a pharmaceutically acceptable salt thereof, wherein;

B is phenyl or a heteroaryl of 5 or 6 ring members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, haloalkanoyl, nitro, alkylamino, alkylthio, aryl, aralkyl, cycloalkyl, cycloalkylalkyl, heteroaryl, heterocyclyl, alkylsulfonamido, amidosulfonyl, alkyl, alkenyl, halo, haloalkyl, haloalkenyl, haloalkoxy, hydroxyalkyl, hydroxyhaloalkyl, aminoalkyl, carboalkoxy, carboxy, carboxamido, cyano, and $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C12 cycloalkyl or a C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

$R^9$, $R^{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkylamino, N-alkyl-N-arylamino, arylamino, aralkylamino, heteroarylamino, heteroaralkylamino, heterocyclylamino, heterocyclylalkylamino, alkylthio, alkylsulfinyl, arylsulfinyl, aralkylsulfinyl, cycloalkylsulfinyl, heteroarylsulfinyl, alkylsulfamido, alkylsulfonyl, arylsulfonyl, aralkylsulfonyl, cycloalkylsulfonyl, heteroarylsulfonyl, amidosulfonyl, alkyl, aryl, aralkyl, cycloalkyl, cycloalkylalkyl, heteroaryl, heterocyclyl, halo, haloalkyl, haloalkoxy, hydroxyalkyl, hydroxyhaloalkyl, aminoalkyl, carboalkoxy, carboxy, carboxyalkyl, carboxamido, and cyano;

A is a single covalent bond or $(CH(R^{15}))_{pa}-(W^7)_{rr}$ wherein rr is 0 or 1, pa is an integer selected from 0 through 3, and $W^7$ is selected from the group consisting of O, S, C(O), $(R^7)NC(O)$, $(R^7)NC(S)$, and $N(R^7)$;

$R^7$ is selected from the group consisting of hydrido, hydroxy and alkyl;

$R^{15}$ is selected from the group consisting of hydrido, hydroxy, halo, alkyl, and haloalkyl;

$R^1$ is selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of covalent single bond, $(CR^{41}R^{42})_q$ wherein q is 1 or 2, $(CH(R^{41}))_g-W^0-(CH(R^{42}))_p$ wherein g and p are integers independently selected from 0 through 3 and $W^0$ is selected from the group consisting of O, S, C(O), S(O), $N(R^{41})$, and $ON(R^{41})$;

$Z^0$ is optionally $(CH(R^{41}))_e-W^{22}-(CH(R^{42}))_h$ wherein e and h are independently 0 or 1 and $W^{22}$ is selected from the group consisting of $CR^{41}=CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein $Z^0$ is directly bonded to the pyrazinone ring and $W^{22}$ is optionally substituted with one or more substituents selected from the group consisting, of $R^9$, $R^{10}$, $R^{11}$, $R^{12}$, and $R^{13}$;

$R^{41}$ and $R^{42}$ are independently selected from the group consisting of hydrido, hydroxy, and amino;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

Q is optionally hydrido with the proviso that $Z^0$ is other than a covalent single bond or $(CR^{41}R^{42})_q$;

K is $CHR^{4a}$ wherein $R^{4a}$ is selected from the group consisting of hydrido, hydroxyalkyl, alkyl, alkoxyalkyl, alkylthioalkyl, and haloalkyl;

$E^0$ is selected from the group consisting of a covalent single bond, C(O)N(H), (H)NC(O), $(R^7)NS(O)_2$, and $S(O)_2N(R^7)$;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the croup consisting of hydrido, amidino, guanidino, carboxy, haloalkylthio, alkoxy, hydroxy, amino, alkoxyamino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano, with the provisos that $R^{16}$ and $R^{19}$ are independently selected from other than the group consisting of hydrido, amino, aminoalkyl, hydroxyalkyl, and alkyl wherein Q is hydrido, $Y^o$ is thiazolyl or imidazolyl and $Z^o$ is $(CH(R^{41}))_e$—$W^{22}$—$(CH(R^{42}))_h$ wherein $W^{22}$ is a cycloalkyl and $R^{16}$ and $R^{19}$ are independently other than hydrido or amino wherein Q is hydrido, $Y^o$ is pyridyl, and $Z^o$ is $(CH(R^{41}))_e$—$W^{22}$—$(CH(R^{42}))_h$ wherein $W^{22}$ is a cycloalkyl or $(CH(R^{41}))_g$—$W^o$—$(CH(R^{42}))_p$ wherein $W^o$ is O, S, or S(O);

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $N(R^{26})C(NR^{25})N(R^{23})(R^{24})$, and $C(NR^{25})NR^{23}R^{24}$, with the provisos that no more than one of $R^{30}$ and $R^{21}$ is selected from the group consisting of hydroxy, amino, alkylamino, and dialkylamino at the same time, that no more than one of $R^{23}$ and $R^{24}$ is selected from the group consisting of hydroxy, amino, alkylamino, and dialkylamino at the same time, that $Q^b$ is other than hydrido or amino wherein Q is hydrido, $Y^o$ is thiazolyl or imidazolyl and $Z^o$ is $(CH(R^{41}))_e$—$W^{22}$—$(CH(R^{42}))_h$ wherein $W^{22}$ is a cycloalkyl, and that $Q^b$ is other than hydrido or amino wherein Q is hydrido, $Y^o$ is pyridyl, and $Z^o$ is $(CH(R^{41}))_e$—$W^{22}$—$(CH(R^{42}))_h$ wherein $W^{22}$ is cycloalkyl or $(CH(R^{41}))_g$—$W^o$—$(CH(R^{42}))_p$ wherein $W^o$ is O, S, or S(O);

$R^{20}$, $R^{21}$, $R^{23}$, $R^{24}$, $R^{25}$, and $R^{26}$ are independently selected from the group consisting of hydrido, alkyl, hydroxy, amino, alkylamino and dialkylamino;

$Q^s$ is selected from the group consisting of a single covalent bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, $S(O)$, $S(O)_2$, $S(O)_2N(R^{14})$, $N(R^{14})S(O)_2$, and $N(R^{14})$, with the provisos that $R^{14}$ is selected from other than halo when directly bonded to N, $Q^s$ is selected from other than a single covalent bond when $Y^o$ is 2-$Q^b$-5-$Q^s$-6-$R^{17}$-4-$R^{18}$-3-$R^{19}$pyridine or 2-$Q^b$-4-$Q^s$-3-$R^{16}$-5-$R^{18}$-6-$R^{19}$pyridine, and that $(CR^{37}R^{38})_b$ and $(CR^{37}R^{38})_b$, and $(CH(R^{14}))_c$ are bonded to $E^o$;

$R^{14}$ is selected from the group consisting of hydrido, halo, alkyl, and haloalkyl;

$R^{37}$ and $R^{38}$ are independently selected from the group consisting of hydrido, alkyl, and haloalkyl;

$R^{38}$ is optionally aroyl or heteroaroyl, wherein $R^{38}$ is optionally substituted at from one through three of the ring carbons with a substituent selected from the group consisting of $R^{16}$, $R^{17}$, $R^{18}$, and $R^{19}$;

$Y^o$ is optionally $Y^{AT}$ wherein $Y^{AT}$ is $Q^b$—$Q^s$;

$Y^o$ is optionally $Q^b$—$Q^{ss}$ wherein $Q^{ss}$ is $(CH(R^{14}))_e$—$W^2$—$(CH(R^{15}))_h$, wherein e and h are independentlyl or 2 and $W^2$ is $CR^{4a}$=CH with the proviso that $(CH(R^{14}))_e$ is bonded to $E^o$.

In an even more preferred embodiment of a compound of Formula I, said compound is the Formula:

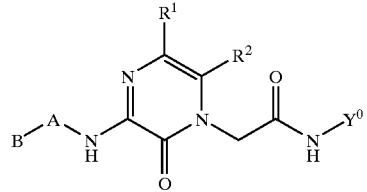

or a pharmaceutically acceptable salt thereof, wherein;

B is phenyl or heteroaryl of 5 or 6 members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, cyano, and $Q^b$;

A is a single covalent bond or $(CH(R^{15}))_{pa}$—$(W^7)_{rr}$ wherein rr is 0 or 1, pa is an integer selected from 0 through 3, and $W^7$ is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^o$—Q;

$Z^o$ is selected from the group consisting of a covalent single bond, $CH_2$, $CH_2CH_2$, $W^o$—$(CH(R^{42}))_p$ wherein p is 0 or 1 and $W^o$ is selected from the group consisting of O, S, and $N(R^{41})$;

$R^{41}$ and $R^{42}$ are independently hydrido or alkyl;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a single covalent bond, $CH_2$, and $CH_2CH_2$.

In another even more preferred embodiment of a compound of Formula I, said compound is the Formula:

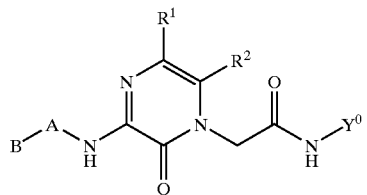

or a pharmaceutically acceptable salt thereof, wherein;
B is selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, cyano, and $Q^b$;

A is a single covalent bond or $(CH(R^{15}))_{pa}$—$(W^7)_{rr}$ wherein rr is 0 or 1, pa is an integer selected from 0 through 3, and $W^7$ is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is selected from the group consisting of a covalent single bond, $CH_2$, $CH_2CH_2$, $W^0$—$(CH(R^{42}))_p$ wherein p is 0 or 1 and $W^0$ is selected from the group consisting of O, S, and $N(R^{41})$;

$R^{41}$ and $R^{42}$ are independently hydrido or alkyl;

Q is phenyl or a heteroaryl of 5 or 6 ring members, wherein a carbon adjacent to the carbon at the point of attachment is optionally substituted by $R^9$ the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$ and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, alkyl, and hydroxy;

$Q^s$ is selected from the group consisting of a single covalent bond, $CH_2$, and $CH_2CH_2$.

In still another even more preferred embodiment of a compound of Formula I, said compound is the Formula:

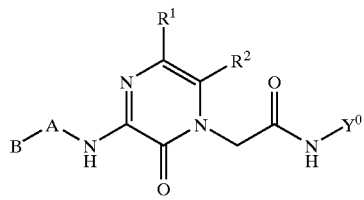

or a pharmaceutically acceptable salt thereof, wherein;

B is a C3–C7 cycloalkyl or a C4–C6 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

$R^{33}$ and $R^{34}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, and cyano;

$R^{33}$ is optionally $Q^b$;

A is a single covalent bond or $(CH(R^{15}))_{pa}$—$(W^7)_{rr}$ wherein rr is 0 or 1, pa is an integer selected from 0 through 3, and $W^7$ is $(R^7)NC(O)$ or $N(R^7)$;

$R^7$ is selected from the group consisting of hydrido hydroxy and alkyl;

$R^{15}$ is selected from the group consisting of hydrido, halo, alkyl, and haloalkyl;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is selected from the group consisting of a covalent single bond, $CH_2$, $CH_2CH_2$, $W^0$—$(CH(R^{42}))_p$ wherein p is 0 or 1 and $W^0$ is selected from the group consisting of O, S, and $N(R^{41})$;

$R^{41}$ and $R^{42}$ are independently hydrido or alkyl;

Q is phenyl or a heteroaryl of 5 or 6 ring members, wherein a carbon adjacent to the carbon at the point of attachment is optionally substituted by $R^9$ the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$Y^0$ is phenyl or a heteroaryl of 5 or 6 ring members, wherein one carbon of said phenyl or said heteroaryl is substituted by $Q^s$ a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a single covalent bond, $CH_2$, and $CH_2CH_2$.

In still a further even more preferred embodiment of a compound of Formula I, said compound is the Formula:

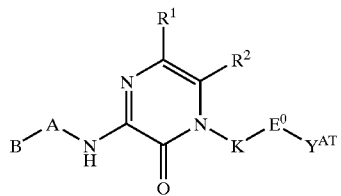

or a pharmaceutically acceptable salt thereof, wherein;

B is phenyl or a heteroaryl of 5 or 6 ring members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{36}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, haloalkanoyl, nitro, alkylamino, alkylthio, aryl, aralkyl, cycloalkyl, cycloalkylalkyl, heteroaryl, heterocyclyl, alkylsulfonamido, amidosulfonyl, alkyl, alkenyl, halo, haloalkyl, haloalkenyl, haloalkoxy, hydroxyalkyl, alkylamino, carboalkoxy, carboxy, carboxamido, cyano, and $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C12 cycloalkyl or a C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^9$, $R^{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkylamino, N-alkyl-N-arylamino, arylamino, aralkylamino, heteroarylamino, heteroaralkylamino, heterocyclylamino, heterocyclylalkylamino, alkylthio, alkylsulfinyl, arylsulfinyl, aralkylsulfinyl, cycloalkylsulfinyl, heteroarylsulfinyl, alkylsulfamido, alkylsulfonyl, arylsulfonyl, aralkylsulfonyl, cycloalkylsulfonyl, heteroarylsulfonyl, amidosulfonyl, alkyl, aryl, aralkyl, cycloalkyl, cycloalkylalkyl, heteroaryl, heterocyclyl, halo, haloalkyl, haloalkoxy, hydroxyalkyl, hydroxyhaloalkyl, aminoalkyl, carboalkoxy, carboxy, carboxyalkyl, carboxamido, and cyano;

A is a single covalent bond or $(CH(R^{15}))_{pa}$—$(W^7)_{rr}$ wherein rr is 0 or 1, pa is an integer selected from 0 through 3, and $W^7$ is selected from the group consisting of O, S, C(O), $(R^7)NC(O)$, $(R^7)NC(S)$, and $N(R^7)$;

$R^7$ is selected from the group consisting of hydrido, hydroxy and alkyl;

$R^{15}$ is selected from the group consisting of hydrido, hydroxy, halo, alkyl, and haloalkyl;

$R^1$ is selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of covalent single bond, $(CR^{41}R^{42})_q$ wherein q is 1 or 2, $(CH(R^{41}))_g$—$W^0$—$(CH(R^{42}))_p$ wherein g and p are integers independently selected from 0 through 3 and $W^0$ is selected from the group consisting of O, S, C(O), S(O), $N(R^{41})$, and $ON(R^{41})$;

$Z^0$ is optionally $(CH(R^{41}))_e$—$W^{22}$—$(CH(R^{42}))_h$ wherein e and h are independently 0 or 1 and $W^{22}$ is selected from the group consisting of $CR^{41}=CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein $Z^0$ is directly bonded to the pyrazinone ring and $W^{22}$ is optionally substituted with one or more substituents selected from the group consisting of $R^9$, $R^{10}$, $R^{11}$, $R^{12}$, and $R^{13}$;

$R^{41}$ and $R^{42}$ are independently selected from the group consisting of hydrido, hydroxy, and amino;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

Q is optionally hydrido with the proviso that $Z^0$ is other than a covalent single bond;

K is $CHR^{4a}$ wherein $R^{4a}$ is selected from the group consisting of hydrido, hydroxyalkyl, alkyl, alkoxyalkyl, alkylthioalkyl, and haloalkyl;

$E^0$ is selected from the group consisting of a covalent single bond, C(O)N(H), (H)NC(O), $(R^7)NS(O)_2$, and $S(O)_2N(R^7)$;

$Y^{AT}$ is $Q^b$—$Q^s$;

$Q^s$ is $(CR^{37}R^{38})_b$ wherein b is an integer selected from 1 through 4, $R^{37}$ is selected from the group consisting of hydrido, alkyl, and haloalkyl, and $R^{38}$ is selected from the group consisting of hydrido, alkyl, haloalkyl, aroyl, and heteroaroyl with the provisos that there is at least one aroyl or heteroaroyl substituent, that no more than one aroyl or heteroaroyl is bonded to $(CR^{37}R^{38})_b$ at the same time, that said aroyl and said heteroaroyl are optionally substituted at from one through three of the ring carbons with a substituent selected from the group consisting of $R^{16}$, $R^{17}$, $R^{18}$, and $R^{19}$, that said aroyl and said heteroaroyl are bonded to the $CR^{37}R^{38}$ that is directly bonded to $E^0$, that no more than one alkyl or one haloalkyl is bonded to a $CR^{37}R^{38}$ at the same time, and that said alkyl and haloalkyl are bonded to a carbon other than the one bonding said aroyl or said heteroaroyl;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkoxyamino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $N(R^{26})C(NR^{25})N(R^{23})(R^{24})$, and $C(NR^{25})NR^{23}R^{24}$, with the provisos that no more than one of $R^{20}$ and $R^{21}$ is hydroxy, amino, alkylamino, or dialkylamino at the same time and that no more than one of $R^{23}$ and $R^{24}$ is hydroxy, amino, alkylamino, or dialkylamino at the same time;

$R^{20}$, $R^{21}$, $R^{23}$, $R^{24}$, $R^{25}$, and $R^{26}$ are independently selected from the group consisting of hydrido, alkyl, hydroxy, amino, alkylamino and dialkylamino.

In a most preferred embodiment of a compound of Formula I, said compound is the Formula:

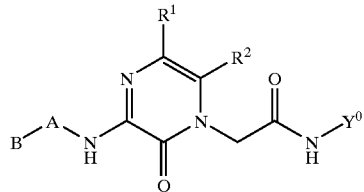

or a pharmaceutically acceptable salt thereof, wherein;

B is phenyl or a heteroaryl of 5 or 6 ring members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, cyano, and $Q^b$;

A is a single covalent bond or $(CH(R^{15}))_{pa}$—$(W^7)_{rr}$ wherein rr is 0 or 1, pa is an integer selected from 0 through 3, and $W^7$ is $N(R^7)$;

$R^7$ is hydrido or alkyl;

$R^{15}$ is selected from the group consisting of hydrido, halo, alkyl, and haloalkyl;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^1$ is $Z^0$—Q;

$Z^0$ is a covalent single bond;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

$R^{10}$ and $R^{12}$ are optionally independently selected from the group consisting of hydrido, amidino, guanidino, aryl, aralkyl, cycloalkyl, cycloalkylalkyl, heteroaryl, heterocyclyl, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, and aminoalkyl;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the Group consisting of $NR^{20}R^{21}$, hydrido, and $C(NR^{25})NR^{23}R^{24}$;

$R^{20}$, $R^{21}$, $R^{23}$, $R^{24}$, and $R^{25}$ are independently hydrido or alkyl;

$Q^s$ is $CH_2$.

In another most preferred embodiment of a compound of Formula I, said compound is the Formula:

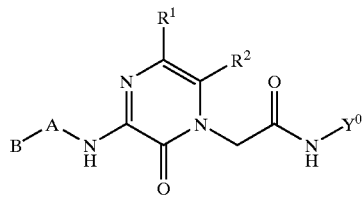

or a pharmaceutically acceptable salt thereof, wherein;
B is selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, cyano, and $Q^b$;

A is a single covalent bond or $(CH(R^{15}))_{pa}$—$(W^7)_{rr}$ wherein rr is 0 or 1, pa is an integer selected from 0 through 3, and $W^7$ is $N(R^7)$;

$R^7$ is hydrido or alkyl;

$R^{15}$ is selected from the group consisting of hydrido, halo, alkyl, and haloalkyl;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is a covalent single bond;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

$R^{10}$ and $R^{12}$ are optionally independently selected from the group consisting of hydrido, amidino, guanidino, aryl, aralkyl, cycloalkyl, cycloalkylalkyl, heteroaryl, heterocyclyl, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, and aminoalkyl;

$Y^0$ is phenyl or a heteroaryl of 5 or 6 ring members, wherein one carbon of said phenyl or said heteroaryl is substituted by $Q^s$ a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and C(NR$^{25}$)NR$^{23}$R$^{24}$, with the proviso that R$^{16}$, R$^{19}$, and Q$^b$ are not simultaneously hydrido;

Q$^b$ is selected from the group consisting of NR$^{20}$R$^{21}$, hydrido, N(R$^{26}$)C(NR$^{25}$)N(R$^{23}$)(R$^{24}$), and C(NR$^{25}$)NR$^{23}$R$^{24}$;

R$^{20}$, R$^{21}$, R$^{23}$, R$^{24}$, R$^{25}$, and R$^{26}$ are independently hydrido or alkyl;

Q$^s$ is CH$_2$.

In still another most preferred embodiment of a compound of Formula I, said compound is the Formula:

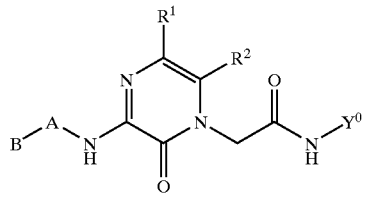

or a pharmaceutically acceptable salt thereof, wherein;

B is a C3–C7 cycloalkyl or a C4–C6 saturated heterocyclyl, wherein each ring carbon is optionally substituted with R$^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with R$^9$ or R$^{13}$, a ring carbon or nitrogen adjacent to the R$^9$ position and two atoms from the point of attachment is optionally substituted with R$^{10}$, a ring carbon or nitrogen adjacent to the R$^{13}$ position and two atoms from the point of attachment is optionally substituted with R$^{12}$, a ring carbon or nitrogen three atoms from the point of attachment and adjacent to the R$^{10}$ position is optionally substituted with R$^{11}$, a ring carbon or nitrogen three atoms from the point of attachment and adjacent to the R$^{12}$ position is optionally substituted with R$^{33}$, and a ring carbon or nitrogen four atoms from the point of attachment and adjacent to the R$^{11}$ and R$^{33}$ positions is optionally substituted with R$^{34}$;

R$^9$, R$^{11}$, and R$^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

R$^{10}$ and R$^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

R$^{10}$ and R$^{12}$ are optionally independently selected from the group consisting of hydrido, amidino, guanidino, aryl, aralkyl, cycloalkyl, cycloalkylalkyl, heteroaryl, heterocyclyl, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, and aminoalkyl;

R$^{33}$ and R$^{34}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, and cyano;

R$^{33}$ is optionally Q$^b$;

A is a single covalent bond or (CH(R$^{15}$))$_{pa}$—(W$^7$)$_{rr}$ wherein rr is 0 or 1, pa is an integer selected from 0 through 3, and W$^7$ is N(R$^7$);

R$^7$ is hydrido or alkyl;

R$^{15}$ is selected from the group consisting of hydrido, halo, alkyl, and haloalkyl;

R$^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

R$^2$ is Z$^0$—Q;

Z$^0$ is a covalent single bond;

Q is phenyl or a heteroaryl of 5 or 6 ring members, wherein a carbon adjacent to the carbon at the point of attachment is optionally substituted by R$^9$, the other carbon adjacent to the carbon at the point of attachment is optionally substituted by R$^{13}$, a carbon adjacent to R$^9$ and two atoms from the carbon at the point of attachment is optionally substituted by R$^{10}$, a carbon adjacent to R$^{13}$ and two atoms from the carbon at the point of attachment is optionally substituted by R$^{12}$, and any carbon adjacent to both R$^{10}$ and R$^{12}$ is optionally substituted by R$^{11}$;

Y$^0$ is phenyl or a heteroaryl of 5 or 6 ring members, wherein one carbon of said phenyl or said heteroaryl is substituted by Q$^s$, a carbon two or three contiguous atoms from the point of attachment of Q$^s$ is substituted by Q$^b$, a carbon adjacent to the point of attachment of Q$^s$ is optionally substituted by R$^{17}$, another carbon adjacent to the point of attachment of Q$^s$ is optionally substituted by R$^{18}$, a carbon adjacent to Q$^b$ is optionally substituted by R$^{16}$, and another carbon adjacent to Q$^b$ is optionally substituted by R$^{19}$;

R$^{16}$, R$^{17}$, R$^{18}$, and R$^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

R$^{16}$ or R$^{19}$ is optionally NR$^{20}$R$^{21}$ or C(NR$^{25}$)NR$^{23}$R$^{24}$, with the proviso that R$^{16}$, R$^{19}$, and Q$^b$ are not simultaneously hydrido;

Q$^b$ is selected from the group consisting of NR$^{20}$R$^{21}$, hydrido, and C(NR$^{25}$)NR$^{23}$R$^{24}$;

R$^{20}$, R$^{21}$, R$^{23}$, R$^{24}$, and R$^{25}$ are independently hydrido or alkyl;

Q$^s$ is CH$_2$.

In a preferred specific embodiment of Formula I, compounds have the Formula I-S:

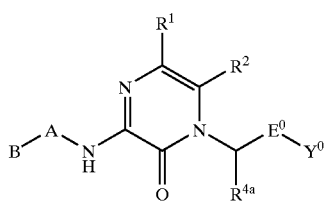

(I-S)

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, 1,2,3-triazin-4-yl, and 1,2,3-triazin-5-yl, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, carboxy, methyl, ethyl, isopropyl, propyl, methoxy, ethoxy, isopropoxy, propoxy, hydroxy, amino, methoxyamino, ethoxyamino, acetamido, trifluoroacetamido, nitro, aminomethyl, 1-aminoethyl, 2-aminoethyl, N-methylamino, dimethylamino, N-ethylamino, methylthio, ethylthio, isopropylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, cyano, and $Q^b$;

B is selected from the group consisting of hydrido, trimethylsilyl, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-3-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 1-octyl, 2-octenyl, 3-octenyl, 4-octenyl, 5-octenyl, 6-octenyl, 7-octenyl, 2-octynyl, 3-octynyl, 4-octynyl, 5-octynyl, 6-octynyl, 2-octyl, 1-methyl-2-heptenyl, 1-methyl-3-heptenyl, 1-methyl-5-heptenyl, 1-methyl-5-heptenyl, 1-methyl-6-heptenyl, 1-methyl-2-heptynyl, 1-methyl-3-heptynyl, 1-methyl-4-heptynyl, 1-methyl-5-heptynyl, 1-methyl-6-heptynyl, 1-methyl-2-heptynyl, 1-methyl-3-heptynyl, 1-methyl-4-heptynyl, 1-methyl-5-heptynyl, 3-octyl, 1-ethyl-2-hexenyl, 1-ethyl-3-hexenyl, 1-ethyl-4-hexenyl, 1-ethyl-2-hexynyl, 1-ethyl-3-hexynyl, 1-ethyl-4-hexynyl, 1-ethyl-5-hexenyl, 1-pentyl-2-propenyl, 4-octyl, 1-propyl-2-pentenyl, 1-propyl-3-pentenyl, 1-propyl-4-pentenyl, 1-butyl-2-butenyl, 1-propyl-2-pentynyl, 1-propyl-3-pentynyl, 1-butyl-2-butynyl, 1-butyl-3-butenyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

B is optionally selected from the group consisting of cyclopropyl, cyclobutyl, oxetan-2-yl, oxetan-3-yl, azetidin-1-yl, azetidin-2-yl, azetidin-3-yl, thiaetan-2-yl, thiaetan-3-yl, cyclopentyl, cyclohexyl, adamantyl, norbornyl, 3-trifluoromethylnorbornyl, 7-oxabicyclo[2.2.1]heptan-2-yl, bicyclo[3.1.0]hexan-6-yl, cycloheptyl, cyclooctyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 4H-2-pyranyl, 4H-3-pyranyl, 4H-4-pyranyl, 4H-pyran-4-one-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, a ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, and a ring carbon or nitrogen atom adjacent to the $R^{13}$ position and two atoms from the point of attachment is optionally substituted with $R^{12}$;

$R^9$, $R^{10}$, $R^{11}$, $R^{12}$, and $R^{13}$ are independently selected from the group consisting of hydrido, amidino, guanidino, carboxy, carboxymethyl, methyl, ethyl, isopropyl, propyl, methoxy, ethoxy, isopropoxy, propoxy, hydroxy, amino, methoxyamino, ethoxyamino, acetamido, trifluoroacetamido, nitro, aminomethyl, 1-aminoethyl, 2-aminoethyl, N-methylamino, dimethylamino, N-ethylamino, methylthio, ethylthio, isopropylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, and cyano;

A is selected from the group consisting of single covalent bond, O, S, NH, N(CH$_3$), N(OH), C(O), CH$_2$, CH$_3$CH, CF$_3$CH, NHC(O), N(CH$_3$)C(O), C(O)NH, C(O)N(CH$_3$), CF$_3$CC(O), C(O)CCH$_3$, C(O)CCF$_3$, CH$_2$C(O), (O)CCH$_2$, CH$_2$CH$_2$, CH$_2$CH$_2$CH$_2$, CH$_3$CHCH$_2$, CF$_3$CHCH$_2$, CH$_3$CC(O)CH$_2$, CF$_3$CC(O)CH$_2$, CH$_2$C(O)CCH$_3$, CH$_2$C(O)CCF$_3$, CH$_2$CH$_2$C(O), and CH$_2$(O)CCH$_2$;

A is optionally selected from the group consisting of CH$_2$N(CH$_3$), CH$_2$N(CH$_2$CH$_3$), CH$_2$CH$_2$N(CH$_3$), and CH$_2$CH$_2$N(CH$_2$CH$_3$) with the proviso that B is hydrido;

R$^1$ is selected from the group consisting of hydrido, cyano, methyl, ethyl, propyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, and bromo;

R$^2$ is Z$^0$—Q;

Z$^0$ is selected from the group consisting of covalent single bond, CH$_2$, CH$_2$CH$_2$, CH(OH), CH(NH$_2$), CH$_2$CH(OH), CH$_2$CHNH$_2$, CH(OH)CH$_2$, and CH(NH$_2$)CH$_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, 1,2,3-triazin-4-yl, and 1,2,3-triazin-5-yl, wherein a carbon adjacent to the carbon at the point of attachment is optionally substituted by R$^9$, the other carbon adjacent to the carbon at the point of attachment is optionally substituted by R$^{13}$, a carbon adjacent to R$^9$ and two atoms from the carbon at the point of attachment is optionally substituted by R$^{10}$, a carbon adjacent to R$^{13}$ and two atoms from the carbon at the point of attachment is optionally substituted by R$^{12}$, and any carbon adjacent to both R$^{10}$ and R$^{12}$ is optionally substituted by R$^{11}$;

K is CHR$^{4a}$ wherein R$^{4a}$ is selected from the group consisting of methyl, ethyl, propyl, isopropyl, hydroxymethyl, 1-hydroxyethyl, methoxymethyl, trifluoromethyl, pentafluoroethyl, 2,2,2-trifluoromethyl, methylthiomethyl, and hydrido;

E$^0$ is a covalent single bond, C(O)N(H), (H)NC(O), and S(O)$_2$N(H);

Y$^0$ is selected from the group of formulas consisting of:

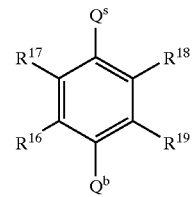

1-Q$^b$-4-Q$^s$-2-R$^{16}$-3-R$^{17}$-5-R$^{18}$-6-R$^{19}$benzene,

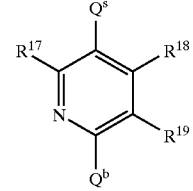

2-Q$^b$-5-Q$^s$-6-R$^{17}$-4-R$^{18}$-3-R$^{19}$pyridine,

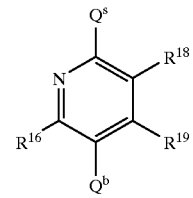

3-Q$^b$-6-Q$^s$-2-R$^{16}$-5-R$^{18}$-4-R$^{19}$pyridine,

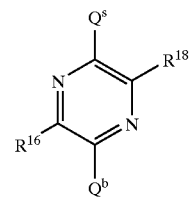

2-Q$^b$-5-Q$^s$-3-R$^{16}$-6-R$^{18}$pyrazine,

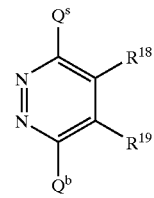

3-Q$^b$-6-Q$^s$-2-R$^{18}$-5-R$^{18}$-4-R$^{19}$pyridazine,

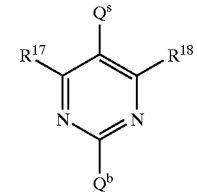

2-Q$^b$-5-Q$^s$-4-R$^{17}$-6-R$^{18}$pyrimidine,

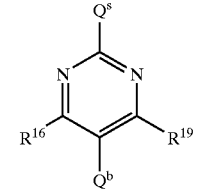

5-Q$^b$-2-Q$^s$-4-R$^{16}$-6-R$^{19}$pyrimidine,

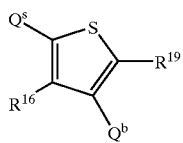

3-$Q^b$-5-$Q^s$-4-$R^{16}$-2-$R^{19}$thiophene,

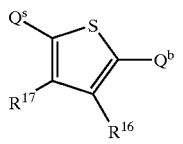

2-$Q^b$-5-$Q^s$-3-$R^{16}$-4-$R^{17}$thiophene,

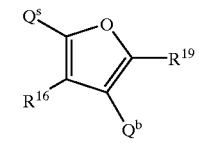

3-$Q^b$-5-$Q^s$-4-$R^{16}$-2-$R^{19}$furan,

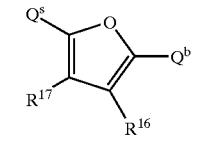

2-$Q^b$-5-$Q^s$-3-$R^{16}$-4-$R^{17}$furan,

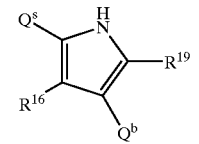

3-$Q^b$-5-$Q^s$-4-$R^{16}$-2-$R^{19}$pyrrole,

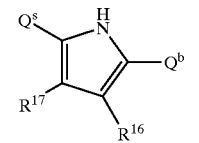

2-$Q^b$-5-$Q^s$-3-$R^{16}$-4-$R^{17}$pyrrole,

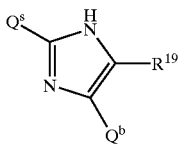

4-$Q^b$-2-$Q^s$-5-$R^{19}$imidazole,

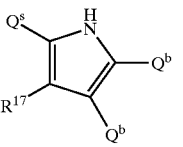

2-$Q^b$-4-$Q^s$-5-$R^{17}$imidazole,

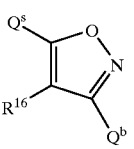

3-$Q^b$-5-$Q^s$-4-$R^{16}$isoxazole,

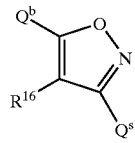

5-$Q^b$-3-$Q^s$-4-$R^{16}$isoxazole,

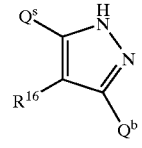

2-$Q^b$-5-$Q^s$-4-$R^{16}$pyrazole,

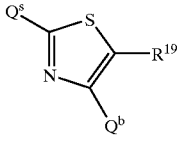

4-$Q^b$-2-$Q^s$-5-$R^{19}$thiazole, and

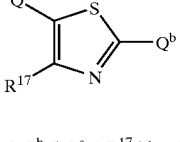

2-$Q^b$-5-$Q^s$-4-$R^{17}$thiazole;

$R^{16}$, $R^{17}$, $R^{18}$, and $R^{19}$ are independently selected from the group consisting of hydrido, methyl, ethyl, isopropyl, propyl, amidino, guanidino, carboxy, methoxy, ethoxy, isopropoxy, propoxy, hydroxy, amino, methoxyamino, ethoxyamino, aminomethyl, 1-aminoethyl, 2-aminoethyl, N-N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $C(NR^{25})NR^{23}R^{24}$ and $N(R^{26})C(NR^{25})N(R^{23})(R^{24})$, with the proviso that no more than one of $R^{20}$ and $R^{21}$ is hydroxy, N-methylamino, and N,N-dimethylamino at the same time and that no more than one of $R^{23}$ and $R^{24}$ is hydroxy, N-methylamino, and N,N-dimethylamino at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, hydroxy, 2-aminoethyl, 2N-methylamino)ethyl, and 2-(N,N-dimethylamino)ethyl;

$Q^s$ is selected from the group consisting of a single covalent bond, $CH_2$, $CH_2CH_2$, $CH_3CH$, $CF_3CH$, $CH_3CHCH_2$, $CF_3CHCH_2$, $CH_2(CH_3)CH$, $CH=CH$, CF=CH, C(CH₃)=CH, CH=CHCH₂, CF=CHCH₂, C(CH₃)=CHCH₂, CH₂CH=CH, CH₂CF=CH, CH₂C(CH₃)=CH, CH₂CH=CHCH₂, CH₂CF=CHCH₂, CH₂C(CH₃)=CHCH₂, CH₂CH=CHCH₂CH₂, CH₂CF=CHCH₂CH₂, and CH₂C(CH₃)=CHCH₂CH₂.

In a more preferred specific embodiment of Formula I, compounds have the Formula I-MPS wherein B is an aromatic:

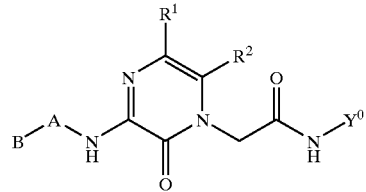

(I-MPS wherein B is aromatic)
or a pharmaceutically acceptable salt thereof, wherein;
B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methyl amino, dimethyl amino, N-ethyl amino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of single covalent bond, NH, N(CH₃), N(OH), CH₂, CH₃CH, CF₃CH, NHC(O), N(CH₃)C(O), C(O)NH, C(O)N(CH₃), CH₂CH₂, CH₂CH₂CH₂, CH₃CHCH₂, and CF₃CHCH₂;

$R^{16}$ or $R^{19}$ is optionally $C(NR^{25})NR^{23}R^{24}$ with the proviso that $R^{16}$, $R^{19}$, and $Q^b$ are not simultaneously hydrido;

$Q^b$ is $C(NR^{25})NR^{23}R^{24}$ or hydrido, with the proviso that no more than one of $R^{23}$ and $R^{24}$ is hydroxy at the same time;

$R^{23}$, $R^{24}$, and $R^{25}$ are independently selected from the group consisting of hydrido, methyl, ethyl, and hydroxy.

In another more preferred specific embodiment of Formula I, compounds have the Formula I-MPS wherein B is a non-cyclic substituent:

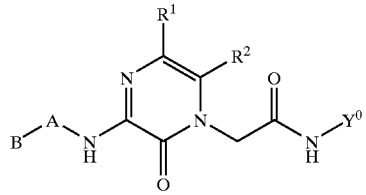

(I-MPS wherein B is a non-cyclic substituent)
or a pharmaceutically acceptable salt thereof, wherein;
B is selected from the group consisting of hydrido, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of single covalent bond, NH, N(CH₃), N(OH), CH₂, CH₃CH, CF₃CH, NHC(O), N(CH₃)C(O), C(O)NH, C(O)N(CH₃), CH₂CH₂, CH₂CH₂CH₂, CH₃CHCH₂, and CF₃CHCH₂;

A is optionally selected from the group consisting of CH₂N(CH₃), CH₂N(CH₂CH₃), CH₂CH₂N(CH₃), and CH₂CH₂N(CH₂CH₃) with the proviso that B is hydrido;

$R^{16}$ or $R^{19}$ is optionally selected from the group consisting of $NR^{20}R^{21}$, $C(NR^{25})NR^{23}R^{24}$, and $N(R^{26})C(NR^{25})N(R^{23})(R^{24})$, with the proviso that $R^{16}$, $R^{19}$, and $Q^b$ are not simultaneously hydrido;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, and hydroxy.

In still another more preferred specific embodiment of Formula I, compounds have the Formula I-MPS wherein B is a non-aromatic cyclic substituent:

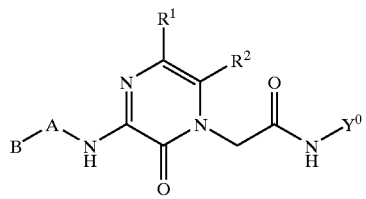

(I-MPS wherein B is a non-aromatic cyclic substituent) or a pharmaceutically acceptable salt thereof, wherein;

B is optionally selected from the group consisting of cyclopropyl, cyclobutyl, oxetan-3-yl, azetidin-1-yl, azetidin-2-yl, azetidin-3-yl, thiaetan-3-yl, cyclopentyl, cyclohexyl, norbornyl, 7-oxabicyclo[2.2.1]heptan-2-yl, bicyclo[3.1.0]hexan-6-yl, cycloheptyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 4H-2-pyranyl, 4H-3-pyranyl, 4H-4-pyranyl, 4H-pyran-4-one-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, a ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, and a ring carbon or nitrogen atom adjacent to the $R^{13}$ position and two atoms from the point of attachment is optionally substituted with $R^{12}$;

A is selected from the group consisting of single covalent bond, NH, $N(CH_3)$, N(OH), $CH_2$, $CH_3CH$, $CF_3CH$, NHC(O), $N(CH_3)C(O)$, C(O)NH, $C(O)N(CH_3)$, $CH_2CH_2$ $CH_2CH_2CH_2$, $CH_3CHCH_2$, and $CF_3CHCH_2$;

$R^{33}$ is selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

$R^{16}$ or $R^{19}$ is optionally $C(NR^{25})NR^{23}R^{24}$ with the proviso that $R^{16}$, $R^{19}$, and $Q^b$ are not simultaneously hydrido;

$Q^b$ is $C(NR^{25})NR^{23}R^{24}$ or hydrido, with the proviso that no more than one of $R^{23}$ and $R^{24}$ is hydroxy at the same time;

$R^{23}$, $R^{24}$, and $R^{25}$ are independently selected from the group consisting of hydrido, methyl, ethyl, and hydroxy.

The more preferred specific embodiment (I-MPS) compounds of the present invention having the Formula:

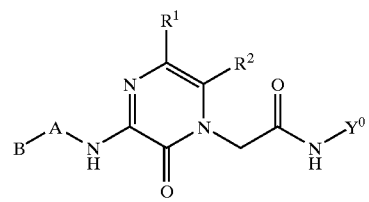

or a pharmaceutically acceptable salt thereof, have common structural units, wherein, $R^1$ is selected from the group consisting of hydrido, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;

$R^2$ is $Z^0$—Q;

$Z^0$ is selected from the group consisting of covalent single bond, $CH_2$, $CH_2CH_2$, O, S, NH, $N(CH_3)$, $OCH_2$, $SCH_2$, $N(H)CH_2$, and $N(CH_3)CH_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl)amidocarbonyl, N-(2-trifluoromethylbenzyl) amidocarbonyl, N-(1-phenylethyl)amidocarbonyl, N-(1-methyl-1-phenylethyl)amidocarbonyl, N-benzylamidosulfonyl, N-(2-chlorobenzyl) amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, fluoro, chloro, bromo, cyano, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-S methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy;

$Y^o$ is selected from the group of formulas consisting of:

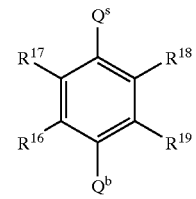

1-$Q^b$-4-$Q^s$-2-$R^{16}$-3-$R^{17}$-5-$R^{18}$-6-$R^{19}$benzene,

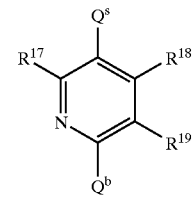

2-$Q^b$-5-$Q^s$-6-$R^{17}$-4-$R^{18}$-3-$R^{19}$pyridine,

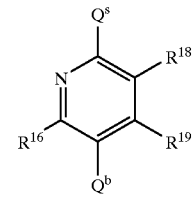

3-$Q^b$-6-$Q^s$-2-$R^{16}$-5-$R^{18}$-4-$R^{19}$pyridine,

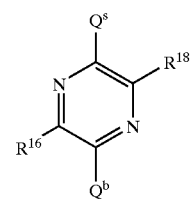

2-$Q^b$-5-$Q^s$-3-$R^{16}$-6-$R^{18}$pyrazine,

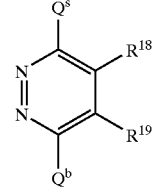

3-$Q^b$-6-$Q^s$-2-$R^{18}$-5-$R^{18}$-4-$R^{19}$pyridazine,

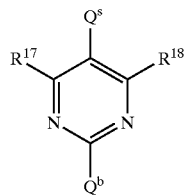

2-Q$^b$-5-Q$^s$-4-R$^{17}$-6-R$^{18}$pyrimidine,

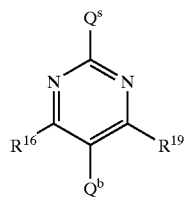

5-Q$^b$-2-Q$^s$-4-R$^{16}$-6-R$^{19}$pyrimidine,

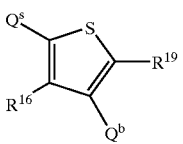

3-Q$^b$-5-Q$^s$-4-R$^{16}$-2-R$^{19}$thiophene,

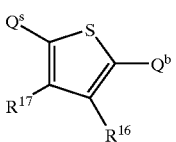

2-Q$^b$-5-Q$^s$-3-R$^{16}$-4-R$^{17}$thiophene,

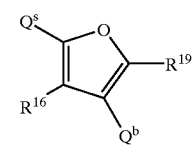

3-Q$^b$-5-Q$^s$-4-R$^{16}$-2-R$^{19}$furan,

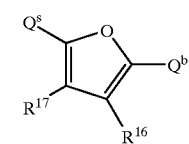

2-Q$^b$-5-Q$^s$-3-R$^{16}$-4-R$^{17}$furan,

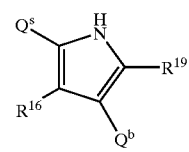

3-Q$^b$-5-Q$^s$-4-R$^{16}$-2-R$^{19}$pyrrole,

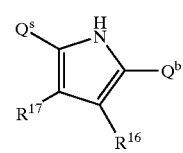

2-Q$^b$-5-Q$^s$-3-R$^{16}$-4-R$^{17}$pyrrole,

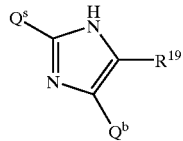

4-Q$^b$-2-Q$^s$-5-R$^{19}$imidazole,

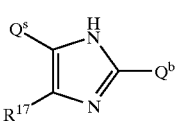

2-Q$^b$-4-Q$^s$-5-R$^{17}$imidazole,

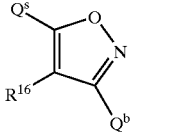

3-Q$^b$-5-Q$^s$-4-R$^{16}$isoxazole,

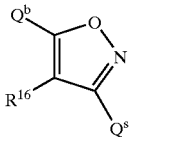

5-Q$^b$-3-Q$^s$-4-R$^{16}$isoxazole,

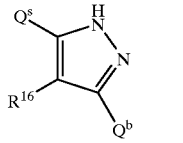

2-Q$^b$-5-Q$^s$-4-R$^{16}$pyrazole,

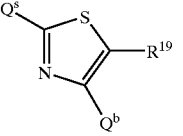

4-Q$^b$-2-Q$^s$-5-R$^{19}$thiazole, and

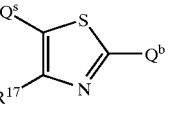

2-Q$^b$-5-Q$^s$-4-R$^{17}$thiazole;

R$^{16}$, R$^{17}$, R$^{18}$, and R$^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano;

$Q^s$ is selected from the group consisting of a single covalent bond, $CH_2$, and $CH_2CH_2$.

In a most preferred specific embodiment of Formula I, compounds have the Formula I-EMPS wherein B is an aromatic:

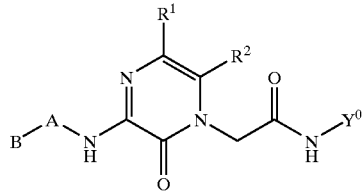

(I-EMPS wherein B is aromatic)

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, and 5-isoxazolyl, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of single covalent bond, NH, $N(CH_3)$, $CH_2$, $CH_3CH$, and $CH_2CH_2$;

$Q^b$ is $NR^{20}R^{21}$ or $C(NR^{25})NR^{23}R^{24}$;

$R^{20}$, $R^{21}$, $R^{22}$, $R^{24}$, and $R^{25}$ are independently selected from the group consisting of hydrido, methyl, and ethyl.

In another most preferred specific embodiment of Formula I, compounds have the Formula I-EMPS wherein B is a non-cyclic substituent:

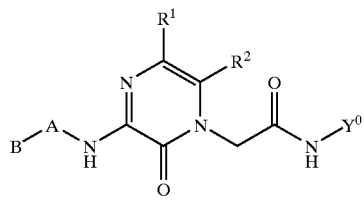

(I-EMPS wherein B is a non-cyclic substituent)

or a pharmaceutically acceptable salt thereof, wherein;

B is selected from the group consisting of hydrido, ethyl, 2-propenyl, 2-propynyl, propyl, isopropyl, butyl, 2-butenyl, 2-butynyl, sec-butyl, tert-butyl, isobutyl, 2-methylpropenyl, 1-pentyl, 2-pentenyl, 3-pentenyl, 2-pentynyl, 3-pentynyl, 2-pentyl, 3-pentyl, 2-methylbutyl, 2-methyl-2-butenyl, 3-methylbutyl, 3-methyl-2-butenyl, 1-hexyl, 2-hexenyl, 3-hexenyl, 4-hexenyl, 2-hexynyl, 3-hexynyl, 4-hexynyl, 2-hexyl, 1-methyl-2-pentenyl, 1-methyl-3-pentenyl, 1-methyl-2-pentynyl, 1-methyl-3-pentynyl, 3-hexyl, 1-ethyl-2-butenyl, 1-heptyl, 2-heptenyl, 3-heptenyl, 4-heptenyl, 5-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-2-pentynyl, 1-ethyl-3-pentynyl, 2,2,2-trifluoroethyl, 2,2-difluoropropyl, 4-trifluoromethyl-5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of single covalent bond, NH, $N(CH_3)$, $CH_2$, $CH_3CH$, and $CH_2CH_2$;

A is optionally selected from the group consisting of $CH_2N(CH_3)$, $CH_2N(CH_2CH_3)$, $CH_2CH_2N(CH_3)$, and $CH_2CH_2N(CH_2CH_3)$ with the proviso that B is hydrido;

$Q^b$ is selected from the group consisting of $NR^{20}R^{21}$, $C(NR^{25})NR^{23}R^{24}$, and $N(R^{26})C(NR^{25})N(R^{23})(R^{24})$;

$R^{20}$, $R^{21}$, $R^{23}$, $R^{24}$, $R^{25}$, and $R^{26}$ are independently selected from the group consisting of hydrido, methyl, and ethyl.

In still another most preferred specific embodiment of Formula I, compounds have the Formula I-EMPS wherein B is a non-aromatic cyclic substituent:

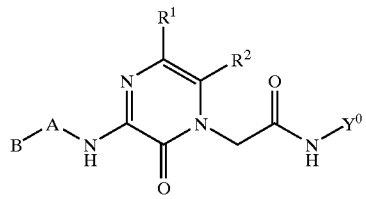

(I-EMPS wherein B is a non-aromatic cyclic substituent)

or a pharmaceutically acceptable salt thereof, wherein;

B is selected from the group consisting of cyclopropyl, cyclobutyl, cyclopentyl, cyclohexyl, cycloheptyl, oxalan-2-yl, 2-(2R)-bicyclo[2.2.1]-heptyl, oxetan-3-yl, azetidin-1-yl, azetidin-2-yl, azetidin-3-yl, bicyclo [3.1.0]hexan-6-yl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, f-pyrrolidinyl, 2-pyrrolidinyl, 3-pyrrolidinyl, 2-dioxanyl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment are optionally substituted with $R^{10}$, and a ring carbon or nitrogen atom adjacent to the $R^{13}$ position and two atoms from the point of attachment is optionally substituted with $R^{12}$;

$R^{33}$ is selected from the group consisting of hydrido, amidino, guanidino, methyl, ethyl, methoxy, ethoxy, hydroxy, carboxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, cyano, and $Q^b$;

A is selected from the group consisting of single covalent bond, NH, N(CH$_3$), CH$_2$, CH$_3$CH, and CH$_2$CH$_2$;

$Q^b$ is $NR^{20}R^{21}$ or $C(NR^{25})NR^{23}R^{24}$;

$R^{20}$, $R^{21}$, $R^{23}$, $R^{24}$, and $R^{25}$ are independently selected from the group consisting of hydrido, methyl, and ethyl.

The most preferred specific embodiment (I-EMPS) compounds of the present invention having the Formula:

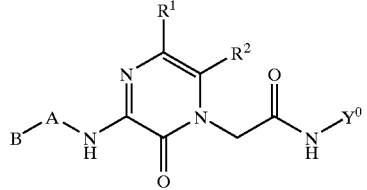

or a pharmaceutically acceptable salt thereof, have common structural units, wherein;

$R^1$ is selected from the group consisting of hydrido, hydroxy, hydroxymethyl, amino, aminomethyl, methylamino, cyano, methyl, trifluoromethyl, methoxy, methylthio, trifluoromethoxy, fluoro, and chloro;

$R^2$ is selected from the group consisting of phenyl, 2-thienyl, 2-furyl, 2-pyrrolyl, 2-imidazolyl, 2-thiazolyl, 3-isoxazolyl, 2-pyridyl, and 3-pyridyl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrido, amidino, amidocarbonyl, N-methylamidocarbonyl, N-benzylamidocarbonyl, N-(2-chlorobenzyl)amidocarbonyl, N-(3-fluorobenzyl) amidocarbonyl, N-(2-trifluoromethylbenzyl) amidocarbonyl, N-(1-phenylethyl)amidocarbonyl, N-(1-methyl-1-phenylethyl)amidocarbonyl, N-benzylamidosulfonyl, N-(2-chlorobenzyl) amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, methoxyamino, amidosulfonyl, N-methylamidosulfonyl, N,N-dimethylamidosulfonyl, methanesulfonamido, methoxycarbonyl, fluoro, chloro, bromo, and cyano;

$R^{10}$ and $R^{12}$ are optionally independently selected from the group consisting of hydrido, amidino, guanidino, hydroxy, hydroxymethyl, 1-hydroxyethyl, 2-hydroxyethyl, amino, aminomethyl, N-methylamino, dimethylamino, methoxyamino, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy;

$Y^o$ is selected from the group of formulas consisting of:

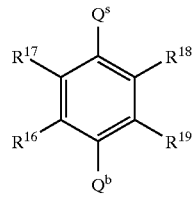

1-$Q^b$-4-$Q^s$-2-$R^{16}$-3-$R^{17}$-5-$R^{18}$-6-$R^{19}$benzene,

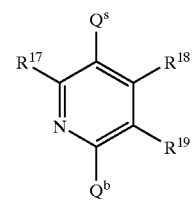

2-$Q^b$-5-$Q^s$-6-$R^{17}$-4-$R^{18}$-3-$R^{19}$pyridine,

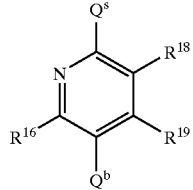

3-$Q^b$-6-$Q^s$-2-$R^{16}$-5-$R^{18}$-4-$R^{19}$pyridine,

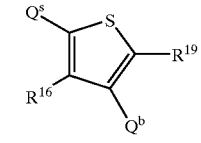

3-$Q^b$-5-$Q^s$-4-$R^{16}$-2-$R^{19}$thiophene,

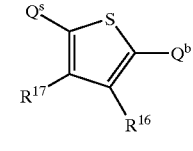

2-$Q^b$-5-$Q^s$-3-$R^{16}$-4-$R^{17}$thiophene,

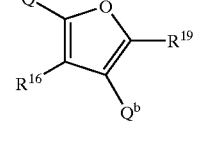

3-$Q^b$-5-$Q^s$-4-$R^{16}$-2-$R^{19}$furan,

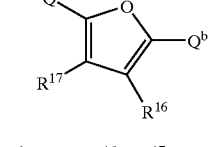

2-$Q^b$-5-$Q^s$-3-$R^{16}$-4-$R^{17}$furan,

-continued

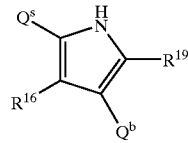

3-$Q^b$-5-$Q^s$-4-$R^{16}$-2-$R^{19}$pyrrole,

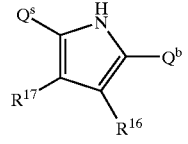

2-$Q^b$-5-$Q^s$-3-$R^{16}$-4-$R^{17}$pyrrole,

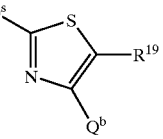

4-$Q^b$-2-$Q^s$-5-$R^{19}$thiazole, and

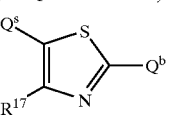

2-$Q^b$-5-$Q^s$-4-$R^{17}$thiazole;

$R^{16}$, $R^{17}$, $R^{18}$, and $R^{19}$ are independently selected from the group consisting of hydrido, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, hydroxymethyl, carboxy, and cyano;

$Q^s$ is $CH_2$.

The compounds of this invention can be used in anticoagulant therapy for the treatment and prevention of a variety of thrombotic conditions including coronary artery and cerebrovascular disease. The compounds of this invention can be used to inhibit serine protease associated with the coagulation cascade and factors II, VII, VIII, IX, X, XI, or XII. The compounds of the invention can inhibit the formation of blood platelet aggregates, inhibit the formation of fibrin, inhibit thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The compounds can also be used in prophylactic treatment of subjects who are at risk of developing such disorders. The compounds can be used to lower the risk of atherosclerosis. The compounds of Formula (I) would also be useful in prevention of cerebral vascular accident (CVA) or stroke.

Besides being useful for human treatment, these compounds are also useful for veterinary treatment of companion animals, exotic animals and farm animals, including mammals, rodents, and the like. More preferred animals include horses, dogs, and cats.

In yet another embodiment of the present invention, the novel compounds are selected from the compounds set forth in Examples 1 through Example 166, Tables 1 through Table 7, Example Table 1, and Example Table 2.

The use of generic terms in the description of the compounds are herein defined for clarity.

Standard single letter elemental symbols are used to represent specific types of atoms unless otherwise defined. The symbol "C" represents a carbon atom. The symbol "O" represents an oxygen atom. The symbol "N" represents a nitrogen atom. The symbol "P" represents a phosphorus atom. The symbol "S" represents a sulfur atom. The symbol "H" represents a hydrido atom. Double letter elemental symbols are used as defined for the elements of the periodical table (i.e., Cl represents chlorine, Se represents selenium, etc.).

As utilized herein, the term "alkyl", either alone or within other terms such as "haloalkyl" and "alkylthio", means an acyclic alkyl radical containing from 1 to about 10, preferably from 3 to about 8 carbon atoms and more preferably 3 to about 6 carbon atoms. Said alkyl radicals may be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical in so much as it contains at least one double bond. Such alkenyl radicals contain from about 2 to about 10 carbon atoms, preferably from about 3 to about 8 carbon atoms and more preferably 3 to about 6 carbon atoms. Said alkenyl radicals may be optionally substituted with groups as defined below. Examples of suitable alkenyl radicals include propenyl, 2-chloropropenyl, buten-1-yl, isobutenyl, penten-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, preferably having from about 3 to about 8 carbon atoms and more preferably having 3 to about 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "hydrido" denotes a single hydrogen atom (H). This hydrido radical may be attached, for example, to an oxygen atom to form a "hydroxyl" radical, one hydrido radical may be attached to a carbon atom to form a "methine" radical —CH=, or two hydrido radicals may be attached to a carbon atom to form a "methylene" (—CH$_2$—) radical.

The term "carbon" radical denotes a carbon atom without any covalent bonds and capable of forming four covalent bonds.

The term "cyano" radical denotes a carbon radical having three of four covalent bonds shared by a nitrogen atom.

The term "hydroxyalkyl" embraces radicals wherein any one or more of the alkyl carbon atoms is substituted with a hydroxyl as defined above. Specifically embraced are monohydroxyalkyl, dihydroxyalkyl and polyhydroxyalkyl radicals.

The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl.

The term "alkylene" radical denotes linear or branched radicals having from 1 to about 10 carbon atoms and having attachment points for two or more covalent bonds. Examples of such radicals are methylene, ethylene, methylethylene, and isopropylidene.

The term "alkenylene" radical denotes linear or branched radicals having from 2 to about 10 carbon atoms, at least one double bond, and having attachment points for two or more covalent bonds. Examples of such radicals are 1,1-vinylidene (CH$_2$=C), 1,2-vinylidene (—CH=CH—), and 1,4-butadienyl (—CH=CH—CH=CH—).

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "haloalkyl" radicals having one to about six carbon atoms. Examples of such haloalkyl radicals include fluoromethyl, difluoromethyl, trifluoromethyl, chloromethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl and dichloropropyl.

The term "hydroxyhaloalkyl" embraces radicals wherein any one or more of the haloalkyl carbon atoms is substituted with hydroxy as defined above. Examples of "hydroxyhaloalkyl" radicals include hexafluorohydroxypropyl.

The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred haloalkylene radicals are "haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "alkoxy" radicals having one to six carbon atoms. Examples of such radicals include methoxy, ethoxy, propoxy, butoxy, isopropoxy and tert-butoxy alkyls. The "alkoxy" radicals may be further substituted with one or more halo atoms, such as fluoro, chloro or bromo, to provide "haloalkoxy" and "haloalkoxyalkyl" radicals. Examples of such haloalkoxy radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy. Examples of such haloalkoxyalkyl radicals include fluoromethoxymethyl, chloromethoxyethyl, trifluoromethoxymethyl, difluoromethoxyethyl, and trifluoroethoxymethyl.

The terms "alkenyloxy" and "alkenyloxyalkyl" embrace linear or branched oxy-containing radicals each having alkenyl portions of two to about ten carbon atoms, such as ethenyloxy or propenyloxy radical. The term "alkenyloxyalkyl" also embraces alkenyl radicals having one or more alkenyloxy radicals attached to the alkyl radical, that is, to form monoalkenyloxyalkyl and dialkenyloxyalkyl radicals. More preferred alkenyloxy radicals are "alkenyloxy" radicals having two to six carbon atoms. Examples of such radicals include ethenyloxy, propenyloxy, butenyloxy, and isopropenyloxy alkyls. The "alkenyloxy" radicals may be further substituted with one or more halo atoms, such as fluoro, chloro or bromo, to provide "haloalkenyloxy" radicals. Examples of such radicals include trifluoroethenyloxy, fluoroethenyloxy, difluoroethenyhloxy, and fluoropropenyloxy.

The term "haloalkoxyalkyl" also embraces alkyl radicals having one or more haloalkoxy radicals attached to the alkyl radical, that is, to form monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals.

The term "alkylenedioxy" radicals denotes alkylene radicals having at least two oxygens bonded to a single alkylene group. Examples of "alkylenedioxy" radicals include methylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoroethylenedioxy, tetrachloroethylenedioxy, alkylsubstituted monofluoromethylenedioxy, and arylsubstituted monofluoromethylenedioxy.

The term "aryl", alone or in combination, means a carbocyclic aromatic system containing one, two or three rings wherein such rings may be attached together in a pendant manner or may be fused. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indane and biphenyl.

The term "perhaloaryl" embraces aromatic radicals such as phenyl, naphthyl, tetrahydronaphthyl, indane and biphenyl wherein the aryl radical is substituted with 3 or more halo radicals as defined below.

The term "heterocyclyl" embraces saturated and partially saturated heteroatom-containing ring-shaped radicals having from 4 through 15 ring members, herein referred to as "C4–C15 heterocyclyl", selected from carbon, nitrogen, sulfur and oxygen, wherein at least one ring atom is a heteroatom. Heterocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclyl radicals include dihydrothiophene, dihydropyran, dihydrofuran and dihydrothiazole. Non-limiting examples of heterocyclic radicals include 2-pyrrolinyl, 3-pyrrolinyl, pyrrolindinyl, 1,3-dioxolanyl, 2H-pyranyl, 4H-pyranyl, piperidinyl, 1,4-dioxanyl, morpholinyl, 1,4-dithianyl, thiomorpholinyl, and the like. Said "heterocyclyl" group may be substituted as defined herein. Preferred heterocyclic radicals include five to twelve membered fused or unfused radicals.

The term "heteroaryl" embraces fully unsaturated heteroatom-containing ring-shaped aromatic radicals having from 4 through 15 ring members selected from carbon, nitrogen, sulfur and oxygen, wherein at least one ring atom is a heteroatom. Heteroaryl radicals may contain one, two or three rings wherein such rings may be attached in a pendant manner or may be fused. Examples of "heteroaryl" radicals, include the unsaturated heteromonocyclyl group of 5 to 6 contiguous members containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heteroaryl" group may be substituted as defined herein. Preferred heteroaryl radicals include five and six membered unfused radicals. Non-limiting examples of heteroaryl radicals include 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5- yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 13,5-triazin-2-yl, 1,2,4-triazin-3-yl, 1,2,4-triazin-5-yl, 1,2,4-triazin-6-yl, 1,2,3-triazin-4-yl, and 1,2,3-triazin-5-yl, and the like.

The term "sulfonyl", whether used alone or linked to other terms such as alkylsulfonyl, denotes respectively divalent radicals —SO$_2$—. "Alkylsulfonyl", embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals attached to a sulfonyl radical, where haloalkyl is defined as above. "Haloalkylsulfonylalkyl", embraces haloalkylsulfonyl radicals attached to an alkyl radical, where alkyl is defined as above.

The term "amidosulfonyl" embraces amino, monoalkylamino, dialkylamino, monocycloalkylamino, alkyl cycloalkylamino, dicycloalkylamino, N-alkyl-N-arylamino, arylamino, aralkylamino, nitrogen containing heterocyclyl, heterocyclylamino, N-alkyl-N-heterocyclylamino, heteroarylamino, and heteroaralkylamino radicals, attached to one of two unshared bonds in a sulfonyl radical.

The term "sulfinyl", whether used alone or linked to other terms such as alkylsulfinyl, denotes respectively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfinylalkyl", embraces haloalkylsulfinyl radicals attached to an alkyl radical, where alkyl is defined as above.

The term "aralkyl" embraces aryl-substituted alkyl radicals. Preferable aralkyl radicals are "aralkyl" radicals having aryl radicals attached to alkyl radicals having one to six carbon atoms. Examples of such radicals include benzyl, diphenylmethyl, triphenylmethyl, phenylethyl and diphenylethyl. The terms benzyl and phenylmethyl are interchangeable.

The term "heteroaralkyl" embraces heteroaryl-substituted alkyl radicals wherein the heteroaralkyl radical may be additionally substituted with three or more substituents as defined above for aralkyl radicals. The term "perhaloaralkyl" embraces aryl-substituted alkyl radicals wherein the aralkyl radical is substituted with three or more halo radicals as defined above.

The term "aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above.

The term "aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above.

The term "cycloalkyl" embraces radicals having three to 15 carbon atoms. More preferred cycloalkyl radicals are "cycloalkyl" radicals having three to seven carbon atoms. Examples include radicals such as cyclopropyl, cyclobutyl, cyclopentyl, cyclohexyl and cycloheptyl. The term cycloalkyl embraces radicals having seven to 15 carbon atoms and having two to four rings. Exmaples incude radicals such as norbornyl (i.e., bicyclo[2.2.1]heptyl) and adamantyl. The term "cycloalkylalkyl" embraces cycloalkyl-substituted alkyl radicals. Preferable cycloalkylalkyl radicals are "cycloalkylalkyl" radicals having cycloalkyl radicals attached to alkyl radicals having one to six carbon atoms. Examples of such radicals include cyclohexylhexyl. The term "cycloalkenyl" embraces radicals having three to ten carbon atoms and one or more carbon-carbon double bonds. Preferred cycloalkenyl radicals are "cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. More preferred halocycloalkyl radicals are "halocycloalkyl" radicals having three to about eight carbon atoms.

Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals.

The term "cycloalkoxy" embraces cycloalkyl radicals attached to an oxy radical. Examples of such radicals includes cyclohexoxy and cyclopentoxy. The term "cycloalkoxyalkyl" also embraces alkyl radicals having one or more cycloalkoxy radicals attached to the alkyl radical, that is, to form monocycloalkoxyalkyl and dicycloalkoxyalkyl radicals. Examples of such radicals include cyclohexoxyethyl. The "cycloalkoxy" radicals may be further substituted with one or more halo atoms, such as fluoro, chloro or bromo, to provide "halocycloalkoxy" and "halocycloalkoxyalkyl" radicals. The term "cycloalkylalkoxy" embraces cycloalkyl radicals attached to an alkoxy radical. Examples of such radicals includes cyclohexylmethoxy and cyclopentylmethoxy.

The term "cycloalkenyloxy" embraces cycloalkenyl radicals attached to an oxy radical. Examples of such radicals includes cyclohexenyloxy and cyclopentenyloxy. The term "cycloalkenyloxyalkyl" also embraces alkyl radicals having one or more cycloalkenyloxy radicals attached to the alkyl radical, that is, to form monocycloalkenyloxyalkyl and dicycloalkenyloxyalkyl radicals. Examples of such radicals include cyclohexenyloxyethyl. The "cycloalkenyloxy" radicals may be further substituted with one or more halo atoms, such as fluoro, chloro or bromo, to provide "halocycloalkenyloxy" and "halocycloalkenyloxyalkyl" radicals.

The term "cycloalkylenedioxy" radicals denotes cycloalkylene radicals having at least two oxygens bonded to a single cycloalkylene group. Examples of "alkylenedioxy" radicals include 1,2-dioxycyclohexylene.

The term "cycloalkylsulfinyl", embraces cycloalkyl radicals attached to a sulfinyl radical, where cycloalkyl is defined as above. "Cycloalkylsulfinylalkyl", embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalkylsulfonyl radicals attached to an alkyl radical, where alkyl is defined as above.

The term "cycloalkylalkanoyl" embraces radicals wherein one or more of the cycloalkyl carbon atoms are substituted with one or more carbonyl radicals as defined below. Specifically embraced are monocarbonylcycloalkyl and dicarbonylcycloalkyl radicals. Examples of monocarbonylcycloalkyl radicals include cyclohexylcarbonyl, cyclohexylacetyl, and cyclopentylcarbonyl. Examples of dicarbonylcycloalkyl radicals include 1,2-dicarbonylcyclohexane.

The term "alkylthio" embraces radicals containing a linear or branched alkyl radical, of one to ten carbon atoms, attached to a divalent sulfur atom. More preferred alkylthio radicals are "alkylthio" radicals having one to six carbon atoms. An example of "alkylthio" is methylthio ($CH_3$—S—). The "alkylthio" radicals may be further substituted with one or more halo atoms, such as fluoro, chloro or bromo, to provide "haloalkylthio" radicals. Examples of such radicals include fluoromethylthio, chloromethylthio, trifluoromethylthio, difluoromethylthio, trifluoroethylthio, fluoroethylthio, tetrafluoroethylthio, pentafluoroethylthio, and fluoropropylthio.

The term "alkyl aryl amino" embraces radicals containing a linear or branched alkyl radical, of one to ten carbon atoms, and one aryl radical both attached to an amino radical. Examples include N-methyltmethoxyaniline, N-ethyltmethoxyaniline, and N-methyl-4-trifluoromethoxyaniline.

The term alkylamino denotes "monoalkylamino" and "dialkylamino" containing one or two alkyl radicals, respectively, attached to an amino radical. One or two alkyl radicals of the alkylamino may be optionally substituted with hydrogen bonding substitutents selected from the group consisting of hydroxy, amino, monoalkylamino, dialkylamino, amidino, guanidino, thiol, and alkoxy provided the alkyl radicals comprises two or more carbons.

The terms arylamino denotes "monoarylamino" and "diarylamino" containing one or two aryl radicals, respectively, attached to an amino radical. Examples of such radicals include N-phenylamino and N-naphthylamino.

The term "aralkylamino", embraces aralkyl radicals attached to an amino radical, where aralkyl is defined as above. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "arylsulfinyl" embraces radicals containing an aryl radical, as defined above, attached to a divalent S(O) atom. The term "arylsulfinylalkyl" denotes arylsulfinyl radicals attached to a linear or branched alkyl radical, of one to ten carbon atoms.

The term "arylsulfonyl", embraces aryl radicals attached to a sulfonyl radical, where aryl is defined as above. "arylsulfonylalkyl", embraces arylsulfonyl radicals attached to an alkyl radical, where alkyl is defined as above. The term "heteroarylsulfinyl" embraces radicals containing an heteroaryl radical, as defined above, attached to a divalent S(O) atom. The term "heteroarylsulfinylalkyl" denotes heteroarylsulfinyl radicals attached to a linear or branched alkyl radical, of one to ten carbon atoms. The term "Heteroarylsulfonyl", embraces heteroaryl radicals attached to a sulfonyl radical, where heteroaryl is defined as above. "Heteroarylsulfonylalkyl", embraces heteroarylsulfonyl radicals attached to an alkyl radical, where alkyl is defined as above.

The term "aryloxy" embraces aryl radicals, as defined above, attached to an oxygen atom. Examples of such radicals include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 3-pentafluoroethylphenoxy, 3-(1,1,2,2-tetrafluoroethoxy)-phenoxy, and 4-tert-butylphenoxy.

The term "aroyl" embraces aryl radicals, as defined above, attached to an carbonyl radical as defined above. Examples of such radicals include benzoyl and toluoyl.

The term "aralkanoyl" embraces aralkyl radicals, as defined herein, attached to an carbonyl radical as defined above. Examples of such radicals include, for example, phenylacetyl.

The term "aralkoxy" embraces oxy-containing aralkyl radicals attached through an oxygen atom to other radicals. More preferred aralkoxy radicals are "aralkoxy" radicals having phenyl radicals attached to alkoxy radical as described above. Examples of such radicals include benzyloxy, 1-phenylethoxy, 3-trifluoromethoxybenzyloxy, 3-trifluoromethylbenzyloxy, 3,5-difluorobenyloxy, 3-bromobenzyloxy, 4-propylbenzyloxy, 2-fluoro-3-trifluoromethylbenzyloxy, and 2-phenylethoxy.

The term "aryloxyalkyl" embraces aryloxy radicals, as defined above, attached to an alkyl group. Examples of such radicals include phenoxymethyl.

The term "haloaryloxyalkyl" embraces aryloxyalkyl radicals, as defined above, wherein one to five halo radicals are attached to an aryloxy group.

The term "heteroaroyl" embraces heteroaryl radicals, as defined above, attached to an carbonyl radical as defined above. Examples of such radicals include furoyl and nicotinyl.

The term "heteroaralkanoyl" embraces heteroaralkyl radicals, as defined herein, attached to an carbonyl radical as defined above. Examples of such radicals include, for example, pyridylacetyl and furylbutyryl.

The term "heteroaralkoxy" embraces oxy-containing heteroaralkyl radicals attached through an oxygen atom to other radicals. More preferred heteroaralkoxy radicals are "heteroaralkoxy" radicals having heteroaryl radicals attached to alkoxy radical as described above. The term "heterocyclylalkoxy" embraces oxy-containing heterocyclylalkyl radicals attached through an oxygen atom to other radicals.

The term "haloheteroaryloxyalkyl" embraces heteroaryloxyalkyl radicals, as defined above, wherein one to four halo radicals are attached to an heteroaryloxy group.

The term "heteroarylamino" embraces heteroaryl radicals, as defined above, attached to an amino group. Examples of such radicals include pyridylamino. The term "heterocyclylamino" embraces heterocyclyl radicals, as defined above, attached to an amino group.

The term "heteroaralkylamino" embraces heteroaralkyl radicals, as defined above, attached to an amino group. Examples of such radicals include pyridylmethylamino. The term "heterocyclylalkylamino" embraces heterocyclylalkyl radicals, as defined above, attached to an amino group.

The term "heteroaryloxy" embraces heteroaryl radicals, as defined above, attached to an oxy group. Examples of such radicals include 2-thiophenyloxy, 2-pyrimidyloxy, 2-pyridyloxy, 3-pyridyloxy, and 4-pyridyloxy. The term "heterocyclyloxy" embraces heterocyclyl radicals, as defined above, attached to an oxy group.

The term "heteroaryloxyalkyl" embraces heteroaryloxy radicals, as defined above, attached to an alkyl group. Examples of such radicals include 2-pyridyloxymethyl, 3-pyridyloxyethyl, and 4-pyridyloxymethyl. The term "heterocyclyloxyalkyl" embraces heterocyclyloxy radicals, as defined above, attached to an alkyl group.

The term "arylthio" embraces aryl radicals, as defined above, attached to an sulfur atom. Examples of such radicals include phenylthio.

The term "arylthioalkyl" embraces arylthio radicals, as defined above, attached to an alkyl group. Examples of such radicals include phenylthiomethyl.

The term "alkylthioalkyl" embraces alkylthio radicals, as defined above, attached to an alkyl group. Examples of such radicals include methylthiomethyl. The term "alkoxyalkyl" embraces alkoxy radicals, as defined above, attached to an alkyl group. Examples of such radicals include methoxymethyl.

The term "carbonyl" denotes a carbon radical having two of the four covalent bonds shared with an oxygen atom. The term "carboxy" embraces a hydroxyl radical, as defined above, attached to one of two unshared bonds in a carbonyl group. The term "carboxamido" embraces amino, monoalkylamino, dialkylamino, monocycloalkylamino, alkylcycloalkylamino, dicycloalkylamino, N-alkyl-N-arylamino, arylamino, aralkylamino, nitrogen containing heterocyclyl, heterocyclylamino, N-alkyl-N-heterocyclylamino, heteroarylamino, and heteroaralkylamino radicals, attached to one of two unshared bonds in a carbonyl group. The term "carboxamidoalkyl" embraces carboxamido radicals, as defined above, attached to an alkyl group. The term "carboxyalkyl" embraces a carboxy radical, as defined above, attached to an alkyl group. The term "carboalkoxy" embraces alkoxy radicals, as defined above, attached to one of two unshared bonds in a carbonyl group. The term "carboaralkoxy" embraces aralkoxy radicals, as defined above, attached to one of two unshared bonds in a carbonyl group. The term "monocarboalkoxyalkyl" embraces one carboalkoxy radical, as defined above, attached to an alkyl group. The term "dicarboalkoxyalkyl" embraces two carboalkoxy radicals, as defined above, attached to an alkylene group. The term "monocyanoalkyl" embraces one cyano radical, as defined above, attached to an alkyl group. The term "dicyanoalkylene" embraces two cyano radicals, as defined above, attached to an alkyl group. The term "carboalkoxycyanoalkyl" embraces one cyano radical, as defined above, attached to an carboalkoxyalkyl group.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like. The term "haloalkanoyl" embraces one or more halo radicals, as defined herein, attached to an alkanoyl radical as defined above. Examples of such radicals include, for example, chloroacetyl, trifluoroacetyl, bromopropanoyl, and heptafluorobutanoyl.

The term "phosphono" embraces a pentavalent phosphorus attached with two covalent bonds to an oxygen radical. The term "dialkoxyphosphono" denotes two alkoxy radicals, as defined above, attached to a phosphono radical with two covalent bonds. The term "diaralkoxyphosphono" denotes two aralkoxy radicals, as defined above, attached to a phosphono radical with two covalent bonds. The term "dialkoxyphosphonoalkyl" denotes dialkoxyphosphono radicals, as defined above, attached to an alkyl radical. The term "diaralkoxyphosphonoalkyl" denotes diaralkoxyphosphono radicals, as defined above, attached to an alkyl radical.

The term "amino" denotes a nitrogen atom containing two substituents such as hydrido, hydroxy or alkyl and having one covalent bond available for bonding to a single atom such as carbon. Examples of such amino radicals include, for example, —NH$_2$, —NHCH$_3$, —NHOH, and —NHOCH$_3$. The term "imino" denotes a nitrogen atom containing one substituent such as hydrido, hydroxy or alkyl and having two covalent bonds available for bonding to a single atom such as carbon. Examples of such imino radicals include, for example, =NH, =NCH$_3$, =NOH, and =NOCH$_3$. The term "imino carbonyl" denotes a carbon radical having two of the four covalent bond sites shared with an imino group. Examples of such imino carbonyl radicals include, for example, C=NH, C=NCH$_3$, C=NOH, and C=NOCH$_3$. The term "amidino" embraces a substituted or unsubstituted amino group bonded to one of two available bonds of an iminocarbonyl radical. Examples of such amidino radicals include, for example, NH$_2$—C=NH, NH$_2$—C=NCH$_3$, NH$_2$—C=NOCH$_3$ and CH$_3$NH—C=NOH. The term "guanidino" denotes an amidino group bonded to an amino group as defined above where said amino group can be bonded to a third group. Examples of such guanidino radicals include, for example, NH$_2$—C(NH)—NH—, NH$_2$—C(NCH$_3$)—NH—, NH$_2$—C(NOCH$_3$)—NH—, and CH$_3$NH—C(NOH)—NH—.

The term "sulfonium" denotes a positively charged trivalent sulfur atom where said sulfur is substituted with three carbon based groups such as alkyl, alkenyl, aralkyl, or aryl. The term "dialkyl sulfonium" denotes a sulfonium group where said sulfur is substituted with two alkyl groups. Examples of such dialkylsulfonium radicals include, for example, (CH$_3$)$_2$S$^+$—. The term "dialkyl sulfonium alkyl" denotes a dialkyl sulfonium group where said group is bonded to one bond of an alkylene group as defined above. Examples of such dialkylsulfoniumalkyl radicals include (CH$_3$)$_2$S$^+$—CH$_2$CH$_2$—.

The term "phosphonium" denotes a positively charged tetravalent phosphorus atom where said phosphorus is substituted with four carbon based groups such as alkyl, alkenyl, aralkyl, or aryl. The term "trialkyl phosphonium" denotes a phosphonium group where said phosphorus is substituted with three alkyl groups. Examples of such trialkylphosphonium radicals include, for example, (CH$_3$)$_3$P$^+$—.

Said "alkyl", "alkenyl", "alkynyl", "alkanoyl", "alkylene", "alkenylene", "hydroxyalkyl", "haloalkyl", "haloalkylene", "haloalkenyl", "alkoxy", "alkenyloxy", "alkenyloxyalkyl", "alkoxyalkyl", "aryl", "perhaloaryl", "haloalkoxy", "haloalkoxyalkyl", "haloalkenyloxy", "haloalkenyloxyalkyl", "alkylenedioxy", "haloalkylenedioxy", "heterocyclyl", "heteroaryl", "hydroxyhaloalkyl", "alkylsulfonyl", "haloalkylsulfonyl", "alkylsulfonylalkyl", "haloalkylsulfonylalkyl", "alkylsulfinyl", "alkylsulfinylalkyl", "haloalkylsulfinylalkyl", "aralkyl", "heteroaralkyl", "perhaloaralkyl", "aralkylsulfonyl", "aralkylsulfonylalkyl", "aralkylsulfinyl", "aralkylsulfinylalkyl", "cycloalkyl", "cycloalkylalkanoyl", "cycloalkylalkyl", "cycloalkenyl", "halocycloalkyl", "halocycloalkenyl", "cycloalkylsulfinyl", "cycloalkylsulfinylalkyl", "cycloalkylsulfonyl", "cycloalkylsulfonylalkyl", "cycloalkoxy", "cycloalkoxyalkyl", "cycloalkylalkoxy", "cycloalkenyloxy", "cycloalkenyloxyalkyl", "cycloalkylenedioxy", "halocycloalkoxy", "halocycloalkoxyalkyl", "halocycloalkenyloxy", "halocycloalkenyloxyalkyl", "alkylthio", "haloalkylthio", "alkylsulfinyl", "amino", "oxy", "thio", "alkylamino", "arylamino", "aralkylamino", "arylsulfinyl", "arylsulfinylalkyl", "arylsulfonyl", "arylsulfonylalkyl", "heteroarylsulfinyl", "heteroarylsulfinylalkyl", "heteroarylsulfonyl", "heteroarylsulfonylalkyl", "heteroarylamino", "heteroaralkylamino", "heteroaryloxy", "heteroaryloxylalkyl", "aryloxy", "aroyl", "aralkanoyl", "aralkoxy", "aryloxyalkyl", "haloaryloxyalkyl", "heteroaroyl", "heteroaralkanoyl", "heteroaralkoxy", "heteroaralkoxyalkyl", "arylthio", "arylthioalkyl", "alkoxyalkyl", "acyl", "amidino", "guanidino", "dialkylsulfonium", "trialkylphosphonium", and "dialkylsulfoniumalkyl" groups defined above may optionally have 1 or more non-hydrido substituents such as amidino, guanidino, dialkylsulfonium, trialkylphosphorium, dialkylsulfoniumalkyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroaralkyl, arylalkenyl, heteroarylalkenyl, carboxyalkyl, carboalkoxy, alkoxycarbonyl, carboaralkoxy, carboxamido, carboxamidoalkyl, cyano, carbohaloalkoxy, phosphono, phosphonoalkyl, diaralkoxyphosphono, and diaralkoxyphosphonoalkyl.

The term "spacer" can include a covalent bond and a linear moiety having a backbone of 1 to 7 contiguous atoms. The spacer may have 1 to 7 atoms of a univalent or multi-valent chain. Univalent chains may be constituted by a radical selected from =C(H)—, =C(R$^{2a}$)—, —O—, —S—, —S(O)—, —S(O)$_2$—, —NH—, —N(R$^{2a}$)—, —N=, —CH(OH)—, =C(OH)—, —CH(OR$^{2a}$)—, =C(OR$^{2a}$)—, and —C(O)— wherein R$^{2a}$ is selected from alkyl, alkenyl, alkynyl, aryl, heteroaryl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl. Multi-valent chains may consist of a straight chain of 1 or 2 or 3 or 4 or 5 or 6 or 7 atoms or a straight chain of 1 or 2 or 3 or 4 or 5 or 6 atoms with a side chain. The chain may be constituted of one or more radicals selected from: alkylene, alkenyl, —O—, —O—CH$_2$—, —S—CH$_2$—, —CH$_2$CH$_2$—, ethenyl, —CH=CH(OH)—, —OCH$_2$O—, —O(CH$_2$)$_2$O—, —NHCH$_2$—, —OCH(R$^{2a}$)O—, —O(CH$_2$CHR$^{2a}$)O—, —OCF$_2$O—, —O(CF$_2$)$_2$O—, —S—, —S(O)—, —S(O)$_2$—, —N(H)—, —N(H)O—, —N(R$^{2a}$)O—, —N(R$^{2a}$)—, —C(O)—, —C(O)NH—, —C(O)NR$^{2a}$—, —N=, —OCH$_2$—, —SCH$_2$—, S(O) CH$_2$—, —CH$_2$C(O)—, —CH(OH)—, =C(OH)—, —CH (OR$^2$, =C(OR$^{2a}$)—, S(O)$_2$CH$_2$—, and —NR$^{2a}$CH$_2$— and many other radicals defined above or generally known or ascertained by one of skill-in-the art. Side chains may include substituents such as 1 or more non-hydrido substituents such as amidino, guanidino, dialkylsulfonium, trialkylphosphonium, dialkylsulfoniumalkyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, carboaralkoxy, carboxamido, carboxamidoalkyl, cyano, carbohaloalkoxy, phosphono, phosphonoalkyl, diaralkoxyphosphono, and diaralkoxyphosphonoalkyl.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, 1-isomers, the racemic mixtures thereof and other mixtures thereof, as falling within the scope of the invention. Pharmaceutically acceptable sales of such tautomeric, geometric or stereoisomeric forms are also included within the invention.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

Some of the compounds described herein may contain one or more amide carbonyl groups or combinations thereof alone or as part of a heterocyclic ring system. Such carbonyl groups may exist in part or principally in the "keto" form and in part or principally as one or more "enol" forms of each amide group present. Compounds of the present invention having amidic carbonyl groups are meant to include both "keto" and "enol" tautomeric forms. Said amide carbonyl groups may be both oxo (C=O) and thiono (C=S) in type.

Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

The present invention also comprises a treatment and prophylaxis in anticoagulant therapy for the treatment and prevention of a variety of thrombotic conditions including coronary artery and cerebrovascular disease in a subject, comprising administering to the subject having such disorder a therapeutically-effective amount of a compound of Formula (I):

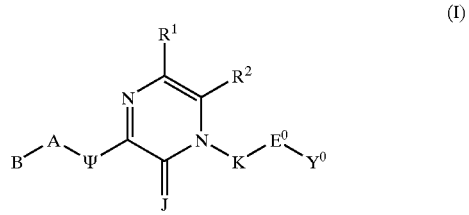

(I)

or a pharmaceutically-acceptable salt thereof.

As a further embodiment, compounds of the present invention of Formula (I) or a pharmaceutically-acceptable salt thereof as defined above, comprise a treatment and prophylaxis of coronary artery disease, cerebrovascular disease and other coagulation cascade related disorders in a subject, comprising administering to the subject having such disorder a therapeutically-effective amount of compounds of formula (I) of the present invention or a pharmaceutically-acceptable salt thereof.

Compounds of the present invention of Formula (I) or a pharmaceutically-acceptable salt thereof can also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prothesis, cardiac prosthesis, and extracorporeal circulation systems.

Compounds of Formula (I) are capable of inhibiting activity of serine proteases related to the coagulation cascade, and thus could be used in the manufacture of a medicament, a method for the prophylactic or therapeutic treatment of diseases mediated by coagulation cascade serine proteases, such as inhibiting the formation of blood platelet aggregates, inhibiting the formation of fibrin, inhibiting thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The compounds also can be used to study the mechanism of action of coagulation cascade serine proteases to enable the design of better inhibitors and development of better assay methods. The compounds of Formula (I) would be also useful in prevention of cerebral vascular accident (CVA) or stroke.

Also included in the family of compounds of Formula (I) are the pharmaceutically-acceptable salts thereof. The term "pharmaceutically-acceptable salt" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula (I) may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula (I) include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula (I) by reacting, for example, the appropriate acid or base with the compound of Formula (I).

The present invention also comprises a pharmaceutical composition comprising a therapeutically-effective amount of a compound of Formulas (I) in association with at least one pharmaceutically-acceptable carrier, adjuvant or diluent. Pharmaceutical compositions of the present invention can comprise the active compounds of Formula (I) in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

The active compounds and composition may, for example, be administered orally, intravascularly, intraperitoneally, subcutaneously, intramuscularly, ocularly, or topically. For treating ocular build up of fibrin, the compounds may be administered intraocularly or topically as well as orally or parenterally.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other silicon containing polymers.

The compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or ployethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphitpathic block copolymers of hydrogels.

For oral administration, the pharmaceutical composition may be in the form of, for example, tablets, capsules (each of which includes sustained release or timed release formulations), pills, powders, granules, elixers, tinctures, suspensions, liquids including syrups, and emulsions. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low.

Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of the present invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

In practicing the methods of the present invention for the treatment and prevention of a variety of thrombotic conditions including coronary artery and cerebrovascular disease, the compounds and pharmaceutical compositions of the present invention are administered alone or in combination with one another, or in combination with other therapeutics or in vivo diagnostic agents. The coagulation cascade inhibitors of the present invention can also be co-administered with suitable anti-platelet agreggation agents, including, but not limited to ticlopidine or clopidrogel, fibrinogen receptor antagonists (e.g. to treat or prevent unstable angina or to prevent reocculsion after angioplasty and restenosis), anticoagulants such as aspirin, warfarin or heparins, thrombolytic agents such as plasminogen activators or streptokinase to achieve synergistic effects in the treatment of various pathologies, lipid lowering agents including antihypercholesterolemics (e.g. HMG CoA reductase inhibitors such as mevastatin, lovastatin, simvastatin, pravastatin, and fluvastatin, HMG CoA synthatase inhibitors, etc.), anti-diabetic drugs, or other cardiovascular agents (loop diuretics, thiazide type diuretics, nitrates, aldosterone antagonistics (i.e., spironolactone and epoxymexlerenone), angiotensin converting enzyme (e.g. ACE) inhibitors, angiotensin II receptor antagonists, beta-blockers, antiarrythmics, anti-hypertension agents, and calcium channel blockers) to treat or prevent atherosclerosis. For example, patients suffering from coronary artery disease, and patients subjected to angioplasty procedures, would benefit from coadministration of fibrinogen receptor antagonists and coagulation cascade inhibitors of the present invention. Also, coagulation cascade inhibitors could enhance the efficiency of tissue plasminogen activator-mediated thrombolytic reperfusion.

Typical doses of coagulation cascade inhibitors of the present invention with other suitable anti-platelet agents, anticoagulation agents, cardiovascular therapeutic agents, or thrombolytic agents may be the same as those doses of coagulation cascade inhibitors administered without coadministration of additional anti-platelet agents, anticoagulation agents, cardiovascular therapeutic agents, or thrombolytic agents, or may be substantially less than those doses of coagulation cascade inhibitors administered without coadministration of additional anti-platelet agents, anticoagulation agents, cardiovascular therapeutic agents, or thrombolytic agents, depending on a patient's therapeutic needs.

The present novel methods preferably employ compounds which selectively inhibit human TF-VIIA over the inhibition of both human Thrombin II and human factor Xa. Preferably, the compounds have a human TF-VIIA $IC_{50}$ of less than 0.5 $\mu$M and also have a selectivity ratio of TF-VIIA inhibition over both human Thrombin II and human factor Xa inhibition of at least 10, and more preferably at least 100. Even more preferably, the compounds have a human TF-VIIA $IC_{50}$ of less than 0.1 $\mu$M and also have a selectivity ratio of TF-VIIA inhibition over both human Thrombin II and human factor Xa inhibition of at least 1000, and most preferably at least 10,000.

All mentioned references are incorporated by reference as if here written.

Although this invention has been described with respect to specific embodiments, the details of these embodiments are not to be construed as limitations. The following examples are provided to illustrate the present invention and are not intended to limit the scope thereof. Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the schemes or the following Examples are also contemplated. Those skilled in the art will readily understand that known variations of the conditions and processes of the following preparative procedures can be used to prepare these compounds.

One skilled in the art may use these generic methods to prepare the following specific examples, which have been or may be properly characterized by $^1$H NMR, mass spectrometry, elemental composition, and similar procedures. These compounds also may be formed in vivo. The following examples contain detailed descriptions of the methods of preparation of compounds of Formula (I). These detailed descriptions fall within the scope and are presented for illustrative purposes only and are not intended as a restriction on the scope of the invention. All parts are by weight and temperatures are Degrees centigrade unless otherwise indicated.

The following general synthetic sequences are useful in making the present invention. Abbreviations used in the schemes and tables include: "AA" represents amino acids, "AcCN" represents acetonitrile, "AcOH" represents acetic acid, "BINAP" represents 2,2'-bis(diphenylphosphino)-1,1'-binaphthyl. "BnOH" represents benzyl alcohol, "BnCHO" represents 2-phenylethanal, "BnSO$_2$Cl" represents benzyl-sulfonyl chloride, "Boc" represents tert-butyloxycarbonyl, "BOP" represents benzotriazol-1-yl-oxy-tris-(dimethylamino), "bu" represents butyl, "dba" represents dibenzylidene-acetone, "DCC" represents 1,3- dicyclohexylcarbodiimide, "DCM" represents dichloromethane or methylene chloride, "DIBAH" or "DIBAL" represents diisobutylaluminum hydride, "DMF" represents dimethylformamide, "DMSO" represents dimethylsulfoxide, "DPPA" represents "diphenylphosphoryl azide", "EDC" represents 1-[3-(dimethylamino)propyl]-3-ethylcarbodiimide hydrochloride, "Ex. No." represents Example Number, "Fmoc" represents 9-fluorenylmethoxycarbonyl, "HOBt" represents "hydroxybenzoltriazole", "LDA" represents lithium diisopropylamide, "MW" represents molecular weight, "NMM" represents N-methylmorpholine, "Ph" represents phenyl or aryl, "PHTH" represents a phthaloyl group, "pnz" represents 4-nitrobenzyloxy-carbonyl, "PTC" represents a phase transfer catalyst, "py" represents pyridine, "RNH$_2$" represents a primary organic amine, "p-TsOH" represents paratoluenesulfonic acid, "TBAF" represents tetrabutylammonium fluoride, "TBTU" represents 2-(1H-benzotriozole-1-yl)-1,1,3,3-tetramethyl uronium tetrafluoroborate, "TEA" represents triethylamine, "TFA" represents trifluoroacetic acid, "THF" represents tetrahydrofuran, "TMS" represents trimethylsilyl, "TMSCN" represents trimethylsilyl cyanide, and "Cbz" or "Z" represents benzyloxycarbonyl.

GENERAL SYNTHETIC PROCEDURES AND SPECIFIC

EXAMPLES

The compounds of the present invention can be synthesized, for example, according to the following procedures and Schemes given below.

The general synthetic approach to substituted pyrazinones is shown in Schemes 1 and 2 below. Treatment of benzyl glycine under Strecker reaction conditions followed by cyclocondensation with oxalyl chloride provides the pyrazinone heterocyclic core with an acetic acid ester at N-1. Heating a solution of the pyrazinone in ethyl acetate in the presence of excess amine results in the nucleophilic displacement of the C-3 chlorine atom by the amine. Stirring the substituted pyrazinone in the presence of lithium hydroxide results in the unmasking of the acid functional group. Alternatively, treatment of the pyrazinone with potassium hydroxide and catalytic palladium on carbon under an atmosphere Scheme 1
General Pyrazinone Synthesis

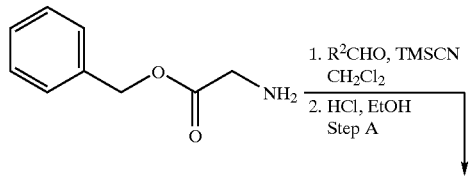

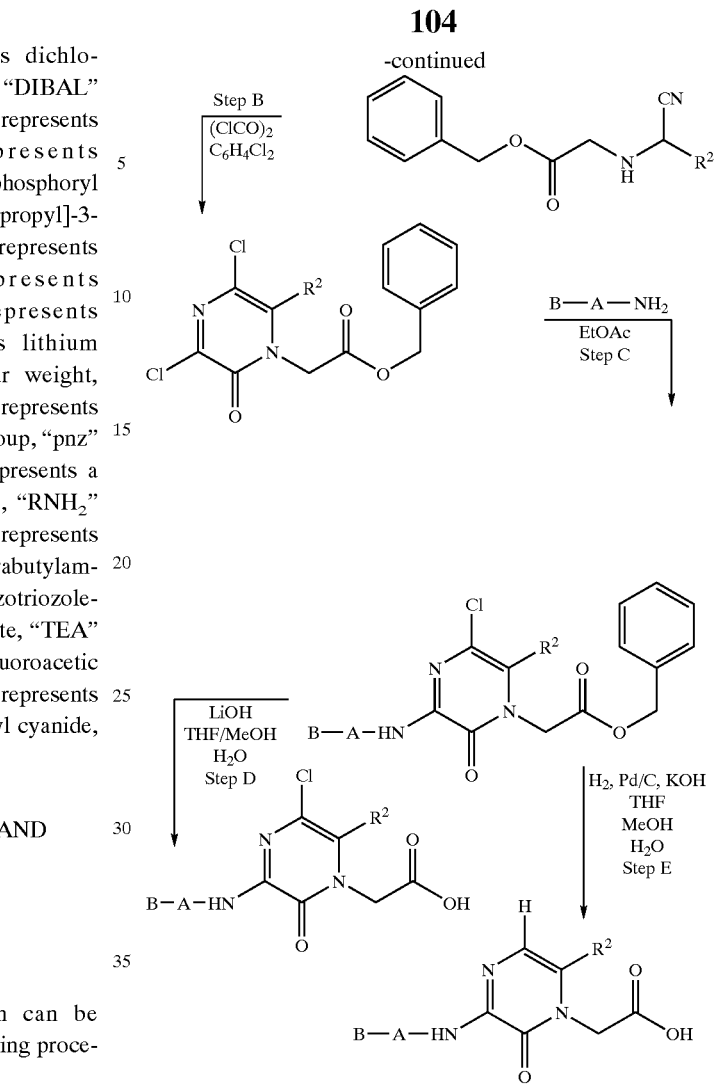

Scheme 2
General Pyrazinone Synthesis (Continued)

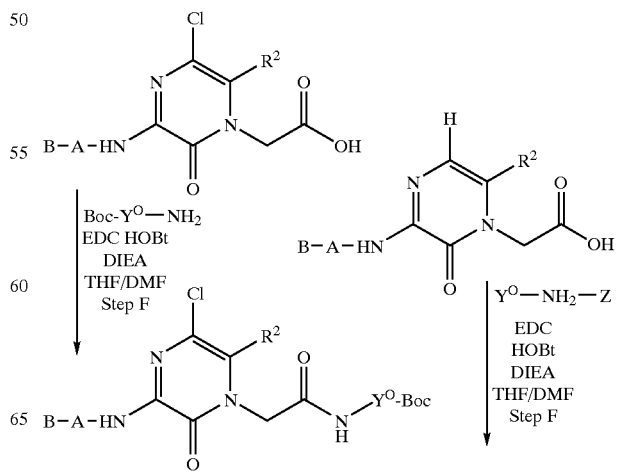

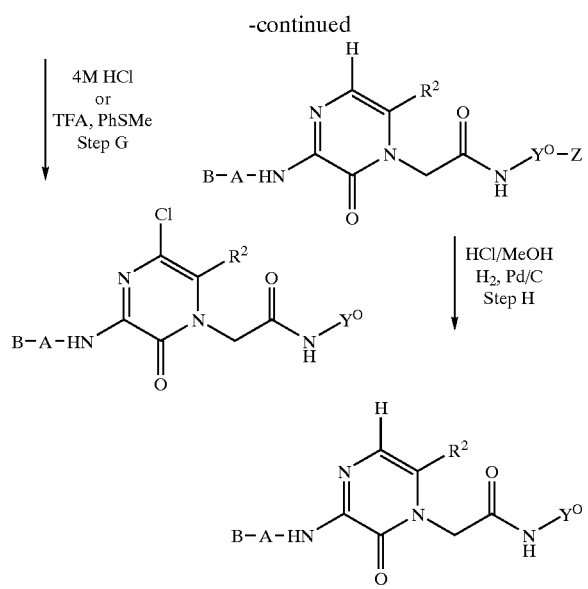

of hydrogen results in the reductive dechlorination of the C-5 chlorine atom as well as the unmasking of the acid functional group. These acids are then coupled under standard peptide coupling conditions with various amines. These amines are typically multi-functional, and are introduced in a protected form. Removal of these protecting groups in any of several ways provides the compounds for screening. These synthetic schemes are exemplified in specific examples disclosed herein.

Example 1

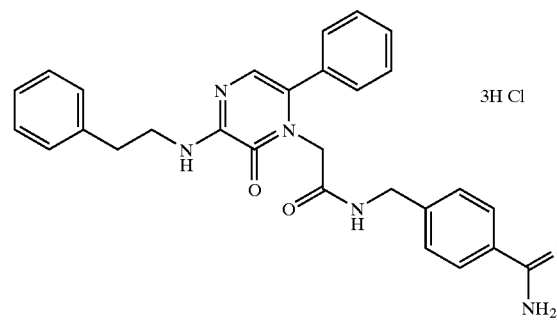

A solution of benzyl glycine hydrochloride (78.00 g, 386.8 mmol) in 1.2 L ethyl acetate was washed with brine and saturated $Na_2CO_3$ (1:1, 3×1 L). The organic solution was dried ($MgSO_4$), filtered, and concentrated. The resulting light yellow oil was placed on the high vacuum for approximately 15 minutes to remove residual solvent. The yellow oil was then diluted with 137.0 mL dichloromethane (2.82 M) and added benzaldehyde (39.30 mL, 386.6 mmol) slowly by syringe at room temperature. The reaction becomes slightly exothermic and turbid. The mixture was then added trimethylsilyl nitrile (51.60 mL, 386.9 mmol) drop wise via syringe over a 10 minute period, upon which a slight exotherm occurs and the reaction becomes clear and golden brown in color. The reaction was stirred for 4 hours at room temperature. The reaction mixture was then concentrated under reduced pressure. The resulting brown oil was diluted with ethyl acetate (500.0 mL), washed with brine (3×150 mL), dried ($MgSO_4$), and concentrated to leave a yellow oil.

The oil was diluted ethyl acetate (80 mL) and added 9.9 M HCl (406.4 mmol) in ethanol (prepared by addition of 28.90 mL acetyl chloride to 41.0 mL cold ethanol). Upon which a white precipitate forms exothermically. The precipitate was collected by filtration, washed with ethyl ether, and dried which gave pure benzyl-N-(1-cyanobenzyl)glycine hydrochloride (EX-1A) in 35% yield: $^1H$ NMR (300 MHz, DMSO) δ 9.13–9.00 (br s, 1H) 7.68–7.60 (m, 2H), 7.55–7.32 (m, 8H) 5.70 (s, 1H), 5.19 (s, 2H), 3.81 (d, J=5.4 Hz, 1H); $^{13}C$ NMR (75 MHz, DMSO) d 168.6, 136.1, 130.7, 129.78, 129.49, 129.17, 128.99, 128.92, 127.10, 67.3, 51.7, 47.1; HRMS (ES) calcd for $C_{17}H_{17}N_2O_2$ 281.1290, found 281.1311.

A suspension of benzyl-N-(1-cyanobenzyl)glycine hydrochloride (EX-1A) (42.90 g, 135.4 mmol) in 135.0 mL dry 1,2-dichlorobenzene (1.0 M) was added to oxalyl chloride (47.50 mL, 544.5 mmol) with stirring at room temperature. The resulting light brown suspension was heated to 100° C. for approximately 18 hours. Upon heating to mixture 100° C., the mixture became homogeneous and dark brown in color with gaseous HCl being evolved. The reaction was allowed to cool to room temperature and the volatiles were removed under reduced pressure. The remaining solution was passed through a silica gel column (1 L hexane flush, followed by 2 L 50% ethyl acetate/hexanes). Concentration of the solution gave a dark brown solid. The crude product was purified by MPLC (2 L hexane flush to 25% ethyl acetate/hexanes) to gave pure 1-Benzyloxycarbonylmethyl-3,5-dichloro-6-phenylpyrazinone (EX-1B) in 60% yield as a yellow solid: $^1H$ NMR (300 MHz, $CDCl_3$) δ 7.58–7.37 (m, 6H), 7.31–7.26 (m, 4H), 5.18 (s, 2H), 4.53 (s, 2H); $^{13}C$ NMR (75 MHz, $CDCl_3$) δ 166.4, 152.4, 146.0, 138.3, 134.9, 131.1, 130.0, 129.8, 129.1, 129.0, 128.8, 1243, 68.2, 49.5; HRMS (ES) calcd for $C_{19}H_{15}Cl_2N_2O_3$ 389.0460, found 389.0475.

A solution of 1-benzyloxycarbonylmethyl-3,5-dichloro-6-phenylpyrazinone (EX-1B) (10.19 g, 26.19 mmol) in 103.0 mL ethyl acetate (0.255M) was added 9.90 mL phenethyl amine in one portion at room temperature. The resulting solution was heated to reflux for 18 hours. The solution was allowed to cool to room temperature which resulted in a thick precipitate forming. The reaction mixture was diluted with ethyl acetate (750.0 mL) and was washed with 0.5 N HCl (1×250 mL), saturated $NaHCO_3$ (1×250 mL) and brine (1×250 mL). The organic solution was dried ($MgSO_4$), filtered and concentrated to give the crude product. Recrystallization from ethyl acetate and hexanes afforded pure 3-(2-phenylethylamino)-5-chloro-6-phenyl-1-benzyloxycarbonylmethylpyrazinone (EX-1C) as light yellow crystals in 96% yield: $^1H$ NMR (300 MHz, $CDCl_3$) δ 7.46–7.28 (m, 15H), 6.39 (br s, 1H), 5.25 (s, 2H), 4.54 (s, 2H), 3.81–3.79 (m, 2H), 3.04–3.00 (m, 2H); $^{13}C$ NMR (75 MHz, $CDCl_3$) δ 167.2, 151.3, 149.2, 138.9, 135.2, 131.9, 130.7, 129.9, 129.3, 129.0, 128.95, 128.86, 128.83, 128.7, 126.9, 123.3, 67.7, 47.9, 42.5, 35.4; HRMS (EI) calcd for $C_{27}H_{25}ClN_3O_3$ 474.1584, found 474.1591.

A suspension of 3-(2-phenylethylamino)-5-chloro-6-phenyl-1-benzyloxycarbonylmethylpyrazinone (EX-1C) (1.26 g, 2.66 mmol) in 27.0 mL tetrahydrofuran and ethanol (1:1, 0.12 M) was added potassium hydroxide (463.1 mg, 8.25 mmol) in 4.0 mL water. The resulting solution was degassed (via high vacuum) three times. The solution was then added 421.1 mg 5% Pd/C in one portion. The resulting mixture was then stirred under an atmosphere of hydrogen overnight. The reaction mixture was filtered through a pad of Celite 545 then concentrated under reduced pressure to half of the original volume. The solution was then diluted with brine and acidified with 20% (w/w) $KHSO_4$ to a pH of 1.

The resulting turbid solution was extracted with ethyl acetate (4×25 mL). The combined organic solutions were washed with brine (1×25 mL), dried (MgSO$_4$), filtered, concentrated to give pure 3-(2-phenethylamino)-6-phenyl-1-methylenecarboxypyrazinone (EX-1D) in 97% yield as a white solid: $^1$H NMR (300 MHz, DMSO) δ 7.49–7.48 (m, 3H), 7.40–7.23 (m, 7H), 6.77 (s, 1H), 4.52 (s, 1H), 4.40 (s, 2H), 3.64–3.57 (m, 2H), 2.93 (t, J=7.4 Hz, 2H); $^{13}$C NMR (75 MHz, DMSO) δ 169.6, 151.8, 150.6, 150.5, 143.2, 140.3, 133.2, 130.2, 129.6, 129.4, 129.3, 129.1, 128.8, 128.7, 127.3, 127.1, 126.8, 122.3, 63.6, 47.5, 42.5, 35.2; HRMS (EI) calcd for C$_{20}$H$_{20}$N$_3$O$_3$ 350.1505, found 350.1502.

p-Cyanobenzaldehyde (38.13 mmoles, 5 g) was stirred in 50 mL of tetrahydrofuran at 0° C. under nitrogen while lithium bis(trimethylsilyl)amide (83.89 mmoles, 84 mL of a 1.0M solution in tetrahydrofuran) was added dropwise over 10 min. After addition the mixture was allowed to warm to room temperature and stirred for 3 hr. Water (50 mL) was then added and stirring continued for 30 min. Then 2.5N sodium hydroxide (763 mmoles, 305 mL) and di-tert-butyl dicarbonate (83.89 mmoles, 18.309 g) were added along with tetrahydrofuran (100 mL) and the mixture was allowed to stir for 3 hr. The layers were then separated. The tetrahydrofuran layer was diluted with ethyl acetate and washed with brine. The water layer was extracted twice with ethyl acetate. The combined organic layers were dried over magnesium sulfate, filtered, the solvent removed in vacuo. The residue was chromatographed medium pressure liquid chromatography with 30% ethyl acetate/hexanes to give 4.03 g of desired 4-(t-butoxycarbonylamidino)benzaldehyde in 43% yield. $^1$H NMR (300 MHz, CDCl$_3$) δ 10.03 (s, 1H), 7.97 (d, 2H) 7.89 (d, 2H), 1.53 (s, 9H).

The 4-(t-butoxycarbonylamidino)benzaldehyde (4.03 mmoles, 1.0 g) was stirred in tetrahydrofuran (20 mL) at room temperature under nitrogen while allylamine (6.05 mmoles, 453 uL) was added dropwise. After addition the mixture was allowed to stir for 6 hr. The mixture was diluted with methanol (20 mL) and cooled to 0° C. Then sodium borohydride (6.04 mmoles, 22.8 mg) added in small amounts and allowed to warm to room temperature. After 2 hr the reaction was quenched with water and extracted with dichloromethane. The organic layer was dried over magnesium sulfate, filtered, and the solvent removed in vacuo. The oily residue solidified on standing. The N-allyl-4-(t-butoxycarbonylamidino)-benzylamine product was used without further purification. $^1$H NMR (300 MHz, CDCl$_3$) δ 7.79 (d, 2H), 7.37 (d, 2H), 5.90–6.10 (m, 1H), 5.19 (dd, 2H), 3.81 (s, 2H), 3.24 (d, 2H), 1.53 (s, 9H)

The N-allyl-4-(t-butoxycarbonylamidino)benzylamine (3.97 mmoles, 1.15 g) and chlorotris(triphenylphosphine)-rhodium(I) (0.21 mmoles, 195 mg) was stirred in acetonitrile/water (84:16, 92 mL) under nitrogen. The mixture was refluxed for 3 hr and allowed to cool to room temperature. Then the mixture was filtered through a pad of celite and the solvent removed in vacuo. The residue was dried on a high vacuum pump to yield an orange glassy product. 4-(t-Butoxycarbonylamidino)benzylamine product was verified by HPLC/MS and used without further purification.

A solution of 3-(2-phenethylamino)-6-phenyl-1-methylenecarboxypyrazinone (EX-1D) (521.1 mg, 1.491 mmol) in 15.0 mL tetrahydrofuran and dimethylformamide (1:1, 0.1 M) was added N,N-diisopropylethylamine (1.30 mL, 7.463 mmol), N-hydroxybenzotriazole (610.5 mg, 4.518 mmol), and 1-[3-(dimethylamino)propyl]-3-ethylcarbodiimide hydrochloride (855.3 mg, 4.461 mmol).

The resulting mixture was allowed to stir for 30 minutes. The reaction mixture was then added 4-(t-butoxycarbonyl-amidino)benzylamine (763.1 mg, 3.061 mmol) prepared above in one portion. The resulting mixture was allowed to stir over night. The reaction mixture was diluted with ethyl acetate (50 mL) and washed with 5% citric acid (1×25 mL), saturated NaHCO$_3$ (1×25 mL), and brine (1×25 mL). The organic solution was dried (MgSO$_4$), filtered and concentrated. The crude reaction was purified by MPLC (75% ethyl acetate/hexanes) to give the product (EX-1E): $^1$H NMR (300 MHz. DMSO) δ 9.06 (br s, 1H), 8.65 (t, J=5.6 Hz, 1H), 7.94 (d, J=8.1 Hz, 2H), 7.47–7.40 (m, 6H), 7.35–7.21 (m, 8H), 6.75 (s, 1H), 4.41 (s, 2H), 4.36–4.34 (m, 2H). 3.63–3.57 (m, 2H), 2.93 (t, J=7.3 Hz, 2H), 1.48 (s, 9H); $^{13}$C NMR (75 MHz, DMSO) δ 167.3, 151.9, 150.7, 143.7, 140.4, 133.8, 133.4, 130.3, 129.4, 129.34, 129.29, 129.15, 129.10, 128.3, 127.6, 126.8, 122.2, 78.5, 48.7, 42.6, 35.2, 28.7; HRMS (EI) calcd for C$_{33}$H$_{37}$N$_6$O$_4$ 581.2876. found 581.2871.

A flask of protected pyrazinone (260.7 mg, 0.449 mmol) was added 5.0 mL of 4 M HCl in dioxane. The resulting solution was allowed to stir overnight (approximately 18 hours). The solution was concentrated and the crude product was triturated from ethyl ether. The resulting white solid was collected by filtration, washed with ethyl ether and dried to give pure product: $^1$H NMR (300 MHz, DMSO) δ 9.57 (br s, 2H), 938 (br s, 2H), 9.06 (br s, 1H), 7.88 (d, J=7.9 Hz, 2H), 7.55–7.52 (m, 3H), 7.42–7.24 (m, 9H), 6.66 (s, 1H), 4.43 (s, 2H), 4.38–4.37 (m, 2H), 3.83 (br s, 2H), 3.03–2.98 (m, 2H); HRMS (EI) calcd for C$_{28}$H$_{29}$N$_6$O$_2$ 481.2352, found 481.2348.

Example 2

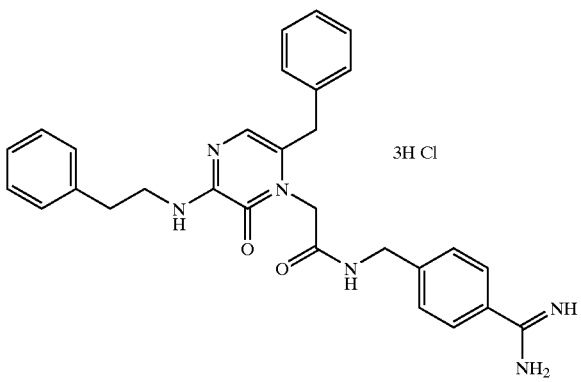

By following the method of Example 1 and substituting phenylacetaldehyde for benzaldehyde, the compound was prepared: $^1$H NMR (400 MHz, DMSO) δ 9.43 (s, 2H), 9.25 (s, 2H), 8.84 (br s, 1H), 7.79 (d, J=8.1 Hz, 2H), 7.40–7.16 (m, 12H), 6.61 (s, 1H), 4.47 (s, 2H), 4.27 (s, 2H), 3.86 (s, 2H), 3.75 (br s, 2H), 2.94–2.90 (m, 2H); HRMS (EI) calcd for C$_{29}$H$_{30}$N$_6$O$_2$ 494.2430, found 494.2438.

Example 3

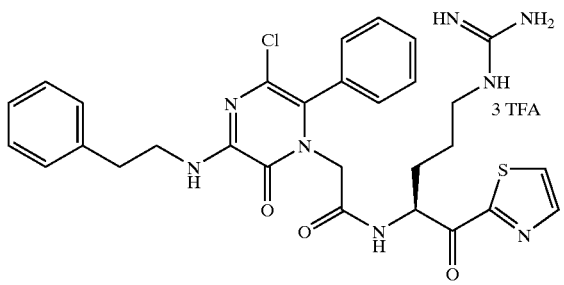

A suspension of 3-(2-phenylethylamino)-5-chloro-6-phenyl-1-benzyloxycarbonylmethylpyrazinone (1.35 g, 2.85 mmol) in 28.0 mL tetrahydrofuran, methanol and water (3:3:1, 0.10 M) was added potassium hydroxide (0.50 g, 8.93 mmol). The mixture was then stirred 3 hours. The reaction mixture was concentrated under reduced pressure to half of the original volume. The solution was then diluted with brine and acidified with 20% (w/w) $KHSO_4$ to a pH of 1. The resulting turbid solution was extracted with ethyl acetate (4×25 mL). The combined organic solutions were washed with brine (1×25 mL), dried ($MgSO_4$), filtered, concentrated to give pure EX-3A (3-(2-phenethylamino)-5-chloro-6-phenyl-1-methylenecarboxypyrazinone) in 88% yield as a white solid: $^1$H NMR (300 MHz, DMSO) δ 13.15 (br s, 1H), 7.84 (br s, 1H), 7.51–7.50 (br m, 3H), 7.33–7.24 (m, 7H), 4.24 (s, 2H), 3.58 (br s, 2H), 2.94 (br s, 2H); $^{13}$C NMR (75 MHz, DMSO) δ 169.2, 151.0, 149.6, 140.1, 132.4, 131.1, 130.2, 129.6, 129.3, 129.1, 126.9, 125.4, 123.4, 48.1, 42.8, 34.8; HRMS (EI) calcd for $C_{20}H_{19}ClN_3O_3$ 384.1115, found 384.1118.

A solution of (S)-N-[[[4-amino-5-oxo-5-(thiazolyl)pentyl]amino]iminomethyl]-4-methoxy-2,3,6-trimethylbenzenesulfonamide dihydrochloride (1.664 g, 3.161 mmol) in 29.0 mL tetrahydrofuran and dimethylformamide (1:1, 0.10 M) was added N,N-diisopropylethylamine (5.00 mL, 28.70 mmol). The resulting mixture was allowed to stir for 10 minutes at room temperature. The solution was then added 3-(2-Phenylethylamino)-5-chloro-6-phenyl-1-methylenecarboxypyrazinone (1.104 g, 2.877 mmol), N-hydroxybenzotriazole (466.8 mg, 3.454 mmol), and 1-[3-(dimethylamino)propyl]-3-ethylcarbodiimide hydrochloride (673.1 mg, 3.511 mmol). After the addition was complete the solution was allowed to stir over night. The reaction mixture was diluted with ethyl acetate (50 mL). The organic solution was washed with 5% citric acid (1×25 mL), saturated $NaHCO_3$ (1×25 mL), and brine (1×25 mL). The organic solution was dried ($MgSO_4$), filtered and concentrated. The crude reaction mixture was purified by MPLC (75% ethyl acetate/hexanes) to give pure product EX-3B: $^1$H NMR (300 MHz, $CDCl_3$) δ 8.04 (d, J=3.0 Hz, 1H), 7.75 (d, J=2.8 Hz, 1H), 7.57 (br s, 1H), 7.42–7.21 (m, 11H), 6.54 (s, 2H), 6.31 (s, 2H), 5.63 (br s, 1H), 4.60 (d, J=1H), 1H), 4.21 (d, J=16.5 Hz, 1H), 3.84 (s, 3H), 3.77–3.66 (m, 2H), 3.17 (br s, 1H), 2.96 (d, J=7.2 Hz, 2H), 2.68 (s, 3H), 2.60 (s, 3H), 2.14 (s, 3H), 1.79–1.66 (m, 3H); HRMS (EI) calcd for $C_{39}H_{44}ClN_8O_6S_2$ 819.2514, found 819.2512.

A solution of material EX-3B (928.1 mg, 1.133 mmol) in 113 mL trifluoroacetic acid (0.1 M) was added to thioanisole (0.400 mL, 3.407 mmol) at room temperature with stirring. The resulting mixture was allowed to stir 6 hours. The reaction mixture was concentrated under reduced pressure. The crude product was purified by trituration from ethyl ether. A yellow powder was collected by filtration, washed with ethyl ether to give the pure product: $^1$H NMR (300 MHz, DMF) δ 8.76 (d, J=7.2 Hz, 1H), 8.51–8.50 (m, 1H), 8.42–8.41 (m, 1H), 8.17 (br s, 1H), 7.92–7.45 (m, 10H), 5.74 (br s, 1H), 4.67–4.65 (m, 2H), 3.89–3.87 (m, 2H), 3.52 (br s, 2H), 3.23–3.20 (m, 2H), 2.73 (s, 2H), 2.19 (br s, 1H), 1.88 (br s, 3H); HRMS (EI) calcd for $C_{29}H_{32}ClN_8O_3S$ 607.2007, found 607.2000.

Example 4

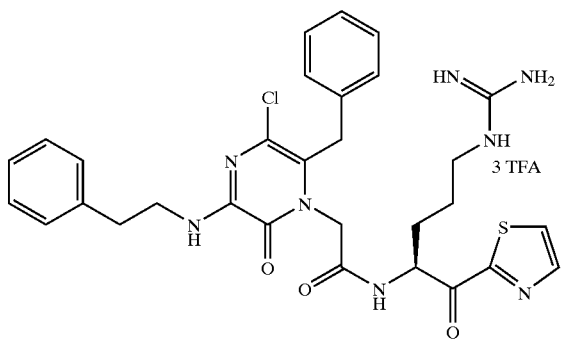

By following the method of Example 3 and substituting 3-(2-phenethylamino)-5-chloro-6-benzyl-1-methylenecarboxypyrazinone for 3-(2-phenethylamino)-5-chloro-6-phenyl-1-methylenecarboxypyrazinone, the title compound was prepared: HRMS (EI) calcd for $C_{30}H_{34}ClN_8O_3S$ 621.2163, found 621.2171.

Example 5

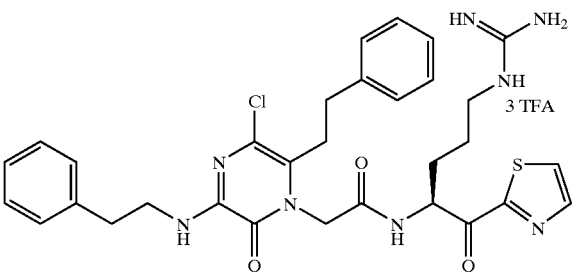

By following the method of Example 3 and substituting 3-(2-phenethylamino)-5-chloro-6-(2-phenylethyl)-1-methylenecarboxypyrazinone for 3-(2-phenethylamino)-5-chloro-6-phenyl-1-methylenecarboxypyrazinone, the title compound was prepared: HRMS (EI) calcd for $C_{31}H_{36}ClN_8O_3S$ 635.2320, found 635.2330.

Example 6

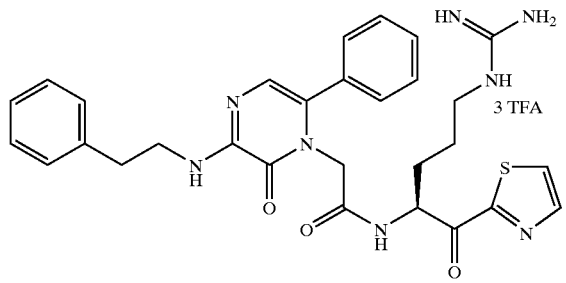

By following the method of Example 3 and substituting 3-(2-phenethylamino)-6-phenyl-1-methylenecarboxypyrazinone for 3-(2-phenethylamino)-5-chloro-6-phenyl-1-methylenecarboxypyrazinone, the title compound was prepared: HRMS (EI) calcd for $C_{29}H_{33}N_6O_3S$ 573.2396, found 573.2399.

Example 7

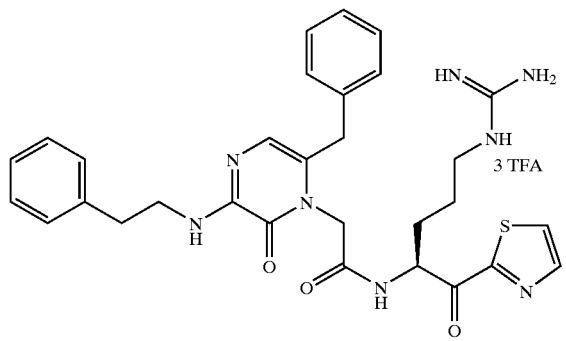

By following the method of Example 3 and substituting 3-(2-phenethylamino)-6-benzyl-1-methylenecarboxypyrazinone for 3-(2-phenethylamino)-5-chloro-6-phenyl-1-methylenecarboxypyrazinone, the title compound was prepared: HRMS (EI) calcd for $C_{30}H_{35}N_8O_3S$ 587.2553, found 587.2564

Example 8

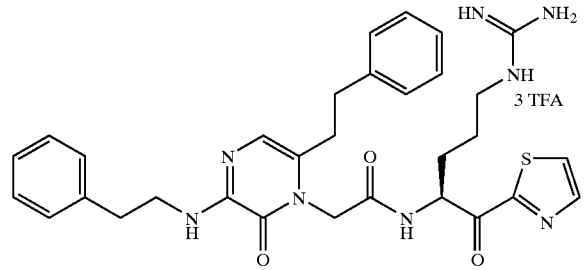

By following the method of Example 3 and substituting 3-(2-phenethylamino)-6-(2-phenylethyl)-1-methylenecarboxypyrazinone for 3-(2-phenethylamino)-5-chloro-6-phenyl-1-methylenecarboxypyrazinone, the title compound was prepared: HRMS (EI) calcd for $C_{31}H_{37}N_8O_3S$ 601.2709, found 601.2714.

Example 9

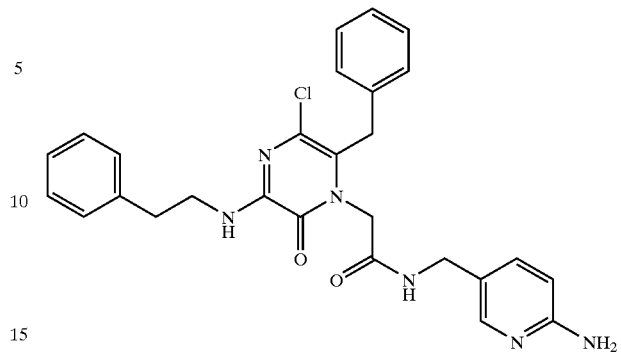

A solution of 2-amino-5-aminomethylpyridine in 1.60 mL tetrahydrofuran (0.13 M) was added to N,N-diisopropylethylamine (0.145 mL, 0.832 mmol). The resulting mixture was allowed to stir for 10 minutes at room temperature. The solution was then added to 3-(2-Phenylethylamino)-6-benzyl-5-chloro-1-methylenecarboxypyrazinone (81.6 mg, 0.2051 mmol), N-hydroxybenzotriazole (38.1 mg, 0.2819 mmol), and 1-[3-(dimethylamino)propyl]-3-ethylcarbodiimide hydrochloride (49.6 mg, 3.511 mmol). The reaction mixture was then allowed to stir over night. The reaction mixture was diluted with ethyl acetate (50 mL). The organic solution was washed with 5% citric acid (1×25 mL), saturated NaHCO$_3$ (1×25 mL), and brine (1×25 mL). The organic solution was dried (MgSO$_4$), filtered and concentrated. The crude reaction mixture was purified by MPLC (ethyl acetate) to give pure product: $^1$H NMR (300 MHz, DMSO) δ 8.50 (br s, 1H), 7.83 (s, 1H), 7.68 (br s, 1H), 7.34–7.19 (m, 13H), 6.4–6.43 (m, 1H), 5.90 (br s, 1H), 4.42 (s, 2H), 4.09 (br s, 2H), 3.98 (br s, 2H), 3.56 (br s, 3H), 2.94 (br s, 3H); HRMS (EI) calcd for $C_{27}H_{28}ClN_6O_2$ 503.1962, found 503.1968.

Example 10

3-(2-Phenylethylamino)-5-chloro-6-phenethyl-1-(2-amino-5-methylcarboxamidomethylpyridinyl)pyrazinone

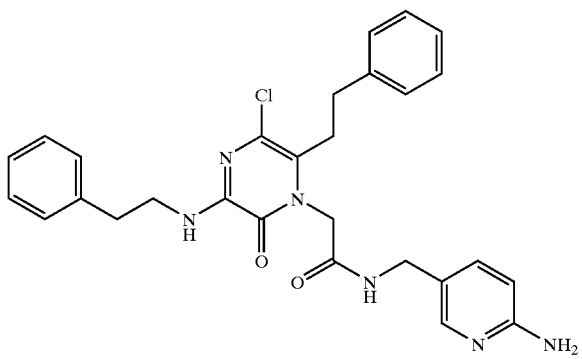

By following the method of Example 9 and substituting 3-(2-phenethylamino)-5-chloro-6-(2-phenylethyl)-1-methylenecarboxypyrazinone for 3-(2-phenethylamino)-5-chloro-6-benzyl-1-methylenecarboxypyrazinone, the title compound was prepared: HRMS (EI) calcd for $C_{28}H_{30}N_6O_2$ 517.2119, found 517.2127.

Example 11

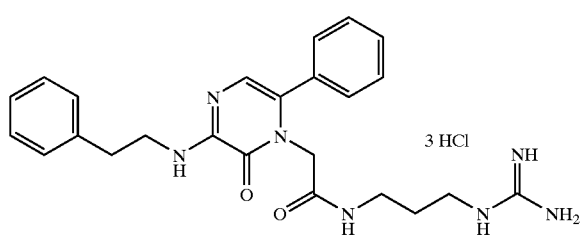

A solution of 3-(2-phenethylamino)-6-phenyl-1-methylenecarboxy-pyrazinone (217.6 mg, 0.6228 mmol) in 6.3 mL tetrahydrofuran and dimethylformamide (1:1, 0.1 M) was added N,N-diisopropylethylamine (1.00 mL, 5.741 mmol), N-hydroxybenzotriazole (171.1 mg, 1.266 mmol), and 1-[3-(dimethylamino)propyl]-3-ethylcarbodiimide hydrochloride (240.0 mg, 1.252 mmol). The resulting mixture was allowed to stir for 30 minutes. The reaction mixture was then added to the 3-(di-Boc-guanidino)propanamine (1.30 mg, 3.684 mmol) in one portion. The resulting mixture was allowed to stir over night. The reaction mixture was diluted with ethyl acetate (50 mL) and washed with 5% citric acid (1×25 mL), saturated NaHCO$_3$ (1×25 mL), and brine (1×25 mL). The organic solution was dried (MgSO$_4$), filtered and concentrated. The crude reaction was purified by MPLC (75% ethyl acetate/hexanes) to give the product EX-11A: $^1$H NMR (300 MHz, DMSO) δ 11.42 (s, 1H), 8.46 (t, J=6.3 Hz, 1H), 7.92 (t, J=6.0 Hz, 1H), 7.46–7.41 (m, 5H), 7.37–7.23 (m, 5H), 6.86 (s, 1H), 6.24 (br s, 1H), 4.49 (s, 2H), 3.79–3.72 (m, 2H), 3.48–3.42 (m, 2H), 3.31–3.25 (m, 2H), 3.00 (t, J=7.1 Hz, 2H), 1.53 (s, 9H), 1.40 (s, 9H); HRMS (EI) calcd for C$_{34}$H$_{45}$N$_7$O$_6$ 648.3510, found 648.3498.

A flask of protected guanidine EX-11A (260.7 mg, 0.449 mmol) was added to 5.0 mL of 4 M HCl in dioxane. The resulting solution was allowed to stir for 4 hours. The solution was concentrated and the crude product was triturated from ethyl ether. The resulting white solid was collected by filtration, washed with ethyl ether and dried to give pure product: $^1$H NMR (300 MHz, DMSO) δ 9.65 (br s, 1H), 8.48 (t, J=5.1 Hz, 1H), 7.96 (t, J=5.4 Hz, 1H), 7.60–7.22 (m, 13H), 6.66 (s, 1H), 4.32 (s, 2H), 3.82 (br s, 2H), 3.13–3.09 (m, 2H), 3.03–2.98 (m, 2H), 1.59–1.54 (m, 2H); HRMS (EI) calcd for C$_{24}$H$_{29}$N$_7$O$_2$ 448.2461, found 448.2425.

Example 12

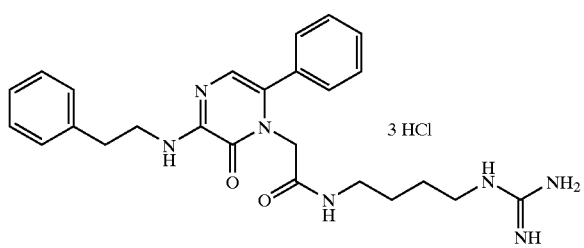

By following the method of Example 11 and using the appropriate butanamine, the title compound was prepared: HRMS (EI) calcd for C$_{25}$H$_{31}$N$_7$O$_2$ 462.2617, found 462.2575.

Example 13

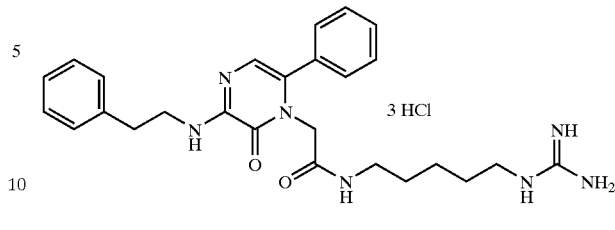

By following the method of Example 11 and using the appropriate pentanamine, the title compound was prepared: HRMS (EI) calcd for C$_{26}$H$_{33}$N$_7$O$_2$ 476.2774, found 476.2783.

Example 14

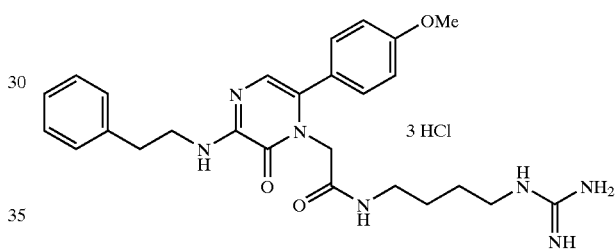

By following the method of Example 11 and using the appropriate butanamine with 3-(2-phenethylamino)-6-(4-methoxyphenyl)-1-methylenecarboxypyrazinone, title compound was prepared: HRMS (EI) calcd for C$_{26}$H$_{34}$N$_7$O$_3$ 492.2723, found 492.2693.

Example 15

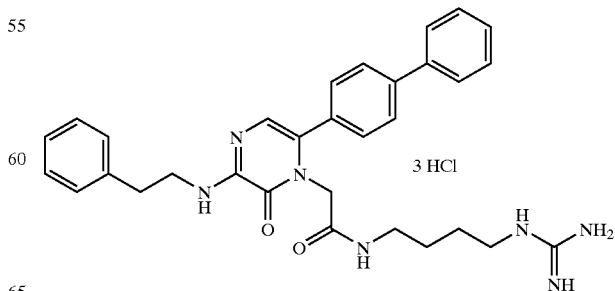

By following the method of Example 11 and using the appropriate butanamine with 3-(2-phenethylamino)-6-(4-biphenyl)-1-methylenecarboxypyrazinone, the title compound was prepared: HRMS (EI) calcd for $C_{31}H_{36}N_7O_2$ 538.2930, found 538.2918.

Example 16

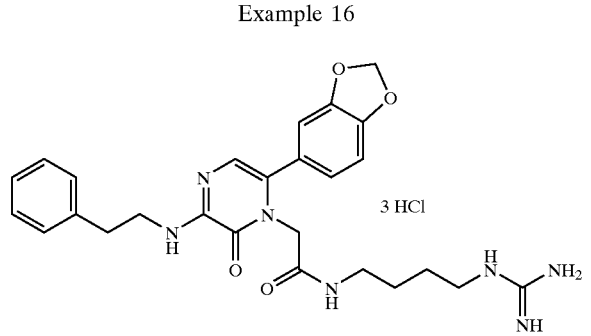

By following the method of Example 11 and using the appropriate butanamine with 3-(2-phenethylamino)-6-(3,4-methylenedioxyphenyl)-1-methylenecarboxypyrazinone, the title compound was prepared: HRMS (EI) calcd for $C_{26}H_{32}N_7O_4$ 506.2516, found 506.2506.

Example 17

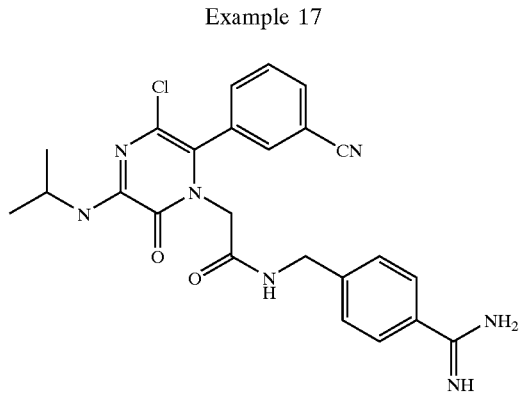

Using the procedures of Schemes 1 and 2 and Example 1, 2-{5-chloro-6-(3-bromophenyl)-3 [(methylethyl)amino]-2-oxohydropyrazinyl}acetic acid was prepared.

A solution of 2-{5-chloro-6-(3-bromophenyl)-3-[(methylethyl)amino]-2-oxohydropyrazinyl}acetic acid (7.4 g, 18.47 mmol) and copper (I) cyanide (1.75 g, 19.55 mmol) in 75.0 mL dimethylsulfoxide was heated at 150° C. for 20 hours. The flask was then cooled and the contents were poured into a solution of 500 mL water and 100 mL 1M HCl. The mixture was then extracted with ethyl acetate (2×1 L). The ethyl acetate layers were separated, combined, dried over magnesium sulfate, filtered, and stripped of solvent under reduced pressure. Purification by HPLC (25% ethyl acetate in hexanes) provided 2-{5-chloro-6-(3-cyanophenyl)-3-[(methylethyl)amino]-2-oxohydropyrazinyl}acetic acid (EX-17A) of adequate purity: $^1$H NMR (400 MHz, CDCl$_3$) d 7.8–7.4 (br, 4H), 4.4 (br, 2H), 2.2 (br, 1H), 1.3 (br d, 6H); MS (ES) calcd for $C_{15}H_{15}ClN_4O_3$ 346, found 347 (M+H).

2-{5-chloro-6-(3-cyanophenyl)-3-[(methylethyl)amino]-2-oxohydropyrazinyl}acetic acid (EX-17A) was converted to the product as described in Example 1. Mass spectral analysis gave an m/z+1 of 478.

Example 18

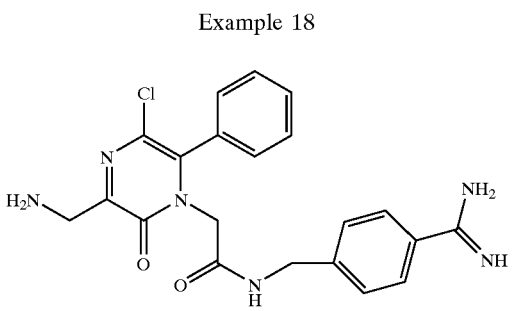

A solution of 3.90 g (10 mmol) of EX-1B in 50 mL of $CH_3NO_2$ was treated with 4.5 mL of 1,8-diazabicyclo[5.4.0]undec-7-ene (DBU). After 30 minutes, the reaction was poured into 300 mL of ethyl acetate and washed with 2×25 mL 1 N HCl (aq). The excess organic solvent was removed under reduced pressure. The resulting oil was treated with 25 mL $H_2O$ and 25 mL $CH_3OH$. The solution was treated with 2.8 g of KOH. After 60 minutes, the reaction was diluted with 300 mL of acetonitrile. The resulting solid was washed with 100 mL of acetonitrile. The solid was dissolved in 50 mL 1N HCl (aq) and extracted with 2×100 mL $CH_2Cl_2$. The organic layer was dried with $MgSO_4$, and the excess solvent removed under reduced pressure. The resulting solid was washed with diethyl ether and dried in ambient conditions to give 2.1 g (6.4 mmol; 64% yield) of desired product (EX-18A). LC/MS showed a single peak at 254 nm and a M+Na at 346. $^1$H-NMR (dmso-d$_6$): 4.4 ppm (2H, s); 5.6 ppm (2H, s); 7.3–7.5 ppm (5H, m)

The product was obtained using standard coupling conditions and deprotection methods under reducing conditions of Example 1 to give the desired product after purification by HPLC. LC/MS showed a single peak at 254 nm and a M+H at 425. $^1$H-NMR (dmso-d$_6$): 4.2 ppm (2H, s); 4.4 ppm (2H, m); 4.6 ppm (2H, m); 7.4 ppm (5H, m) 7.6–7.8 ppm (4H, m); 8.4 ppm (2H, bs); 8.7 (1H,m); 9.1 ppm (2H, bs); 9.3 ppm (2H,bs).

Using the procedures of Scheme 1, Scheme 2, and Example 1 through Example 18 with suitable reagents, starting materials, intermediates, and additional pyrazinones of the present invention were prepared by one skilled in the art using, similar methods and these pryazinones summarized in Table 1.

TABLE 1

Additional Substituted Pyrazinones Prepared by Procedures of
Scheme 1, Scheme 2, and Examples 1 through 18

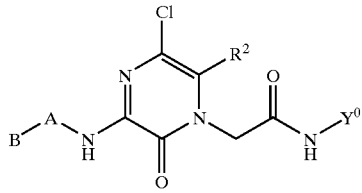

General Structure

| Ex. No. | R² | B—A | Y⁰ | MW (m/z + 1) |
|---|---|---|---|---|
| 19 | phenyl | 2-(4-pyridyl)ethyl | 4-amidinobenzyl | 516.3 |
| 20 | benzyl | 2-phenylethyl | 4-amidinobenzyl | 528.9 |
| 21 | biphenyl | 2-(3-pyridyl)ethyl | 4-amidinobenzyl | 591.9 |
| 22 | biphenyl | 2-(4-chlorophenyl)ethyl | 4-amidinobenzyl | 625.5 |
| 23 | 3-chlorophenyl | benzyl | 4-amidinobenzyl | 535.3 |
| 24 | biphenyl | 2-phenylethyl | 4-amidinobenzyl | 591.5 |

Example 25

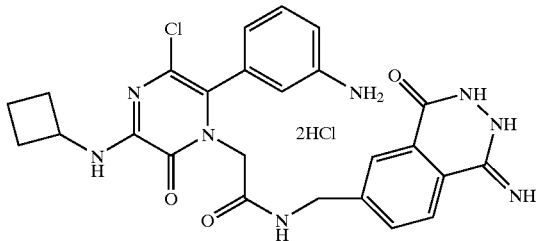

To a solution of 2-iodo-5-methyl benzoic acid (10.0 g, 0.038 mol) in toluene (200 mL) was added trimethylorthoacetate (25 mL) at room temperature. The reaction mixture was refluxed for 12 hours. The reaction mixture was cooled to room temperature and diluted with saturated sodium bicarbonate and ethyl acetate. The layers were separated and the organic layer washed with brine. The organic layer was dried (MgSO$_4$) and solvent removed to give 1035 g of methyl 2-iodo-5-methylbenzoate (EX-25A) as a yellow oil with an m/z+1=277.

A degasssed mixture of ester EX-25A (10.35 g, 0.037 mol)), Pd(dba)$_3$ (0.017 g, 0.018 mmol)), dppf (0.025 g, 0.045 mmol)) and Zn(CN)$_2$ (2.6 g, 0.02 mol) in DMF (100 mL) was heated to 120° C. for 2 hours. The reaction mixture was poured into water and ethyl acetate. The organic layer was washed with water (2x) and brine (1x). The organic layer was collected, dried (MgSO$_4$) and the solvent removed in vacuo to give 5.28 g methyl 2-cyano-5-methylbenzoate (EX-25B) as a brownish oil with m/z+1=176

To a solution of EX-25B (5.28 g, 0.03 mol) in CCl$_4$ (100 mL) was added NBS (5.37 g, 0.03 mol) and benzoyl peroxide (0.36 g, 0.0015 mol) at room temperature. The reaction mixture was heated to reflux for 15 hours. The reaction was cooled and the precipitate filtered away. The organic filtrate was diluted with ether and washed with saturated sodium bicarbonate. The organic layer was dried (MgSO$_4$) and the solvent removed in vacuo to give an oil, which after chromatography (silica, hexanes to 30% ether/hexanes) gave 1.57 g methyl 2-cyano-5-bromomethylbenzoate (EX-25C) as a tan solid with m/z+1=255.

To a solution of di-tert-butyl iminodicarboxylate (1.48 g, 7.5 mmol) in THF at 0° C. was added NaH (0.31 e, 7.8 mmol). After stirring at room temperature for 30 minutes, EX-25C (1.57 g, 6.0 mmol) was added as a solution in THF via canula. The reaction was complete after 2.5 hours at room temperature. The reaction was quenched by addition of water and ether. The layers were separated and the organic layer washed with brine (2x), dried (MgSO$_4$) and the solvent removed in vacuo to give 2.36 g methyl 2-cyano-5-(N,N-bis-Bocaminomethylbenzoate (EX-25D) as a yellowish solid with m/z+1=391.

To a solution of EX-25D (0.20 g, 0.5 mmol) in anhydrous methanol (10 mL) was added anhydrous hydrazine (1 mL, 32 mmol)) at room temperature. The reaction was heated to 70° C. overnight. The solvent was removed in vacuo to give a solid, which was suspended in ether and filtered to give 0.11 g of the product EX-25E as a white solid with an m/z+1=291.

To a solution of EX-25E (0.22 g, 0.78 mmol) in dichloromethane (5 mL) at room temperature was added trifluoroacetic acid (5 mL). After 30 min, the solvent was removed in vacuo to give a clear residue, which upon drying on high vacuum became a white solid EX-25F (0.39 g) with m/z+1=191.

To a solution of 2-{5-chloro-6-(3-aminophenyl)-3-cyclobutylamino-2-oxohydropyrazinyl}acetic acid (0.93 g, 2.6 mmol) in DMF (20 mL) was added EDC (0.64 g, 3.3 mmol) and HOBt (0.44 g, 3.2 mmol) at room temperature. After 30 min, the amine EX-25F in a solution of DMF and triethylamine (1.76 mL, 0.01 mol) was added to the acid. The reaction mixture was stirred for 1 hour and then poured into NaHCO$_3$ (aq) and ethyl acetate. The layers were separated and the aqueous layer extracted with ethyl acetate (2x) The organic layer was washed with brine (1x), dried (MgSO$_4$), and the solvent removed in vacuo to give a brown oil, which after chromatography (silica, dicholoromethane to 10% methanol/dichloromethane) gave the product EX-25G (0.29 g) with m/z+1=521.

To a suspension of EX-25G (0.29 g, 5.6 mmol) in ether (5 mL) was added 25 mL of 2.0 M HCl in ether. The reaction was stirred for 30 min to give a fine precipitate which was filtered and dried to give the product (0.37 g) with m/z+1=

521. Analysis $C_{25}H_{25}Cl_2N_8O_3 + 1.8$ HCl + 2.15$H_2O$ gave C, 47.78%; H, 5.22%; N, 16.29%; O, 12.59%; Cl, 15.43%.

Example 26

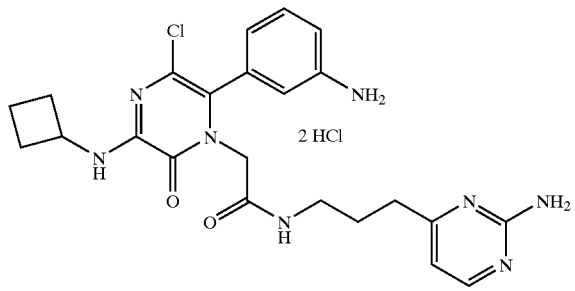

To a solution of 2-Amino-4-methylpyrimidine (1.0 g, 9.0 mmol) in THF (100 mL) at 0° C. was added TMEDA (4.15 mL, 27.0 mmol) and n-butyl lithium (17.2 mL; 27.0 mmol). After stirring at 0° C. for 30 min, (2-bromoethoxy)-tert-butyldimethylsilane (2.16 mL, 10 mmol) was added in a solution of THF (20 mL) dropwise via canula. The reaction was allowed to warm to room temperature overnight. The reaction was diluted with water and ether. The aqueous layer was extracted (2×) with ether. The organic layer was washed with brine, dried (MgSO$_4$), and solvent removed in vacuo to give a brown oil, which after chromatography (silica, dichloromethane to 10% methanol/dicholoromethane) gave EX-26A (1.26 g) with m/z+1=268.

To a solution of EX-26A (4.36 g, 16.0 mmol) in dichloromethane (100 mL) was added triethylamine (3.4 mL, 24 mmol), di-tert-butyl dicarbonate (4.53 g, 24 mmol) and DMAP (0.2 g, 0.16 mmol). After stirring at room temperature for 24 hours the reaction was poured into aqueous sodium bicarbonate and ether. The layers were separated and the aqueous layer extracted (2×) with ether. The organic layer was washed with brine, and the solvent removed in vacuo to give a red oil (4.4 g). The oil was purified by chromatography (silica, 60% ethyl acetate/hexanes) to give a yellow oil EX-26B (2.77 g) with m/z+1=468.

To a solution of EX-26B (2.77 g, 6.0 mmol) in THF (100 mL) was added TBAF (7.1 mL, 1 M in THF) dropwise. After 4 hours at room temperature the reaction was complete. The reaction mixture was poured into ethyl acetate and brine. The aqueous layer was extracted 2× with ethyl acetate. The organic layer was dried (MgSO$_4$) and the solvent removed to give a yellow oil, which after chromatography (silica, 70% ethyl acetate/hexanes to 100% ethyl acetate) gave 1.51 g of the alcohol 2-(bis-Boc-amino)$_4$-(3-hydroxypropyl) pyrimidine (EX-26C) as a yellow oil with an m/z+1=354.

To a solution of EX-26C (1.38 g, 4.0 mmol) in toluene (20 mL) was added triethylamine (0.54 mL, 4.0 mmol) and methanesulfonyl chloride (0.30 mL, 4.0 mmol). After 10 min, no starting material was observed by TLC. The reaction mixture was poured into dichloromethane and water. The layers were separated and the organic layer was washed with brine and dried (Na$_2$SO$_4$). The solvent was removed to give a yellow oil EX-26D which was used without further purification. To the crude mesylate EX-26D (1.73 g, 4.0 mmol) in DMF (10 mL) was added NaN$_3$ (2.6 g, 40 mmol) and water (1 mL). The reaction mixture was stirred at room temperature for 18 hours. The reaction was diluted with ether and water. The layers were separated and the organic layer washed with brine and dried (Na$_2$SO$_4$). The solvent was removed to give an oil, which after chromatography (silica, 60% ethyl acetate/hexanes) gave the azide EX-26E (0.91 g) with a m/z+1=379.

To a solution of 2-(bis-Boc-amino)-4-(3-azidopropyl) pyrimidine (EX-26E) (0.39 g, 1.0 mmol) in ethanol at room temperature was added 10% Pd/C and a hydrogen balloon. After stirring at room temperature for 3 hours the reaction was complete by TLC. The reaction mixture was filtered through a pad of celite and washed with ethanol. The solvent was removed in vacuo to give an oil (035 g) which was a mixture of Boc derivatives EX-26F. To a solution of EX-26F (0.32 g) in dichloromethane (7 mL) was added trifluoroacetic acid (3 mL) dropwise. After 30 min, the solvent was removed in vacuo to give 0.34 g of the free amine 2-amino-4-(3-aminopropyl)pyrimidine (EX-26G) as an oil with an m/z+1=353.

To a solution of anilino-acid 2-{5-chloro-6-(3-aminophenyl)-3-cyclobutylamino-2-oxohydropyrazinyl}acetic acid (1.46 g, 4.2 mmol) in DMF (30 mL) was added HOBt (0.91 g, 6.7 mmol) and EDAC (1.29 g, 6.7 mmol) at room temperature. After stirring for 30 min, EX-26G (1.59 g, 4.2 mmol) in DMF (8 mL) and triethylamine (3.5 mL, 25.2 mmol) was added. After 30 min, the reaction was diluted with aqueous sodium bicarbonate and ethyl acetate. The layers were separated and aqueous layer extracted (2×) with ethyl acetate. The organic layer was washed with brine and dried (MgSO$_4$). The solvent was removed in vacuo to give an oil, which after chromatography (dichloromethane to 15% methanol dichloromethane) gave the product EX-26H (1.20 g) as a yellow foam with an m/z+1=483.

To a solution of EX-26H (0.32 g, 0.67 mmol) in 5 mL of ether was added 20 mL of 3.0 M HCl in ether at room temperature. The reaction mixture was stirred at room temperature for 20 minutes to give a precipitate which was filtered to give a yellow solid (0.34 g) of the di-hydrochloride salt. The solid was purified by RP-HPLC to give (0.22 g) with an m/z+1=483.

Example 27

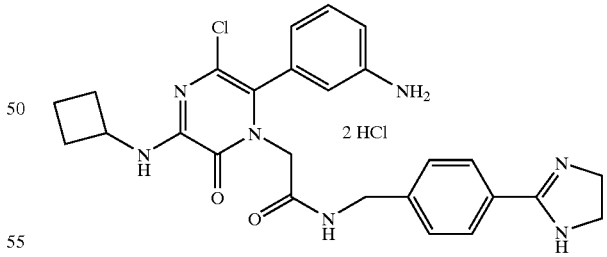

To a solution of the mixture N-Boc and N,N-bis-Boc 4-(N'-Z-amidino)benzylamines (3.0 g, 6.2 mmol) in 50 mL of EtOH and 20 mL THF was added 300 mg of 5% Pd(C). The solution was hydrogenated at 40 psi H$_2$ in a Parr shaker for 18 hrs. The catalyst was filtered off, and the filtrate concentrated in-vacuo to afford the mixture EX-27A (2.1 g, 6.0 mmol) of N-Boc and N,N-bis-Boc 4-amidinobenzylamines as a brownish oil with M+H of 250 (monoBoc) and M+H of 350 (diBoc).

A solution of EX-27A (2.1 g, 6.0 mmol) in MeOH was treated with ethylenediamine (1.13 g, 18.9 mmol). The mixture was heated to reflux for 18 hrs, cooled to room temperature and concentrated in vacuo. 50 mL of H₂O was added and extracted 3×with CH₂Cl₂. The organic extracts were dried over MgSO₄, filtered and condensed in vacuo to afford the mixture EX-27B (2.2 g, 5.9 mmol) as a tan solid with M+H of 276 (monoBoc) and M+H of 376 (diBoc).

A solution of the mixture EX-27B (2.2 g, 5.9 mmol) in 20 mL methylene chloride and 5 mL pyridine was treated with benzyl chloroformate (1.3 g, 7.7 mmol). The mixture was stirred for 1.5 hrs and then was added 100 mL methylene chloride and 100 mL 0.5 N HCl. The layers were seperated, and the aqueous extracted 2×with methylene chloride The organics were combined, washed 1× with brine, dried over MgSO₄, filtered and condensed in vacuo. Purification by column chromatography (silica gel 200–400 mesh) using 50% ethyl acetate as elutant afforded the mixture EX-27C (1.1 g, 2.2 mmol) as a tan oil with M+H 410 (monoBoc) and M+H 510 (diBoc).

A solution of the mixture EX-27C (800 mg, 1.6 mmol) in 10 mL of methylene chloride was treated with 5 mL of 4N HCl in dioxane. The mixture was stirred for 1.5 hrs. and then diethyl ether was added to precipitate the product. The precipitate was filtered off and washed extensively with diethyl ether to afford the HCl salt EX-27D (520 mg, 1.7 mmol) as a tan soild with an M+H of 310.

A solution of 2-{5-chloro-6-(3-nitrophenyl)-3-cyclobutylamino-2-oxohydropyrazinyl}acetic acid (329 mg, 0.86 mmol) in 10 mL of methylene chloride was treated with HOBt (127 mg, 0.94 mmol) for 20 min. Then was added EDC (180 mg, 0.94 mmol), DIEA (335 mg, 2.6 mmol), and EX-27D (300 mg, 0.86 mmol), and the reaction was allowed to stir for 1 hr. Water was then added, and the reaction mixture extracted 3×with methylene chloride. The organics were then washed 1× with brine, dried over MgSO₄, filtered and condensed in vacuo. Purification by column chromatography (silica gel 200400 mesh) eluting with 90% ethyl acetate/hexane and then 100% ethyl acetate afforded EX-27E (325 mg, 0.48 mmol) as a yellow solid which gave an M+H of 670.

A solution of EX-27E (325 mg, 0.48 mmol) in 10 mL of MeOH was treated with 0.7 mL of 3N HCl in MeOH and 5% Pd(C) (50 mg). The mixture was hydrogenated at 45 psi on a Parr shaker apparatus for 2 hrs. The catalyst was then filtered off and washed extensively with MeOH. The filtrate was concentrated in vacuo. The residue was dissolved in EtOH and triturated with diethyl ether. The solid formed was filtered and extensively washed with diethyl ether to afford the HCl salt product (220 mg, 0.43 mmol) as an off-white solid which gave M+H's of 506 (100%) and 508 (60%).

Example 28

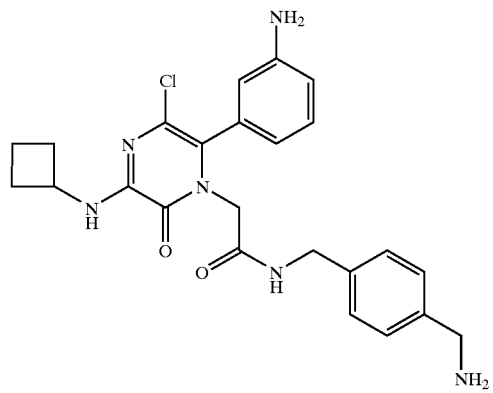

Using the procedures of Scheme 1, Scheme 2, and Example 1 through Example 18 with suitable reagents, starting materials, 2-{5-chloro-6-(3-nitrophenyl)-3-cyclobutylamino-2-oxohydropyrazinyl}acetic acid and 4-(N-Boc-aminomethyl)benzylamine prepared according to the literature reference (Callahan, J. F., Ashton-Shue, D., et al., *J. Med. Chem.* 1989,32, 391–396), the product was obtained and gave an m/z(M+H)⁺ of 467.

Example 29

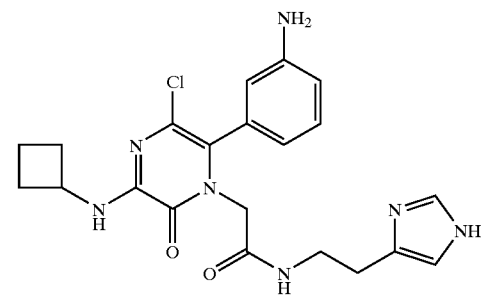

Using the procedures of Scheme 1, Scheme 2, and Example 1 through Example 18 with suitable reagents, starting materials, 2-{5-chloro-6-(3-nitrophenyl)-3-cyclobutylamino-2-oxohydropyrazinyl}acetic acid, and 2-(4-imidazoyl)ethanamine commercially available form Fluka, the product was obtained and gave an m/z(M+H)⁺ of 442.

Example 30

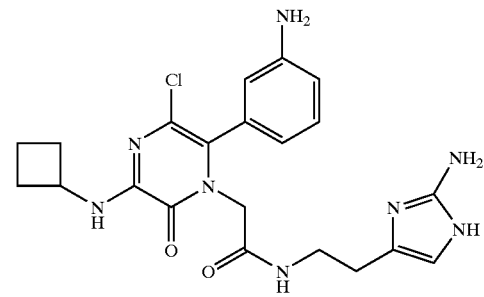

Using the procedures of Scheme 1, Scheme 2, and Example 1 through Example 18 with suitable reagents, starting materials, 2-{5-chloro-6-(3-nitrophenyl)-3-cyclobutylamino-2-oxohydropyrazinyl}acetic acid and 2-(4-(2-aminoimidazoyl))ethanamine prepared according to the literature reference (Nagai, W. Kirk, K. L., Cohen, L. A., *J. Org. Chem.* 1973,33, 1971–1974), the product was obtained and gave an m/z(M+H)+ of 457.

Example 31

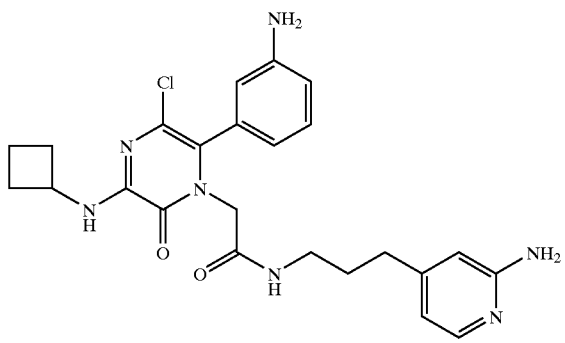

2-Amino-4-picoline (5.00 g, 46.2 mmol) and 11.20 a of di-tert-butyl dicarbonate (50.8 mmol) were stirred in 100 mL of tert-butanol at 30° C. overnight. The reaction mixture was concentrated in vacuo and chromatographed on silica gel with 25% EtOAc/Hexane to give 8.20 g (85% yield) of the product EX-31A.

To a solution of 3.00 g of N-Boc-2-amino-6-picoline (EX-31A, 14.4 mmol) in 150 mL of THF at −78° C. was added 14.4 mL of 2.5 M n-BuLi/Hexanes solution. The reaction mixture was allowed to warm up to room temperature and stirred for 40 min. The reaction mixture was cooled down to −78° C. and 1-bromo-2-chloroethane was added. The mixture was stirred at −78° C. for overnight. The reaction mixture was quenched with HOAc at −78° C. and concentrated in vacuo. The crude was dissolved in EtOAc and washed with brine. The EtOAc layer was dried over MgSO$_4$ and concentrated in vacuo. The crude product was purified by silica gel chromatography with 20% EtOAc/Hexane to give 2.00 g (50%) of the product EX-31B To a solution of 2.00 g of the chloride EX-31B (6.91 mmol) and 0.50 g of sodium azide (7.69 mmol) in 80 mL of DMF was added 10 mL of water and 0.52 g of sodium iodide. The reaction mixture was stirred at 55° C. overnight. The mixture was washed with brine and extracted with EtOAc. The EtOAc layer was dried over MgSO$_4$ and concentrated in vacuo. The crude product was chromatographed on silica gel with 20% EtOAc/Hexane to give 1.80 g (94%) of the product EX-31C.

To a solution of 1.74 g of the azide EX-31C (6.27 mmol) in 30 mL of THF was added 1.64 g of triphenylphosphine (6.27 mmol) and 1 mL of water. The reaction mixture was stirred at room temperature overnight. The reaction mixture was concentrated in vacuo and chromatographed on silica gel with 10% CH$_3$OH/CH$_2$Cl$_2$ to give 1.26 g (80%) of the amine product EX-31D.

To a solution of 0.77 g of 2-{5-chloro-6-(3-aminophenyl)-3-cyclobutylamino-2-oxohydropyrazinyl}acetic acid (2.21 mmol) in 50 mL of DMF was added 0.47 g of EDC.HCl and 033 g of HOBt. The mixture was stirred at room temperature for 30 min. After the addition of 0.61 g of the amine EX-31D (2.43 mmol) and 0.50 g of triethylamine the reaction mixture was stirred at room temperature overnight. The mixture was washed with water and extracted with EtOAc. The EtOAc layer was washed with brine and concentrated in vacuo. The crude product was chromatographed on silica gel with 3% CH$_3$OH/CH$_2$Cl$_2$ to afford 1.10 g (86%) of the Boc protected product EX-31E.

The Boc protected product EX-31E (0.50 g) was treated with 2.0 M of HCl/ether solution for overnight. The mixture was concentrated in vacuo and chromatographed by DeltaPrep with 10% CH$_3$CN/H$_2$O to give 0.32 g of the product (78%) as a TFA salt. The TFA salt was converted to the HCl salt by ion exchange chromatography with BioRad AG 2-X8 resin and 10% CH$_3$CN/H$_2$O and analyzed by mass sprectrometry to give an (M+H) of 482.16.

Example 32

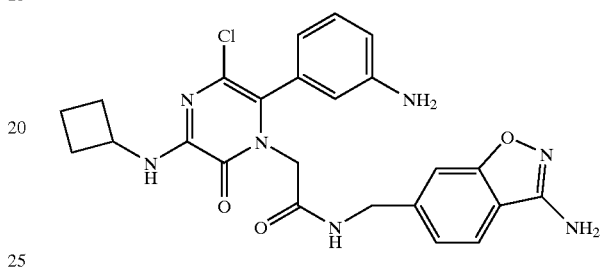

A mixture of 26.5 mmol of 4-bromo-3-fluorotoluene, 29 mmol of copper cyanide and 25 ml of dry DMF is refluxed for 12 hr, then 150 ml water was added and the reaction mixture filtered. The precipitate was triturated with 100 ml of concentrated ammonium hydroxide, extracted twice with 50 ml of dichloromethane. The organic layer was washed with ammonium hydroxide (100 ml) and water (100) and then concentrated and recrystallized (hexane) to yield 2 g solid 4-cyano-3-fluorotoluene (EX-32A). NMR and MS confirmed the structure of EX-32A.

A mixture of 2-fluoro-4-methylbenzonitrile (EX-32A) (2 g, 14.8 mmol), NBS (2.6 g, 14.8 mmol) and benzoyl peroxide (178 mg, 0.74 mmol) in CCl$_4$ (30 ml) was refluxed for 16 hr, then cooled and filtered. The mixture was then concentrated and purified with silica-gel column to yield 1.5 g oil EX-32B. NMR and MS confirmed the structure of EX-32B.

N,N-(Boc)$_2$NH (1.1 g, 5.17 mmol) in THF (20 ml) was cooled to 0° C. and NaH (60%, 0.25 g, 6.11 mmol) was added. The mixture was kept stirring for 30 min., then benzylbromide EX-32B (1 g, 4.7 mmol) in THF (2 ml) was added. The mixture was stirred for 3 hr. Then water was added and extracted with EtOAc (3×15 ml). The combined EtOAc was then concentrated and recrystalized in hexane to yield 0.6 g white solid EX-32C. NMR and MS all confirmed the structure of EX-32C.

To the compound EX-32C (200 mg) in CH$_2$Cl$_2$ (3 ml) was added TFA (1.5 ml). The reaction mixture was stirred at RT for 3 h and concentrated to afford oil EX-32D which was directly used for next amide coupling reaction.

To 2-{5-chloro-6-(3-nitrophenyl)-3-cyclobutylamino-2-oxohydropyrazinyl}acetic acid (227 mg, 0.6 mmol) was added HOBt (106.1 mg, 0.7 mmol) and EDC (126.7 mg, 0.7 mmol) in DMF (3 ml). The mixture was stirred at RT for 30 min. Then the amine TFA salt EX-32D in DMF (1 ml) and triethyl amine (0.2 ml) was added to the mixture which was stirred overnight. The mixture was concentrated, purified to yield 200 mg solid EX-32E, confirmed by NMR and MS.

EX-32E (0.2 g) in THF (5 ml) was added with Pd/C (10%, 20 mg). The mixture was stirred at RT under N$_2$, and then H$_2$ gas balloon was connected to the flask. The reaction was stirred for 24 hr to complete reaction. The mixture was filtered, washed with ethanol, and then dried to yield 0.16 g white solid EX-32F which was directly used for next cyclization reaction.

To acetohydroxamic acid (37 mg, 0.5 mmol) in DMF (2 ml) was added potassium t-butoxide (1M, 0.5 ml, 0.5 mmol) at room temperature. After stirring for 30 min, benzonitrile EX-32F (160 mg, 0.33 mmol) in DMF (2 ml) was added. The reaction mixture was stirred overnight, and then poured into a mixture of brine and ethyl acetate. The aqueous layer was extracted with EtOAc (3×2 ml), and the combined EtOAc was washed with brine, dried, concentrated and purified on reverse-phase HPLC to yield 60 mg of the HCl salt. NMR and MS both confirmed the structure of product.

Example 33

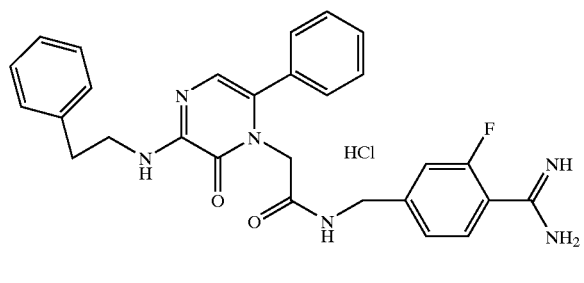

By substituting 2-fluoro-4-methylbenzonitrile for 4-methylbenzonitrile, 2-fluoro-4-methylbenzonitrile (EX-32A) was converted to the protected amidine, 4-(N-benzyloxycarbonylamidino)-3-fluorobenzylamine hydrogen chloride salt (EX-33A), using the procedure outlined in Synthetic Communications, 28(23), 4419–4429 (1998) for preparing 4-(N-benzyloxycarbonylamidino)benzylamine hydrogen chloride salt. EX-33A was characterized by: MS (LR-ESI) m/z 302 (M+H)$^+$; $^1$HNMR (DMSO, 300 MHz) δ 8.75 (bs, 3H, CH$_2$NH$_3$), δ 7.79–7.02 (m, 8H, aromatic CH), δ 5.31–5.07 (m, 2H, C$_6$H$_5$CH$_2$), δ 4.10 (s, 2H, CH$_2$NH$_3$).

Using the procedure of Example 44 by substituting 2-[3-(N-{2-phenylethyl}amino)-2-oxo-6-phenylhydropyrazinyl] acetic acid (EX-1D) for 2-[3-({2-[(tert-butoxy) carbonylamino]ethyl}amino)-5-chloro-2-oxo-6-phenylhydropyrazinyl]acetic acid, EX-33A was converted to the product which gave an m/z+1 of 499.

Example 34

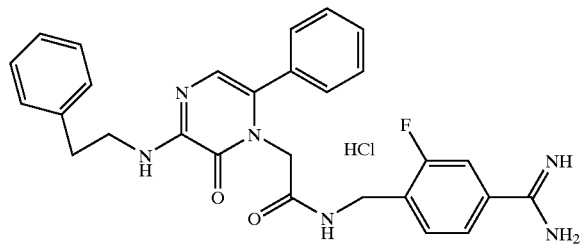

By substituting 3-fluoro-4-methylbenzonitrile for 4-methylbenzonitrile, 3-fluoro-4-methylbenzonitrile was converted to the protected amidine, 4-(N-benzyloxycarbonylamidino)-2-fluorobenzylamine hydrogen chloride salt (EX-34A), using the procedure outlined in Synthetic Communications, 28(23), 4419–4429 (1998) for preparing 4-(N-benzyloxycarbonylamidino)benzylamine hydrogen chloride salt. EX-34A was characterized by: MS (LR-ESI) m/z 302 (M+H)$^+$; $^1$HNMR (DMSO, 300 MHz) δ 8.82 (bs, 3H, CH$_2$NH$_3$), δ 7.92–7.26 (m, 8H, aromatic CH), δ 5.32 (s, 2H, C$_6$H$_5$CH$_2$), δ 4.10 (s, 2H, CH$_2$NH$_3$).

Using the procedure of Example 44 by substituting 2-[3-(N-{2-phenylethyl}amino)-2-oxo-6-phenylhydropyrazinyl] acetic acid (EX-1D) for 2-[3-({2-[(tert-butoxy) carbonylamino]ethyl}amino)-5-chloro-2-oxo-6-phenylhydropyrazinyl]acetic acid, EX-34A was converted to the product which gave an m/z+1 of 499.

Example 35

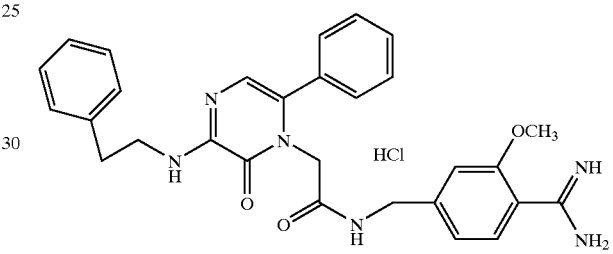

By substituting 2-methoxy-4-methylbenzonitrile for 4-methylbenzonitrile, 2-methoxy-4-methylbenzonitrile was converted to the protected amidine, 4-(N-benzyloxycarbonylamidino)-3-methoxybenzylamine hydrogen chloride salt (EX-35A), using the procedure outlined in Synthetic Communications, 28(23), 4419–4429 (1998) for preparing 4-(N-benzyloxycarbonylamidino)benzylamine hydrogen chloride salt. EX-35A was characterized by: MS (LR-ESI) m/z 314 (M+H)$^+$; $^1$HNMR (DMSO, 300 MHz) δ 7.77–6.95 (m, 8H, aromatic CH), δ 4.74 (bs, 2H, C$_6$H$_5$CH$_2$), δ 4.10–3.95 (m, 2H, CH$_2$NH$_3$), δ 3.80 (s, 3H, OCH$_3$).

Using the procedure of Example 44 by substituting 2-[3-(N-{2-phenylethyl}amino)-2-oxo-6-phenylhydropyrazinyl] acetic acid (EX-1D) for 2-[3-({2-[(tert-butoxy) carbonylamino]ethyl}amino)-5-chloro-2-oxo-6-phenylhydropyrazinyl]acetic acid, EX-35A was converted to the product which gave an m/z+1 of 511.

Using the procedures of Scheme 1, Scheme 2, and the Examples herein with suitable reagents, starting materials, and intermediates, additional pyrazinones of the present invention were prepared and these pryazinones are summarized in Table 2.

TABLE 2

Additional Substituted Pyrazinones of the Present Invention Prepared based on the Procedures of Scheme 1, Scheme 2, and Examples herein.

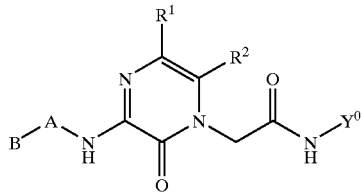

General Structure

| Ex. No. | R¹ | R¹ | B—A— | Y° | MW (m/z + 1) |
|---|---|---|---|---|---|
| 36 | Phenyl | H | 2-phenethyl | 1-(4-guanidino)-2-butynyl | 458 |
| 37 | Phenyl | H | 2-phenylethyl | 1-(4-guanidino)-cis-2-butenyl | 460 |
| 38 | Phenyl | H | 2-phenylethyl | (3-aminoindazol-5-yl)methyl | 494 |
| 39 | Phenyl | H | 2-phenylethyl | (3-aminoindazol-6-yl)methyl | 494 |
| 40 | 3-aminophenyl | Cl | cyclobutyl | (4-amidino-3-fluoro)benzyl | 498 |
| 41 | 3-aminophenyl | Cl | cyclobutyl | (4-amidino-2-fluoro)benzyl | 511 |
| 42 | 3-aminophenyl | Cl | isopropyl | (4-amidino-3-fluoro)benzyl | 486 |
| 43 | 3-aminophenyl | H | isopropyl | (4-amidino-3-fluoro)benzyl | 452 |

Example 44

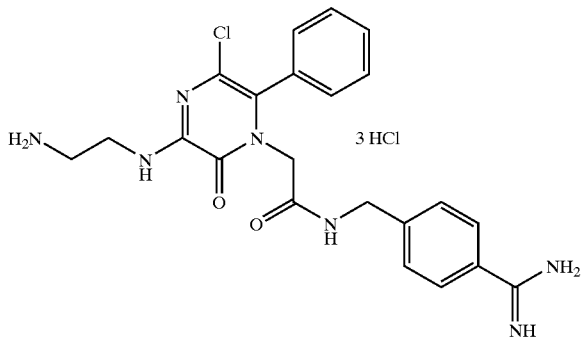

To a solution of 2-[3-({2-[(tert-butoxy)carbonylamino]ethyl}amino)-5-chloro-2-oxo-6-phenylhydropyrazinyl]acetic acid (6.50 e, 15.38 mmol) prepared as described in EX-1C using 2-(tert-butoxycarbonylamino)ethylamine in place of 2-phenylethylamine in 100.0 mL dimethylformamide was added N,N-diisopropylethylamine (21.0 mL, 120.56 mmol), N-hydroxybenzotriazole (2.73 g, 20.21 mmol), and 1-[3-(dimethylamino)propyl]-3-ethylcarbodiimide hydrochloride (3.84 g, 20.04 mmol). The resulting mixture was stirred for 30 minutes. To the reaction mixture was added in one portion (5.9723 g, 18.68 mmol) of the protected amidine, 4-(N-benzyloxycarbonylamidino)benzylamine hydrogen chloride salt, prepared using the procedure outlined Synthetic Communications, 28(23), 4419–4429 (1998). The resulting mixture was stirred overnight. The reaction mixture was diluted with ethyl acetate (250 mL) and washed with 5% citric acid (1×50 mL), saturated NaHCO₃ (1×50 mL), and brine (1×50 mL). The organic solution was dried (MgSO₄), filtered and concentrated. The crude reaction was purified by MPLC (80% ethyl acetate/hexanes) to give pure product EX-44A: ¹H NMR (300 MHz, DMSO) δ 8.59–8.53 (1H), 7.99–7.96 (m, 2H), 7.81–7.75 (m, 1H), 7.51–7.25 (m, 12H), 6.99 (br m, 1H), 5.14 (s, 2H), 4.32–4.27 (m, 4H), 3.42–3.35 (m, 4H), 3.24–3.20 (m, 2H), 1.41 (s, 9H); ¹³C NMR (75 MHz, CDCl₃) δ 166.6, 163.0, 156.5, 151.3, 149.9, 143.9, 137.8, 133.5, 132.6, 131.3, 130.1, 129.5, 129.2, 129.1, 128.9, 128.7, 128.4, 127.7, 124.0, 78.5, 66.8, 49.3, 42.6, 36.5, 31.5, 29.0; HRMS (EI) calcd for C₃₅H₃₈ClN₇O₆ 688.2650, found 688.2614.

A solution of pyrazinone EX-44A (334.4 mg, 0.4593 mmol) in 5.0 mL ethanol/4 M HCl in dioxane (3:1, 0.1 M) was flushed with hydrogen gas. To the solution was then added 113.1 mg 10% Pd/C (wet), and the resulting suspension was stirred at room temperature under an atmosphere of hydrogen (balloon pressure) for approximately 18 hours. The reaction mixture was filtered through a pad of Celite 545 and rinsed with ethanol. The solvent was removed under reduced pressure. The resulting oil was triturated with ethyl ether to provide pure product as a white solid: ¹H NMR (400 MHz, DMSO) d 9.50 (s, 2H), 9.29 (s, 2H), 8.8/0 (s, 1H), 8.22 (s, 3H), 7.85–7.80 (m, 3H), 7.44 (br s, 3H), 7.27–7.24 (m, 4H), 4.23 (s, 4H), 3.58–3.54 (m, 4H); HRMS (ES) calcd for C₂₂H₂₅ClN₇O₂ 454.1758, found 454.1741.

Example 45

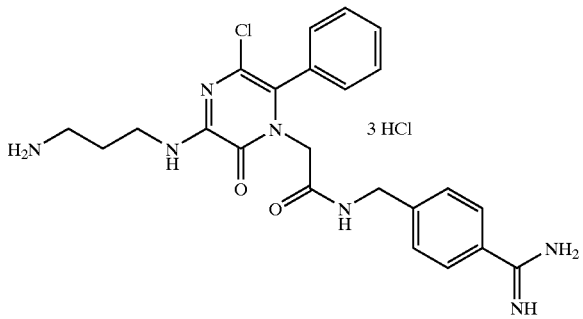

By following the method of Example 44 and substituting 2-[3-({3-[(tert-butoxy)carbonylamino]propyl}amino)-5-chloro-2-oxo-6-phenylhydropyrazinyl]acetic acid for 2-[3-({2-[(tert-butoxy)carbonylamino]ethyl}amino)-5-chloro-2-oxo-6-phenylhydropyrazinyl]acetic acid, the product was prepared: ¹H NMR (400 MHz, DMSO) d 9.51 (br s, 2H), 8.28 (br s, 2H), 8.77 (s, 1H), 8.15 (3, 3H), 7.86–7.79 (m, 3H), 7.42 (s, 3H), 7.26–7.24 (m, 4H), 5.37 (br s, 2H), 4.21 (s 4H), 3.39–3.29 (m, 2H), 2.81–2.76 (br s, 2H), 1.86 (br s, 2H); $^{13}$C NMR (100 MHz, DMSO) d 166.7, 166.0, 151.2, 149.7, 146.0, 132.5, 131.1, 129.5, 128.8, 127.9, 126.8, 125.1, 123.9, 65.6, 56.6, 49.2, 42.4, 38.1, 37.3, 34.6, 26.7, 19.2, 15.8; HRMS (EI) calcd for $C_{23}H_{26}ClN_3O_6$ 469.1755, found 469.1725.

Example 46

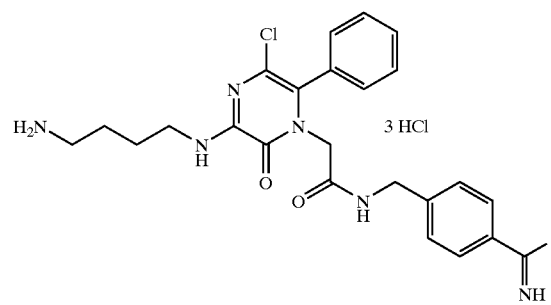

By following the method of Example 44 and substituting 2-[3-({4[(tert-butoxy)carbonylamino]butyl}amino)-5-chloro-2-oxo-6-phenylhydropyrazinyl]acetic acid for 2-[3-({2-[(tert-butoxy)carbonylamino]ethyl}amino)-5-chloro-2-oxo-6-phenylhydropyrazinyl]acetic acid, the product was prepared: $^1$H NMR (400 MHz, DMSO) d 9.49 (br s, 2H), 9.28 (s, 2H), 8.75 (s, 1H), 8.08 (s, 3H), 7.89–7.76 (m, 3H), 7.42 (s, 3H), 7.26–7.24 (m, 4H), 4.70 (br s, 4H), 4.23421 (m, 3H), 2.73 (br s, 2H), 1.57 (br s, 3H), 1.03–0.96 (m, 2H); HRMS (EI) calcd for $C_{24}H_{29}ClN_7O_2$ 482.2071, found 482.2040.

Example 47

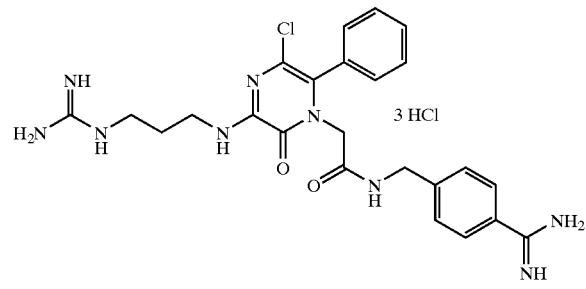

A solution of 1-(N-{4-[N-benzyloxycarbonylamidino]benzylamido}carbonylmethyl)-3-({3-[(tert-butoxy)carbonylamino]propyl}amino)-5-chloro-6-phenylpyrazinone hydrochloride (2.0075 g, 2.859 mmol), prepared as an intermediate in Example 45, in 28.0 mL ethanol/4 M HCl in dioxane (1:1, 0.1 M) was allowed to stir at room temperature for approximately 4 hours. The solvent was removed under reduced pressure. Purification by trituration with ethyl ether gave pure product EX-47A as a yellow solid: $^1$H NMR (400 MHz, DMSO) d 11.67 (br s, 1H), 10.53 (br s, 1H), 8.90–8.87 (m, 1H), 8.30–8.25 (m, 3H), 7.89–7.83 (m, 1H), 7.75–7.73 (m, 2H), 7.46–7.23 (m, 13H), 5.532 (s, 2H), 4.26–4.23 (m, 3H), 3.50 (s, 2H), 3.36–3.35 (m, 2H), 2.75 (br m, 2H); HRMS (EI) calcd for $C_{31}H_{32}ClN_7O_4$ 602.2283, found 602.2253.

To a solution of amino pyrazinone EX-47A (1.9093 g, 2.684 mmol) in 10.0 mL dimethyl formamide (0.25 M) was added triethylamine (1.90 mL, 13.63 mmol) To the resulting mixture was then added N,N'-di-BOC-N'-triflylguanidine (1.4021 g, 3.583 mmol, prepared according to Feichtinger, K., Zapf, C. Sings, H. L., and Goodman, M., *J. Org. Chem.,* 63, 3804–3805 (1998)) in one portion at room temperature. The resulting suspension was allowed to stir over night. The reaction mixture was diluted ethyl acetate (250 mL) and washed with saturated NaHCO$_3$ (2×100 mL) and brine (2×100 mL). The organic solution was dried (MgSO$_4$), filtered and concentrated. Purification by MPLC (75% ethyl acetate/hexanes) afforded EX-47B: $^1$H NMR (400 MHz, CDCl$_3$) d 11.53 (s, 1H), 8.55–8.48 (m, 2H), 7.97–7.93 (m, 4H), 7.49–7.24 (m, 13H), 5.13 (s, 2H), 4.30–4.25 (m, 4H), 3.90–3.33 (m, 4H), 1.84–1.79 (m, 2H), 1.49 (s, 9H), 1.41 (s, 9H); HRMS (EI) calcd for $C_{42}H_{51}ClN_9O_8$ 844.3549, found 844.3521.

A solution of pyrazinone EX-47B (1.5450 g, 1.8298 mmol) in 18.0 mL ethanol/4 M HCl in dioxane (3:1, 0.1 M) was flushed with hydrogen gas. To the solution was then added 157.2 mg 10% Pd/C (wet), and the resulting suspension was stirred at room temperature under an atmosphere of hydrogen (balloon pressure) for approximately 18 hours. The reaction mixture was filtered through a pad of Celite 545 and rinsed with ethanol. The solvent was removed under reduced pressure. The resulting oil was triturated with ethyl ether to provide the pure product in 63% yield: $^1$H NMR (400 MHz, DMSO) d 9.50 (s, 2H), 9.28 (s, 2H), 8.77 (s, 1H), 7.91 (s, 1H), 7.81–7.79 (m, 31H), 7.42 (br s, 4H), 7.26–7.24 (m, 5H), 6.28 (br s, 2H), 4.23–4.21 (m, 4H), 3.36–3.27 (m, 2H), 3.14–3.13 (br m, 2H), 1.77–1.74 (m, 2H); HRMS (ES) calcd for $C_{24}H_{29}ClN_9O_2$ 510.2133, found 510.2080.

Example 48

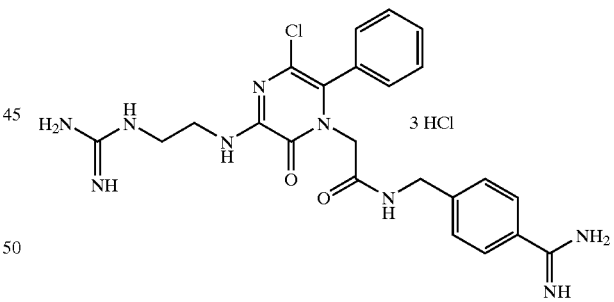

Using the method of Example 47 and substituting 1-(N-{[N-benzyloxycarbonylamidino]benzylamido}carbonylmethyl)-3-({2-[(tert-butoxy)carbonylamino]ethyl}amino)-5-chloro-6-phenylpyrazinone hydrochloride, prepared as an intermediate in Example 44, for the propyl analog used in Example 47, the product was prepared: $^1$H NMR (400 MHz, DMSO) d 9.51 (s, 2H), 9.29 (s, 2H), 8.80 (s, 1H), 7.90–7.78 (m, 5H), 7.43–737 (m, 5H), 7.35–7.23 (m, 5H), 4.23 (s, 4H), 4.03 (s, 2H), 3.43.34 (m, 4H); HRMS (EI) calcd for $C_{23}H_{27}ClN_9O_2$ 496.1976, found 496.1952.

Example 49

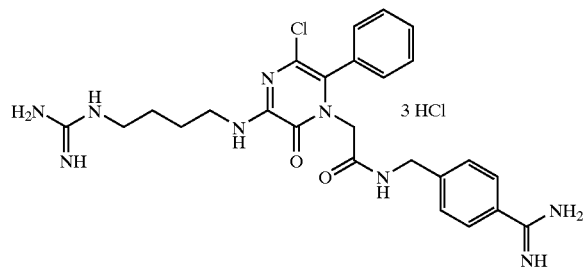

By following the method of Example 47 and substituting 1-(N-{4[N-benzyloxycarbonylamidino]benzylamido}carbonylmethyl)-3-({4[(tert-butoxy)carbonylamino]butyl}amino)-5-chloro-6-phenylpyrazinone hydrochloride (2.0075 g, 2.859 mmol), prepared as an intermediate in Example 46, for the propyl analog used in Example 47, the product was prepared: $^1$H NMR (400 MHz, DMSO) d 9.47 (s, 2H), 9.28 (s, 2H), 8.74–8.72 (m, 1H), 7.88 (br s, 1H), 7.80–7.73 (m, 3H), 7.43–7.31 (m, 4H), 7.27–7.20 (m, 5H), 5.36–5.32 (n, 3H), 4.25–4.21 (m, 4H), 3.28–3.27 (m, 2H), 3.10–3.08 (m, 2H), 1.58–1.53 (m, 2H), 1.48–1.43 (m, 2H); HRMS (EI) calcd for $C_{25}H_{31}ClN_9O_2$ 524.2289, found 524.2292.

Example 50

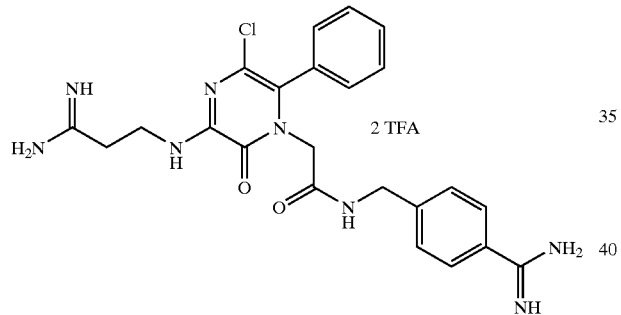

To a solution of 2-{5-chloro-3-[(2-cyanoethyl)amino]-2-oxo-6-phenylhydropyrazinyl}acetic acid (2.09 g, 6.28 mmol) in 31.0 mL dimethylformamide/tetrahydrofuran (1:1) was added N,N-diisopropylethylamine (5.50 mL, 31.57 mmol), N-hydroxybenzotriazole (1.02 g, 7.6 mmol), and 1-[3-(dimethylamino)propyl]-3-ethylcarbodiimide hydrochloride (1.45 g, 7.51 mmol). The resulting mixture was stirred for 30 minutes. To the reaction mixture was then added 4-cyanobenzylamine (1.28 o, 7.57 mmol) in one portion. The resulting mixture was allowed to stir over night. The reaction mixture was diluted with ethyl acetate (250 mL) and washed with 5% citric acid (1×50 mL), saturated NaHCO$_3$ (1×50 mL), and brine (1×50 mL). The organic solution was dried (MgSO$_4$), filtered and concentrated. The crude reaction was purified trituration with ethyl ether to give EX-50A: $^1$H NMR (300 MHz, DMSO) δ 8.59 (t, J=5.6 Hz, 1H), 8.10 (t, J=5.6 Hz, 1H), 7.82 (d, J=8.1 Hz, 2H), 7.53–7.46 (m, 3H), 7.35–7.32 (m, 4H) 4.33–4.29 (m, 4H), 3.63–3.57 (m, 2H), 2.89 (t, J=6.3 Hz, 2H); $^{13}$C NMR (75 MHz, DMSO) δ 166.7, 151.1, 149.6, 145.6, 132.93, 132.45, 131.16, 130.21, 129.55, 128.63, 124.97, 124.72, 120.0, 119.6, 110.4, 49.3, 42.6, 37.3, 17.3; HRMS (EI) calcd for $C_{23}H_{20}ClN_6O_2$ 447.1336, found 447.1330.

To a suspension of bis-nitrile pyrazinone EX-50A (2.26, 58.07 mmol) in 50 mL ethanol/H$_2$O (2.6:1, 0.1 M) was added hydroxyl amine hydrochloride (2.61 g, 37.6 mmol) followed by potassium carbonate (3.08 g, 22.3 mmol). The resulting white suspension was stirred and heated to 60° C. over night. The reaction mixture was cooled to room temperature and diluted with water (75.0 mL). The mixture was placed in an ice bath, and the pH was adjusted to approximately 7 using dilute acid. The precipitate that formed was collected by filtration, washed with cold water and dried under vacuum to afford pure EX-50B: $^1$H NMR (300 MHz, DMSO) δ 9.63 (s, 1H), 8.95 (s, 1H), 8.47 (br s, 1H), 7.6–7.61 (m, 2H), 7.53–7.47 (m, 4H), 7.32 (d, J=5.2 Hz), 7.16–7.13 (m, 2H), 5.83 (s, 2H), 5.47 (s, 2H), 4.25 (s, 4H), 3.61–3.53 (m, 2H), 2.39–2.35 (m, 2H); $^{13}$C NMR (75 MHz, DMSO) δ 166.5, 151.68, 151.35, 151.23, 149.6, 140.3, 132.70, 132.63, 131.3, 130.1, 129.5, 127.6, 126.0, 125.3, 49.2, 42.6, 38.4, 30.6; HRMS (EI) calcd for $C_{23}H_{26}ClN_8O_4$ 513.1766, found 513.1735.

To a solution of Bis-hydroxyamidine EX-50B (2.40 g, 4.67 mmol) in 19.0 mL acetic acid (0.25 M) was added acetic anhydride (1.80 mL, 19.1 mmol). The resulting mixture was stirred for 10 minutes and flushed with hydrogen gas. To the solution was then added Pd/C (wet) and the resulting mixture was allowed to stir under an atmosphere of hydrogen (balloon pressure) at room temperature, over night. The reaction mixture was filtered through a pad of Celite 545 and concentrated under vacuum. Purification by HPLC (1% acetonitrile to 60% acetonitrile/H$_2$O/0.1% trifluoroacetic acid) afford pure product: $^1$H NMR (400 MHz, DMSO) δ 9.51 (s, 2H), 9.30 (s, 2H), 9.03 (s, 2H), 8.93 (s, 2H), 8.62–8.59 (m, 1H), 7.89–7.86 (m, 2H), 7.74 (d, J=8.3 Hz, 2H), 7.47–7.40 (m, 3H), 7.28–7.23 (m, 4H), 4.27–4.24 (m, 4H), 3.63–3.59 (m, 2H), 2.70–2.68 (m, 2H); HRMS (EI) calcd for $C_{23}H_{26}ClN_8O_2$ 481.1867, found 481.1836.

Example 51

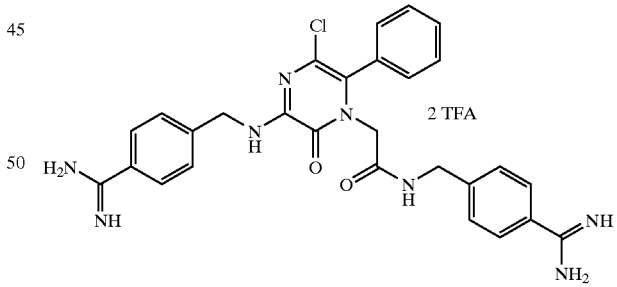

By following the method of Example 50 and substituting 2-{5-chloro-3-[(4-cyanobenzyl)amino]-2-oxo-6-phenylhydropyrazinyl}acetic acid for the 2-cyanoethylamino analog, the product was prepared: $^1$H NMR (400 MHz, DMSO) d 9.44 (d, J=16.9 Hz, 3H), 9.26 (d, J=17.2 Hz, 8.61 (br s, 1H), 8.47–8.44 (m, 1H), 7.74 (d, J=7.0 Hz, 4H), 7.52 (d, J=Hz, 2H), 7.43–7.42 (m, 3H), 7.28–7.22 (m, 4H), 4.56–4.55 (m, 2H), 4.25 (s, 4H); HRMS (EI) calcd for $C_{28}H_{28}ClN_8O_2$ 543.2024, found 543.1986.

Example 52

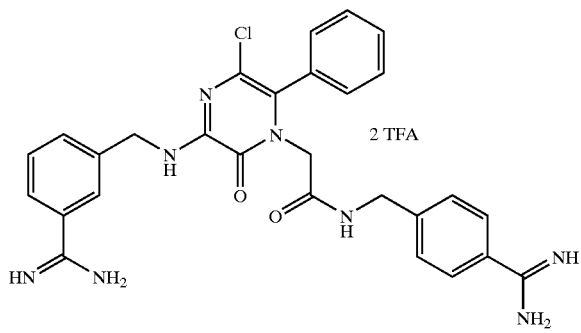

By following the method of Example 50 and substituting 2-{5-chloro-3-[(3-cyanobenzyl)amino]-2-oxo-6-phenylhydropyrazinyl}acetic acid for the 2-cyanoethylamino analog, the product was prepared: $^1$H NMR (400 MHz, DMSO) d 9.41 (s, 4H), 9.28 (d, J=11.0 Hz, 4H), 8.61–8.58 (m, 1H), 8.35–8.32 (m, 1H), 7.77–7.72 (m, 3H), 7.66–7.64 (m, 2H), 7.55–7.52 (m, 1H), 7.45–7.39 (m, 3H), 7.29–7.23 (m, 4H), 4.57–4.55 (m, 2H), 4.26–4.21 (m, 4H); $^{13}$C NMR (100 MHz, DMSO) d 166.7, 166.1, 159.8, 159.4, 151.2, 149.6, 145.9, 140.6, 133.3, 132.4, 131.1, 130.1, 129.6, 129.5, 129.1, 128.7, 127.93, 127.86, 127.3, 124.9, 124.5, 49.1, 44.0, 42.4; HRMS (EI) calcd for $C_{28}H_{28}ClN_8O_2$ 543.2024, found 543.2032.

Example 53

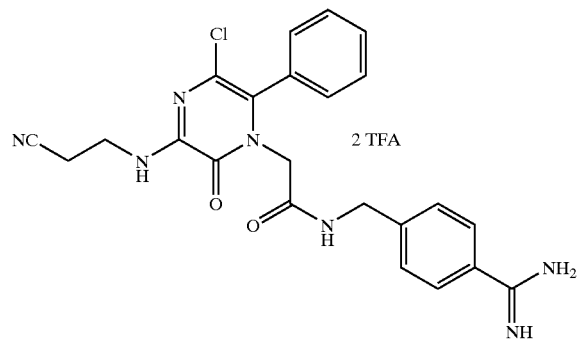

To a solution of 2-{5-chloro-3-[(2-cyanoethyl)amino]-2-oxo-6-phenylhydropyrazinyl}acetic acid (1.45 g, 3.25 mmol) in 17.0 mL dimethylformamide was added N,N-diisopropylethylamine (3.00 mL, 17.2 mmol), N-hydroxybenzotriazole (0.536 mg, 3.96 mmol), and 1-[3-(dimethylamino)propyl]-3-ethylcarbodiimide hydrochloride (0.752 mg, 3.923 mmol). The resulting mixture was allowed to stir for 30 minutes. The reaction mixture was then added the Cbz protected amidine (1.263 g, 3.950 mmol) prepared and used in Example 44 in one portion. The resulting mixture was allowed to stir over right. The reaction mixture was diluted with ethyl acetate (250 mL) and washed with 5% citric acid (1×50 mL), saturated NaHCO$_3$ (1×50 mL), and brine (1×50 mL). The organic solution was dried (MgSO$_4$), filtered and concentrated. The crude reaction was purified by MPLC (100% ethyl acetate) to give pure EX-53A in 82% yield: $^1$H NMR (400 MHz, DMSO) δ 9.06 (br s, 1H), 8.50–8.47 (m, 1H), 8.05–8.02 (m, 1H), 7.89 (d, J=8.2 Hz, 2H) 7.46–7.26 (m, 11H), 7.18 (d, J=8.2 Hz, 2H), 5.07 (s, 2H), 4.24–4.21 (m, 4H), 3.55–3.51 (m, 2H), 2.83–2.80 (m, 2H); HRMS (EI) calcd for $C_{31}H_{28}ClN_7O_4$ 598.1970, found 598.1970.

To a solution of pyrazinone EX-53A (1.497 g, 2.50 mmol) in 25.0 mL ethanol/4 M HCl in dioxane (3:1, 0.1 M) was flushed with hydrogen gas. To the solution was then added 10% Pd/C (wet) and the resulting suspension was allowed to stir at room temperature under an atmosphere of hydrogen (balloon pressure) for approximately 18 hours. The reaction mixture was filtered through a pad of Celite 545 and rinsed with ethanol. The solvent was removed under reduced pressure. Purification by HPLC (5% acetonitrile to 95% acetonitrile/H$_2$O/0.1% trifluoroacetic acid) provided pure product: $^1$H NMR (400 MHz, DMSO) d 9.51 (s, 2H), 9.29 (s, 2H), 8.63–8.60 (m, 1H), 8.03–8.00 (m, 1H), 7.74 (d, J=8.3 Hz, 2H), 7.44–7.40 (m, 3H), 7.29–7.27 (m, 4H), 4.27–4.24 (m, 4H), 3.55–3.51 (m, 3H), 2.83–2.80 (m, 3H); HRMS (ES) calcd for $C_{23}H_{23}ClN_7O_2$ 464.1602, found 464.1624.

Example 54

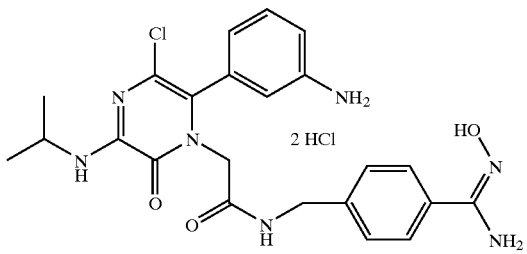

A solution of p-bromophenethylamine (40 g, 199.92 mmol) and phthalic anhydride (29.6 g, 199.84 mmol) in 250 mL of dioxane and 25 mL of dimethylformamide was heated at 120° C. for 24 hours. The flask was then cooled, and the resulting white precipitate was filtered and washed with methanol (200 mL) to give EX-54A in exceptional yield and purity: $^1$H NMR (400 MHz, CDCl$_3$) d 7.8 (m, 2H), 7.7 (m, 2H), 7.4 (d, 2H), 7.1 (d, 2H), 3.8 (t, 2H), 2.95 (t, 2H); MS (ES) calcd for $C_{16}H_{12}BrNO_2$ 330, found 331 (M+H).

A nitrogen purged solution of EX-54A (40 g, 121.15 mmol) and copper (I) cyanide (16.28 g, 181.72 mmol) in 500 mL of dimethylformamide was heated at 170° C. for 24 hours. The solvent was removed under vacuum, and the resulting material was taken up in ethyl acetate. The ethyl acetate suspension was flashed through celite and concentrated under vacuum. The resulting white precipitate EX-54B was of exceptional yield and purity: $^1$H NMR (300 MHz, CDCl$_3$) d 7.82 (m, 2H), 7.75 (m, 2H), 7.6 (d, 2H), 7.35 (d, 2H), 3.95 (t, 2H), 3.05 (t, 2H); MS (ES) calcd for $C_{17}H_{12}N_2O_2$ 276, found 277 (M+H).

A solution of p-cyanophenethylamine EX-54B (25 g, 90.48 mmol) and hydroxylamine hydrochloride (8 g, 115.12 mmol) in 1 L of ethanol and 20 mL (114.82 mmol) of diisopropylethylamine was heated at reflux for 16 hours. The flask was then cooled, and the resulting white precipitate was filtered and air dried to give EX-54C in an adequate yield and purity: $^1$H NMR (300 MHz, DMSO) d 7.75 (d, 2H), 7.55 (d, 2H), 7.25 (d, 2H), 7.2 (d, 2H), 3.8 (m, 2H), 2.95 (m, 2H); MS (ES) calcd for $C_{17}H_{15}N_3O_3$ 309, found 310 (M+H).

A solution of p-(N-hydroxy)amidinophenethyl phthalimide (EX-54C) (4.53 g, 14.64 mmol) in 200 mL of chloroform was treated with hydrazine monohydrate (1 mL, 20.62 mmol). The reaction was stirred vigorously at 50° C. for 24 hours. The flask was then cooled and the resulting white precipitate was filtered and washed with chloroform (200 mL). A 50:50 mixture of product EX-54D and phthalhydrazide was obtained and used as is: $^1$H NMR (300 MHz, DMSO) d 7.6 (d, 2H), 7.2 (d, 2H), 2.8 (t, 2H), 2.7 (m, 2H); MS (ES) calcd for $C_{17}H_{15}N_3O_3$ 179, found 180 (M+H).

Reacting EX-54D containing phthalhydrazide with 2-{5-chloro-6-(3-nitrophenyl)-3-[N-(-methylethyl)amino]-2-oxohydropyrazinyl}acetic acid in place of 2-{5-chloro-6-(3-nitrophenyl)-3-cyclobutylamino-2-oxohydropyrazinyl}acetic acid and EX-27D and then hydrogenating the resulting intermediate according to the final two procedures described in Example 27 gave the product with an m/z+1 of 484.

Example 55

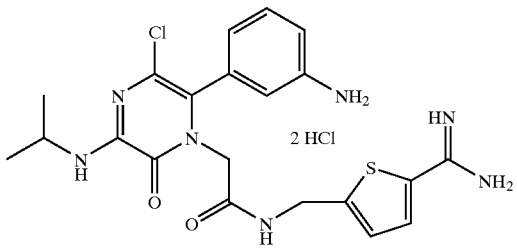

A solution of diisopropylamine (35.3 ml, 0.251 moles) in tetrahydrofuran (500 ml) was cooled to −78° C. under a nitrogen blanket. To this was added 1.6M n-butyllithium in hexanes (157 ml, 0.251 moles) and allowed to stir for 5 min. Then slowly added thiopene-2-carbonitrile (21.33 ml, 0.229 moles) in tetrahydrofuran (115 ml) and allowed to stir. After 45 min. was added N,N-dimethylformamide (88.66 ml, 1.145 moles) at −78° C. Citric acid (40 g) was added after 2 h. followed by water (240 ml) and stirred for 18 h. The reaction was concentrated in vacuo, transferred to a separatory funnel, diluted with brine, and extracted twice with ether. The combined ether layers were washed with brine, dried over magnesium sulfate, filtered, and the solvent removed in vacuo. Chromatography yielded 15.8 g (50%) of 2-cyano-5-formylthiophene (EX-55A) as a brown solid: $^1$H NMR (300 MHZ, CDCl$_3$) d 10.02 (s, 1H), 7.79 (m, 1H), 7.30 (m, 1H).

2-Cyano-5-formylthiophene (EX-55A) (15.8 g, 0.229 moles) was stirred in ethanol (375 ml), and sodium borohydride (4.36 g, 0.115 moles) added in small portions. After 15 min., the solvent was removed in vacuo, and residue taken up in ethyl acetate. After the ethyl acetate was washed with 1N potassium hydrogen sulfate and brine, the organic layer was dried over magnesium sulfate, filtered, and solvent removed in vacuo. The residue was dried on vacuum pump to yield 9.57 g (59%) of the alcohol EX-55B as a brown-orange oil: $^1$H NMR (300 MHz, CDCl$_3$) d 7.53 (m, 1H), 7.00 (m, 1H), 4.88 (s, 2H), 2.84 (br s, 1H).

To a stirring solution of EX-55B (9.57 g, 0.069 moles) in tetrahydrofuran (80 ml) was added triphenylphosphine (19.86 g, 0.075 moles) and carbon tetrabromide (25.11 g, 0.075 moles). After 18 h. the reaction was concentrated in vacuo, and the crude material chromatographed to yield EX-55C as a brown oil: $^1$H NMR (300 MHz, CDCl$_3$) d 7.52 (m, 1H), 7.14 (m, 1H), 4.69 (s,2H).

2-Aminomethyl-5-carbobenzyloxyamidinothiophene dihydrogen chloride salt (EX-55D) was prepared by the method outlined in Synthetic Communications, 28(23), 44194429 (1998) by substituting 5-bromomethyl-2-cyanothiophene (EX-55C) for 4-cyanobenzyl bromide to give after trituration with acetonitrile EX-55D: $^1$H NMR (300 MHz, DMSO) d 9.98 (br s, 1H), 8.83 (br s, 2H), 8.10 (s, 1H), 7.40–7.48 (m, 7H), 5.26 (s, 2H), 4.31 (s, 2H); HRMS calcd for $C_{14}H_{16}N_3O_2S$ 290.0963, found 290.0949.

Reacting EX-55D with 2-{5-chloro-6-(3-nitrophenyl)-3-[N-(1-methylethyl)amino]-2-oxohydropyrazinyl}acetic acid in place of 2-{5-chloro-6-(3-nitrophenyl)-3-cyclobutylamino-2-oxohydropyrazinyl}acetic acid and EX-27D and then hydrogenating the resulting intermediate according to the final two procedures described in Example 27 gave the product with an m/z+1 of 474.

Example 56

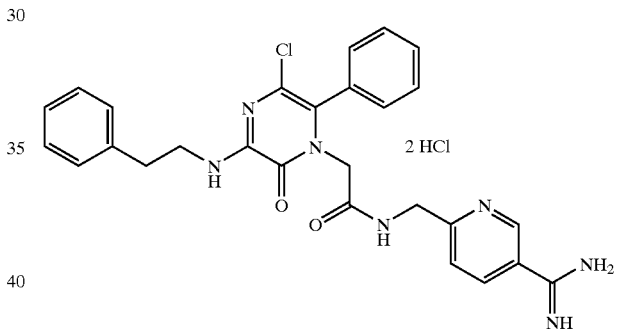

To a stirring solution of 3-cyano-6-methylpyridine (20 g, 0.169 moles) in carbon tetrachloride (850 ml) was added N-bromosuccinimde (30 g, 0.169 moles) and benzoyl peroxide (4.1 g, 0.0169 moles), and the solution was heated to reflux. After 18 h, the heat was discontinued, diluted with carbon tetrachloride (1 L) and washed twice with water (1 L). The solvent was removed in vacou and the crude material chromatographed to yield 12.05 g (36%) of dark brown solid EX-56A: $^1$H NMR (300 MHz, CDCl$_3$) d 8.86 (d, 1H), 7.00 (m, 1H), 7.62 (m, 1H), 4.60 (s, 2H); $^{13}$C NMR (300 MHz, CDCl$_3$) d 15638, 147.70, 135.82, 118.98, 111.75, 104.66, 27.82; HRMS (EI) calcd for $C_7H_6BrN_2$ 196.9714, found 196.9661.

2-Aminomethyl-5-carbobenzyloxyamidinopyridine dihydrogen chloride salt (EX-56B) was prepared by the method outlined in Synthetic Communications, 28(23), 4419–4429 (1998) by substituting 5-bromomethyl-2-cyanopyridine (EX-55A) for 4-cyanobenzyl bromide to give EX-56B: HPLC/LRMS; 98%, (M+H)$^+$ 285.

Reacting EX-56B with 2-{5-chloro-6-phenyl-3-[N-(2-phenylethyl)amino]-2-oxohydropyrazinyl}acetic acid in place of 2-{5-chloro-6-(3-nitrophenyl)-3-cyclobutylamino-2-oxohydropyrazinyl}acetic acid and EX-27D and then hydrogenating the resulting intermediate according to the final two procedures described in Example 27 gave the product with an m/z+1 of 482.

Example 57

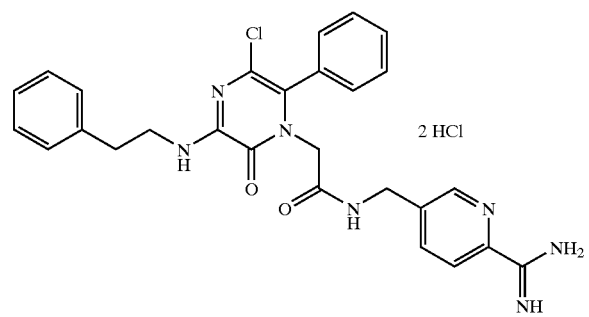

2-Cyano-5-methylpyridine (EX-57A) was prepared following the procedure outlined in Synthetic Communications, 19(13&14), 2371–2374(1989): HRMS (EI) calcd for $C_7H_7N_2$ 119.0609, found 119.0587.

By following the procedure of Example 56 and substituting 2-cyano-5-methylpyridine for 3-cyano-6-methylpyridine, the intermediate 5-bromomethyl-2-cyanopyridine (EX-57B) was prepared.

2-Aminomethyl-5-carbobenzyloxyamidinopyridne dihydrogen chloride salt (EX-57C) was prepared by the method outlined in Example 56 substituting 5-bromomethyl-2-cyanopyridine for 6-bromomethyl-3-cyanopyridine: HPLC/LRMS; 95%, (M+H)$^+$ 285.

Reacting 2-Aminomethyl-5-carbobenzyloxyamidinopyridne dihydrogen chloride salt (EX-57C) with 2-{5-chloro-6-phenyl-3-[N-(2-phenylethyl)amino]-2-oxohydropyrazinyl}acetic acid as described in Example 56 gave the product with an m/z+1 of 482.

Example 58

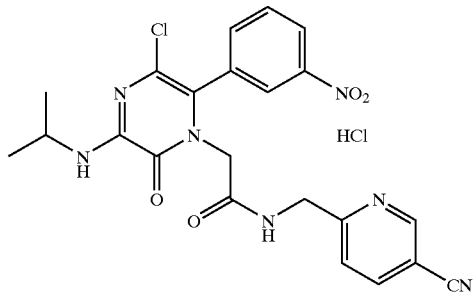

2-Aminomethyl-5-cyanopyridine hydrochloride (EX-58A) was prepared by the deprotection with 4N HCl Dioxane of the intermediate 2-{N,N-bis(tert-butoxycarbonyl)aminomethyl}-5-cyanopyridine used to prepare 2-aminomethyl-5-carbobenzyloxyamidinopyridine dihydrogen chloride salt in Example 56: $^1$H NMR (400 MHz, DMSO) d 9.04 (s, 1H), 8.64 (br s, 2H), 8.34 (m, 1H), 7.69 (m, 1H), 4.25 (s, 2H); HRMS (EI) calcd for $C_7H_8N_3$ 134.0718, found 134.0699.

Using the procedure of Example 44 by substituting 2-[5-chloro-3-(N-{1-methylethyl}amino)-2-oxo-6-phenylhydropyrazinyl]acetic acid (EX-1D) for 2-[3-({2-[(tert-butoxy)carbonylamino]ethyl}amino)-5-chloro-2-oxo-6-phenylhydropyrazinyl]acetic acid, EX-58A was converted to the product which gave an m/z+1 of 482.

Example 59

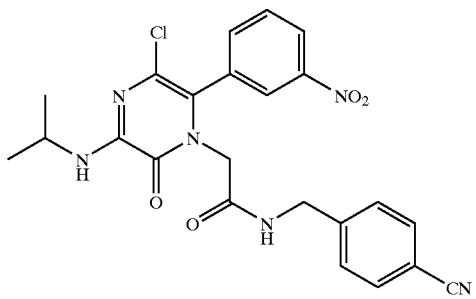

4-cyanobenzylamine hydrochloride (EX-59A) was prepared from 10 g (0.030 moles) of 4{N,N-bis-(tert-butoxycarbonyl)aminomethyl}benzonitrile, prepared following Synthetic Communication, 28(23), 4419–4429 (1998), by stirring it in 4N HCl Dioxane (75 ml). After 3 h, the solution was concentraed in vacuo and triturated with ether. The solid was collected by filtration and vacuum dried to yield 5 g (98%) of EX-59A as a white solid: $^1$H NMR (DMSO) d 8.68 (br s, 2H), 7.84 (m, 2H), 7.67 (m, 2H), 4.06 (s, 2H); HRMS (EI) calcd for $C_8H_8N_2$ 133.0766, found 133.0807

Using the procedure of Example 58, EX-59A was converted to the product which gave an m/z+1 of 481.

Using the procedures of Scheme 1, Scheme 2, and the Examples herein with suitable reagents, starting materials, and intermediates, additional pyrazinones of the present invention were prepared and these pryazinones are summarized in Table 3.

TABLE 3

Additional Substituted Pyrazinones of the Present Invention Prepared based on the Procedures of Scheme 1, Scheme 2, and Examples herein.

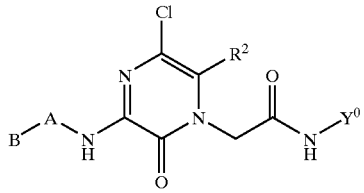

General Structure

| Ex. No. | R² | B—A— | Y° | MW (m/z + 1) |
|---|---|---|---|---|
| 60 | Phenyl | 2-phenylethyl | 4-amidinobenzyl | 487 |
| 61 | 3-Nitrophenyl | isopropyl | 4-(N-hydroxyamidino)benzyl | 514 |
| 62 | 3-Aminophenyl | isopropyl | 2-(4-amidinophenyl)ethyl | 482 |
| 63 | Phenyl | 2-phenylethyl | 2-(4-amidinophenyl)ethyl | 495 |
| 64 | 3-Carbomethoxyphenyl | isopropyl | 4-amidinobenzyl | 511 |
| 65 | 3-Carboxyphenyl | isopropyl | 4-amidinobenzyl | 497 |
| 66 | 2-hydroxyphenyl | cyclobutyl | 4-amidinobenzyl | 481 |
| 67 | 3-hydroxyphenyl | cyclobutyl | 4-amidinobenzyl | 481 |
| 68 | 3-acetamidophenyl | isopropyl | 2-(4-amidinophenyl)ethyl | 524 |

Example 69

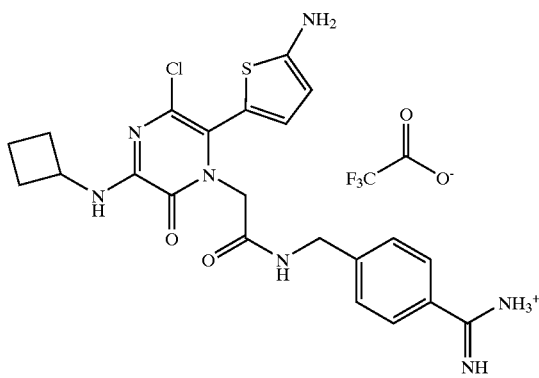

1-Benzyloxycarbonylmethyl-6-(5-bromothiophen-2-yl)-3,5-dichloro pyrazinone (EX-69A) was synthesized as described in the general schemes of the patent and as described, for example, specifically for EX-LB substituting 5-bromothiophenecarbaldehyde for benzaldehyde. EX-69A is a yellow crystalline solid: HPLC-MS (5 to 95% AcCN/6 min @ 1.0 mL/Min @ 254 nm @ 50° C.): retention time 4.38 min, M+Na⁺=494.9 for formula $C_{17}H_{11}BrCl_2N_2O_3SNa$; ¹H NMR (400 MHz, CDCl₃): d 4.62 (s, 2H), 5.19 (s, 2H), 6.79 (d, J=4.0 Hz, 1H), 7.00 (d, J=4.0 Hz, 1H) 7.32 (m, 2H), 7.37 (m, 3H); ¹³C NMR (101 MHz, CDCl₃): d 49.0, 68.1, 117.8, 126.5, 128.6, 128.7, 128.8, 130.1, 130.7, 132.0, 134.5, 147.8, 151.9, 166.2.

EX-69A (12.15 g, 25.75 mmol) was treated with cyclobutylamine (3.80 g, 53.52 mmol) in 250 ml toluene at room temperature for 4 hours. The toluene solution was washed with saturated ammonium chloride solution and dried over anhydrous MgSO₄. After removing the toluene, the pure product EX-69B was obtained as a yellow solid (13.05 g, 99%): HPLC-MS (5 to 95% AcCN/6 min @ 1.0 mL Min @ 254 nm @ 50° C.): retention time 4.90 min, M+H⁺=508.0 for formula $C_2H_{20}BrClN_3O_3S$.

Potassium phthalimide (4.56 g, 24.6 mmol) and CuI (18.0 g, 940.7 mmol) were mixed in 200 ml dimethylacetamide. The mixture was stirred at room temperature for 10 minutes. To this mixture was added compound EX-69B (12.0 g, 23.7 mmol). The resulting mixture was heated to 160° C. and stirred for 5 hours at an open air atmosphere. The reaction solution was filtered to remove all the insoluble solid and was concentrated via high vacuum distillation at a rotavapor. Aqueous work-up and silica gel flush chromatography yielded the pure product EX-69C as light yellow solid (6.8 g, 50%) with the des-bromo side product formation the reason for the low yield: HPLC-MS (5 to 95% AcCN/6 min @ 1.0 mL/Min @ 254 nm @ 50° C.): retention time 3.82 min, M+H⁺=575.5 for formula $C_{29}H_{24}ClN_4O_5S$; ¹H NMR (400 MHz, CDCl₃): d 1.69 (m, 2H), 1.92 (m, 2H), 2.36 (m, 2H), 4.45 (m, 1H), 4.49 (s, 2H), 5.07 (s, 2H), 6.54 (d, J=8.0 Hz, 1H), 6.75 (d, J=3.6 Hz, 1H), 7.17–7.25 (m, 7H), 7.50 (d, J=4.0 Hz, 1H), 7.71 (dd, J=2.8, 5.2 Hz, 2H), 7.85 (dd, J=2.8, 5.2 Hz, 2H); ¹³C NMR (101 MHz, CDCl₃): d 15.2, 30.9, 45.8, 47.4, 67.4, 114.7, 118.2, 123.9, 126.5, 128.28, 128.33, 128.36, 128.39, 128.42, 128.45, 129.5, 129.9, 131.1, 134.8, 134.9, 135.7, 148.5, 150.8, 165.2, 166.9.

EX-69C (0.55 g, 0.96 mmol) was treated with 1 ml hydrazine in 10 ml methanol and 5 ml dichloromethane for 4 hours. The reaction solution was acidified with 1N HCl and filtered to remove the solid by-product. Aqueous work-up yield the crude (90% pure) product EX-69D (0.49 g): HPLC-MS (5 to 95% AcCN/6 min @ 1.0 mL/Min @ 254 nm @ 50° C.): retention time 3.29 min, M+H⁺=445.3 for formula $C_{21}H_{22}ClN_4O_3S$.

EX-69D (0.48 g, 1.08 mmol) was mixed with Boc anhydride (0.28 g, 1.30 mmol), triethylamine (0.22 g, 2.16 mmol) and DMAP (12 mg, 0.1 mmol). The reaction mixture was stirred for 4 hours at room temperature. After an aqueous work-up, the crude product in 2 ml CH₃CN and 2 ml THF was treated with 2 ml 1M LiOH for 3 hours. Aqueous work-up yield the crude carboxylic acid EX-69E: HPLC-MS (5 to 95% AcCN/6 min (@ 1.0 mL/Min @ 254 nmr @ 50° C.): retention time 3.18 min, M+H⁺=455.4 for formula $C_{19}H_{24}ClN_4O_5S$.

EX-69E was coupled with the protected amidine, 4-(N-benzyloxycarbonylamidino)benzylamine hydrogen chloride salt, prepared using the procedure outlined Synthetic Communications, 28(23), 4419–4429 (1998) in the same way as described before using EDC, HOBt and DIEA in DMF to give the protected product EX-69F. EX-69F was purified by reverse phase HPLC using C18 column to give an off-white amorphous solid: HPLC-MS (5 to 95% AcCN/6 min @ 1.0 mL/Min @ 254 nm @ 50° C.): retention time 3.28 min, M+H$^+$=720.9 for formula $C_{35}H_{38}ClN_7O_6S$; $^1$H NMR (400 MHz, CDCl$_3$): d 1.49 (s, 9H), 1.80 (m, 2H), 2.03 (m, 2H), 2.45 (m, 2H), 4.3 (b, 2H), 4.49 (b, 3H), 5.07 (s, 2H), 6.66–6.78 (m, 2H), 7.0–7.18 (m, 2H), 7.33–7.47 (m, 5H).

EX-69F was converted to the product by hydrogenation as described before. After the hydrogenation, it was treated with HCl saturated methanol solution to remove the Boc group. The product was purified by reverse phase HPLC with a C18 column with amobile phase was 0.1% TFA in water and acetonitrile to give the product as a TFA salt and an off-white amorphous solid: HPLC-MS (5 to 95% AcCN/6 min @ 1.0 mL/Min @ 254 nm @ 50° C.): retention time 1.94 min, M+H$^+$=486.4 for formula $C_{22}H_{25}ClN_7O_2S$; $^1$H NMR (400 MHz, methanol-d$_4$): d 1.79 (m, 2H), 2.06 (m, 2H), 2.39 (m, 2H), 4.45 (s, 2H), 4.46 (m, 1H), 4.57 (s, 1H), 4.58 (s, 1H), 6.01 (d, J=4 Hz, 1H), 6.52 (m, 1H), 7.49 (d, J=8.4 Hz, 2H), 7.75 (m, 2H).

Sulfonyl analogs of pyrazinones wherein a sulfonyl is present as a replacement for the carbonyl of the acetamide at the N-I position of the pyrazinone can be prepared using Scheme 3: Sulfonyl Pyrazinone detailed below along with the specific Example 70.

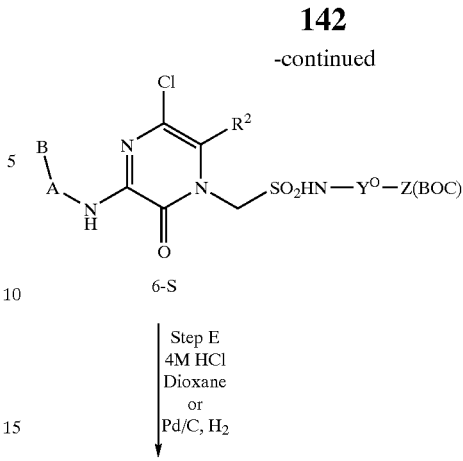

Example 70

Benzaldehyde (1 eq.) is added slowly by syringe to a solution of aminomethanesulfonic acid (1 eq.) in dichloromethane at room temperature. Trimethylsilyl cyanide (1 eq.) is added dropwise via syringe over a 10 minute period. The reaction is stirred for 4 hours at room temperature and then concentrated under reduced pressure. The residue is diluted with ethyl acetate, washed with brine, dried (MgSO$_4$), and concentrated. The residue is diluted with ethyl acetate (80 mL) and 9.9 M HCl (1.05 eq.) in ethanol is added (prepared by addition of 28.90 mL acetyl chloride to 41.0 mL cold ethanol), resulting in precipitation of the intermediate product EX-70A. The precipitate is collected by filtration, washed with ethyl ether, and dried to give pure product EX-70A.

To a suspension of 1 eq. of EX-70A in dry 1,2-dichlorobenzene (1.0 M) is added oxalyl chloride (4 eq.) with stirring at room temperature. The resulting suspension is heated at 100° C. for approximately 18 hours. The reaction is allowed to cool to room temperature and the volatiles are removed under reduced pressure. The remaining solution is passed through a silica gel column (hexane flush, followed by 50% ethyl acetate/hexanes). Concentration of the solution gives crude product EX-70B, which is purified by column chromatography.

Phenethylamine (3 eq.) is added to a solution of EX-70B (1 eq.) in ethyl acetate at room temperature. The resulting solution is heated at reflux for 18 hours. The solution is allowed to cool to room temperature, resulting in formation of a thick precipitate. The reaction mixture is diluted with ethyl acetate, washed with 0.5 N HCl, saturated NaHCO$_3$ and brine. The organic solution is dried (MgSO$_4$), filtered and concentrated to give the crude product. Recrystallization from ethyl acetate and hexanes affords pure product EX-70C.

A solution of 1 eq. of EX-70C in dichloromethane with several drops of dimethylformamide added is cooled to 0° C. Thionyl chloride (1.1 eq.) is added dropwise and the solution is slowly warmed to room temperature. After completion of the reaction, the volatile components are removed under reduced pressure and the product EX-70D is immediately used in the next step.

To the sulfonyl chloride EX-70D (1 eq.) in dichloromethane is added the amine, 4-(N-tert-butoxycarbonylamidino)benzylamine hydrochloride, in DMF with 5 eq. of N-methylmorpholine. After completion of the reaciton, polyaldehyde and/or polyamine resin (10 eq.) are added to remove any unreacted starting materials. The resins are filtered, rinsed with DMF/DCM (1:1) and the solvents are, removed under reduced pressure to give pure product EX-70E.

To 1 eq. of EX-70E is added 40 eq. of 4 M HCl/dioxane. The resulting solution is stirred at room temperature overnight. The solution is concentrated and the crude product is triturated from solvent to afford pure product.

Methylene analogs of pyrazinones wherein a methylene is present as a replacement for the carbonyl of the acetamide at the N-1 position of the pyrazinone can be prepared using Scheme 4: Methylene Pyrazinone detailed below along with the specific Example 71.

Scheme 4
Methylene Pyrazinone

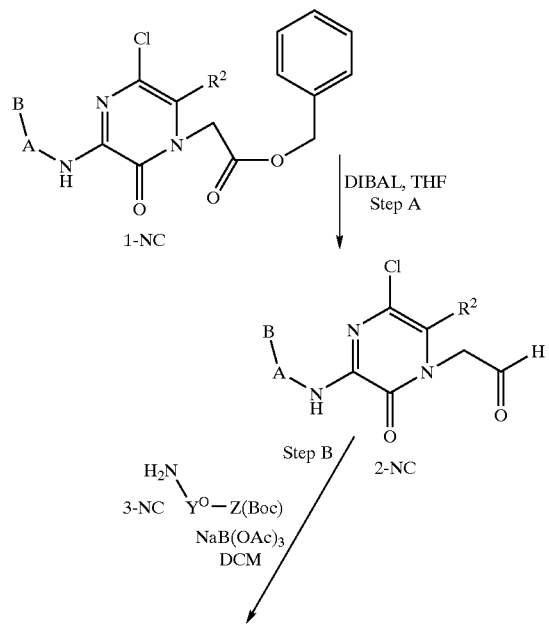

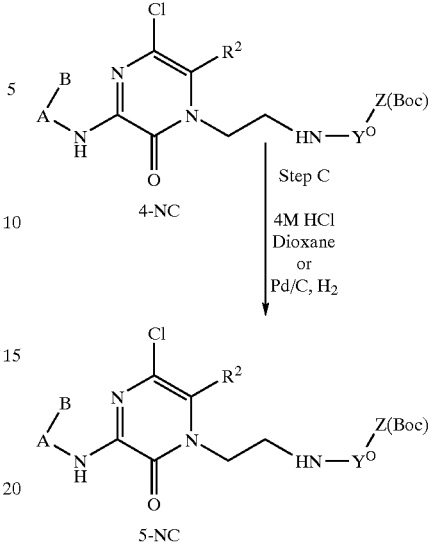

Example 71

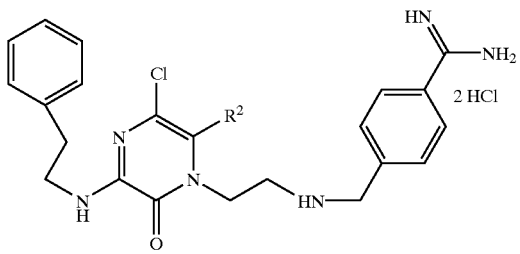

Diisobutylaluminum hydride (1.05 equiv.) is added over a period of 15 min to a cooled solution (−78° C.) of 1 eq. of 1-benzyloxycarbonylmethyl-5-chloro-6-phenyl-3-(2-phenylethylamino)pyrazinone in tetrahydrofuran. After stirring for 1 h at −78° C. the reaction is slowly quenched at −78° C. with cold methanol. The mixture is slowly poured into ice-cold 1N HCl and the aqueous mixture is extracted with ethyl acetate. The combined organic layers are washed with brine, dried with MgSO$_4$, filtered, and the solvents are removed under reduced pressure. The crude product is purified by column chromatography to afford purified product EX-71A.

Sodium triacetoxyborohydride (1.2 eq.) and a catalytic amount of acetic acid are added to a suspension of 1.0 eq. of EX-71A and 1.0 eq. of the amine, 4-(N-tert-butoxycarbonylamidino)benzylamine hydrochloride, in dichloromethane. The suspension quickly clears and becomes homogeneous. The reaction is stirred for several hours. The solution is cooled in an ice bath and basified with 1.0 N NaOH. The reaction mixture is diluted with dichloromethane and washed with brine. The organic solution is dried (MgSO$_4$), filtered and concentrated to give the crude product. The crude product is purified by silica gel chromatagraphy to afford purified product EX-71B.

To 1 eq. of EX-71B is added 40 eq. of 4 M HCl/dioxane. The resulting solution is stirred at room temperature overnight. The solution is concentrated and the crude product is triturated from ethyl ether to afford pure product.

General Robotics and Experimental Procedure for the Robotic Parallel Synthesis of a Series of Amides E-i and Z-i from A-i Scheme 5 specifically illustrates the derivatization of the scaffold A-i to afford the desired product D-i in a parallel array synthesis format. In a parallel array synthesis reaction block, individual reaction products were prepared in each of multiple reaction block vessels in a spatially addressed format. A solution of the desired scaffold A-i (limiting amount) in acetonitrile (ACN) was added to the reaction vessels followed by a three-fold stoichiometric excess solution of the primary amine B-i in acetonitrile. Excess primary amine was used as a base and to effect complete conversion of scaffold A-i to product C-i. The reaction mixtures were incubated at 70° C. for 16–20 h. After cooling to ambient temperature, each reaction vessel was charged with one mL of methanol and an excess (3–4 fold stoichiometric excess) of aqueous potassium hydroxide. The reaction block was shaken vertically for 14–20 h on an orbital shaker at ambient temperature. The contents of each reaction vessel were then acidified with aqueous HCl. Each reaction vessel was then opened, and the solutions were evaporated to dryness under $N_2$ and/or a Savant apparatus. Polyamine resin R-1 (10–15 fold stoichiometric excess) was added to the solid carboxylic acid followed by dichloromethane and water (10:1). The mixture was shaken laterally for 14–20 h on an orbital shaker at ambient temperature (rotating the vials at least once so each side of the vial was agitated for a minimum of 2 h). The desired product D-i was sequestered away from the reaction by-products and excess reactants as the insoluble adduct D-x. Simple filtration of the insoluble resin-adduct D-x and rinsing of the resin cake with DMF, DCM, MeOH, and DCM afforded the desired resin-bound product. After drying the resin under vacuum for 2 h, an excess of HCl/dioxane (7–8 fold stoichiometric excess based on the loading of amine functionality) along with dichloromethane was added to each reaction vessel to cleave the desired product D-i from the resin. The reaction block was shaken laterally for 2–20 h on an orbital shaker at ambient temperature. Simple filtration of the solution, rinsing of the resin cake with dimethylformamide/dichloromethane, and evaporation of the solvents afforded the desired product D-i in purified form.

Scheme 6 and Scheme 7 illustrate the conversion of the carboxylic acid-containing scaffold D-i to the desired amide product E-i in a parallel synthesis format. A unique scaffold D-i was added as a solution in dichloromethane/dimethylformamide to each reaction vessel. A solution of hydroxybenzotriazole B-2 in dichloromethane/dimethylformamide was added to each reaction vessel, followed by the polymer-bound carbodiimide reagent R-2 (1.5 fold stoichiometric excess). The parallel reaction block was agitated vertically on an orbital shaker for 30 min to 1 h. A limiting amount of the same amine B-3 (0.8 equivalents) in DMF, along with a 3 fold stoichiometric excess of NMM if the amine B-3 was a salt, was added to the unique contents of each vessel. The parallel reaction block was then agitated vertically on an orbital shaker for 2–3 h at ambient temperature. An excess of the amine-functionalized resin R-1 and aldehyde resin R-3, along with dichloromethane solvent were added to each reaction vessel. The resin-charged reaction block was shaken vertically for 2 h on an orbital shaker at ambient temperature. The amine-containing resin R-1 sequestered B-2 and any remaining D-i as their resin-bound adducts, B-4 and D-2, respectively. The aldehyde-containing resin R-3 sequestered any unreacted B-3 as its resin-bound adduct R-5. Filtration of the insoluble resins and resin adducts R-1, R-2, R-3, R-4, R-5, B-4, and D-2 and subsequent rinsing of the vessel resin-bed with dichloromethane/dimethylformamide afforded filtrates containing the purified products E-i. Concentration of the filtrates afforded the purified products E-i, which were weighed and analyzed by LC/MS.

For those amines B-3 which contain a protecting group, a final deprotection step was required after the coupling reaction (Scheme 8). The residues E-i were dissolved in methanol, Pd/C was added, and the reaction mixtures were stirred under 10 psi of $H_2$ for 16–20 h. The mixtures were filtered through Celite, rinsed with methanol and concentrated to afford pure products Z-i, which were weighed and analyzed by LC/MS. If necessary, the products were purified by reverse-phase HPLC. Conversely, the deprotection step was done, as needed, in the presence of ammonium formate (5 fold stoichiometric excess) in place of the 10 psi of $H_2$.

A third method of deprotection uses TMSI generated in situ. The residues E-i were dissolved in acetonitrile. Sodium iodide and TMSCl (5 fold stoichiometric excess of each) were added, and the reaction mixtures were agitated vertically at 55° C. for 14–20 h. Methanol and (N,N-dimethyl) aminomethylpolystyrene resin were added to each vessel, and the mixtures were agitated for another 3 h. The mixtures were filtered through Celite, rinsed with acetonitrile and concentrated to afford products Z-i, which were weighed and analyzed by LC/MS. If necessary, the products were purified by reverse-phase HPLC.

Scheme 5
General RoboticSynthesis

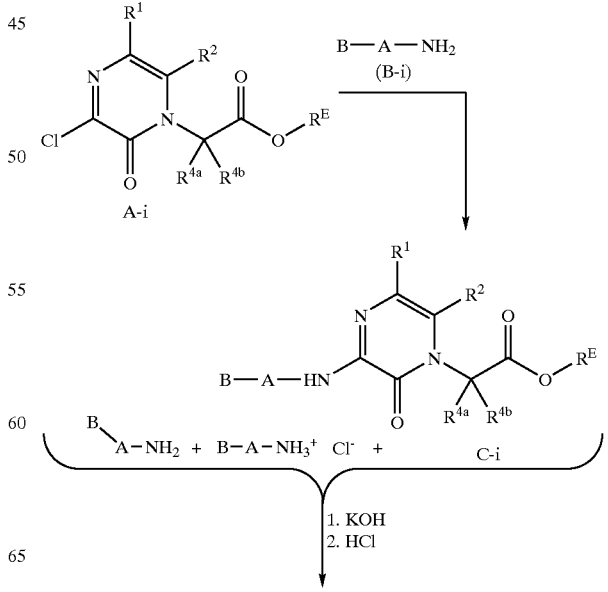

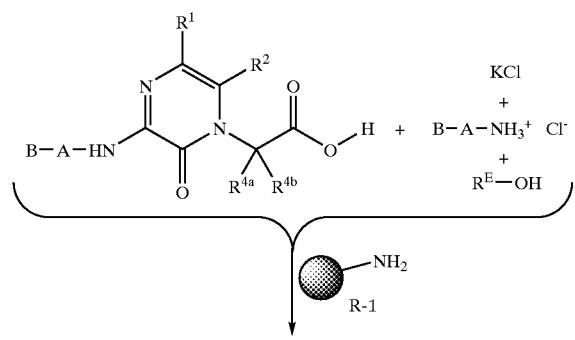
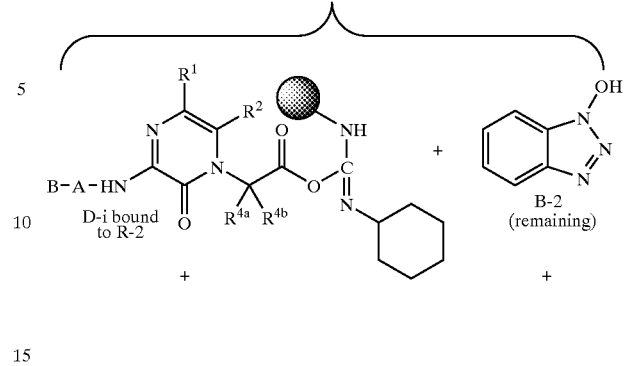
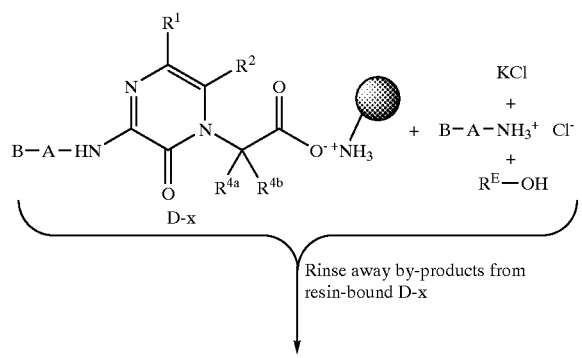
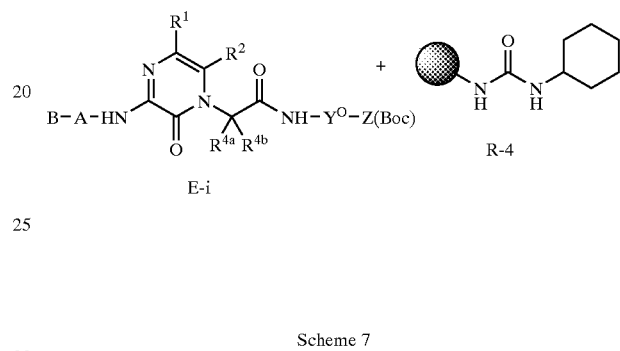
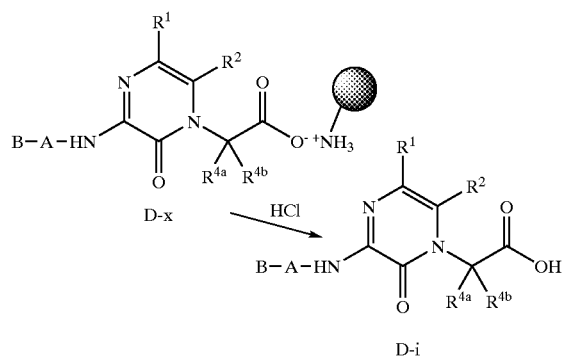
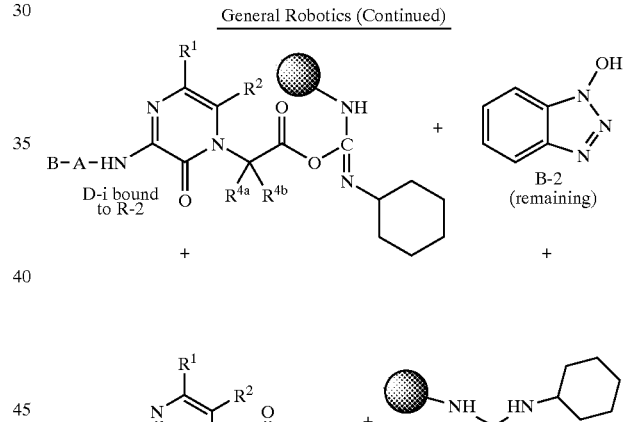
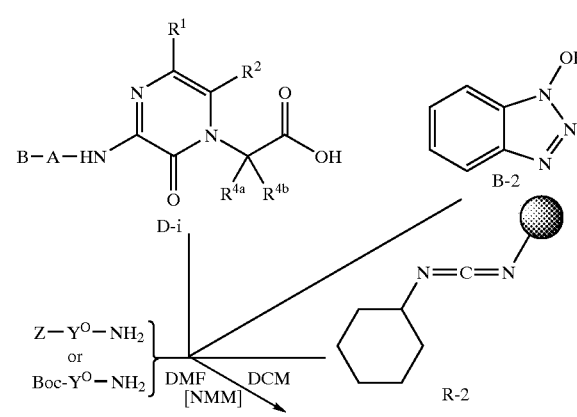
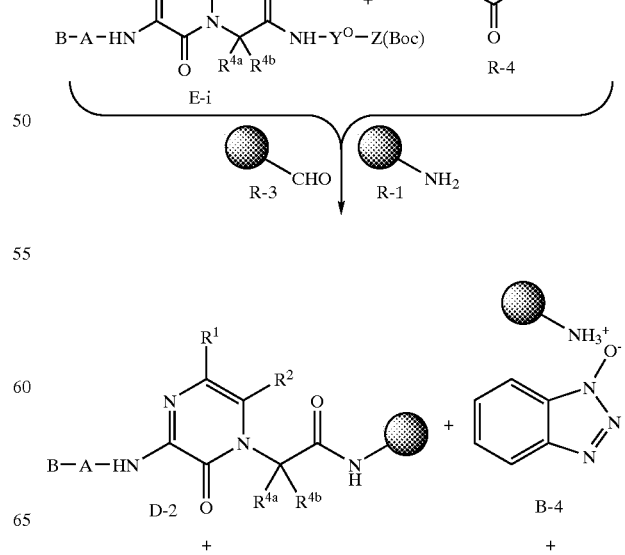

149

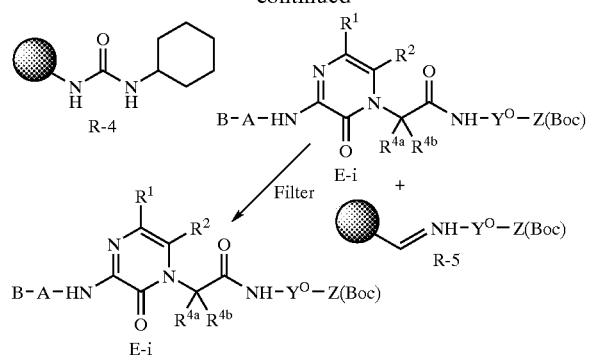

Scheme 8
General Robotic Synthesis (Concluded)

150 the actual structural unit bound to the resin for each) are summarized below as follows:

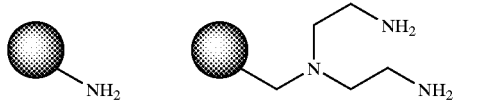

R-1 Reference: Prepared as reported in J. J. Parlow, D. A. Mischke, and S. S. Woodard, *J. Organic Chemistry*, 62, 5908–5919 (1997)

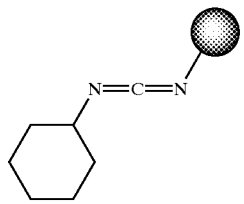

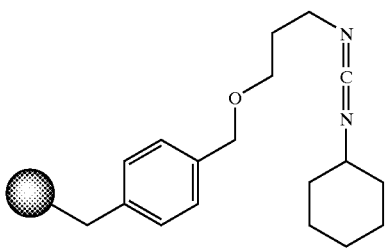

R-2 Reference: Polystyrene bound N-cyclohexylcarbodiimide (Argonaut Catalog Number 800371

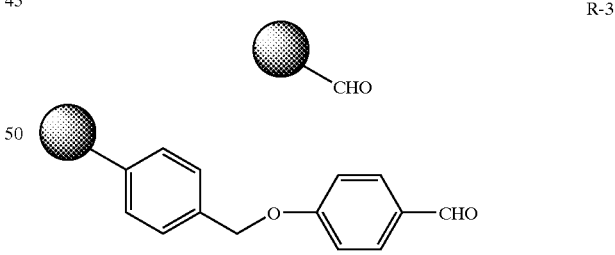

R-3 Reference: Polystyrene bound benzaldehyde Novabiochem Catalog Number 01-640182

Although Schemes 5, 6, 7, and 8 describe the use of parallel array chemical library technology to prepare compounds of general formulae D-i, E-i and Z-i, it is noted that one with ordinary skill in the art of classical synthetic organic chemistry would be able to prepare D-i, E-i, and Z-i by conventional means (one compound prepared at a time in conventional glassware and purified by conventional means such as chromatography and/or crystallization).

The various functionalized resins utilized to prepare and purify parallel reaction mixtures, their source commercially or in the scientific literature, and the three representations (Ie. the R number, an abbreviated functional structure, and The specific compounds prepared, by using the General Robotics and Experimental Procedure, Schemes 5 through 8, and general synthetic methods and processes disclosed herein, are listed below in Tables 4 through Table 7. Tables 4 through Table 7 further summarize the mass spectral characterization data that confirmed the indicated structure for each compound of the present invention disclosed in these tables.

TABLE 4

Structures of Pyrazinones Prepared by General Robotic and Experimental Procedures

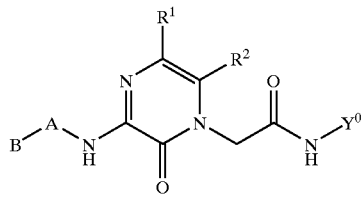

General Structure

| Ex. No. | R² | B—A— | Y⁰ | R¹ | MW (m/z + 1) |
|---|---|---|---|---|---|
| 73 | 5-amino-2-fluorophenyl | isopropyl | 4-amidino-2-fluorobenzyl | Cl | 504 |
| 74 | 2-chloro-5-pyridyl | isopropyl | 4-amidino-2-fluorobenzyl | Cl | 506 |
| 75 | 3-pyridyl | isopropyl | 4-amidinobenzyl | Cl | 454 |
| 76 | 5-amino-2-methylthiophenyl | isopropyl | 4-amidinobenzyl | Cl | 515 |
| 77 | 3-nitrophenyl | 2-phenylethyl | 4-amidinobenzyl | Cl | 560.2 |
| 78 | 2-methylphenyl | 2-phenylethyl | 4-amidinobenzyl | Cl | 529.4 |
| 79 | 4-methylphenyl | 2-phenylethyl | 4-amidinobenzyl | Cl | 529.3 |
| 80 | 1-naphthyl | 2-phenylethyl | 4-amidinobenzyl | Cl | 565.3 |
| 81 | 3-methylphenyl | 2-phenylethyl | 4-amidinobenzyl | Cl | 529.5 |
| 82 | 2-naphthyl | 2-phenylethyl | 4-amidinobenzyl | Cl | 564.9 |
| 83 | 3-methylphenyl | 2-phenylethyl | 4-amidinobenzyl | H | 495.8 |
| 84 | 3-methylphenyl | 2-phenylethyl | 4-amidinobenzyl | H | 495.5 |
| 85 | 3-methylphenyl | 2-phenylethyl | 4-amidinobenzyl | H | 495.4 |
| 86 | 3-aminophenyl | 2-phenylethyl | 4-amidinobenzyl | Cl | 530.3 |
| 87 | 3-aminophenyl | 2-(3-chlorophenyl)ethyl | 4-amidinobenzyl | Cl | 563.9 |
| 88 | 3-aminophenyl | benzyl | 4-amidinobenzyl | Cl | 516.2 |
| 89 | 3-aminophenyl | cyclobutyl | 2-phenylethyl | Cl | 452.3 |
| 90 | 3-aminophenyl | cyclobutyl | 4-amidinobenzyl | Cl | 480.5 |
| 91 | 3-aminophenyl | benzyl | 5-guamdino-1-oxo-1-(2-thiazolyl)-2-pentyl | Cl | 608.4 |
| 92 | 3-aminophenyl | cyclobutyl | 4-amidinobenzyl | H | 446.2 |
| 93 | 3-aminophenyl | t-butyl | 4-amidinobenzyl | Cl | 482 |
| 94 | 3-aminophenyl | N,N-dimethylamino | 4-amidinobenzyl | Cl | 469.2 |
| 95 | 3-(N-methylamino)phenyl | 2-phenylethyl | 4-amidinobenzyl | Cl | 543.9 |
| 96 | 3-(N-methylamino)phenyl | isopropyl | 4-amidinobenzyl | Cl | 481.6 |
| 97 | 2-methyl-3-aminophenyl | isopropyl | 4-aniidinobenzyl | Cl | 482.2 |
| 98 | 2-methyl-3-aminophenyl | isopropyl | 4-amidinobenzyl | H | 448.8 |
| 99 | 3-aminophenyl | cyclobutyl | benzyl | Cl | 438.4 |

TABLE 5

Structures of Pyrazinones Prepared by General Robotic and Experimental Procedures

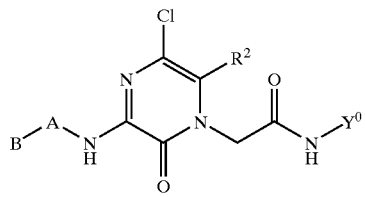

General Structure

| Ex. No. | R² | B—A— | Y⁰ | MW (m/z + 1) |
|---|---|---|---|---|
| E-0001 | methyl | benzyl | 2-(4-pyridyl)ethyl | 412 |
| E-0002 | methyl | 2-phenylethyl | 2-(4-pyridyl)ethyl | 426 |
| E-0003 | methyl | 2-(3-chlorophenyl)ethyl | 2-(4-pyridyl)ethyl | 460 |
| E-0004 | methyl | 2-(4-chlorophenyl)ethyl | 2-(4-pyridyl)ethyl | 460 |
| E-0005 | methyl | 2-(3-pyridyl)ethyl | 2-(4-pyridyl)ethyl | 427 |
| E-0006 | methyl | 2-(4-pyridyl)ethyl | 2-(4-pyridyl)ethyl | 427 |
| E-0007 | methyl | 2-(4-morpholinyl)ethyl | 2-(4-pyridyl)ethyl | 435 |
| E-0008 | methyl | 4-pyridylmethyl | 2-(4-pyridyl)ethyl | 413 |
| E-0009 | phenyl | benzyl | 2-(4-pyridyl)ethyl | 474 |
| E-0010 | phenyl | 2-phenylethyl | 2-(4-pyridyl)ethyl | 488 |
| E-0011 | phenyl | 2-(3-chlorophenyl)ethyl | 2-(4-pyridyl)ethyl | 522 |

TABLE 5-continued

Structures of Pyrazinones Prepared by General Robotic and Experimental Procedures

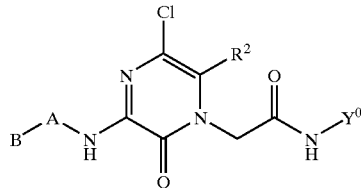

General Structure

| Ex. No. | R² | B—A— | Y⁰ | MW (m/z + 1) |
|---|---|---|---|---|
| E-0012 | phenyl | 2-(4-chlorophenyl)ethyl | 2-(4-pyridyl)ethyl | 522 |
| E-0013 | phenyl | 2-(3-pyridyl)ethyl | 2-(4-pyridyl)ethyl | 489 |
| E-0014 | phenyl | 2-(4-pyridyl)ethyl | 2-(4-pyridyl)ethyl | 489 |
| E-0015 | phenyl | 2-(4-morpholinyl)ethyl | 2-(4-pyridyl)ethyl | 497 |
| E-0016 | phenyl | 4-pyridylmethyl | 2-(4-pyridyl)ethyl | 475 |
| E-0017 | 4-chlorophenyl | benzyl | 2-(4-pyridyl)ethyl | 508 |
| E-0018 | 4-chlorophenyl | 2-phenylethyl | 2-(4-pyridyl)ethyl | 522 |
| E-0019 | 4-chlorophenyl | 2-(3-chlorophenyl)-2-ethyl | (4-pyridyl)ethyl | 557 |
| E-0020 | 4-chlorophenyl | 2-(4-chlorophenyl)-2-ethyl | (4-pyridyl)ethyl | 557 |
| E-0021 | 4-chlorophenyl | 2-(3-pyridyl)ethyl | 2-(4-pyridyl)ethyl | 523 |
| E-0022 | 4-chlorophenyl | 2-(4-pyridyl)ethyl | 2-(4-pyridyl)ethyl | 523 |
| E-0023 | 4-chlorophenyl | 2-(4-morpholinyl)ethyl | 2-(4-pyridyl)ethyl | 531 |
| E-0024 | 4-chlorophenyl | 4-pyridylmethyl | 2-(4-pyridyl)ethyl | 509 |
| E-0025 | 4-chlorophenyl | benzyl | 2-(4-pyridyl)ethyl | 508 |
| E-0026 | 4-chlorophenyl | 2-phenylethyl | 2-(4-pyridyl)ethyl | 522 |
| E-0027 | 4-chlorophenyl | 2-(3-chlorophenyl)ethyl | 2-(4-pyridyl)ethyl | 557 |
| E-0028 | 4-chlorophenyl | 2-(4-chlorophenyl)ethyl | 2-(4-pyridyl)ethyl | 557 |
| E-0029 | 4-chlorophenyl | 2-(3-pyridyl)ethyl | 2-(4-pyridyl)ethyl | 523 |
| E-0030 | 4-chlorophenyl | 2-(4-pyridyl)ethyl | 2-(4-pyridyl)ethyl | 523 |
| E-0031 | 4-chlorophenyl | 2-(4-morpholinyl)ethyl | 2-(4-pyridyl)ethyl | 531 |
| E-0032 | 4-chlorophenyl | 4-pyridylmethyl | 2-(4-pyridyl)ethyl | 509 |
| E-0033 | 4-methoxyphenyl | benzyl | 2-(4-pyridyl)ethyl | 504 |
| E-0034 | 4-methoxyphenyl | 2-phenylethyl | 2-(4-pyridyl)ethyl | 518 |
| E-0035 | 4-methoxyphenyl | 2-(3-chlorophenyl)ethyl | 2-(4-pyridyl)ethyl | 552 |
| E-0036 | 4-methoxyphenyl | 2-(4-chlorophenyl)ethyl | 2-(4-pyridyl)ethyl | 552 |
| E-0037 | 4-methoxyphenyl | 2-(3-pyridyl)ethyl | 2-(4-pyridyl)ethyl | 519 |
| E-0038 | 4-methoxyphenyl | 2-(4-pyridyl)ethyl | 2-(4-pyridyl)ethyl | 519 |
| E-0039 | 4-methoxyphenyl | 2-(4-morpholinyl)ethyl | 2-(4-pyridyl)ethyl | 527 |
| E-0040 | 4-methoxyphenyl | 4-pyridylmethyl | 2-(4-pyridyl)ethyl | 505 |
| E-0041 | 3,4-methylenedioxyphenyl | benzyl | 2-(4-pyridyl)ethyl | 518 |
| E-0042 | 3,4-methylenedioxyphenyl | 2-phenylethyl | 2-(4-pyridyl)ethyl | 532 |
| E-0043 | 3,4-methylenedioxyphenyl | 2-(3-chlorophenyl)ethyl | 2-(4-pyridyl)ethyl | 566 |
| E-0044 | 3,4-methylenedioxyphenyl | 2-(4-chlorophenyl)ethyl | 2-(4-pyridyl)ethyl | 566 |
| E-0045 | 3,4-methylenedioxyphenyl | 2-(3-pyridyl)ethyl | 2-(4-pyridyl)ethyl | 533 |
| E-0046 | 3,4-methylenedioxyphenyl | 2-(4-pyridyl)ethyl | 2-(4-pyridyl)ethyl | 533 |
| E-0047 | 3,4-methylenedioxyphenyl | 2-(4-morpholinyl)ethyl | 2-(4-pyridyl)ethyl | 541 |
| E-0048 | 3,4-methylenedioxyphenyl | 4-pyridylmethyl | 2-(4-pyridyl)ethyl | 519 |
| E-0049 | 4-biphenyl | benzyl | 2-(4-pyridyl)ethyl | 550 |
| E-0050 | 4-biphenyl | 2-phenylethyl | 2-(4-pyridyl)ethyl | 564 |
| E-0051 | 4-biphenyl | 2-(3-chlorophenyl)ethyl | 2-(4-pyridyl)ethyl | 599 |
| E-0052 | 4-biphenyl | 2-(4-chlorophenyl)ethyl | 2-(4-pyridyl)ethyl | 599 |
| E-0053 | 4-biphenyl | 2-(3-pyridyl)ethyl | 2-(4-pyridyl)ethyl | 565 |
| E-0054 | 4-biphenyl | 2-(4-pyridyl)ethyl | 2-(4-pyridyl)ethyl | 565 |
| E-0055 | 4-biphenyl | 2-(4-morpholinyl)ethyl | 2-(4-pyridyl)ethyl | 573 |
| E-0056 | 4-biphenyl | 4-pyridylmethyl | 2-(4-pyridyl)ethyl | 551 |
| E-0057 | benzyl | benzyl | 2-(4-pyridyl)ethyl | 488 |
| E-0058 | benzyl | 2-phenylethyl | 2-(4-pyridyl)ethyl | 502 |
| E-0059 | benzyl | 2-(3-chlorophenyl)ethyl | 2-(4-pyridyl)ethyl | 536 |
| E-0060 | benzyl | 2-(4-chlorophenyl)ethyl | 2-(4-pyridyl)ethyl | 536 |
| E-0061 | benzyl | 2-(3-pyridyl)ethyl | 2-(4-pyridyl)ethyl | 503 |
| E-0062 | benzyl | 2-(4-pyridyl)ethyl | 2-(4-pyridyl)ethyl | 503 |
| E-0063 | benzyl | 2-(4-morpholinyl)ethyl | 2-(4-pyridyl)ethyl | 511 |
| E-0064 | benzyl | 4-pyridylmethyl | 2-(4-pyridyl)ethyl | 489 |
| E-0065 | 2-phenylethyl | benzyl | 2-(4-pyridyl)ethyl | 502 |
| E-0066 | 2-phenylethyl | 2-phenylethyl | 2-(4-pyridyl)ethyl | 516 |
| E-0067 | 2-phenylethyl | 2-(3-chlorophenyl)ethyl | 2-(4-pyridyl)ethyl | 550 |
| E-0068 | 2-phenylethyl | 2-(4-chlorophenyl)ethyl | 2-(4-pyridyl)ethyl | 550 |
| E-0069 | 2-phenylethyl | 2-(3-pyridyl)ethyl | 2-(4-pyridyl)ethyl | 517 |
| E-0070 | 2-phenylethyl | 2-(4-pyridyl)ethyl | 2-(4-pyridyl)ethyl | 517 |

TABLE 5-continued

Structures of Pyrazinones Prepared by General Robotic and Experimental Procedures

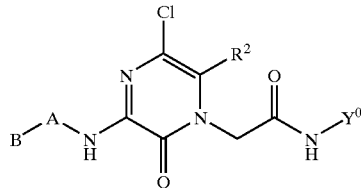

General Structure

| Ex. No. | R² | B—A— | Y⁰ | MW (m/z + 1) |
|---|---|---|---|---|
| E-0071 | 2-phenylethyl | 2-(4-morpholinyl)ethyl | 2-(4-pyridyl)ethyl | 525 |
| E-0072 | 2-phenylethyl | 4-pyridylmethyl | 2-(4-pyridyl)ethyl | 503 |
| E-0073 | 3-chlorophenyl | benzyl | 2-(4-pyridyl)ethyl | 508 |
| E-0074 | 3-chlorophenyl | benzyl | 2-(3-pyridyl)ethyl | 508 |
| E-0075 | 3-chlorophenyl | benzyl | 4-piperidinylmethyl | 573 |
| E-0076 | 3-chlorophenyl | 2-phenylethyl | 2-(4-pyridyl)ethyl | 522 |
| E-0077 | 3-chlorophenyl | 2-phenylethyl | 2-(3-pyridyl)ethyl | 522 |
| E-0078 | 3-chlorophenyl | 2-phenylethyl | 4-piperidinylmethyl | 587 |
| E-0079 | 3-chlorophenyl | 2-(3-chlorophenyl)ethyl | 2-(4-pyridyl)ethyl | 557 |
| E-0080 | 3-chlorophenyl | 2-(3-chlorophenyl)ethyl | 2-(3-pyridyl)ethyl | 557 |
| E-0081 | 3-chlorophenyl | 2-(3-chlorophenyl)ethyl | 4-piperidinylmethyl | 622 |
| E-0082 | 3-chlorophenyl | 2-(4-chlorophenyl)ethyl | 2-(4-pyridyl)ethyl | 557 |
| E-0083 | 3-chlorophenyl | 2-(4-chlorophenyl)ethyl | 2-(3-pyridyl)ethyl | 557 |
| E-0084 | 3-chlorophenyl | 2-(4-chlorophenyl)ethyl | 4-piperidinylmethyl | 622 |
| E-0085 | 3-chlorophenyl | benzyl | 2-(4-pyridyl)ethyl | 508 |
| E-0086 | 3-chlorophenyl | benzyl | 2-(3-pyridyl)ethyl | 508 |
| E-0087 | 3-chlorophenyl | benzyl | 4-piperidinylmethyl | 573 |
| E-0088 | 3-chlorophenyl | 2-phenylethyl | 2-(4-pyridyl)ethyl | 522 |
| E-0089 | 3-chlorophenyl | 2-phenylethyl | 2-(3-pyridyl)ethyl | 522 |
| E-0090 | 3-chlorophenyl | 2-phenylethyl | 4-piperidinylmethyl | 587 |
| E-0091 | 3-chlorophenyl | 2-(3-chlorophenyl)ethyl | 2-(4-pyridyl)ethyl | 557 |
| E-0092 | 3-chlorophenyl | 2-(3-chlorophenyl)ethyl | 2-(3-pyridyl)ethyl | 557 |
| E-0093 | 3-chlorophenyl | 2-(3-chlorophenyl)ethyl | 4-piperidinylmethyl | 622 |
| E-0094 | 3-chlorophenyl | 2-(4-chlorophenyl)ethyl | 2-(4-pyridyl)ethyl | 557 |
| E-0095 | 3-chlorophenyl | 2-(4-chlorophenyl)ethyl | 2-(3-pyridyl)ethyl | 557 |
| E-0096 | 3-chlorophenyl | 2-(4-chlorophenyl)ethyl | 4-piperidinylmethyl | 622 |
| E-0097 | 4-methoxyphenyl | benzyl | 2-(4-pyridyl)ethyl | 504 |
| E-0098 | 4-methoxyphenyl | benzyl | 2-(3-pyridyl)ethyl | 504 |
| E-0099 | 4-methoxyphenyl | benzyl | 4-piperidinylmethyl | 569 |
| E-0100 | 4-methoxyphenyl | 2-phenylethyl | 2-(4-pyridyl)ethyl | 518 |
| E-0101 | 4-methoxyphenyl | 2-phenylethyl | 2-(3-pyridyl)ethyl | 518 |
| E-0102 | 4-methoxyphenyl | 2-phenylethyl | 4-piperidinylmethyl | 583 |
| E-0103 | 4-methoxyphenyl | 2-(3-chlorophenyl)ethyl | 2-(4-pyridyl)ethyl | 552 |
| E-0104 | 4-methoxyphenyl | 2-(3-chlorophenyl)ethyl | 2-(3-pyridyl)ethyl | 552 |
| E-0105 | 4-methoxyphenyl | 2-(3-chlorophenyl)ethyl | 4-piperidinylmethyl | 617 |
| E-0106 | 4-methoxyphenyl | 2-(4-chlorophenyl)ethyl | 2-(4-pyridyl)ethyl | 552 |
| E-0107 | 4-methoxyphenyl | 2-(4-chlorophenyl)ethyl | 2-(3-pyridyl)ethyl | 552 |
| E-0108 | 4-methoxyphenyl | 2-(4-chlorophenyl)ethyl | 4-piperidinylmethyl | 617 |
| E-0109 | 4-biphenyl | benzyl | 2-(4-pyridyl)ethyl | 550 |
| E-0110 | 4-biphenyl | benzyl | 2-(3-pyridyl)ethyl | 550 |
| E-0111 | 4-biphenyl | beuzyl | 4-piperidinylmethyl | 615 |
| E-0112 | 4-biphenyl | 2-phenylethyl | 2-(4-pyridyl)ethyl | 564 |
| E-0113 | 4-biphenyl | 2-phenylethyl | 2-(3-pyridyl)ethyl | 564 |
| E-0114 | 4-biphenyl | 2-phenylethyl | 4-piperidinylmethyl | 629 |
| E-0115 | 4-biphenyl | 2-(3-chlorophenyl)ethyl | 2-(4-pyridyl)ethyl | 599 |
| E-0116 | 4-biphenyl | 2-(3-chlorophenyl)ethyl | 2-(3-pyridyl)ethyl | 599 |
| E-0117 | 4-biphenyl | 2-(3-chlorophenyl)ethyl | 4-piperidinylmethyl | 663 |
| E-0118 | 4-biphenyl | 2-(4-chlorophenyl)ethyl | 2-(4-pyridyl)ethyl | 599 |
| E-0119 | 4-biphenyl | 2-(4-chlorophenyl)ethyl | 2-(3-pyridyl)ethyl | 599 |
| E-0120 | 4-biphenyl | 2-(4-chlorophenyl)ethyl | 4-piperidinylmethyl | 663 |
| E-0121 | methyl | benzyl | 4-piperidinylmethyl | 477 |
| E-0122 | methyl | 2-phenylethyl | 4-piperidinylmethyl | 491 |
| E-0123 | methyl | 2-(3-chlorophenyl)ethyl | 4-piperidinylmethyl | 525 |
| E-0124 | methyl | 2-(4-chlorophenyl)ethyl | 4-piperidinylmethyl | 525 |
| E-0125 | methyl | 2-(3-pyridyl)ethyl | 4-piperidinylmethyl | 528 |
| E-0126 | methyl | 2-(4-pyridyl)ethyl | 4-piperidinylmethyl | 528 |
| E-0127 | methyl | 2-(4-morpholinyl)ethyl | 4-piperidinylmethyl | 536 |
| E-0128 | methyl | 2-(1-methylimidazol-4-yl)ethyl | 4-piperidinylmethyl | 531 |
| E-0129 | methyl | 2-(1-methylimidazol-5-yl)ethyl | 4-piperidinylmethyl | 531 |

TABLE 5-continued

Structures of Pyrazinones Prepared by General Robotic and Experimental Procedures

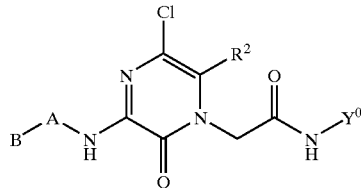

General Structure

| Ex. No. | R² | B—A— | Y⁰ | MW (m/z + 1) |
|---|---|---|---|---|
| E-0130 | methyl | 4-pyridylmethyl | 4-piperidinylmethyl | 514 |
| E-0131 | phenyl | benzyl | 4-piperidinylmethyl | 539 |
| E-0132 | phenyl | 2-phenylethyl | 4-piperidinylmethyl | 553 |
| E-0133 | phenyl | 2-(3-chlorophenyl)ethyl | 4-piperidinylmethyl | 587 |
| E-0134 | phenyl | 2-(4-chlorophenyl)ethyl | 4-piperidinylmethyl | 587 |
| E-0135 | phenyl | 2-(3-pyridyl)ethyl | 4-piperidinylmethyl | 590 |
| E-0136 | phenyl | 2-(4-pyridyl)ethyl | 4-piperidinylmethyl | 590 |
| E-0137 | phenyl | 2-(4-morpholinyl)ethyl | 4-piperidinylmethyl | 598 |
| E-0138 | phenyl | 2-(1-methylimidazol-4-yl)ethyl | 4-piperidinylmethyl | 593 |
| E-0139 | phenyl | 2-(1-methylimidazol-5-yl)ethyl | 4-piperidinylmethyl | 593 |
| E-0140 | phenyl | 4-pyridylmethyl | 4-piperidinylmethyl | 576 |
| E-0141 | 4-chlorophenyl | benzyl | 4-piperidinylmethyl | 573 |
| E-0142 | 4-chlorophenyl | 2-phenylethyl | 4-piperidinylmethyl | 587 |
| E-0143 | 4-chlorophenyl | 2-(3-chlorophenyl)ethyl | 4-piperidinylmethyl | 622 |
| E-0144 | 4-chlorophenyl | 2-(4-chlorophenyl)ethyl | 4-piperidinylmethyl | 622 |
| E-0145 | 4-chlorophenyl | 2-(3-pyridyl)ethyl | 4-piperidinylmethyl | 625 |
| E-0146 | 4-chlorophenyl | 2-(4-pyridyl)ethyl | 4-piperidinylmethyl | 625 |
| E-0147 | 4-chlorophenyl | 2-(4-morpholinyl)ethyl | 4-piperidinylmethyl | 633 |
| E-0148 | 4-chlorophenyl | 2-(1-methylimidazol-4-yl)ethyl | 4-piperidinylmethyl | 628 |
| E-0149 | 4-chlorophenyl | 2-(1-methylimidazol-5-yl)ethyl | 4-piperidinylmethyl | 628 |
| E-0150 | 4-chlorophenyl | 4-pyridylmethyl | 4-piperidinylmethyl | 611 |
| E-0151 | 4-chlorophenyl | benzyl | 4-piperidinylmethyl | 573 |
| E-0152 | 4-chlorophenyl | 2-phenylethyl | 4-piperidinylmethyl | 587 |
| E-0153 | 4-chlorophenyl | 2-(3-chlorophenyl)ethyl | 4-piperidinylmethyl | 622 |
| E-0154 | 4-chlorophenyl | 2-(4-chlorophenyl)ethyl | 4-piperidinylmethyl | 622 |
| E-0155 | 4-chlorophenyl | 2-(3-pyridyl)ethyl | 4-piperidinylmethyl | 625 |
| E-0156 | 4-chlorophenyl | 2-(4-pyridyl)ethyl | 4-piperidinylmethyl | 625 |
| E-0157 | 4-chlorophenyl | 2-(4-morpholinyl)ethyl | 4-piperidinylmethyl | 633 |
| E-0158 | 4-chlorophenyl | 2-(1-methylimidazol-4-yl)ethyl | 4-piperidinylmethyl | 628 |
| E-0159 | 4-chlorophenyl | 2-(1-methylimidazol-5-yl)ethyl | 4-piperidinylmethyl | 628 |
| E-0160 | 4-chlorophenyl | 4-pyridylmethyl | 4-piperidinylmethyl | 611 |
| E-0161 | 4-methoxyphenyl | benzyl | 4-piperidinylmethyl | 569 |
| E-0162 | 4-methoxyphenyl | 2-phenylethyl | 4-piperidinylmethyl | 583 |
| E-0163 | 4-methoxyphenyl | 2-(3-chlorophenyl)ethyl | 4-piperidinylmethyl | 617 |
| E-0164 | 4-methoxyphenyl | 2-(4-chlorophenyl)ethyl | 4-piperidinylmethyl | 617 |
| E-0165 | 4-methoxyphenyl | 2-(3-pyridyl)ethyl | 4-piperidinylmethyl | 620 |
| E-0166 | 4-methoxyphenyl | 2-(4-pyridyl)ethyl | 4-piperidinylmethyl | 620 |
| E-0167 | 4-methoxyphenyl | 2-(4-morpholinyl)ethyl | 4-piperidinylmethyl | 628 |
| E-0168 | 4-methoxyphenyl | 2-(1-methylimidazol-4-yl)ethyl | 4-piperidinylmethyl | 623 |
| E-0169 | 4-methoxyphenyl | 2-(1-methylimidazol-5-yl)ethyl | 4-piperidinylmethyl | 623 |
| E-0170 | 4-methoxyphenyl | 4-pyridylmethyl | 4-piperidinylmethyl | 606 |
| E-0171 | 3,4-methylene-dioxyphenyl | benzyl | 4-piperidinylmethyl | 583 |
| E-0172 | 3,4-methylenedioxyphenyl | 2-phenylethyl | 4-piperidinylmethyl | 597 |
| E-0173 | 3,4-methylenedioxyphenyl | 2-(3-chlorophenyl)ethyl | 4-piperidinylmethyl | 631 |
| E-0174 | 3,4-methylenedioxyphenyl | 2-(4-chlorophenyl)ethyl | 4-piperidinylmethyl | 631 |
| E-0175 | 3,4-methylenedioxyphenyl | 2-(3-pyridyl)ethyl | 4-piperidinylmethyl | 634 |
| E-0176 | 3,4-methylenedioxyphenyl | 2-(4-pyridyl)ethyl | 4-piperidinylmethyl | 634 |
| E-0177 | 3,4-methylenedioxyphenyl | 2-(4-morpholinyl)ethyl | 4-piperidinylmethyl | 642 |
| E-0178 | 3,4-methylenedioxyphenyl | 2-(1-methylimidazol-4-yl)ethyl | 4-piperidinylmethyl | 637 |
| E-0179 | 3,4-methylenedioxyphenyl | 2-(1-methylimidazol-5-yl)ethyl | 4-piperidinylmethyl | 637 |

TABLE 5-continued

Structures of Pyrazinones Prepared by General Robotic and Experimental Procedures

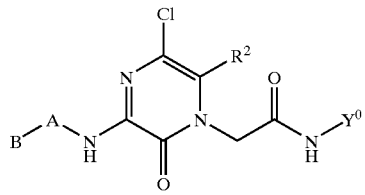

General Structure

| Ex. No. | R² | B—A— | Y⁰ | MW (m/z + 1) |
|---|---|---|---|---|
| E-0180 | 3,4-methylenedioxyphenyl | 4-pyridylmethyl | 4-piperidinylmethyl | 620 |
| E-0181 | 4-biphenyl | benzyl | 4-piperidinylmethyl | 615 |
| E-0182 | 4-biphenyl | 2-phenylethyl | 4-piperidinylmethyl | 629 |
| E-0183 | 4-biphenyl | 2-(3-chlorophenyl)ethyl | 4-piperidinylmethyl | 663 |
| E-0184 | 4-biphenyl | 2-(4-chlorophenyl)ethyl | 4-piperidinylmethyl | 663 |
| E-0185 | 4-biphenyl | 2-(3-pyridyl)ethyl | 4-piperidinylmethyl | 666 |
| E-0186 | 4-biphenyl | 2-(4-pyridyl)ethyl | 4-piperidinylmethyl | 666 |
| E-0187 | 4-biphenyl | 2-(4-morpholinyl)ethyl | 4-piperidinylmethyl | 675 |
| E-0188 | 4-biphenyl | 2-(1-methylimidazol-4-yl)ethyl | 4-piperidinylmethyl | 669 |
| E-0189 | 4-biphenyl | 2-(1-methylimidazol-5-yl)ethyl | 4-piperidinylmethyl | 669 |
| E-0190 | 4-biphenyl | 4-pyridylmethyl | 4-piperidinylmethyl | 652 |
| E-0191 | benzyl | benzyl | 4-piperidinylmethyl | 553 |
| E-0192 | benzyl | 2-phenylethyl | 4-piperidinylmethyl | 567 |
| E-0193 | benzyl | 2-(3-chlorophenyl)ethyl | 4-piperidinylmethyl | 601 |
| E-0194 | benzyl | 2-(4-chlorophenyl)ethyl | 4-piperidinylmethyl | 601 |
| E-0195 | benzyl | 2-(3-pyridyl)ethyl | 4-piperidinylmethyl | 604 |
| E-0196 | benzyl | 2-(4-pyridyl)ethyl | 4-piperidinylmethyl | 604 |
| E-0197 | benzyl | 2-(4-morpholinyl)ethyl | 4-piperidinylmethyl | 612 |
| E-0198 | benzyl | 2-(1-methylimidazol-4-yl)ethyl | 4-piperidinylmethyl | 607 |
| E-0199 | benzyl | 2-(1-methylimidazol-5-yl)ethyl | 4-piperidinylmethyl | 607 |
| E-0200 | benzyl | 4-pyridylmethyl | 4-piperidinylmethyl | 590 |
| E-0201 | 2-phenylethyl | benzyl | 4-piperidinylmethyl | 567 |
| E-0202 | 2-phenylethyl | 2-phenylethyl | 4-piperidinylmethyl | 581 |
| E-0203 | 2-phenylethyl | 2-(3-chlorophenyl)ethyl | 4-piperidinylmethyl | 615 |
| E-0204 | 2-phenylethyl | 2-(4-chlorophenyl)ethyl | 4-piperidinylmethyl | 615 |
| E-0205 | 2-phenylethyl | 2-(3-pyridyl)ethyl | 4-piperidinylmethyl | 618 |
| E-0206 | 2-phenylethyl | 2-(4-pyridyl)ethyl | 4-piperidinylmethyl | 618 |
| E-0207 | 2-phenylethyl | 2-(4-morpholinyl)ethyl | 4-piperidinylmethyl | 626 |
| E-0208 | 2-phenylethyl | 2-(1-methylimidazol-4-yl)ethyl | 4-piperidinylmethyl | 621 |
| E-0209 | 2-phenylethyl | 2-(1-methylimidazol-4-yl)ethyl | 4-piperidinylmethyl | 621 |
| E-0210 | 2-phenylethyl | 4-pyridylmethyl | 4-piperidinylmethyl | 604 |

TABLE 6

Structures of Pyrazinones Prepared by General Robotic and Experimental Procedures

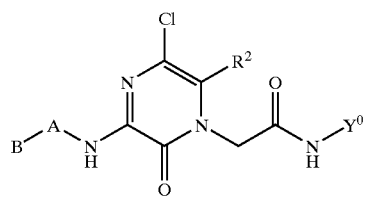

General Structure

| Ex. No. | R² | B—A— | Y⁰ | MW (m/z + 1) |
|---|---|---|---|---|
| 1471-1 | methyl | benzyl | 4-amidinobenzyl | 439 |
| 1471-2 | methyl | 2-(4-chlorophenyl)ethyl | 4-amidinobenzyl | 488 |
| 1471-3 | methyl | 4-pyridylmethyl | 4-amidinobeuzyl | 440 |

TABLE 6-continued

Structures of Pyrazinones Prepared by General Robotic and Experimental Procedures

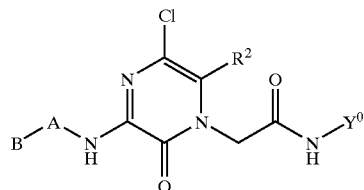

General Structure

| Ex. No. | R² | B—A— | Y⁰ | MW (m/z + 1) |
|---|---|---|---|---|
| 1471-4 | methyl | 2-(4-morpholinyl)ethyl | 4-amidinobenzyl | 462 |
| 1471-5 | methyl | 2-(4-pyridyl)ethyl | 4-amidinobenzyl | 454 |
| 1471-6 | methyl | 2-(3-chlorophenyl)ethyl | 4-amidinobenzyl | 488 |
| 1471-7 | methyl | 2-phenylethyl | 4-amidinobenzyl | 453 |
| 1471-8 | methyl | 2-(3-pyridyl)ethyl | 4-amidinobenzyl | 454 |
| 1471-9 | phenyl | benzyl | 4-arnidinobenzyl | 501 |
| 1471-10 | phenyl | 2-(4-chlorophenyl)ethyl | 4-amidinobenzyl | 550 |
| 1471-11 | phenyl | 4-pyridylmethyl | 4-amidinobenzyl | 502 |
| 1471-12 | phenyl | 2-(4-morpholinyl)ethyl | 4-amidinobenzyl | 525 |
| 1471-13 | phenyl | 2-(4-pyridyl)ethyl | 4-amidinobenzyl | 517 |
| 1471-14 | phenyl | 2-(3-chlorophenyl)ethyl | 4-amidinobenzyl | 550 |
| 1471-15 | phenyl | 2-phenylethyl | 4-amidinobenzyl | 516 |
| 1471-16 | phenyl | 2-(3-pyridyl)ethyl | 4-amidinobenzyl | 517 |
| 1471-17 | 4-Cl-phenyl | benzyl | 4-amidinobenzyl | 536 |
| 1471-18 | 4-Cl-phenyl | 2-(4-chlorophenyl)ethyl | 4-anidinobenzyl | 584 |
| 1471-19 | 4-Cl-phenyl | 4-pyridylmethyl | 4-amidinobenzyl | 537 |
| 1471-20 | 4-Cl-phenyl | 2-(4-morpholinyl)ethyl | 4-amidinobenzyl | 559 |
| 1471-21 | 4-Cl-phenyl | 2-(4-pyridyl)ethyl | 4-amidinobenzyl | 551 |
| 1471-22 | 4-Cl-phenyl | 2-(3-chlorophenyl)ethyl | 4-amidinobenzyl | 584 |
| 1471-23 | 4-Cl-phenyl | 2-phenylethyl | 4-amidinobenzyl | 550 |
| 1471-24 | 4-Cl-phenyl | 2-(3-pyridyl)ethyl | 4-amidinobenzyl | 551 |
| 1471-25 | 3-Cl-phenyl | benzyl | 4-amidinobenzyl | 536 |
| 1471-26 | 3-Cl-phenyl | 2-(4-chlorophenyl)ethyl | 4-amidinobenzyl | 584 |
| 1471-27 | 3-Cl-phenyl | 4-pyridylmethyl | 4-amidinobenzyl | 537 |
| 1471-28 | 3-Cl-phenyl | 2-(4-morpholinyl)ethyl | 4-amidinobenzyl | 559 |
| 1471-29 | 3-Cl-phenyl | 2-(4-pyridyl)ethyl | 4-amidinobenzyl | 551 |
| 1471-30 | 3-Cl-phenyl | 2-(3-chlorophenyl)ethyl | 4-amidinobenzyl | 584 |
| 1471-31 | 3-Cl-phenyl | 2-phenylethyl | 4-amidinobenzyl | 550 |
| 1471-32 | 3-Cl-phenyl | 2-(3-pyridyl)ethyl | 4-amidinobenzyl | 551 |
| 1471-33 | 4-methoxyphenyl | benzyl | 4-amidinobenzyl | 532 |
| 1471-34 | 4-methoxyphenyl | 2-(4-chlorophenyl)ethyl | 4-amidinobenzyl | 580 |
| 1471-35 | 4-methoxyphenyl | 4-pyridylmethyl | 4-amidinobenzyl | 533 |
| 1471-36 | 4-methoxyphenyl | 2-(4-morpholinyl)ethyl | 4-amidinobenzyl | 555 |
| 1471-37 | 4-methoxyphenyl | 2-(4-pyridyl)ethyl | 4-amidinobenzyl | 547 |
| 1471-38 | 4-methoxyphenyl | 2-(3-chlorophenyl)ethyl | 4-amidinobenzyl | 580 |
| 1471-39 | 4-methoxyphenyl | 2-phenylethyl | 4-amidinobenzyl | 546 |
| 1471-40 | 4-methoxyphenyl | 2-(3-pyridyl)ethyl | 4-amidinobenzyl | 547 |
| 1471-41 | 3,4-methylenedioxyphenyl | benzyl | 4-amidinobenzyl | 545 |
| 1471-42 | 3,4-methylenedioxyphenyl | 2-(4-chlorophenyl)ethyl | 4-amidinobenzyl | 594 |
| 1471-43 | 3,4-methylenedioxyphenyl | 4-pyridylmethyl | 4-amidinobenzyl | 546 |
| 1471-44 | 3,4-methylenedioxyphenyl | 2-(4-morpholinyl)ethyl | 4-amidinobenzyl | 569 |
| 1471-45 | 3,4-methylenedioxyphenyl | 2-(4-pyridyl)ethyl | 4-amidinobenzyl | 561 |
| 1471-46 | 3,4-methylenedioxyphenyl | 2-(3-chlorophenyl)ethyl | 4-amidinobenzyl | 594 |
| 1471-47 | 3,4-methylenedioxyphenyl | 2-phenylethyl | 4-amidinobenzyl | 560 |
| 1471-48 | 3,4-methylenedioxyphenyl | 2-(3-pyridyl)ethyl | 4-amidinobenzyl | 561 |
| 1471-57 | ethyl | benzyl | 4-amidinobenzyl | 553 |
| 1471-58 | ethyl | 2-(4-chlorophenyl)ethyl | 4-amidinobenzyl | 502 |
| 1471-59 | ethyl | 4-pyridylmethyl | 4-amidinobenzyl | 454 |
| 1471-60 | ethyl | 2-(4-morpholinyl)ethyl | 4-amidinobenzyl | 476 |
| 1471-61 | ethyl | 2-(4-pyridyl)ethyl | 4-amidinobenzyl | 468 |
| 1471-62 | ethyl | 2-(3-chlorophenyl)ethyl | 4-amidinobenzyl | 502 |
| 1471-63 | ethyl | 2-phenylethyl | 4-amidinobenzyl | 467 |
| 1471-64 | ethyl | 2-(3-pyridyl)ethyl | 4-amidinobenzyl | 468 |
| 1471-67 | 4-biphenyl | 4-pyridylmethyl | 4-amidinobenzyl | 579 |
| 1471-70 | 4-biphenyl | 2-(3-chlorophenyl)ethyl | 4-amidinobenzyl | 626 |
| 1471-71 | 4-biphenyl | 2-phenylethyl | 4-amidinobenzyl | 592 |
| 1471-72 | 4-biphenyl | 2-(3-pyridyl)ethyl | 4-amidinobenzyl | 593 |
| 1507-01 | phenyl | 3-trifluoromethylbenzyl | 4-amidinobenzyl | 569 |
| 1507-02 | phenyl | 1-indanyl | 4-amidinobenzyl | 528 |
| 1507-03 | phenyl | 2-Cl-benzyl | 4-amidinobenzyl | 536 |
| 1507-04 | phenyl | 4-trifluoromethoxybenzyl | 4-amidinobenzyl | 585 |
| 1507-05 | phenyl | 3-(1-imidazolyl)propyl | 4-amidinobenzyl | 520 |

TABLE 6-continued

Structures of Pyrazinones Prepared by General Robotic and Experimental Procedures

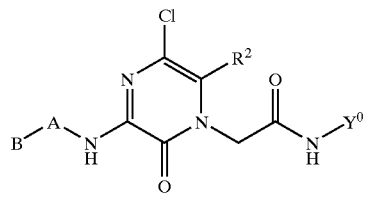

General Structure

| Ex. No. | R² | B—A— | Y⁰ | MW (m/z + 1) |
|---|---|---|---|---|
| 1507-06 | phenyl | 2-(4-bromophenyl)ethyl | 4-amidinobenzyl | 594 |
| 1507-07 | phenyl | 1,2-(diphenyl)ethyl | 4-amidinobenzyl | 592 |
| 1507-08 | phenyl | 2-indanyl | 4-amidinobenzyl | 528 |
| 1507-09 | phenyl | 2,2-(diphenyl)ethyl | 4-amidinobenzyl | 592 |
| 1507-10 | phenyl | 3,3-(diphenyl)propyl | 4-amidinobenzyl | 606 |
| 1507-11 | phenyl | 2-(4-methoxyphenyl)ethyl | 4-amidinobenzyl | 546 |
| 1507-12 | phenyl | 2-(3-methoxyphenyl)ethyl | 4-amidinobenzyl | 546 |
| 1507-13 | phenyl | 4-methoxybenzyl | 4-amidinobenzyl | 532 |
| 1507-15 | phenyl | 2-trifluoromethylbenzyl | 4-amidinobenzyl | 569 |
| 1507-16 | phenyl | 1,2,3,4-tetrahydro-1-naphthyl | 4-amidinobenzyl | 542 |
| 1507-17 | phenyl | 2-(cyclohex-1-enyl)ethyl | 4-amidinobenzyl | 520 |
| 1507-18 | phenyl | 2-(2-thienyl)ethyl | 4-amidinobenzyl | 522 |
| 1507-19 | phenyl | 3-[1-(pyrrolidinyl-2-one)]propyl | 4-amidinobenzyl | 537 |
| 1507-20 | phenyl | 1-carboethoxypiperidin-4-yl | 4-amidinobenzyl | 567 |
| 1507-21 | phenyl | cyclobutyl | 4-amidinobenzyl | 465 |
| 1507-22 | phenyl | 2,4-dichlorobenzyl | 4-amidinobenzyl | 570 |
| 1507-23 | phenyl | 2-(3-chlorophenyl)ethyl | 4-amidinobenzyl | 516 |
| 1507-24 | phenyl | 2-pyridylmethyl | 4-amidinobenzyl | 502 |
| 1507-25 | phenyl | cyclopentyl | 4-amidinobenzyl | 479 |
| 1507-26 | phenyl | 2,4-difluorobenzyl | 4-amidinobenzyl | 537 |
| 1507-28 | phenyl | 1-naphthylmethyl | 4-amidinobenzyl | 552 |
| 1507-29 | phenyl | cycloheptyl | 4-amidinobenzyl | 508 |
| 1507-30 | phenyl | 4-bromobenzyl | 4-amidinobenzyl | 580 |
| 1507-31 | phenyl | cyclopropyl | 4-amidinobenzyl | 451 |
| 1507-32 | phenyl | 2-methylpropyl | 4-amidinobenzyl | 467 |
| 1507-33 | phenyl | 2-methoxyethyl | 4-amidinobenzyl | 469 |
| 1507-34 | phenyl | (S)-α-methylbenzyl | 4-amidinobenzyl | 516 |
| 1507-35 | phenyl | 1,1-diphenylmethyl | 4-amidinobenzyl | 578 |
| 1507-36 | phenyl | 3-(2,3,4,5-tetrahydro-1,1-dioxothiophenyl) | 4-amidinobenzyl | 530 |
| 1507-38 | phenyl | 3-chlorobenzyl | 4-amidinobenzyl | 536 |
| 1507-40 | phenyl | 3,5-bis-trifluoromethylbenzyl | 4-amidinobenzyl | 637 |
| 1507-41 | phenyl | 2,2,2-trifluoroethyl | 4-amidinobenzyl | 493 |
| 1507-42 | phenyl | 3-fluorobenzyl | 4-amidinobenzyl | 519 |
| 1507-43 | phenyl | 4-phenylbutyl | 4-amidinobenzyl | 544 |
| 1507-44 | phenyl | 2-(3,4-dichlorophenyl)ethyl | 4-amidinobenzyl | 584 |
| 1507-45 | phenyl | 2-(4-methylphenyl)ethyl | 4-amidinobenzyl | 530 |
| 1507-46 | phenyl | 4-chlorobenzyl | 4-amidinobenzyl | 536 |
| 1507-47 | phenyl | 3-(dimethylamino)propyl | 4-amidinobenzyl | 497 |
| 1507-48 | phenyl | 3,4-difluorobenzyl | 4-amidinobenzyl | 537 |
| 1512-01 | phenyl | 2H,3H-benzo[e]1,4-dioxan-2-ylmethyl | 4-amidinobenzyl | 560 |
| 1512-02 | phenyl | 2,3-dimethoxybenzyl | 4-amidinobenzyl | 562 |
| 1512-04 | phenyl | 3,4-methylenedioxyphenyl | 4-amidinobenzyl | 545 |
| 1512-05 | phenyl | 2-(3,4-dimethoxyphenyl)ethyl | 4-amidinobenzyl | 576 |
| 1512-06 | phenyl | 3-(phenyl)propyl | 4-amidinobenzyl | 530 |
| 1512-07 | phenyl | 2-(3-methoxy)propyl | 4-amidinobenzyl | 483 |
| 1512-11 | phenyl | 2-ethoxybenzyl | 4-amidinobenzyl | 546 |
| 1512-12 | phenyl | 3-heptyl | 4-amidinobenzyl | 510 |
| 1512-14 | phenyl | butyl | 4-amidinobenzyl | 467 |
| 1512-15 | phenyl | 2-(dimethylamino)ethyl | 4-arnidinobenzyl | 482 |
| 1512-16 | phenyl | cycloheptyl | 4-amidinobenzyl | 508 |
| 1512-17 | phenyl | 4-t-butylcyclohexyl | 4-amidinobenzyl | 550 |
| 1512-19 | phenyl | 3-(2,3,4,5-tetrahydro-1,1-dioxothiophenyl) | 4-amidinobenzyl | 530 |
| 1512-20 | phenyl | phenylamino | 4-amidinobenzyl | 487 |
| 1512-23 | phenyl | 2,3-dimethylcyclohexyl | 4-amidinobenzyl | 522 |
| 1512-26 | phenyl | 2-fluoro-4-trifluoromethylbenzyl | 4-amidinobenzyl | 587 |
| 1512-27 | phenyl | 2-fluoro-5-trifluoromethylbenzyl | 4-amidinobenzyl | 587 |
| 1512-29 | phenyl | 3-fluoro-5-trifluoromethylbenzyl | 4-amidinobenzyl | 587 |
| 1512-31 | phenyl | 2-chloro-6-methylbenzyl | 4-amidinobenzyl | 550 |
| 1512-32 | phenyl | 3,4,5-trifluorobenzyl | 4-amidinobenzyl | 555 |
| 1512-35 | phenyl | 2,5-dichlorobenzyl | 4-amidinobenzyl | 570 |
| 1512-36 | phenyl | 2,5-difluorobenzyl | 4-amidinobenzyl | 537 |
| 1512-39 | phenyl | 3,5-difluorobenzyl | 4-amidinobenzyl | 537 |

TABLE 6-continued

Structures of Pyrazinones Prepared by General Robotic and Experimental Procedures

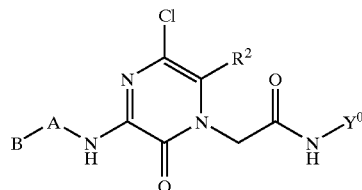

General Structure

| Ex. No. | R² | B—A— | Y⁰ | MW (m/z + 1) |
|---|---|---|---|---|
| 1512-40 | phenyl | 3-trifluoromethoxybenzyl | 4-amidinobenzyl | 585 |
| 1512-41 | phenyl | 2-(3-trifluoromethylphenyl)ethyl | 4-amidinobenzyl | 584 |
| 1512-42 | phenyl | 2-trifluoromethoxybenzyl | 4-amidinobenzyl | 585 |
| 1512-43 | phenyl | 2,6-difluorobenzyl | 4-amidinobenzyl | 537 |
| 1512-44 | phenyl | 2-fluoro-6-trifluoromethylbenzyl | 4-amidinobenzyl | 587 |
| 1512-45 | phenyl | 2,4-dichloro-6-methylbenzyl | 4-amidinobenzyl | 584 |
| 1512-46 | phenyl | 2-(1-methyl-pyrrolidin-2-yl)-ethyl | 4-amidinobenzyl | 523 |
| 1512-47 | phenyl | 2-(pyrid-2-yl)ethyl | 4-amidinobenzyl | 517 |
| 1515-10 | 3-trifluoromethylphenyl | benzyl | 4-amidinobenzyl | 569 |
| 1515-02 | 2-methoxyphenyl | benzyl | 4-amidinobenzyl | 532 |
| 1515-03 | 1-(2-bromothienyl) | benzyl | 4-amidinobenzyl | 586 |
| 1515-04 | 2-chlorophenyl | benzyl | 4-amidinobenzyl | 536 |
| 1515-05 | 3-methoxyphenyl | benzyl | 4-amidinobenzyl | 532 |
| 1515-06 | 2-thienyl | benzyl | 4-amidinobenzyl | 508 |
| 1515-07 | 4-fluorophenyl | benzyl | 4-amidinobenzyl | 519 |
| 1515-08 | 4-trifluoromethylphenyl | benzyl | 4-amidinobenzyl | 569 |
| 1515-09 | 3-fluorophenyl | benzyl | 4-amidinobenzyl | 519 |
| 1515-10 | 3-bromophenyl | benzyl | 4-amidinobenzyl | 580 |
| 1515-11 | 2-fluorophenyl | benzyl | 4-amidinobenzyl | 519 |
| 1515-12 | 2-trifluoromethylphenyl | benzyl | 4-amidinobenzyl | 569 |
| 1515-13 | 3-trifluoromethylphenyl | cyclobutyl | 4-amidinobenzyl | 533 |
| 1515-14 | 2-methoxyphenyl | cyclobutyl | 4-amidinobenzyl | 495 |
| 1515-15 | 1-(2-bromothienyl) | cyclobutyl | 4-amidinobenzyl | 550 |
| 1515-16 | 2-chlorophenyl | cyclobutyl | 4-amidinobenzyl | 500 |
| 1515-17 | 3-methoxyphenyl | cyclobutyl | 4-amidinobenzyl | 495 |
| 1515-18 | 2-thienyl | cyclobutyl | 4-amidinobenzyl | 471 |
| 1515-19 | 4-fluorophenyl | cyclobutyl | 4-amidinobenzyl | 483 |
| 1515-20 | 4-trifluoromethylphenyl | cyclobutyl | 4-amidinobenzyl | 533 |
| 1515-22 | 3-bromophenyl | cyclobutyl | 4-amidinobenzyl | 544 |
| 1515-23 | 2-fluorophenyl | cyclobutyl | 4-amidinobenzyl | 483 |
| 1515-24 | 2-trifluoromethylphenyl | cyclobutyl | 4-amidinobenzyl | 533 |
| 1515-25 | 3-trifluoromethylphenyl | 2-phenylethyl | 4-amidinobenzyl | 584 |
| 1515-26 | 2-methoxyphenyl | 2-phenylethyl | 4-amidinobenzyl | 546 |
| 1515-27 | 3-bromo-2-thienyl) | 2-phenylethyl | 4-amidinobenzyl | 600 |
| 1515-28 | 2-chlorophenyl | 2-phenylethyl | 4-amidinobenzyl | 550 |
| 1515-29 | 3-methoxyphenyl | 2-phenylethyl | 4-amidinobenzyl | 546 |
| 1515-30 | 2-thienyl | 2-phenylethyl | 4-amidinobenzyl | 522 |
| 1515-31 | 4-fluorophenyl | 2-phenylethyl | 4-amidinobenzyl | 534 |
| 1515-32 | 4-trifluoromethylphenyl | 2-phenylethyl | 4-amidinobenzyl | 584 |
| 1515-33 | 3-fluorophenyl | 2-phenylethyl | 4-amidinobenzyl | 534 |
| 1515-34 | 3-bromophenyl | 2-phenylethyl | 4-amidinobenzyl | 594 |
| 1515-35 | 2-fluorophenyl | 2-phenylethyl | 4-amidinobenzyl | 534 |
| 1515-36 | 2-trifluoromethylphenyl | 2-phenylethyl | 4-amidinobenzyl | 584 |
| 1515-37 | 3-trifluoromethylphenyl | 2-(3,4-dichlorophenyl)ethyl | 4-amidinobenzyl | 618 |
| 1515-38 | 2-methoxyphenyl | 2-(3,4-dichlorophenyl)ethyl | 4-amidinobenzyl | 580 |
| 1515-39 | 1-(2-bromo-thienyl) | 2-(3,4-dichlorophenyl)ethyl | 4-amidinobenzyl | 635 |
| 1515-40 | 2-chlorophenyl | 2-(3,4-dichlorophenyl)ethyl | 4-amidinobenzyl | 584 |
| 1515-41 | 3-methoxyphenyl | 2-(3,4-dichlorophenyl)ethyl | 4-amidinobenzyl | 580 |
| 1515-42 | 2-thienyl | 2-(3,4-dichlorophenyl)ethyl | 4-amidinobenzyl | 556 |
| 1515-43 | 4-fluorophenyl | 2-(3,4-dichlorophenyl)ethyl | 4-amidinobenzyl | 568 |
| 1515-44 | 4-trifluoromethylphenyl | 2-(3,4-dichlorophenyl)ethyl | 4-amidinobenzyl | 618 |
| 1515-45 | 3-fluorophenyl | 2-(3,4-dichlorophenyl)ethyl | 4-amidinobenzyl | 568 |
| 1515-46 | 3-bromophenyl | 2-(3,4-dichlorophenyl)ethyl | 4-amidinobenzyl | 629 |
| 1515-47 | 2-fluorophenyl | 2-(3,4-dichlorophenyl)ethyl | 4-amidinobenzyl | 568 |
| 1515-48 | 2-trifluoromethylphenyl | 2-(3,4-dichlorophenyl)ethyl | 4-amidinobenzyl | 618 |
| 1522-02 | phenyl | 2-hydroxyethyl | 4-amidinobenzyl | 455 |
| 1522-05 | phenyl | 4-hydroxybutyl | 4-amidinobenzyl | 484 |
| 1522-06 | phenyl | (R)-2-butyl | 4-amidinobenzyl | 468 |
| 1522-07 | phenyl | 6-hydroxyhexyl | 4-amidinobenzyl | 512 |
| 1522-08 | phenyl | 2-(pyrrolidin-1-yl)-ethyl | 4-amidinobenzyl | 509 |
| 1522-09 | phenyl | (S)-2-butyl | 4-amidinobenzyl | 468 |
| 1522-11 | phenyl | 3-pentyl | 4-amidinobenzyl | 482 |

TABLE 6-continued

Structures of Pyrazinones Prepared by General Robotic and Experimental Procedures

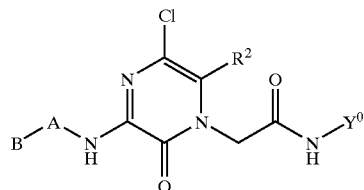

General Structure

| Ex. No. | R² | B—A— | Y⁰ | MW (m/z + 1) |
|---|---|---|---|---|
| 1522-12 | phenyl | (S)-2-methylbutyl | 4-amidinobenzyl | 482 |
| 1522-13 | phenyl | 2-methylbutyl | 4-amidinobenzyl | 482 |
| 1522-14 | phenyl | 3-methylbutyl | 4-amidinobenzyl | 482 |
| 1522-15 | phenyl | 2-(3-methyl)butyl | 4-amidinobenzyl | 482 |
| 1522-17 | phenyl | 2-(4-methyl)pentyl | 4-amidinobenzyl | 496 |
| 1522-18 | phenyl | 3,3-dimethylbutyl | 4-amidinobenzyl | 496 |
| 1522-19 | phenyl | tricyclo[53.1.1<3,9>]dodec-3-yl | 4-amidinobenzyl | 546 |
| 1522-20 | phenyl | tricyclo[53.1.1<3,9>]dodec-3-ylmethyl | 4-amidinobenzyl | 560 |
| 1522-21 | phenyl | 2-propynyl | 4-amidinobenzyl | 449 |
| 1522-23 | phenyl | 2-(dimethylamino)propyl | 4-amidinobenzyl | 497 |
| 1522-27 | phenyl | N,N-butano | 4-amidinobenzyl | 465 |
| 1522-28 | phenyl | N,N-propano | 4-amidinobenzyl | 451 |
| 1522-31 | phenyl | benzylthio | 4-amidinobenzyl | 519 |
| 1522-33 | phenyl | 2-methoxyethyl | 4-amidinobenzyl | 469 |
| 1522-34 | phenyl | 2-methylpropyl | 4-amidinobenzyl | 468 |
| 1522-35 | phenyl | 1,2-diethylpyrazolidinyl | 4-amidinobenzyl | 538 |
| 1522-36 | phenyl | cycloheptyl | 4-amidinobenzyl | 508 |
| 1522-37 | phenyl | N-(3-chloro-5-trifluoromethyl-pyrid-2-yl)-2-aminoethyl | 4-amidinobenzyl | 634 |
| 1522-38 | phenyl | N-(3-trifluoromethyl-pyrid-2-yl)-2-aminoethyl | 4-amidinobenzyl | 600 |
| 1522-40 | phenyl | 6-cyanohexyl | 4-amidinobenzyl | 507 |
| 1522-41 | phenyl | 3-hydroxypropyl | 4-amidinobenzyl | 469 |
| 1522-42 | phenyl | 4-(pyrrolidin-1-yl)butyl | 4-amidinobenzyl | 537 |
| 1522-43 | phenyl | (S)-1-cyclohexylethyl | 4-amidinobenzyl | 522 |
| 1522-44 | phenyl | 2-(2R)-bicyclo-[2.2.1]heptyl | 4-amidinobenzyl | 506 |
| 1522-46 | phenyl | 3-(2,3,4,5-tetrahydro-1,1-dioxothiophenyl) | 4-amidinobenzyl | 530 |
| 1522-47 | phenyl | 4-t-butylcyclohexyl | 4-amidinobenzyl | 550 |
| 1526-01 | 3-aminophenyl | cyclopropyl | 4-amidinobenzyl | 466 |
| 1526-03 | 3-aminophenyl | cyclopentyl | 4-amidinobenzyl | 495 |
| 1526-04 | 3-aminophenyl | 2,2,2-trifluoroethyl | 4-amidinobenzyl | 508 |
| 1526-05 | 3-aminophenyl | 2-(3-methoxypropyl) | 4-amidinobenzyl | 499 |
| 1526-06 | 3-aminophenyl | 2-(2-methylbutyl) | 4-amidinobenzyl | 497 |
| 1526-07 | 3-aminophenyl | t-butyl | 4-amidinobenzyl | 483 |
| 1526-09 | 3-aminophenyl | (S)-2-butyl | 4-amidinobenzyl | 483 |
| 1526-11 | 3-aminophenyl | 3-pentyl | 4-amidinobenzyl | 497 |
| 1526-12 | 3-aminophenyl | ethyl | 4-amidinobenzyl | 454 |
| 1526-13 | 3-aminophenyl | propyl | 4-amidinobenzyl | 469 |
| 1526-14 | 3-aminophenyl | 2-butyl | 4-amidinobenzyl | 483 |
| 1526-15 | 3-aminophenyl | 2-(3-methylbutyl) | 4-amidinobenzyl | 497 |
| 1526-16 | 3-aminophenyl | (R)-2-butyl | 4-amidinobenzyl | 483 |
| 1526-17 | 3-aminophenyl | 2-(4-methylpentyl) | 4-amidinobenzyl | 511 |
| 1526-19 | 3-aminophenyl | 2-propenyl | 4-amidinobenzyl | 466 |
| 1526-21 | 3-aminophenyl | 2-propynyl | 4-amidinobenzyl | 464 |
| 1526-23 | 3-aminophenyl | cyclobutyl | 4-amidinobenzyl | 481 |
| 1526-24 | 3-aminophenyl | isopropyl | 4-amidinobenzyl | 469 |
| 1526-25 | 3-aminophenyl | 2-methoxyethyl | 4-amidinobenzyl | 485 |
| 1526-26 | 3-aminophenyl | 2-methylpropyl | 4-amidinobenzyl | 483 |
| 1526-29 | 3-aminophenyl | (1S)-1-cyclohexylethyl | 4-amidinobenzyl | 537 |
| 1526-30 | 3-aminophenyl | 2-(2R)bicyclo[2.2.1]-heptyl | 4-amidinobenzyl | 521 |
| 1526-33 | 3-aminophenyl | (2S)-oxalan-2-ylmethyl | 4-amidinobenzyl | 511 |
| 1526-40 | 3-aminophenyl | butyl | 4-amidinobenzyl | 483 |
| 1526-41 | 3-aminophenyl | cyclopropylmethyl | 4-amidinobenzyl | 481 |
| 1543-03 | 3-aminophenyl | 2-(pyrrolidin-1-yl)ethyl | 4-amidinobenzyl | 524 |
| 1543-05 | 3-aminophenyl | methyl | 4-amidinobenzyl | 440 |
| 1543-07 | 3-aminophenyl | 3-(1-imidazolyl)propyl | 4-amidinobenzyl | 535 |
| 1543-09 | 3-aminophenyl | 2-dimethylaminoethyl | 4-amidinobenzyl | 498 |
| 1543-11 | 3-aminophenyl | 6-amidocarbonylhexyl | 4-amidinobenzyl | 540 |
| 1543-13 | 3-aminophenyl | 3-hydroxypropyl | 4-amidinobenzyl | 485 |
| 1543-15 | 3-aminophenyl | 2-(piperid-1-yl)ethyl | 4-amidinobenzyl | 538 |
| 1543-19 | 3-aminophenyl | 2-dimethylaminopropyl | 4-amidinobenzyl | 512 |
| 1543-21 | 3-aminophenyl | 4-(pyrrolidin-1-yl)butyl | 4-amidinobenzyl | 552 |
| 1543-25 | 3-aminophenyl | 2-(3-diethylamino)propyl | 4-amidinobenzyl | 540 |
| 1543-27 | 3-aminophenyl | 3-(pyrrolidin-1-yl)propyl | 4-amidinobenzyl | 538 |

TABLE 6-continued

Structures of Pyrazinones Prepared by General Robotic and Experimental Procedures

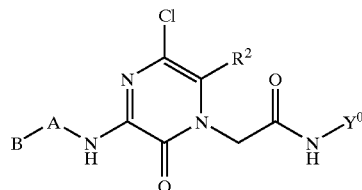

General Structure

| Ex. No. | R² | B—A— | Yº | MW (m/z + 1) |
|---|---|---|---|---|
| 1543-31 | 3-aminophenyl | ethyl | 4-amidino-2-fluorobenzyl | 472 |
| 1543-33 | 3-aminophenyl | cyclopropyl | 4-amidino-2-fluorobenzyl | 484 |
| 1543-34 | 3-aminophenyl | cyclopentyl | 4-amidino-2-fluorobenzyl | 513 |
| 1543-35 | 3-aminophenyl | propyl | 4-amidino-2-fluorobenzyl | 486 |
| 1543-36 | 3-aminophenyl | butyl | 4-amidino-2-fluorobenzyl | 501 |
| 1543-37 | 3-aminophenyl | 2-(pyrrolidin-1-yl)ethyl | 4-amidino-2-fluorobenzyl | 542 |
| 1543-38 | 3-aminophenyl | 2-methylpropyl | 4-amidino-2-fluorobenzyl | 501 |
| 1543-39 | 3-aminophenyl | cyclobutyl | 4-amidino-2-fluorobenzyl | 499 |
| 1543-40 | 3-aminophenyl | isopropyl | 4-amidino-2-fluorobenzyl | 486 |
| 1543-41 | 3-aminophenyl | cyclobutyl | 8-aza-1,4-dioxaspiro[4.5]decyl | 474 |
| 1543-45 | 3-aminophenyl | cyclobutyl | 3,3-diethylpyrrolidin-1-yl | 462 |
| 1543-46 | 3-aminophenyl | cyclobutyl | 4-(4-amino-phenyl)pyrazinyl | 497 |

TABLE 7

Structures of Pyrazinones Prepared by General Robotic and Experimental Procedures

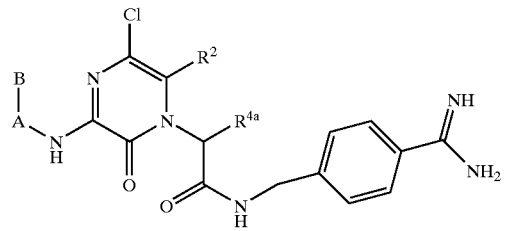

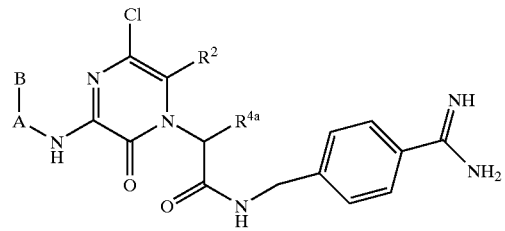

| Ex. No. | R² | B—A— | R⁴ᵃ | MW (m/z + 1) |
|---|---|---|---|---|
| 1517-01 | 3-thienyl | benzyl | H | 508 |
| 1517-03 | phenyl | benzyl | (S)-methyl | 516 |
| 1517-04 | phenyl | benzyl | methylthiomethyl | 562 |
| 1517-05 | phenyl | benzyl | (R)-methyl | 516 |
| 1517-06 | 2,6-dichlorophenyl | benzyl | H | 570 |
| 1517-07 | 3-thienyl | cyclobutyl | H | 472 |
| 1517-08 | phenyl | cyclobutyl | benzyl | 556 |
| 1517-09 | phenyl | cyclobutyl | (S)-methyl | 480 |
| 1517-10 | phenyl | cyclobutyl | methylthiomethyl | 526 |
| 1517-11 | phenyl | cyclobutyl | (R)-methyl | 480 |
| 1517-12 | 2,6-dichlorophenyl | cyclobutyl | H | 534 |
| 1517-13 | 3-thienyl | 2-phenylethyl | H | 522 |
| 1517-14 | phenyl | 2-phenylethyl | benzyl | 606 |
| 1517-15 | phenyl | 2-phenylethyl | (S)-methyl | 530 |
| 1517-16 | phenyl | 2-phenylethyl | methylthiomethyl | 576 |
| 1517-17 | phenyl | 2-phenylethyl | (R)-methyl | 530 |
| 1517-18 | 2,6-dichlorophenyl | 2-phenylethyl | H | 584 |
| 1517-19 | 3-thienyl | 2-(3-chlorophenyl)-ethyl | H | 556 |
| 1517-20 | phenyl | 2-(3-chlorophenyl)-ethyl | benzyl | 640 |
| 1517-23 | phenyl | 2-(3-chlorophenyl)-ethyl | (R)-methyl | 564 |
| 1517-24 | 2,6-dichlorophenyl | 2-(3-chlorophenyl)-ethyl | H | 619 |
| 1517-25 | phenyl | cyclohexyl | H | 494 |
| 1517-26 | phenyl | 4-heptyl | H | 510 |
| 1517-29 | phenyl | 2-hexyl | H | 496 |
| 1517-31 | phenyl | N-methyl N-(1-methylethyl) | H | 468 |
| 1517-33 | phenyl | propyl | H | 453 |
| 1517-35 | phenyl | butyl | H | 468 |
| 1517-36 | phenyl | trimethyl-silylmethyl | H | 498 |
| 1517-37 | phenyl | 2-butyl | H | 468 |
| 1517-38 | phenyl | prop-2-enyl | H | 451 |
| 1517-39 | phenyl | methyl | H | 425 |
| 1517-40 | phenyl | 3-methylbutyl | H | 482 |
| 1517-41 | phenyl | 3,3-dimethylbutyl | H | 496 |
| 1517-43 | phenyl | cyclopropylmethyl | H | 465 |
| 1517-44 | phenyl | isopropyl | H | 453 |
| 1517-46 | phenyl | ethyl | H | 439 |

TABLE 7-continued

Structures of Pyrazinones Prepared by General Robotic and Experimental Procedures

[Chemical structure showing a pyrazinone core with Cl, $R^2$, B-A-NH substituents, connected via N-$R^{4a}$-C(O)-NH-CH$_2$-phenyl-C(NH)NH$_2$]

| Ex. No. | $R^2$ | B—A— | $R^{4a}$ | MW (m/z + 1) |
|---|---|---|---|---|
| 1517-47 | phenyl | 3-heptyl | H | 524 |
| 1517-48 | phenyl | pentyl | H | 482 |

Formula (I) compounds of this invention possessing hydroxyl, thiol, and amine functional groups can be converted to a wide variety derivatives. Alternatively, derivatized Formula (I) compounds can be obtained by first derivatizing one or more intermediates in the processes of preparation before further transforming the derivatized intermediate to comounds of Formula (I). A hydroxyl group in the form of an alcohol or phenol can be readily converted to esters of carboxylic, sulfonic, carbamic, phosphonic, and phosphoric acids. Acylation to form a carboxylic acid ester is readily effected using a suitable acylating reagent such as an aliphatic acid anhydride or acid chloride. The corresponding aryl and heteroaryl acid anhydrides and acid chlorides can also be used. Such reactions are generally carried out using an amine catalyst such as pyridine in an inert solvent. Similarly, carbamic acid esters (urethanes) can be obtained by reacting a hydroxyl group with isocyanates and carbamoyl chlorides. Sulfonate, phosphonate, and phosphate esters can be prepared using the corresponding acid chloride and similar reagents. Compounds of Formula (I) that have at least one thiol group present can be converted to the corresponding thioesters derivatives analogous to those of alcohols and phenols using the same reagents and comparable reaction conditions. Compounds of Formula (I) that have at least one primary or secondary amine group present can be converted to the corresponding amide derivatives. Amides of carboxylic acids can be prepared using the appropriate acid chloride or anhydrides with reaction conditions analogous to those used with alcohols and phenols. Ureas of the corresponding primary or secondary amine can be prepared using isocyanates directly and carbamoyl chlorides in the presence of an acid scavenger such as triethylamine or pyridine. Sulfonamides can be prepared from the corresponding sulfonyl chloride in the presence of aqueous sodium hydroxide or a tertiary amine. Suitable procedures and methods for preparing these derivatives can be found in House's Modern Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis, Volume 1, John Wiley & Sons. Reagents of a wide variety that can be used to derivatize hydroxyl, thiol, and amines of compounds of Formula (I) are available from commercial sources or the references cited above, which are incorporated herein by reference.

Formula (I) compounds of this invention possessing hydroxyl, thio, and amine functional groups can be alkylated to a wide variety of derivatives. Alternatively, alkylated Formula (I) compounds can be obtained by first alkylating one or more intermediates in the processes of preparation before further transforming the alkylated intermediate to comounds of Formula (I). A hydroxyl group of compounds of Formula (I) can be readily converted to ethers. Alkylation to form an ether is readily effected using a suitable alkylating reagent such as an alkyl bromide, alkyl iodide or alkyl sulfonate. The corresponding aralkyl, heteroaralkyl, alkoxyalkyl, aralkyloxyalkyl, and heteroaralkyloxyalkyl bromides, iodides, and sulfonates can also be used. Such reactions are generally carried out using an alkoxide forming reagent such as sodium hydride, potassium t-butoxide, sodium amide, lithium amide, and n-butyl lithium using an inert polar solvent such as DMF, DMSO, THF, and similar, comparable solvents, amine catalyst such as pyridine in an inert solvent. Compounds of Formula (I) that have at least one thiol group present can be converted to the corresponding thioether derivatives analogous to those of alcohols and phenols using the same reagents and comparable reaction conditions. Compounds of Formula (I) that have at least one primary, secondary or tertiary amine group present can be converted to the corresponding secondary, tertiary or quaternary ammonium derivative. Quaternary ammonium derivatives can be prepared using the appropriate bromides, iodides, and sulfonates analogous to those used with alcohols and phenols. Conditions involve reaction of the amine by warming it with the alkylating reagent with a stoichiometric amount of the amine (i.e., one equivalent with a tertiary amine, two with a secondary, and three with a primary). With primary and secondary amines, two and one equivalents, respectively, of an acid scavenger are used concurrently. Secondary or tertiary amines can be prepared from the corresponding primary or secondary amine. A primary amine can be dialkylated by reductive amination using an aldehyde, such as formaldehyde, and sodium cyanoborohydride in the presence of glacial acetic acid. A primary amine can be monoalkylated by first monoprotecting the amine with a ready cleaved protecting group, such as trifluoroacetyl. An alkylating agent, such as dimethylsulfate, in the presence of a non-nucleophilic base, such as Barton's base (2-tert-butyl-1,1,3,3-tetramethylguanidine), gives the monomethylated protected amine. Removal of the protecting group using aqueous potassium hydroxide gives the desired monoalkylated amine. Additional suitable procedures and methods for preparing these derivatives can be found in House's Modem Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis published by John Wiley & Sons. Perfluoroalkyl derivatives can be prepared as described by DesMarteau in J. Chem. Soc. Chem. Commun. 2241 (1998). Reagents of a wide variety that can be used to derivatize hydroxyl, thiol, and amines of compounds of Formula (I) are available from commercial sources or the references cited above, which are incorporated herein by reference.

The examples of synthetic approaches to the preparation pyrazinones derivatized in a nucleophilic substituent such as may be present in B, $R^1$, $R^2$ and $Y^0$ are shown in specific Examples 100 through 104 below. The specific examples recited below should be considered a being merely illustrative of the wide variety possible and not as limiting to one of ordinary skill in the art.

Example 100

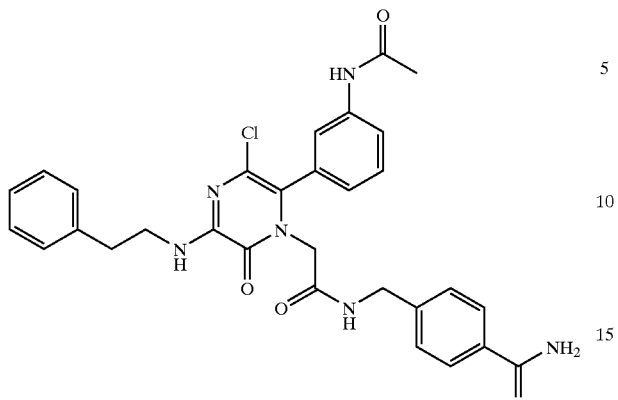

By following the method of Example 1 and substituting 3-nitrobenzaldehyde for benzaldehyde, 1-benzyloxycarbonylmethyl-3,5-dichloro-6-(3-nitrophenyl)pyrazinone (EX-100A) was obtained. The pyrazinone, 1-benzyloxycarbonylmethyl-3,5-dichloro-6-(3-nitrophenyl)pyrazinone (EX-100A), (15.01 g, 34.6 mmol) was taken up in 325 mL of 50% EtOH (w/w) and heated to 75° C. EtOAc was added until the solution was homogeneous (about 80 mL). Iron powder (9.4 g, 168 mmol) was added, followed by 0.57 mL of 12 M HCl (6.8 mmol) in about 0.6 mL of 50% EtOH. The reaction was monitored by TLC (80% EtOAc/hexanes) and was complete within 40 minutes. The reaction mixture was cooled to room temperature, and the iron was removed by filtration through Celite. The yellow solution was diluted with 600 mL of EtOAc and 300 mL of water. Saturated NaCl was added to help separate the layers. The organic phase was washed with saturated NaHCO$_3$ (2×250 mL), saturated NaCl (1×250 mL), dried over MgSO$_4$, filtered, and the solvents were removed under reduced pressure. The residue was taken up in 20–25 mL of 3.4 M HCl in EtOAc. Additional EtOAc (about 25 mL) was added, and the mixture was heated to dissolve all of the compound. The volatile components were removed under reduced pressure. The residue (crusty solid) was taken up in EtOAc and slowly dripped into hexanes. The pale yellow solid that precipitated was filtered and dried under vacuum at room temperature to yield 12.19 g (80% yield) of 1-benzyloxycarbonylmethyl-3,5-dichloro-6-(3-aminophenyl)pyrazinone hydrochloride (EX-100B) as a pale yellow solid: $^1$H NMR (300 MHz, CD$_3$OD) δ 4.61 (AB q, 2H, J=17 Hz), 5.20 (AB q, 2H, J=12 Hz), 7.31–7.51 (m, 7H), 7.63–7.67 (m, 2H); HPLC purity (retention time): 91% (3.0 min); LRMS m/z 404 (M$^+$+H).

The pyrazinone, 1-benzyloxycarbonylmethyl-3,5-dichloro-6-(3-aminophenyl)pyrazinone hydrochloride (EX-100B), (78.2 mg, 0.18 mmol) was taken up in 5 mL of dichloromethane. Pyridine (32 mL, 0.40 mmol) was added, followed by acetyl chloride (26 mL, 0.36 mmol) in 1 mL of dichloromethane. The reaction was stirred at ambient temperature until the reaction was complete by TLC and LC/MS after 24 hours. The reaction solution was then washed with saturated NaHCO$_3$ (4×5 mL), saturated NaCl (1×5 mL), dried over MgSO$_4$ and concentrated to give 68.9 mg (86% yield) of the product 1-benzyloxycarbonyl-methyl-3,5-dichloro-6-(3-acetamidophenyl)pyrazinone (EX-100C): $^1$H NMR (300 MHz, CDCl$_3$) δ 2.21 (s, 3H), 4.55 (AB q, 2H, J=16.6 Hz), 5.17 (s, 2H), 6.96 (d, 1H, J=7.7 Hz), 7.26–7.40 (m, 5H), 7.57 (s, 1H), 7.74–7.79 (m, 1H), 8.19–8.24 (br m, 1H), 8.65 (br s, 1H).

Following the necessary final steps of the procedure of Example 1, EX-100C. was converted to the product: HPLC purity (retention time): 100% (2.9 min); LRMS m/z 572.5 (M$^+$+H).

Example 101

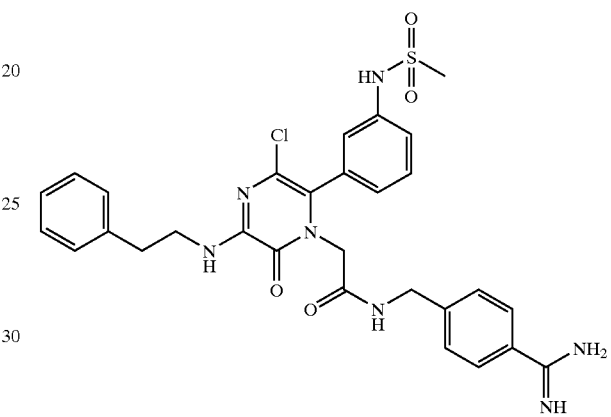

By following the method of Example 100 and substituting methanesulfonyl chloride for acetyl chloride the product was prepared: HPLC purity (retention time): 100% (2.9 min); LRMS m/z 608.2 (M$^+$+H).

Example 102

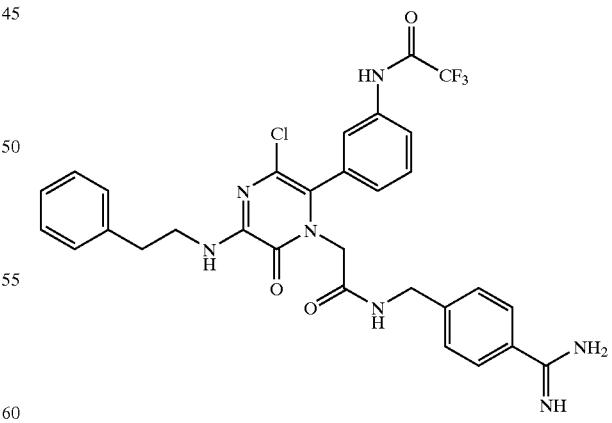

By following the method of Example 100 and substituting trifluoroacetic anhydride for acetyl chloride, the product was prepared: HPLC purity (retention time): 100% (3.3 min); LRMS m/z 626.3 (M$^+$+H).

Example 103

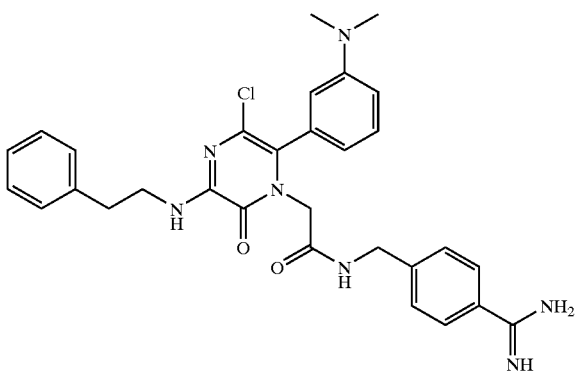

By following the method of Example 1 and substituting 3-nitrobenzaldehyde for benzaldehyde, 1-benzyloxycarbonylmethyl-3,5-dichloro-6-(3-aminophenyl)pyrazinone was obtained.

The 1-benzyloxycarbonylmethyl-3,5-dichloro-6-(3-aminophenyl)pyrazinone (210.6 mg, 0.48 mmol) was taken up in 9 mL of acetonitrile. Polyamine resin (1.05 g, 4.9 mmol) was added, along with about 10 mL of dichloromethane. After agitating about 10 mins the resin was filtered, rinsed with acetonitrile, and the solvents concentrated to about 10 mL. Formaldehyde (37%) (0.4 mL, 4.9 mmol) was added, followed by NaCNBH$_3$ (1.0 M in THF, 1.5 mL, 1.5 mmol) and the dropwise addition of two 50 mL portions of glacial acetic acid (17.4 M, 1.74 mmol). The reaction was monitored by LC/MS. A third 50 mL portion of glacial acetic acid was added after 3.5 h to force the reaction to completion. The solution was diluted with about 40 mL of diethyl ether and washed with 1.2 M NaOH (3×5 mL), saturated NaCl (1×5 mL), dried over MgSO$_4$, and the solvents were removed under reduced pressure to give 0.17 g (82% yield) of 1-benzyloxycarbonylmethyl-3,5-dichloro-6-(3-[N,N-dimethylamino]phenyl)pyrazinone (EX-103A): $^1$H NMR (300 MHz, CDCl$_3$): δ 2.96 (s, 6H), 4.59 (s, 2H), 5.19 (s, 2H), 6.55 (m, 2H), 6.82 (d, 1H), 7.25–7.40 (m, 6H).

Following the necessary final steps of the procedure of Example 1, EX-103A was converted to the product: HPLC purity (retention time): 94% (2.6 min); LRMS m/z 558.4 (M$^+$+H).

Example 104

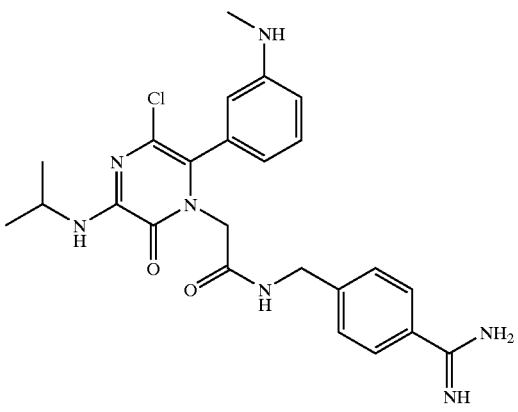

By following the method of Example 100 and replacing phenethylamine with isopropylamine, 1-benzyloxycarbonylmethyl-3-isopropylamino-5-chloro-6-(3-aminophenyl)pyrazinone was obtained.

The 1-benzyloxycarbonylmethyl-3-isopropylamino-5-chloro-6-(3-aminophenyl)pyrazinone (1.01 g, 2.4 mmol) was dissolved in 25 mL of THF. Pyridine (0.37 mL, 4.6 mmol) was added, followed by pentafluoropyridine trifluoroacetate (0.79 mL, 4.6 mmol). After 2 h, polyamine resin (3.1 g, 8.7 mmol) and 25 mL of dichloromethane was added, and the mixture was vigorously stirred for 1–2 h. The resin was filtered, rinsed with dichloromethane (3×5 mL), and the volatiles were removed under reduced presssure to give the desired product EX-104A in quantitative yield: $^1$H NMR (300 MHz, CDCl$_3$) δ 1.30 (d, 3H, J=1.4 Hz), 1.32 (d, 3H, J=1.4 Hz), 4.24 (m, 1H), 4.47 (AB q, 2H, J=16.9 Hz), 5.15 (s, 2H), 6.22 (d, 1H, J=8.2 Hz), 7.12 (d, 1H, J=7.7 Hz), 7.25–7.42 (m, 5H), 7.54 (s, 1H), 7.73–7.81 (m, 1H), 8.62 (d, 1H, J=4.2 Hz), 9.10 (br s, 1H).

The 1-benzyloxycarbonylmethyl-3-isopropylamino-5-chloro-6-(3-[N-trifluoroacetamido]phenyl)pyrazinone (EX-104A) (0.63 g, 1.2 mmol) was dissolved in 20 mL of dichloromethane. Barton's base (2-tert-butyl-1,1,3,3-tetramethylguanidine) (0.5 mL, 2.5 mmol) and dimethylsulfate (0.66 mL, 7 mmol) wee added, and the reaction was stirred at ambient temperature overnight. The reaction was monitored by LC/MS, and after completion the solution was washed with aqueous NH$_4$OH (2×10 mL) and 5% HCl (1×10 mL). The combined aqueous washes were extracted with dichloromethane (1×10 mL). The combined organic phases were washed with saturated NaCl (1×10 mL), dried over MgSO$_4$, filtered, and the volatiles were removed under reduced pressure to give 0.51 g (80% yield) of the desired product (EX-104B): HPLC purity (retention time): 97% (4.4 min); LRMS m/z 537.5 (M$^+$+H).

Following the necessary final steps of the procedure of Example 1, EX-104B was converted to the product: $^1$H NMR (300 MHz, CD$_3$OD) δ 1.31 (s, 3H), 1.33 (s, 3H), 2.94 (s, 3H), 4.22 (m, 1H), 4.40–4.52 (m, 4H), 7.01–7.05 (m, 2H), 7.17–7.19 (m, 1H), 7.42–7.45 (m, 1H), 7.49 (d, 2H, J=8.3 Hz) 7.80 (d, 2H, J=8.3 Hz); HPLC purity (retention time): 100% (2.1 min); LRMS m/z 481.6 (M$^+$+H).

Pyrazinones, wherein a B-A substituent is introduced by reaction of a 3-amino group of an intermediate pyrazinone with an electrophilic reagent, can be prepared using the general procedures and processes shown in Scheme 9 and Scheme 10 and as illustrated below in specific Examples 105–109.

Scheme 9:
Introduction of B—A—N(R$^5$) into Pyrazidone Intermediates and the Resulting Products

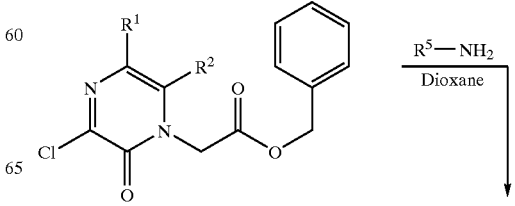

-continued

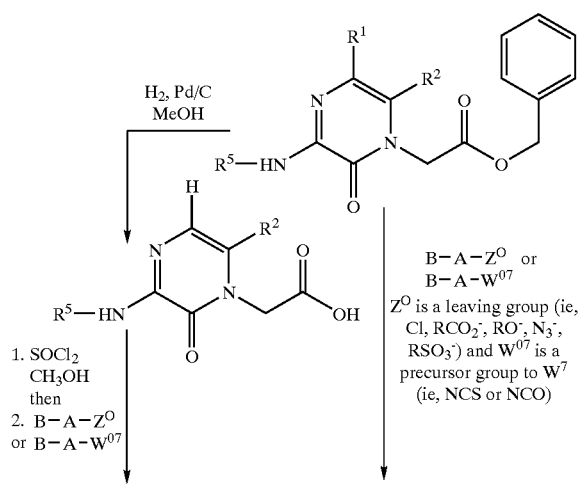

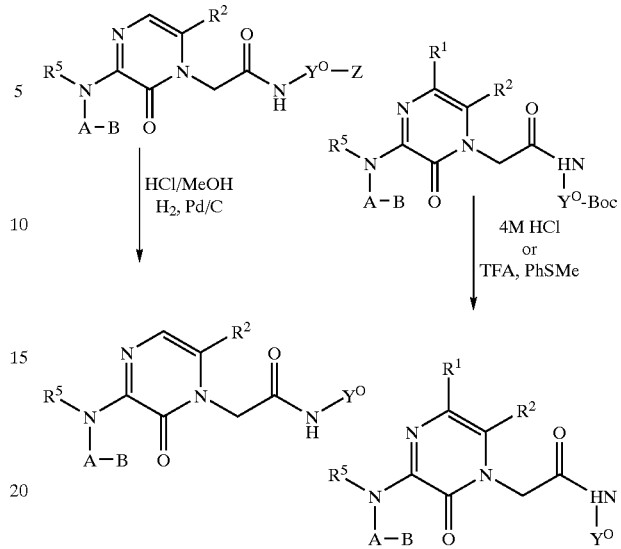

The examples of synthetic approaches to the preparation pyrazinones in which the substituents represented by B-A are introduced by reaction of a 3-amino group of the pyrazinone with an electrophilic reagent are shown in specific Examples 105 through 109 below. The specific examples recited below should be considered a being merely illustrative of the wide variety possible and not construed as limiting to one of ordinary skill in the art.

Example 105

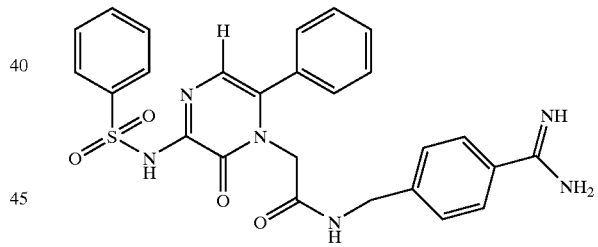

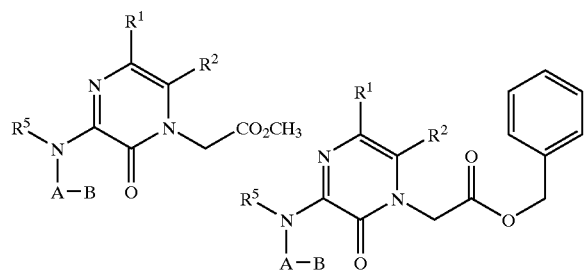

Scheme 10:
Introduction of B—A—N(R$^5$) into Pyrazidone
Intermediates and the Resulting Products (Concluded)

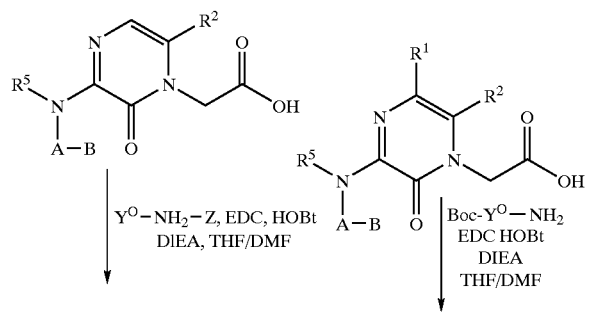

1-Benzyloxycarbonylmethyl-3,5-dichloro-6-phenylpyrazinone (EX-1B) (0.8 g, 2.06 mmol) was mixed with 20 ml 0.5 M ammonia in dioxane in a sealed tube. The tube was heated to 100° C. for 12 hours. After removing the dioxane under reduced pressure, the residue was dissolved in ethyl acetate. The ethyl acetate solution was washed with water and brine and dried over anhydrous $Na_2SO_4$. After removing the solvent, the product was recrystallized in acetone to yield the pure amino pyrazinone EX-105A as a white crystal solid (0.76 g, 99%): HPLC-MS (0 to 95% AcCN/6 min @ 1.0 mL/Min @ 254 nm @ 50° C.): retention time 3.75 min, M+H$^+$=370.0 for formula $C_{19}H_{17}ClN_3O_3$. $^1$H NMR (400 MHz, CDCl$_3$): δ 4.43 (s, 2H), 5.13 (s, 2H), 5.78 (b, 2H), 7.21–7.27 (m, 5H), 735–7.39 (m, 5H).

EX-105A (4.7 g, 12.73 mmol) was mixed with 1.34 g 10% Pd/C in 100 ml methanol. The mixture was stirred under hydrogen atmosphere that was introduced via a balloon for 48 hours. After filtration and removing the solvent, a white crystal solid was obtained as the carboxylic acid product EX-105B (3.0 g, 97%): HPLC-MS (0 to 95% AcCN/6 min @ 1.0 mL Min @ 254 nm @ 50° C.): retention time 1.45 min, M+H+=246.0 for formula $C_{12}H_{12}N_3O_3$.

EX-105B (3.0 g, 12.2 mmol) in 100 ml methanol was cooled down to −50° C. $SOCl_2$ (1.4 ml, 19.1 mmol) was added to the solution. After stirring at room temperature for four hours, the mix was heated to reflux for three hours. After removing the solvent, the residue was subjected to a silica gel plug using ethyl acetate to elute. The pure product was obtained by recrystallization in methanol as a white crystal solid EX-105C (2.22 g, 68%): HPLC-MS (0 to 95% AcCN/6 min @ 1.0 mL/Min @ 254 nm @ 50° C.): retention time 1.94 min, M+H+=260.0 for formula $C_{13}H_{14}N_3O_3$.

EX-105C (0.258 g, 1 mmol) was mixed with benzenesulfonyl chloride (0.353 g, 2 mmol) in 3 ml pyridine. The reaction mixture was heated at 90° C. for 2 hours. After removing the pyridine, the crude product was obtained by an aqueous work-up procedure. The crude product EX-105D was dissolved in 10 ml methanol and treated with 10 ml 1M LiOH solution for 15 minutes. After the solution was acidified with 2 N HCl to a pH of about 2 and the methanol removed under reduced pressure, a yellow precipitate was obtained via filtration and washing with water. The pure sulfonamide EX-105E is a yellow crystalline solid (0.267 g, 70%): HPLC-MS (0 to 95% AcCN/6 min @ 1.0 mL/Min @ 254 nm @ 50° C.): retention time 2.88 min, M+H+=386.0 for formula $C_{18}H_{16}N_3O_5S$. $^1$H NMR (400 MHz, methanol-$d_4$): δ 4.44 (s, 2H), 6.77 (s, 1H), 732 (dd, J=8.0, 1.6 Hz, 2H), 7.42–7.48 (m, 3H), 7.54 (t, J=8.0 Hz, 2H), 7.60–7.64 (m, 1H), 8.09 (d, J=8.0, 2H). $^{13}$C NMR (101 MHz, methanol-$d_4$): δ 48.4, 129.2, 129.9, 130.0, 130.6, 131.0, 132.6, 134.4, 141.4, 146.1, 157.0, 159.0, 160.0, 170.3.

EX-105E (0.106 g, 0.275 mmol) was mixed with EDC (0.055 g, 0.289 mmol) and HOBt (0.044 g, 0.289 mmol) in 2 ml DMF. The mixture was stirred for 10 minutes. To this mixture was then added the protected amidine, 4-(N-benzyloxycarbonylamidino)benzylamine hydrogen chloride salt (0.289 mmol), and DIEA (0.144 ml, 0.825 mmol) in 1 ml DMF. The reaction solution was stirred for 2 hours at room temperature. The DMF was removed under reduced pressure. The remaining residue was triturated in 1 N HCl and washed with water to yield the product EX-105F as an off-white amorphous solid (0.152 g, 85%): HPLC-MS (0 to 95% AcCN/6 min @ 1.0 mL/Min @ 254 nm @ 50° C.): retention time 3.14 min, M+H+=651.3 for formula $C_{34}H_{30}N_5O_7S$. $^1$H NMR (400 MHz, methanol-$d_4$): δ 4.42 (s, 2H), 4.51 (s, 2H), 5.40 (s, 2H), 6.76 (s, 1H), 7.35–7.62 (m, 15H), 7.75 (d, J=8.0 Hz, 2H), 8.08 (d, J=8.0 Hz, 2H). $^{13}$C NMR (101 MHz, methanol-$d_4$): δ 43.6, 49.7, 70.7, 111.6, 118.2, 119.7, 127.3, 128.7, 129.0, 129.1, 129.8, 129.9, 130.0, 130.8, 131.0, 132.6, 134.4, 135.8, 136.2, 141.5, 146.3, 147.6, 153.0, 154.5, 167.9, 169.0.

EX-105F (0.148 g, 0.228 mmol), p-toluenesulfonic acid mono hydrate (0.045 g, 0.24 mmol) and 10% Pd on activated carbon (0.012 g, 0.007 mmol) were mixed with 5 ml methanol. The mixture was stirred for 2 hours under an atmosphere of hydrogen that was introduced through a rubber balloon. After filtering off the catalyst and removing the methanol, the remaining residue was triturated in a solvent of 2:1 ether to methanol to yield a white amorphous solid as the product (0.105 g, 95%) as the mono-salt of p-toluenesulfonic acid: HPLC-MS (0 to 95% AcCN/6 min @ 1.0 mL/Min @ 254 nm @ 50° C.): retention time 2.64 min, M+H+=517.5 for formula $C_{26}H_{25}N_6O_4S$. $^1$H NMR (400 MHz, methanol-$d_4$): δ 2.35 (s, 3H), 4.40 (s, 2H), 4.52 (s, 2H), 6.77 (s, 1H), 7.21 (d, J=7.6 Hz, 2H), 7.34 (d, J=7.2 Hz, 2H), 7.41–7.51 (m, 3H), 7.55 (t, J=7.6 Hz, 2H), 7.64 (t, J=7.2 Hz, 1H), 7.79 (d, J=8.0 Hz, 2H), 7.74 (d, J=8.0 Hz, 2H). $^{13}$C NMR (101 MHz, methanol-$d_4$): δ 21.2, 43.5, 70.7, 119.5, 126.8, 128.0, 128.7, 128.9, 129.0, 129.7, 129.8, 129.9, 130.6, 130.9, 132.4, 134.3, 136.0, 141.3, 141.6, 146.2, 146.4, 152.9, 167.9, 168.7.

Example 106

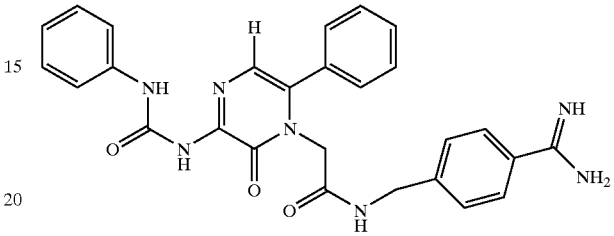

Following the method of Example 105, EX-105C (0.0932 g, 0.36 mmol) was treated with phenyl isocyanate (0.128 g, 1.08 mmol) and 0.2 ml pyridine in 2 ml acetonitrile at 80° C. for 3 hours instead of benzenesulfonyl chloride. After the reaction mixture was kept in a freezer for two days, a nice crystal solid formed as the pure pyrazinone urea EX-106A (0.129 g, 95%): HPLC-MS (0 to 95% AcCN/6 min @ 1.0 mL/Min @ 254 nm @ 50° C.): retention time 3.73 min, M+H+=379.3 for formula $C_{20}H_{19}N_4O_4$. $^1$H NMR (400 MHz, $CDCl_3$): δ 3.75 (s, 3H), 4.55 (s, 2H), 6.97 (s, 1H), 7.10 (t, J=7.6 Hz, 1H), 7.32–7.38 (m, 4H), 7.46–7.52 (m, 3H), 7.58 (d, J=8.0 Hz, 2H), 8.28 (s, 1H), 11.1 (s, 1H). $^{13}$C NMR (101 MHz, $CDCl_3$): δ 47.4, 52.8, 119.6, 120.2, 123.9, 128.9, 129.1, 129.4, 130.1, 130.9, 133.8, 137.8, 145.7, 150.8, 150.9, 167.3.

Saponification of compound EX-106A manner similar to the procedure as described in the synthesis of EX-105D yielded compound EX-106B. HPLC-MS (0 to 95% AcCN/6 min @ 1.0 mL/Min @ 254 nm @ 50° C.): retention time 334 min, M+H+=365.1 for formula $C_{19}H_{16}N_4O_4$. Compound EX-106B was coupled with 4-(N-benzyloxycarbonylamidino)benzylamine hydrogen chloride salt using EDC, HOBt and DIEA as described before to yield the protected product EX-106C as an off-white solid: HPLC-MS (0 to 95% AcCN/6 min @ 1.0 mL/Min @ 254 nm @ 50° C.): retention time 3.58 min, M+H+=630.0 for formula $C_{35}H_{32}N_7O_5$. $^1$H NMR (400 MHz, methanol-$d_4$): δ 4.49 (s, 2H), 4.61 (s, 2H), 5.40 (s, 2H), 7.06 (s, 1H), 7.11 (t, J=7.2 Hz, 1H), 7.32–7.56 (m, 16H), 7.76 (d, J=8 Hz, 2H).

EX-106C was converted to the HCl salt of the product by hydrogenation in methanol in the presence of HCl with Pd/C as the catalyst. The product was an off-white amorphous solid: HPLC-MS (0 to 95% AcCN/6 min @ 1.0 mL/Min @ 254 nm @ 50° C.): retention time 3.01 min, M+H+=496.4 for formula $C_{27}H_{26}N_7O_3$. $^1$H NMR (400 MHz, methanol-$d_4$): δ 4.47 (s, 2H), 4.65 (s, 2H), 6.97 (s, 1H), 7.15 (t, J=7.2 Hz, 1H), 7.27–7.54 (m, 9H), 7.57 (d, J=7.2 Hz, 2H) 7.78 (d, J=8.0 Hz, 2H), 8.76 (s, 1H), 9.26 (s, 1H). HRMS m/z MH+ 496.2036, calcd for $C_{27}H_{26}N_7O_3$ 496.2097.

Example 107

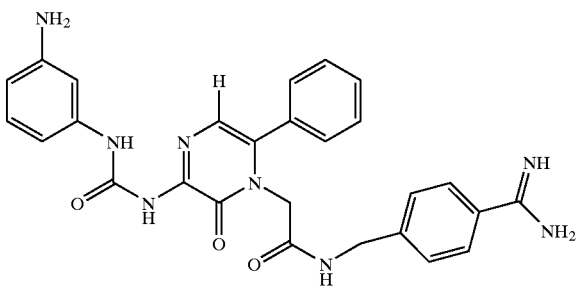

Using the procedure of Example 106 and substituting 3-(benzyloxycarbonylamido)phenyl isocyanate for phenyl isocyanate, the product was obtained as the HCl salt: HPLC-MS (0 to 95% AcCN/6 min @ 1.0 mL/Min @ 254 nm @ 50° C.): retention time 1.84 min, M+H$^+$=511.6 for formula $C_{27}H_{27}N_8O_3$. $^1$H NMR (400 MHz, methanol-d$_4$): δ 4.46 (s, 2H), 4.65 (s, 2H), 6.97 (s, 1H), 7.17 (d, J=6.8 Hz, 1H), 7.45–7.60 (m, 8H), 7.78 (m, 3H) 7.94 (s, 1H), 8.77 (s, 1H), 9.26 (s, 1H). HRMS m/z MH$^+$ 511.2251, calcd for $C_{27}H_{27}N_8O_3$ 511.2206.

Example 108

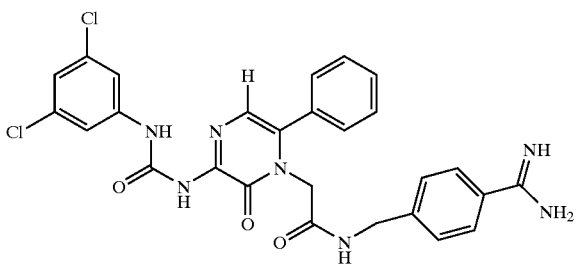

Using the procedure of Example 106 and substituting 3,5-dichlorophenyl isocyanate for phenyl isocyanate, the product was obtained as the HCl salt: HPLC-MS (0 to 95% AcCN/6 min @ 1.0 mL/Min @ 254 nm @ 50° C.): retention time 3.41 min, M+H$^+$=564.4 for formula $C_{27}H_{24}Cl_2N_7O_3$. $^1$H NMR (400 MHz, methanol-d$_4$): δ 4.47 (s, 2H), 4.63 (s, 2H), 7.04 (s, 1H), 7.18 (t, J=1.6 Hz, 1H), 7.45–7.56 (m, 7H), 7.64 (d, J=2 Hz, 2H) 7.78 (d, J=8.0 Hz, 2H), 8.77 (s, 1H), 9.26 (s, 1H). HRMS m/z MH$^+$ 564.1351, calcd for $C_{27}H_{24}Cl_2N_7O_3$ 564.1318.

Example 109

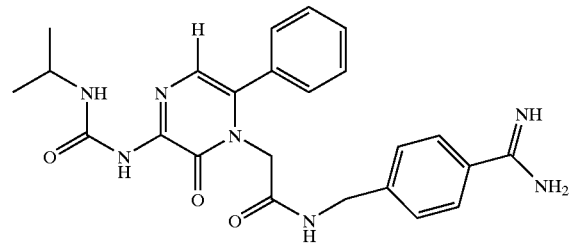

Using the procedure of Example 106 and substituting isopropyl isocyanate for phenyl isocyanate, the product was obtained as the HCl salt: HPLC-MS (0 to 95% AcCN/6 min @ 1.0 mL/Min @ 254 nm @ 50° C.): retention time 2.43 min, M+H$^+$=462.4 for formula $C_{24}H_{28}N_7O_3$. $^1$H NMR (400 MHz, methanol-d$_4$): δ 1.25 (d, J=6.4 Hz, 6H),3.99(m, 1H), 4.45 (s, 2H), 4.64 (s, 2H), 6.82 (s, 1H), 7.43–7.53 (m, 5H), 7.60 (m, 1H) 7.67 (t, J=6.4 Hz, 1H), 7.78 (d, J=8.0 Hz, 2H), 8.77 (s, 1H), 9.26 (s, 1H). HRMS m/z MH$^+$ 462.2230, calcd for $C_{24}H_{28}N_7O_3$ 462.2254.

Example 110

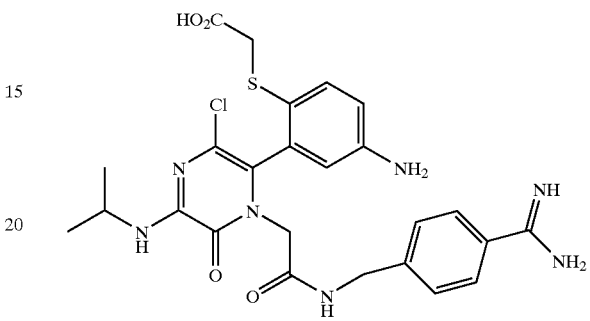

The protected pyrazinone intermediate 1-(N-(4-(N-benzyloxycarbonylamidino)benzyl) amidocarbonylmethylene)-5-chloro-3-(N-isopropylamino)-6-(5-nitro-2-carboxymethylthiophenyl)pyrazinone (prepared from commercially available 2-fluoro-5-nitrobenzaldehyde as described in the general pyrazinone inhibitor synthesis section; Scheme 1, Scheme 2, and Examples disclosed herein; 119 mg, 0.18 mmol) was dissolved in DMF (20 mL) and treated with triethylamine (77 µL). To this solution was added thioglycolic acid (18.6 mg, 0.20 mmol), and the resulting mixture was heated to 50° C. and stirred for 1 hour. At this time LCMS indicated approximately 50% conversion. Sodium hydride (15.0 mg, 0.63 mmol) and another 3 equivalents of thioglycolic acid (55.8 mg) were added over the next two hours and stirring continued. After 5 hours LCMS indicated 96% conversion. The mixture was concentrated to give EX-111A: LRMS (ESI) [M+H]$^+$=723.

EX-111A (:≦0.18 mmol) was placed in a Parr bottle and dissolved in glacial acetic acid (35 mL). Under an argon blanket, 10% Pd/C (52 mg) was added. The resulting heterogeneous mixture was hydrogenated at 60 psi and room temperature for 6 hours. LCMS shows complete reduction of the nitro group to the corresponding amine. The catalyst was filtered and the solvent evaporated. The crude Z-protected intermediate (EX-111B) was taken up into glacial acetic acid (10 mL), treated with 30% HBr in acetic acid (15 mL) and stirred at room temperature for 15 hours. The mixture was then concentrated and purified by reverse phase HPLC (C 18 column, 90% (0.1% TFA in water)/10% acetonitrile gradient to 10% aqueous/90% organic over 10 min) to afford 6 mg of product. Analytical HPLC (Beckman Ultrasphere ODS, 4.6 mm×250 mm, 85% (0.1% TFA in water/15% acetonitrile gradient to 15% aqueous/85% organic over 25 min) showed 100% purity at retention time=10.67 min; LRMS (ESI) [M+H]$^+$=558.

Example 111

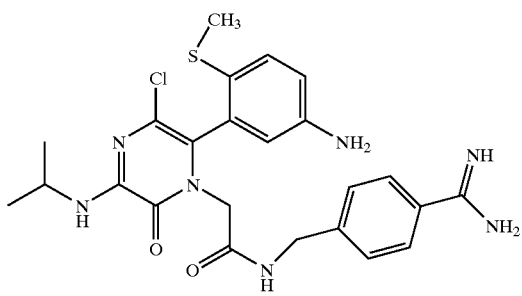

Using the procedure of Example 110 and substituting potassium methanethiolate for thioglycolic acid with no additional base added gave the product: LRMS (ESI) [M+H]$^+$=514.

Example 112

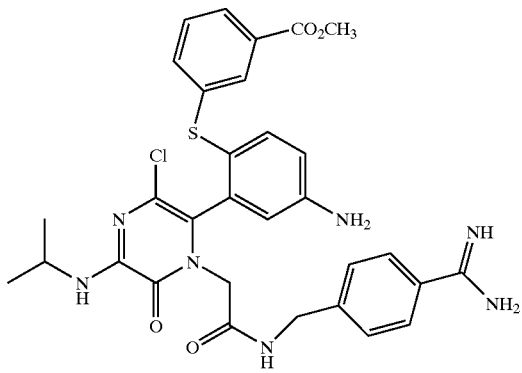

Using the procedure of Example 110 and substituting 3-mercaptobenzoic acid for thioglycolic. The methyl ester of the product was formed quantitatively during hydrogenation/hydrogenolysis conducted in 4 N HCl/MeOH: LRMS (ESI, negative ion mode) [M−H]$^-$=632.

Example 113

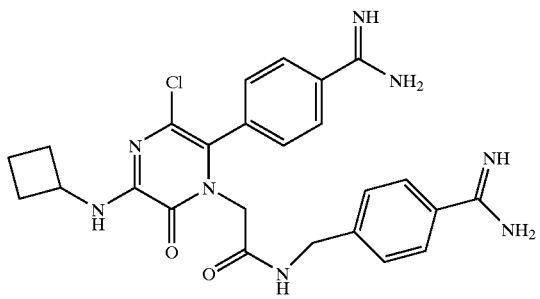

A solution of 1-(tert-butoxycarbonylmethyl)-6-bromo-3-(N-cyclobutylamino)pyrazinone (500 mg, 1.4 mmol) and 4-cyanobenzeneboronic acid (411 mg, 2.8 mmol) in toluene (7.0 mL), ethyl alcohol (5.0 mL), and sodium carbonate (4.4 mL, 2.0 N), was treated with tetrakis(triphenylphosphine) palladium(0) (80 mg, 0.07 mmol) The mixture was deoxygenated three times (hi-vacuum/nitrogen purge), and heated to 75° C. for 18 hrs. The reaction was cooled to room temperature, water (75 mL) was added and extracted three times with ethyl acetate. The organic layer was washed with brine, dried over magnesium sulfate, and concentrated in vacuo. Purification by column chromatography, eluting with 15% ethyl acetate/hexanes and then with 30% ethyl acetate/hexanes afforded EX-113A (270 mg, 0.71 mmol) as a white solid with M+H of 381.

A solution of EX-113A (270 mg, 0.71 mmol) in methylene chloride (5 mL) was treated with trifluoroacetic acid (5 mL) for 18 hrs. The reaction was concentrated in vacuo, toluene added, concentrated, diethyl ether added, and the solution concentrated in vacuo to afford EX-113B (230 mg, 0.70 mmol) as an off white solid.

A solution of EX-113B (200 mg, 0.62 mmol) in methylene chloride (8 mL) was treated with 1-hydroxybenzotriazole (100 mg, 0.74 mmol), EDC (147 mg, 0.74 mmol), diisopropyl ethyl amine (0.08 mL) and 4-cyanobenzylamine (98 mg, 0.74 mmol) for 18 hrs. Water was added and then extracted 3 times with ethyl acetate. The organics were washed with brine, dried over magnesium sulfate, filtered and concentrated in vacuo. Purification by column chromatography eluting with 70% ethyl acetate/hexanes and then 10% methanol/ethyl acetate afforded EX-113C (100 mg, 0.22 mmol) as an off-white solid. M+H 439.

A suspension of EX-113C (90 mg, 0.20 mmol) in ethyl alcohol (10 mL) was cooled to 0° C. and hydrochloric acid (g) was bubbled through the solution for 10 min. The reaction was allowed to warm to room temperature, stirred for 4 hrs, and then concentrated in vacuo. The residue was dissolved in ethyl alcohol (10 mL), cooled to 0° C., treated with ammonia (10 mL, 2.0 M in ethyl alcohol), warmed to room temperature and stirred for 65 hrs. Removal of the solvent, purification by reverse phase HPLC (Waters, delta prep 3000), and lyophilizationyalization afforded the product (80 mg, 0.17 mmol) with an M+H of 473.

Example 114

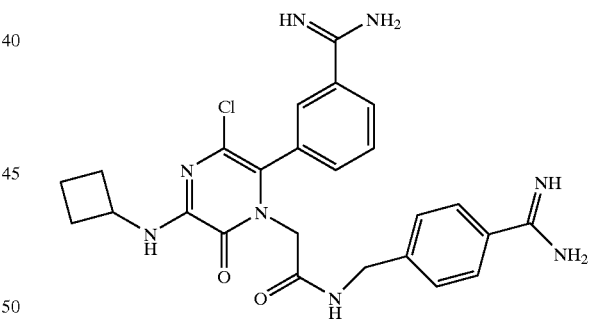

A solution of 1 (tert-butoxycarbonylmethyl)-6-bromo-3-(N cyclobutylamino)pyrazinone (500 mg, 1.4 mmol) and 3-cyanobenzeneboronic acid (411 mg, 2.8 mmol) in toluene (7.0 mL), ethyl alcohol (5.0 mL), and sodium carbonate (4.4 mL, 2.0 N), was treated with tetrakis(triphenylphosphine)-palladium(0) (80 mg, 0.07 mmol). The mixture was deoxygenated three times (hi-vacuum/nitrogen purge), and heated to 75° C. for 18 his. The reaction was cooled to room temperature and water (75 mL) was added, extracted three times with ethyl acetate. The organic layer was washed with brine, dried over magnesium sulfate, and concentrated in vacuo. Purification by column chromatography, eluting with 10% ethyl acetate/hexanes and then with 25% ethyl acetate/hexanes afforded EX-114A (480 mg, 1.2 mmol) as a white solid with M+H of 381.

A solution of EX-114A (480 mg, 1.2 mmol) in methylene chloride (10 mL) was treated with trifluoroacetic acid (10 mL) for 18 hrs. The reaction was concentrated in vacuo, toluene added, concentrated, diethyl ether added, and the solution concentrated in vacuo to afford EX-114B (360 mg, 1.1 mmol) as a brown solid.

A solution of EX-114B (300 mg, 0.92 mmol) in methylene chloride (10 mL) was treated with 1-hydroxybenzotriazole (162 mg, 1.2 mmol), EDC (240 mg, 1.2 mmol), diisopropyl ethyl amine (0.24 mL) and 4-cyanobenzylamine (160 mg, 1.2 mmol) for 18 hrs. Water was added and then extracted 3 times with ethyl acetate. The organics were washed with brine, dried over magnesium sulfate, filtered and concentrated in vacuo. Purification by column chromatography eluting with 70% ethyl acetate/hexanes and then 10% methanol/ethyl acetate afforded EX-114C (210 mg, 0.48 mmol) as an off-white solid. M+H 439.

A suspension of EX-114C (150 mg, 0.34 mmol) in ethyl alcohol (10 mL) was cooled to 0° C. and hydrochloric acid (g) was bubbled through the solution for 10 min. The reaction was allowed to warm to room temperature, stirred for 18 hrs, and then concentrated in vacuo. The residue was dissolved in ethyl alcohol (10 mL), cooled to 0° C., treated with ammonia (10 mL, 2.0 M in ethyl alcohol), warmed to room temperature and stirred for 18 hrs. Removal of the solvent, purification by reverse phase HPLC (Waters, delta prep 3000), and lyophilizationyalizationo afforded the product (103 mg, 0.21 mmol) with an M+H of 473.

Pyrazinones, wherein a wide variety of R substituents can be prepared by a metal catalyzed coupling reaction of a 6-bromo group in an appropriately substituted intermediate pyrazinone, can be prepared using the general procedures and processes shown in Scheme 11 and as illustrated below in specific Examples.

Scheme 11:
Introduction of $R^2$ Groups into Pyrazidone Intermediates and the Resulting Products

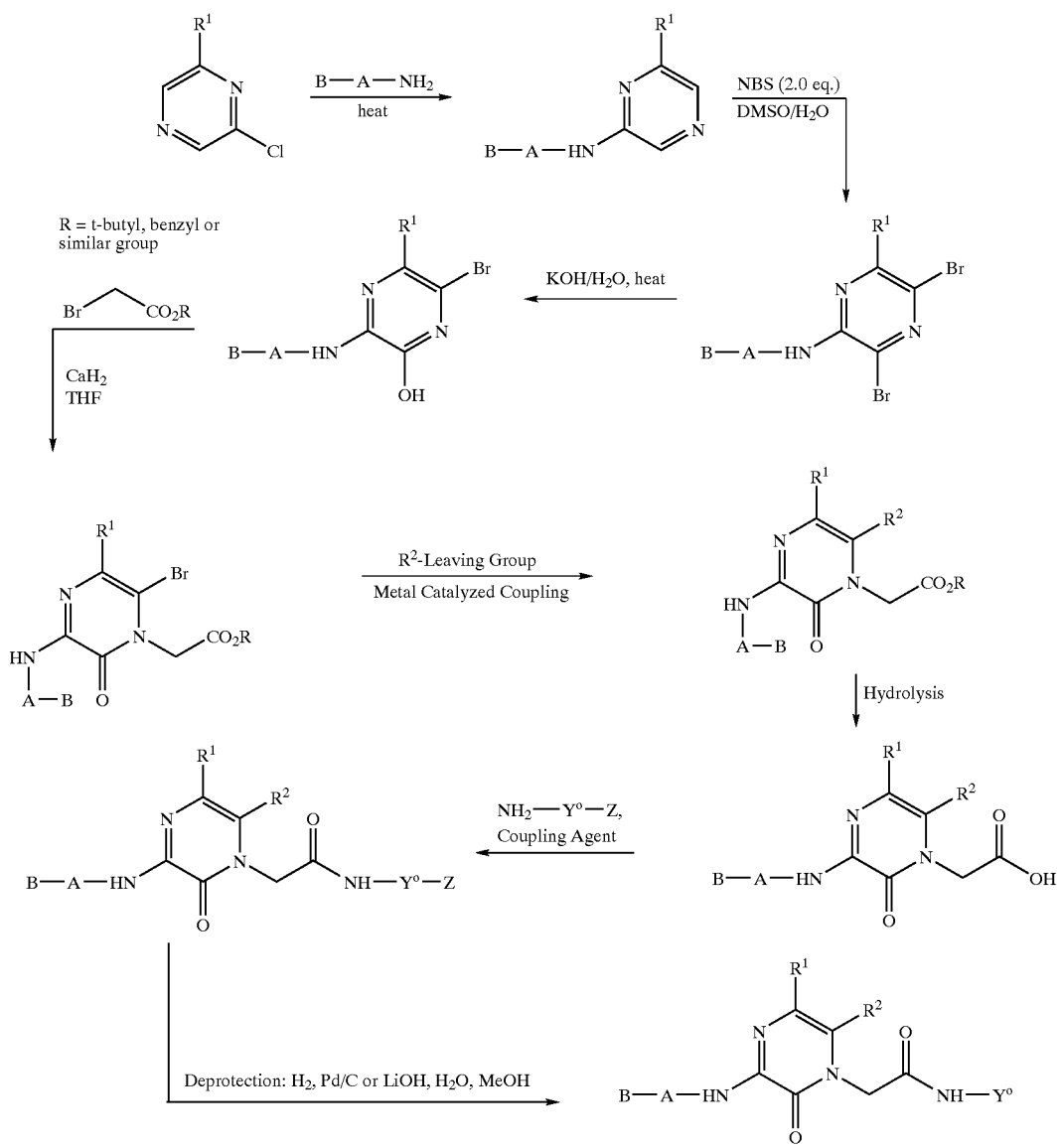

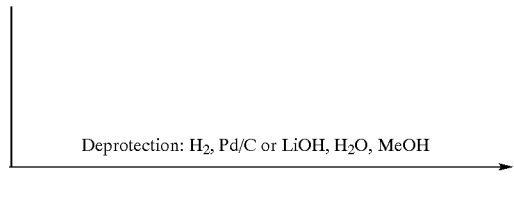

Deprotection: H₂, Pd/C or LiOH, H₂O, MeOH

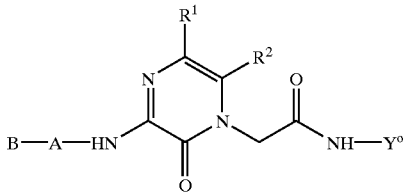

Example 115

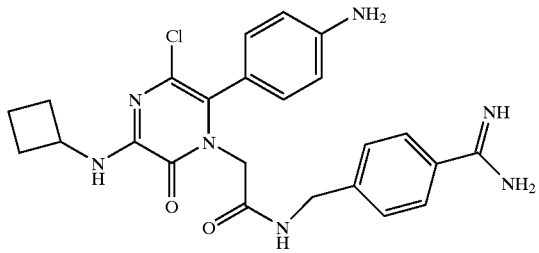

A solution of 2-chloropyrazine (26.12 g, 228.0 mmol) and cyclobutylamine (40.00 mL, 468.5 mmol) was heated in a pressure reaction flask with stirring to 110° C. for 16 hours. The brown reaction was allowed to cool to room temperature and was diluted with water (750 mL). The aqueous solution was extracted with ethyl acetate (2×250 mL). The combined organic solutions were washed with water (1×250 mL), saturated NaHCO₃ (1×250 mL) and brine (2×250 mL). The organic solution was dried (MgSO₄), filtered, and concentrated. The crude product was purified by MPLC (20% ethyl acetate-40% ethyl acetate/hexanes) to afford N-cyclobutylaminopyrazine (EX-115A) in 93% yield: $^1$H NMR (300 MHz, DMSO) δ 7.97–7.96 (m, 1H) 7.82–7.79 (m, 2H), 5.12 (br s, 1H), 430–4.18 (m, 1H) 2.51–2.39 (m, 2H), 1.97–1.73 (m, 4H); $^{13}$C NMR (75 MHz, DMSO) δ 149.3, 137.6, 128.3, 126.9, 42.2, 26.7, 10.7; HRMS (ES) calcd for C₈H₁₂N₃ 150.1031, found 150.0992.

A solution of EX-115A (30.36 g, 203.5 mmol) in 407.0 mL dimethyl sulfoxide and 10.0 mL water was added N-bromosuccinimide (79.17 g, 444.8 mmol) over a 30 minute period with the temperature being kept below 15° C. with an ice water bath. After the addition was completed, the the ice bath was removed, the reaction mixture was allowed to warm to room temperature and stirred for 5 hours. The reaction mixture was then poured into 1.0 L of ice water, and the aqueous solution was extracted with ethyl acetate (5×250 mL). The combined organic solutions were washed with 5% Na₂CO₃ (2×250 mL), water (1×250 mL), and brine (1×250 mL). The organic solution was dried (MgSO₄), filtered, and concentrated to a yellow solid. Purification of the crude product by MPLC (20% ethyl acetate/hexanes) gave pure 2-(N-cyclobutyl)amino-3,5-dibromopyrazine (EX-115B) in 73% yield as a light yellow solid: $^1$H NMR (400 MHz, CDCl₃) δ 7.98 (s, 1H), 5.31 (br d, J=4.8 Hz, 1H), 4.39–4.30 (m, 1H), 2.44–2.37 (m, 2H), 1.95–1.85 (m, 2H), 1.83–1.70 (m, 2H); $^{13}$C NMR (100 MHz, CDCl₃) δ 150.5, 143.0, 125.0, 121.6, 47.2, 31.4, 15.4; HRMS (ES) calcd for C₈H₁₀Br₂N₃ 307.9221, found 307.9214.

A suspension of 2-(N-cyclobutylamino)-3,5-dibromopyrazine (EX-15B) (25.03 g, 81.53 mmol) in 500.0 mL water (0.16 M) was added potassium hydroxide (22.90 g, 408.1 mmol) in 480.0 mL water. The resulting suspension was heated to reflux for approximately 18 hours. The reaction mixture was then added charcoal and refluxed for an additional 15 minutes. The mixture was then allowed to cool for 5 minutes and was filtered through Celite 545. The filtrate was cooled in an ice bath and was acidified to a pH of approximately 5 (litmus paper) upon which a white precipitate forms. The precipitate was collected by filtration, washed twice with water, and dried under vacuum to afford pure 5-bromo-2-(N-cyclobutylamino)-3-hydroxypyrazine (EX-115C) in 80% yield: $^1$H NMR (400 MHz, DMSO) δ 12.43 (s, 1H), 7.18 (br d, J=5.1 Hz, 1H), 6.87 (s, 1H), 4.29–4.19 (m, 1H), 2.16–2.09 (m, 2H), 2.03–1.93 (m, 2H), 1.63–1.51 (m, 2H); $^{13}$C NMR (100 MHz, DMSO) δ 147.0, 144.2, 119.9, 41.3, 26.0, 10.8; HRMS (EI) calcd for C₈H₁₁BrN₃O 244.0085, found 244.0086.

To a suspension of CaH₂ (1.7246 g, 40.96 mmol) in 80.0 mL tetrahydrofuran (0.50 M) was added 5-bromo-2-(N-cyclobutylamino)-3-hydroxypyrazine (EX-115C) (5.0477 g, 20.68 mmol) in 50.0 mL tetrahydrofuran (0.41 M) dropwise via an addition funnel. The resulting suspension was heated to reflux for 30 minutes. To the mixture was then added a solution of tert-butyl bromoacetate (3.40 mL, 23.03 mmol) in tetrahydrofuran (2.3 M). Refluxing of the mixture was continued for 18 hours. The reaction mixture was allowed to cool to room temperature and cautiously poured in to a stirred ice water mixture (600.0 mL). The aqueous layer was extracted with ethyl acetate (4×250 mL). The combined organic solutions were washed with saturated NaHCO₃ (1×250 mL) and brine (2×250 mL). The organic solution was dried (MgSO₄), filtered, and concentrated. Purification of the crude product by MPLC (20% ethyl acetate/hexanes) afforded pure 6-Bromo-1-t-butoxycarbonylmethyl-3-(N-cyclobutylamino)pyrazinone (EX-115D) in 72% yield as an off white solid: $^1$H NMR (400 MHz, CDCl₃) δ 6.97 (s, 1H), 6.18 (br d, J=7.5 Hz, 1H), 4.79 (s, 2H), 4.39–4.29 (m, 1H), 2.41–2.34 (m, 2H), 1.96–1.86 (m, 2H), 1.79–1.68 (m, 2H), 1.45 (s, 9H); $^{13}$C NMR (100 MHz, CDCl₃) δ 165.8, 152.5, 149.0, 124.6, 105.1, 83.3, 49.7, 46.3, 31.3, 28.2, 15.6; HRMS (EI) calcd for C₁₄H₂₁N₃O₃ 358.0766, found 358.0746.

A mixture of 6-bromo-1-t-butoxycarbonylmethyl-3-(N-cyclobutylamino)pyrazinone (EX-115D) (5.0345 g, 14.05 mmol) and 4-nitrophenylboronic acid (2.5204 g, 15.10 mmol) in 47.0 mL THF (0.3M) was stirred for 10 minutes under an atmosphere of nitrogen. To the solution was then added 8.4 mL of 2.0 M sodium carbonate (16.8 mmol) followed by tertakis(triphenylphosphine)palladium(0) (1.6262 g, 10 mol %). The resulting mixture was allowed to stir for 5 minutes at room temperature, then heated to reflux for approximately 18 hours. The reaction mixture was allowed to cool to room temperature and was diluted with ethyl acetate (150.0 mL). The organic solution was washed with saturated NaHCO₃ (2×50 mL) and brine (2×50 mL). The organic solution was dried (MgSO₄), filtered, and concentrated. Purification of the crude product by trituration with ethyl ether afforded pure product (EX-115E) as a bright yellow solid in 53% yield: $^1$H NMR (400 MHz, DMF-d$_7$) δ 8.50 (dd, J=1.9, 7.0 Hz, 2H), 7.87 (dd, J=1.9, 7.0 Hz, 2H), 7.64 (d, J==8.1 Hz, 1H), 4.74–4.64 (m, 3H), 2.49–2.29 (m, 4H), 1.91–1.83 (m, 2H), 1.52 (s, 9H); $^{13}$C NMR (100 MHz, DMF-d$_7$) δ 167.4, 151.7, 150.2, 148.1, 139.9, 131.1, 127.2, 124.3, 123.6, 82.5, 48.2, 46.3.30.8, 27.6, 15.3; HRMS (EI) calcd for $C_{20}H_{25}N_4O_5$ 401.1825, found 401.1846.

A solution of compound EX-115E (2.8013 g, 6.996 mmol) in 35.0 mL dry chloroform (0.2M) was added 5.40 mL trifluoroacetic acid (70.09 mmol) in one portion at room temperature. The resulting clear yellow solution was allowed to stir over night. The solvent was removed under reduced pressure and trituration from ethyl ether/hexanes afforded pure product (EX-115F) as a tan solid in 97% yield: $^1$H NMR (300 MHz, DMF-d$_7$) δ 13.81 (br s, 2H), 8.55 (d, J=8.9 Hz, 2H), 7.95 (d, J=8.9 Hz, 2H), 8.29 (d, J=7.5 Hz, 2H), 7.11 (s, 1H), 4.78–4.71 (m, 3H), 2.60–2.38 (m, 4H), 1.99–1.87 (m, 2H); $^{13}$C NMR (75 MHz, DMF-d$_7$) δ 169.4, 151.9, 149.5, 148.3, 139.5, 131.2, 127.7, 124.4, 121.0, 47.8, 46.7, 30.5, 15.4; HRMS (EI) calcd for $C_{16}H_{17}N_4O_5$ 345.1199, found 345.1193.

To a solution of acid EX-115F (3.0451 g, 8.844 mmol) in 60.0 mL dimethylformamide (0.15 M) was added N,N-diisopropylethylamine (15.0 mL, 86.11 mmol), N-hydroxybenzotriazole (1.4306 g, 10.59 mmol), and 1-[3-(dimethylamino)propyl]-3-ethylcarbodiimide hydrochloride (2.0116 g, 210.49 mmol). The resulting mixture was allowed to stir for 30 minutes. To the reaction mixture was then added 4-(N-benzyloxycarbonylamidino)benzylamine hydrogen chloride salt (3.1106 g, 9.727 mmol) prepared in Example 33 in one portion. The resulting mixture was allowed to stir over night. The reaction mixture was diluted with ethyl acetate (250 mL), washed with 5% citric acid (2×50 mL), saturated NaHCO$_3$ (2×50 mL), and brine (2×50 mL). The organic solution was dried (MgSO$_4$), filtered and concentrated. The crude reaction was purified by trituration (ethyl ether) to give pure product (EX-115G) in 43% yield: $^1$H NMR (400 MHz, DMF-d$_7$) δ 9.68 (br s, 1H), 9.35 (br s, 1H), 8.89 (t, J=5.8 Hz, 1H), 8.47 (d, J=8.9 Hz, 2H), 8.26 (d, J=8.5 Hz, 2H), 7.96 (d, J=8.9 Hz, 2H), 7.67–7.50 (m, 8H), 7.04 (s, 1H), 539 (s, 2H), 4.79–4.64 (m, 5H), 2.52–2.30 (m, 4H), 1.97–1.86 (m, 2H); $^{13}$C NMR (100 MHz, DMF-d$_7$) 6167.78, 167.49, 165.0, 151.9, 150.4, 148.0, 144.1, 140.2, 138.1, 133.8, 131.2, 128.87, 128.45, 128.31, 128.23, 127.8, 124.1, 123.6, 66.8, 49.0, 46.3, 42.9, 30.9, 15.4; HRMS (EI) calcd for $C_{32}H_{32}N_7O_6$ 610.2414, found 610.2454.

A solution of pyrazinone EX-115G (2.0113 g, 3.299 mmol) in 18.5 mL methanol/4 M HCl in dioxane (3:1, 0.1 M) was flushed with hydrogen gas. To the solution was then added 347.2 mg 10% Pd/C (wet), and the resulting suspension was allowed to stir at room temperature under an atmosphere of hydrogen (balloon pressure) for approximately 18 hours. The reaction mixture was filtered through a pad of Celite 545 and rinsed with methanol. The solvent was removed under reduced pressure. The crude product was purified by HPLC (20% acetonitrile to 95% acetonitrile/water/0.1% trifluoroacetic acid) to afford pure product in 74% yield: $^1$H NMR (400 MHz, DMF-d$_7$) δ 10.20 (br s, 2H), 9.41 (br s, 2H), 8.76–8.72 (m, 1H), 7.91 (d, J=8.3 Hz, 2H), 7.45 (d, J=8.3 Hz, 2H), 7.09 (d, J=8.5 Hz, 2H), 6.78 (d, J=8.5 Hz, 2H), 6.70 (s, 1H), 4.56–4.47 (m, 5H), 2.40–2.32 (m, 2H), 2.29–2.19 (m, 2H), 1.79–1.67 (m, 2H); $^{13}$C NMR (100 MHz, DMF-d$_7$) δ 167.17, 167.11, 160.0, 159.7, 152.3, 149.2, 147.6, 146.1, 131.0, 130.7, 128.4, 127.84, 127.51, 120.2, 118.1, 115.83, 115.23, 114.7, 113.9, 48.5, 46.8, 42.4, 30.2, 15.1; HRMS (EI) calcd for $C_{24}H_{28}N_7O_2$ 446.2304, found 446.2322.

Example 116

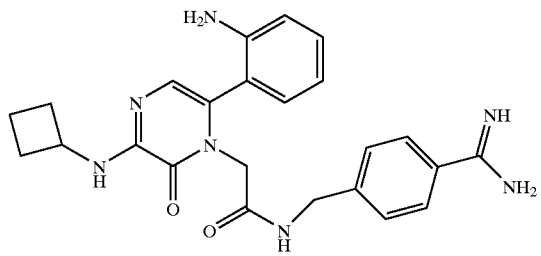

By following the method of Example 115 and substituting 2-nitrophenylboronic acid for 4-nitrophenylboronic acid, the title compound was prepared: $^1$H NMR (400 MHz, DMF-d$_7$) δ 10.60 (br s, 1H), 10.53–10.44 (br m, 1H), 9.68 (br s, 1H), 9.16 (br s, 2H), 8.20–8.16 (m, 3H), 8.04–7.99 (m, 2H), 7.76–7.74 (m, 1H), 7.63–7.59 (m, 1H), 7.55–7.51 (m, 1H), 7.44–7.40 (m, 1H), 7.35–7.31 (m, 1H), 7.18 (s, 1H), 4.69–4.60 (m, 3H), 2.44 (m, 2H), 2.35–2.25 (m, 2H), 1.90–1.82 (m, 2H); HRMS (EI) calcd for $C_{24}H_{28}N_7O_2$ 446.2304, found 446.2301

Example 117

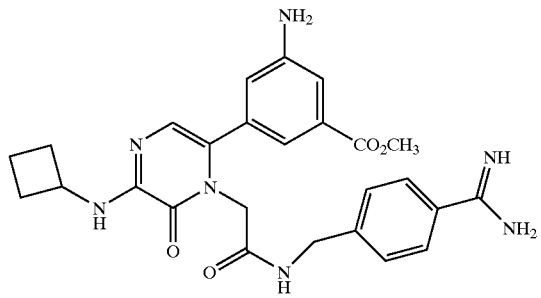

By following the method of Example 115 and substituting (3-methoxycarbonyl-5-nitrophenyl)boronic acid for 4-nitrophenylboronic acid, the title compound was prepared: $^1$H NMR (400 MHz, DMF-d$_7$) δ 10.43 (br s, 2H), 9.37 (br s, 2H), 8.68 (t, J=5.7 Hz, 1H), 7.88 (d, J=8.1 Hz, 2H), 7.46 (d, J=8.1 Hz, 2H), 7.39 (s, 1H), 7.22–7.17 (m, 2H), 6.94 (s, 1H), 6.70 (s, 1H), 5.54 (br s, 2H), 4.56–4.64 (m, 5H), 3.83 (s, 3H), 2.30–2.28 (m, 2H), 2.18–2.09 (m, 2H), 1.73–1.65 (m, 2H); $^{13}$C NMR (100 MHz, DMF-d$_7$) δ 167.3, 166.9, 151.8, 149.98, 149.63, 146.1, 1343, 131.3, 129.3, 128.4, 127.84, 127.49, 121.4, 119.6, 118.2, 115.0, 51.9, 48.3, 46.1, 42.5, 30.8, 15.1; HRMS (EI) calcd for $C_{26}H_{30}N_7O_4$ 504.2359, found 504.2334

Example 118

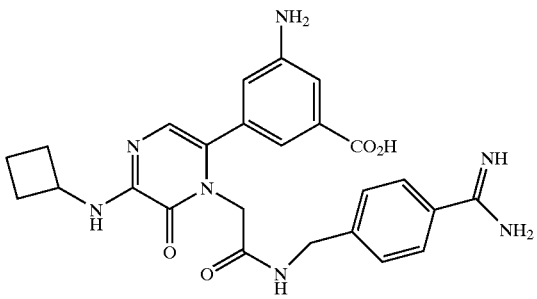

By following the method of Example 115 and substituting (3-carboxy-5-nitrophenyl)boronic acid for 4-nitrophenylboronic acid, the title compound was prepared: $^1$H NMR (400 MHz, DMF-$d_7$) δ 10.22 (br s, 2H), 9.34 (br s, 2H), 8.66–8.63 (m, 1H), 7.99 (s, 2H), 7.86 (d, J=8.1 Hz, 2H), 7.47–7.42 (m, 3H), 7.31–7.25 (m, 2H), 6.90 (s, 1H), 6.71 (s, 1H), 4.56–4.46 (m, 5H), 2.31–2.29 (m, 2H), 2.19–2.09 (m, 2H), 1.74–1.65 (m, 2H); $^{13}$C NMR (100 MHz, DMF-$d_7$) δ 167.85, 167.29, 167.22, 151.8, 149.81, 149.43, 146.1, 134.0, 132.5, 129.5, 128.4, 127.82, 127.46, 120.7, 119.4, 118.6, 115.4, 48.3, 46.2, 42.5, 30.7, 15.1; HRMS (EI) calcd for $C_{25}H_{28}N_7O_4$ 490.2203, found 490.2232.

Example 119

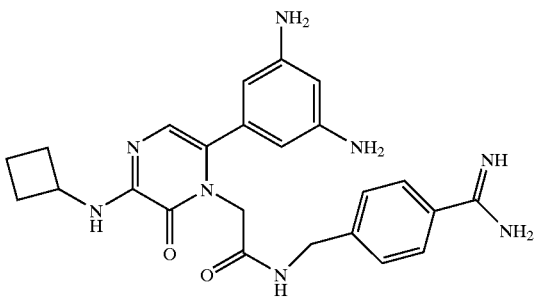

A mixture of methyl 3-nitrobenzoate (122 g, 674 mmol), silver sulphate (100 g, 320.7 mmol) and concentrated sulfuric acid (750 mL) was stirred mechanically and heated at 90° C. To this mixture was added bromine (37 mL), dropwise, over 2 h. The reaction was stirred another hour, cooled and filtered. The filtrate was mixed with 2 L water and 1 Kg crushed ice. The solid was filtered and dried to afford a mixture of the desired methyl ester and free acid hydrolysis product. The mixture was taken up into methanol (1 L), treated with 10 drops concentrated sulfuric acid and refluxed for 12 h. The reaction mixture was allowed to cool and the crystals that were deposited were collected and dried in a desiccator to afford 126 g (72% yield) of methyl 3-bromo-5-nitrobenzoate (EX-119A): $^1$H NMR (300 MHz, CDCl$_3$) δ 8.65 (s, 1 H), 8.44 (s, 1 H), 8.37 (s, 1 H), 3.94 (s, 3H).

To the product EX-119A (5.70 g, 22.0 mmol), dissolved in methanol (200 mL), was added hydrazine hydrate (1.20 mL of 98%, 24.2 mmol). The mixture was heated at reflux for 6 h. The mixture was allowed to cool and the crystals that were deposited were collected and dried in a desiccator to afford 2.85 g (50% yield) of the hydrazide EX-119B: $^1$H NMR (300 MHz, DMSO-$d_6$) a 10.2 (bs, 1 H), 8.60 (s, 1 H), 8.51 (s, 1 H), 8.41 (s, 1 H), 4.65 (bs, 2 H); LRMS (ESI, negative ion mode), [M–H]$^-$=258 (for $C_7H_6N_3^{79}BrO_3$), 260 (for $C_7H_6N_3^{81}BrO_3$).

The hydrazide product EX-119B (4.81 g, 18.6 mmol) was suspended in 2 N HCl (50 mL) and the mixture was cooled to 0° C. with rapid stirring. Sodium nitrite (3.00 g, 43.5 mmol) was added portion-wise over a 1 h period. The reaction was stirred another 1 h at 0° C. and filtered. The solid was dried in a dessicator to afford 3.60 g (72% yield) of the acyl azide EX-119c: $^1$H NMR (300 MHz DMSO-$d_6$) δ 8.70(t, J=1.8 Hz, 1 H), 8.53 (t, J=1.8 Hz, 1 H), 8.42 (t, J=1.8 Hz, 1 H).

The acyl azide product EX-119C (3.60 g, 13.3 mmol) was dissolved in tert-butanol (150 mL) and heated at reflux for 12 h. The reaction was cooled and concentrated to afford 4.00 g (95% crude yield) of the 3-nitro-5-(tert-butoxycarbonylamino)bromobenzene (EX-119D): $^1$H NMR (300 MHz, CDCl$_3$) δ 8.15 (s, 1 H), 7.98 (overlapping s, 2 H), 6.93 (bs, 1 H), 1.53 (s, 9 H); LRMS (ESI, negative ion mode), [M–H]$^-$=315 (for $C_{11}H_{13}N_2^{79}BrO_4$), 317 (for $C_{11}H_{13}N_2^{81}BrO_4$).

A 500 mL round bottom flask, containing a magnetic stir bar, was charged with 3-nitro-5-(tert-butoxycarbonylamino)-bromobenzene (EX-119D) (12.9 g, 40.8 mmol), the commercially available bis(pinacolato) diboron (13.5 g, 53.1 mmol), anhydrous KOAc (12.0 g, 122 mmol) and dichloro[1,1'-bis(diphenylphosphino)ferrocene] palladium (II) dichloromethane adduct (2.99 g, 10 mole %). The mixture was pump/purged (Argon) three times. To this mixture was added anhydrous, degassed dioxane (300 mL) by cannula transfer under a positive pressure of Argon. The resulting reaction mixture was heated at 65° C. for 12 h thereafter. The reaction was cooled, filtered through a medium frit, and concentrated. The residue was crystallized from hot hexanes to afford 13.1 g (88% yield) of 3-(tert-butoxycarbonyl)amino-5-nitrophenylboronic acid pinacol ester (EX-119E) as a tan solid: $^1$H NMR (300 MHz, CDCl$_3$) δ 8.48 (s, 1 H), 8.22 (d, J=1.2 Hz, 1 H), 7.87 (d, J=1.2 Hz, 1 H), 6.88 (bs, 1 H), 1.29 (s, 9 H), 1.21 (s, 12 H); LC-LRMS (ESI, negative ion mode) [M–H]$^-$=281 (for boronic acid hydrolysis product).

By following the method of Example 115 and substituting 3-(tert-butoxycarbonyl)amino-5-nitrophenylboronic acid, pinacol ester (EX-119E) for 4-nitrophenylboronic acid, the compound was prepared: $^1$H NMR (300 MHz, CD$_3$OD) δ 7.79 (d, J=8.1 Hz, 2H), 7.51 (d, J=8.1 Hz, 2H), 6.76 (s, 1H), 6.66 (s,2H), 4.60 (s, 2H), 4.51 (s, 2H), 4.35 (m, 1H), 2.52 (m, 2H), 2.31 (m, 2H), 1.93 (m, 2H); m/z (M+H) 461.4.

Example 120

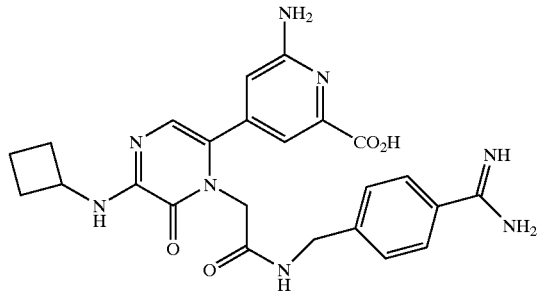

Diethyl 4-bromo-2,6-pyridinecarboxylate (EX-120A) was prepared from commercially available chelidamic acid using the procedure of Takalo, H. and Kankare, J. *Acta. Chemica Scandinavica* 1987, B 41, 219.

To a solution of the bromo-diester product EX-120A (10.0 g, 33.2 mmol) in ethanol (200 mL) at room temperature was added hydrazine hydrate (1.61 mL of 98%, 32.5 mmol), and the resulting mixture was allowed to stir at room temperature for 16 h. At this time the solid was filtered and dried to afford 4.48 g (47% yield) of the desired hydrazide EX-120B as a white solid: $^1$H NMR (CDCl$_3$) δ 9.08 (bs, 1 H), 8.50 (d, J=1.8 Hz, 1 H), 8.38 (d, J=1.8 Hz, 1 H), 4.47 (q, J=7.2 Hz, 2 H), 4.12 (bs, 2 H), 1.45 (t, J=7.2 Hz, 3 H); HRMS (ESI) calc'd for C$_9$H$_{11}$N$_3$O$_3$$^{79}$Br 287.9984, found 287.9974, calc'd for C$_9$H$_{10}$N$_3$O$_3$$^{81}$Br 289.9963, found 289.9982.

To a suspension of the hydrazide product EX-120B (1.0 g, 3.48 mmol) in 2 N HCl (30 mL), at 0–5° C., was added sodium nitrite (480 mg, 6.96 mmol) portion-wise over 1 h. The resulting solution was allowed to stir at 0–5° C. for an addition hour post-addition and filtered. The solid was dried thoroughly in a vacuum dessicator to afford 1.60 g (77% yield) of the desired acyl azide EX-120C: HRMS (ESI) calc'd for C$_9$H$_8$N$_4$O$_3$$^{79}$Br 298.9780, found 298.9788, calc'd for C$_9$H$_8$N$_4$O$_3$$^{81}$Br 300.9760, found 300.9774.

The acyl azide product EX-120C (1.60 g, 5.37 mmol) was dissolved in tert-butanol (50 mL) and the mixture was heated at reflux for 12 h. At this time LCMS indicated the reaction was complete. The mixture was concentrated to afford 1.77 g (96% yield) of the Boc-amino compound EX-120D as an orange oil: $^1$H NMR (CDCl$_3$) δ 8.39 (d, J=1.6 Hz, 1 H), 7.90 (d, J=1.6 Hz, 1 H), 7.59 (bs, 1 H), 4.44 (q, J=7.1 Hz, 2 H), 1.51 (s, 9 H), 1.41 (t, J=7.1 Hz, 3 H); HRMS (ESI) calc'd for C$_{13}$H$_{18}$N$_2$O$_4$$^{79}$Br 345.0450, found 345.0404, calc'd for C$_{13}$H$_{18}$NO$_4$$^{81}$Br 347.0431, found 347.0402.

To an oven-dried 100 mL round bottom flask was added the bromide product EX-120D (586 mg, 1.70 mmol), bis(pinacolato)diboron (2.2 mmol), dichloro[1,1'-bis(diphenylphosphino)ferrocene]palladium (II) dichloromethane adduct (64 mg, 5 mol %), and KOAc (500 mg, 5.10 mmol). This mixture was pump/purged three times with Argon, and dioxane (20 mL) was added by syringe. The mixture was heated to 80° C. for 5 h. LCMS at this time indicates only product. The mixture was cooled, diluted with ethyl acetate (100 mL), and washed with brine (3×75 mL). The layers were separated, and the organic solution was dried (MgSO$_4$), filtered, and concentrated. The residue was purified by radial chromatography (SiO$_2$, 10/1 hexanes-ethyl acetate) to afford 600 mg (90% yield) of pure boronate EX-120E: $^1$H NMR (CDCl$_3$) δ 8.44 (s, 1 H), 8.07 (s, 1 H), 7.61 (bs, 1 H), 4.42 (q, J=7.0 Hz, 2 H), 1.40 (t, J=7.0 Hz, 3 H), 1.33 (s, 9 H), 1.25 (s, 12 H); LC-LRMS (ESI, negative ion mode) [M−1]$^-$=309 (for boronic acid hydrolysis product).

By following the method of Example 115 and substituting 2-(tert-butoxycarbonyl)-6-ethoxycarbonyl-4-pyridineboronic acid, pinacol ester (EX-120E) for 4-nitrophenylboronic acid, the product was isolated as the dihydrochloride: $^1$H NMR (300 MHz, DMSO-d$_6$) δ 9.36 (bs, 1 H), 9.15 (bs, 1 H), 8.89 (t, J=6.0 Hz, 1 H), 7.76 (d, J=8.4 Hz, 2 H), 7.40 (d, J=8.4 Hz, 2 H), 7.35 (s, 1 H), 6.98 (s, 1 H), 6.84 (s, 1 H), 4.32–4.51 (complex m, 4 H), 3.75–3.90 (complex m, 1 H), 2.05–2.28 (m, 4 H), 1.58–1.72 (m, 2 H); HRMS (ESI) calc'd for C$_{24}$H$_{27}$N$_8$O$_4$ 491.2155, found 491.2185.

Example 121

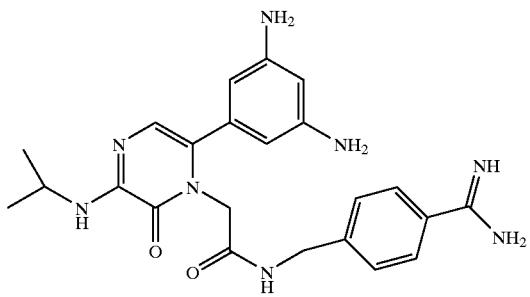

By following the method of Example 115 and substituting isopropylamine for cyclobutylamine and 3-(tert-butoxycarbonyl)amino-5-nitrophenylboronic acid, pinacol ester for 4-nitrophenylboronic acid, the compound was prepared: $^1$H NMR (300 MHz, CD$_3$OD) δ 7.82 (d, J=8.1 Hz, 2H), 7.54–7.50 (m, 3H), 7.43 (s, 2H), 6.78 (s, 1H), 4.66 (s, 2H), 4.51 (s, 2H), 4.20–4.11 (m, 1H), 1.44 (d, J=6.2 Hz, 6H); $^{13}$C NMR (75 MHz, CD$_3$OD) δ 167.5, 166.9, 152.5, 146.2, 145.3, 128.12, 128.00, 127.0, 108.7, 46.0, 42.6, 203. MS (m/z+1) of 449.

Example 122

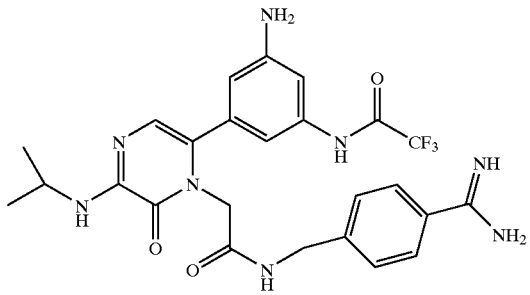

By following the method of Example 115, procedures disclosed herein, and substituting isopropylamine for cyclobutylamine and 3-(tert-butoxycarbonyl)amino-5-nitrophenylboronic acid, pinacol ester for 4-nitrophenylboronic acid, the title compound can be prepared.

Example 123

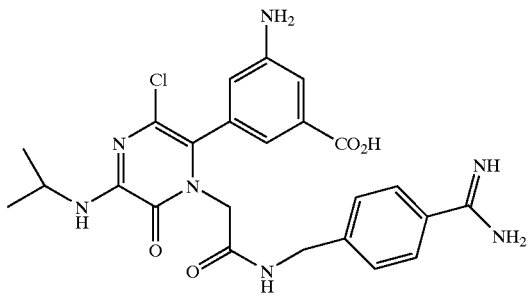

By following the method of Example 115 and substituting 2,6-dichloropyrazine for 2-chloropyrazine, isopropylamine for cyclobutylamine and (3-carboxy-5-nitrophenyl)boronic acid for 4-nitrophenylboronic acid, the compound was prepared $^1$H NMR (300 MHz CD$_3$OD) δ 8.12–8.19 (m, 2H), 7.71–7.78 (m, 3H), 7.46–7.49 (m, 2H), 4.48–4.63 (m, 2H), 4.28–4.42 (m, 2H), 4.18–4.26 (m, 1H), 1.33 (d, J=1.5 Hz, 3H), 130 (d, J=1.5 Hz, 3H); HRMS (EI) calcd for C$_{24}$H$_{27}$ClN$_7$O$_4$ 512.1813, found 512.1819.

Example 124

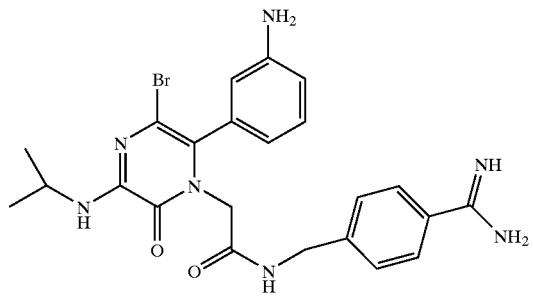

By following the method of Example 115 and substituting 2,6-dichloropyrazine for 2-chloropyrazine, isopropylamine for cyclobutylamine and 3-nitrophenylboronic acid for 4-nitrophenylboronic acid, the compound was prepared: $^1$H NMR (300 MHz CD$_3$OD) δ 7.80 (s, 1H), 7.77 (s, 1H), 7.59–7.40 (m, 4H), 7.37–7.28 (m, 2H), 4.52–4.33 (m, 4H), 4.20 (sept, J=6.6 Hz, 1H), 1.30 (d,J=6.6 Hz, 6H). MS (m/z+1) of 513.

Example 125

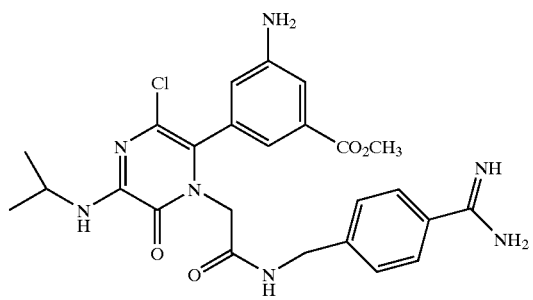

Using the Procedures of Scheme 1, Scheme 2, and Examples disclosed herein, the compound was prepared and showed MS (m/z+1) of 527.

Example 126

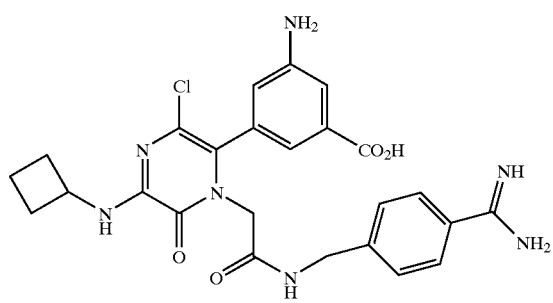

Using the Procedures of Scheme 1, Scheme 2, and Examples disclosed herein, the compound was prepared: $^1$H NMR (300 MHz, CD$_3$OD) δ 1.78–1.90 (m, 2H), 2.05–2.22 (m, 2H), 2.38–2.50 (m, 2H), 4.29–4.64 (m, 5H), 7.43–7.52 (m, 2H), 7.69–7.81 (m, 3H), 8.10–8.21 (m, 2H). MS (m/z+1) of 525.

Example 127

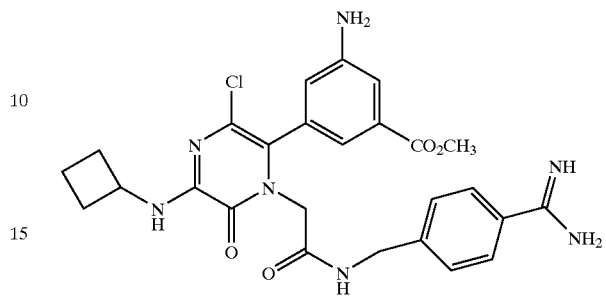

Using the Procedures of Scheme 1, Scheme 2, and Examples disclosed herein, the compound was prepared: $^1$H NMR (300 MHz, CD$_3$OD) δ 1.79–1.85 (m, 2H), 2.07–2.14 (m, 2H), 237–2.51 (m, 2H), 4.38–4.53 (m, 5H), 7.03–7.09 (m, 1H), 7.40–7.80 (m, 6H). MS (m/z+1) of 538.

Example 128

Experimental Procedure for the Robotic Parallel Synthesis of a Series of R$^2$ (3-Amino 5-(N-SubstitutedAmidocarbonyl)Phenyl)Pyrazinones Using a portion of the General Robotics and Experimental Procedure for the Robotic Parallel Synthesis described herein, a parallel array reaction block containing 40 mL vials, each reaction vessel was charged with the carboxylic acid,

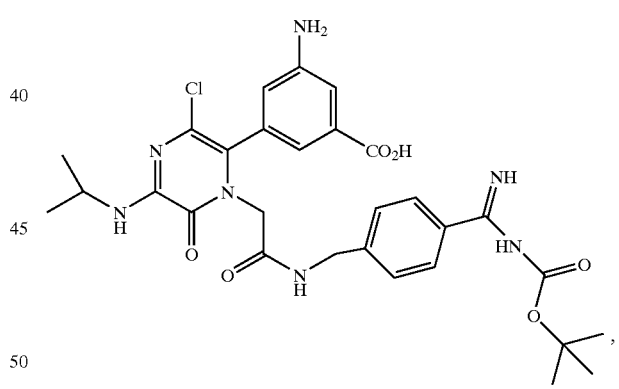

constituted in dichloromethane (2.0 mL). A stock solution of 1-hydroxybenzotriazole in dichloromethane and N-Methyl Morpholine (2 mL per well DCM/2.2 mL per well NMM/ 13.5 mg per well HOBT) were added to each vessel. Each reaction vessel was then charged with 200 mg of carbodiimide resin R-2 (1.0 meq/g resin). The reaction mixtures were agitated on a Labline benchtop orbital shaker at 150 RPM overnight at ambient temperature. An amine corresponding the desired amide product was placed in dichloromethane (0.2 M, 1.0 equiv.) and then added to each reaction vessel and the reaction mixtures were agitated for another 2–3 h. Polyamine polymer R-1 (0.2 grams/2.3 meq. N/g resin) and aldehyde resin R-3 (0.2 grams/2.0 meq per gram) and 2 mL of dichloromethane were added to the reaction mixture in each vessel, and the mixtures were agitated for 2 h. Each reaction vessel was then opened, and the desired solution phase products were separated from the insoluble byproducts by filtration and collected in individual conical vials. Each reaction vessel was rinsed three times with dichloromethane (1 mL), and the rinses were also collected. The solutions obtained were then evaporated to dryness under a nitrogen stream. The samples were then redissolved in 2.5 mL DCM and 0.5 mL TFA for 2 hours, followed by drying under a nitrogen stream, and finally followed by drying under a vacuum overnight. The samples were weighed to afford the desired products as oils or solids. The Examples prepared are summarized in Example Table 1.

Example Table 1. Additional Substituted Pyrazinones of the Present Invention Prepared based on the Procedures of Scheme 9, Scheme 10, Scheme 11, and Example 128.

Example Table 2.
Additional Substituted Pyrazinones Having a Carboxylic Acid Substituent in the B—A—Group.

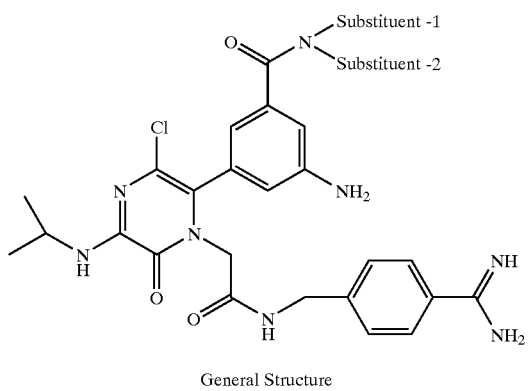

General Structure

| Ex. No. | Substituent-1 | Substituent-2 | Molecular Weight (m/z + 1) |
|---|---|---|---|
| 128-1 | hydrogen | hydrogen | 510.98 |
| 128-2 | methyl | benzyl | 615.13 |
| 128-3 | hydrogen | 1-phenylethyl | 615.13 |
| 128-4 | hydrogen | 2-phenyl-2-propyl | 629.15 |
| 128-5 | hydrogen | 2,4-dichlorobenzyl | 669.99 |
| 128-6 | hydrogen | 3,5-bis-trifluoromethylbenzyl | 737.09 |
| 128-7 | hydrogen | 4-tert-butylbenzyl | 657.2 |
| 128-8 | hydrogen | 4-bromobenzyl | 679.99 |
| 128-9 | hydrogen | benzyl | 601.1 |
| 128-10 | hydrogen | 2-chlorobenzyl | 635.54 |
| 128-11 | hydrogen | 2-trifluoromethylbenzyl | 669.10 |
| 128-12 | hydrogen | 3-fluorobenzyl | 619.09 |
| 128-13 | hydrogen | 3-trifluoromethylbenzyl | 669.10 |
| 128-14 | hydrogen | isobutyl | 567.08 |
| 128-15 | hydrogen | cyclobutyl | 565.07 |
| 128-16 | hydrogen | cyclopentyl | 579.09 |
| 128-17 | hydrogen | cycloheptyl | 607.15 |
| 128-18 | hydrogen | 3-pyridylmethyl | 602.09 |
| 128-19 | hydrogen | 2-pyridylmethyl | 602.09 |
| 128-20 | hydrogen | 2-(4-methoxyphenyl)ethyl | 645.15 |
| 128-21 | hydrogen | 3-phenylpropyl | 629.15 |
| 128-22 | hydrogen | 2,2-diphenylethyl | 691.22 |
| 128-23 | hydrogen | 2-naphthylmethyl | 651.16 |
| 128-24 | hydrogen | 1,2,3,4-tetrahydronaphth-2-yl | 641.16 |

Example 129

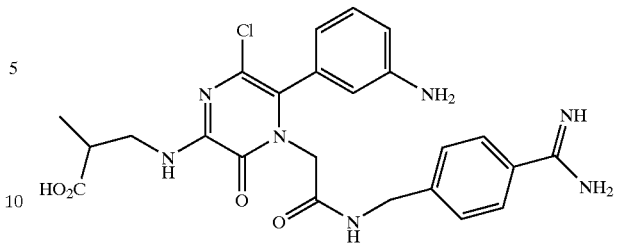

Using the procedures of Scheme 1, Scheme 2, and the Examples herein with suitable reagents, starting materials, and intermediates, 2-{5-chloro-6-(3-nitrophenyl)-3-[N-(2-methoxycarbonylpropyl)amino]-2-oxohydropyrazinyl}acetic acid (EX-129A) was prepared from 2-{3,5-dichloro-6-(3-nitrophenyl)-2-oxohydropyrazinyl}acetic acid by using the methyl ester of 3-amino-2-methylpropionate hydrochloride as the B-A-NH$_2$ reactant along with an equivalent of a non-nucleophilic. The nitro group of EX-129A was hydrogenated to amine as in Example 27 to give EX-129B. EX-129B was reacted with the protected amidine, 4-(N-benzyloxycarbonylamidino) benzylamine hydrogen chloride salt, as described in Example 44, to give the protected product EX-129C.

EX-129C was dissolved in methanol to make approximately a 0.1 M solution. Dissolved in a minimal amount of water, 5.0 eq. of lithium hydroxide monohydrate was added dropwise to the solution turning it cloudy, and the reaction mixture stirred for 24 h. at room temperature. Dropwise, 2 N HCl was added to neutralize the reaction. The methanol and water were concentrated, and the product was purified by reverse phase HPLC: 10 to 50% gradient organic with 0.1% TFA buffer. The product showed a $^1$H NMR (300 MHz, CD$_3$OD) δ 1.35 (d, 3H, 6.9 Hz), 2.68 (ABdq, 2H, Δν=42.6 Hz, J$_{AB}$=15.9), 4.31–4.59 (m, 5H), 7.42–7.80 (8H); LRMS m/z 512.1 (M$^+$+H).

Additional pyrazinones having a carboxylic acid substituent in the B-A-group were prepared as described in Example 129 by using the appropriate amino acid methyl ester hydrochloride in place of methyl ester of 3-amino-2-methylpropionate hydrochloride. Additional examples of these pryazinones are summarized in Example Table 2.

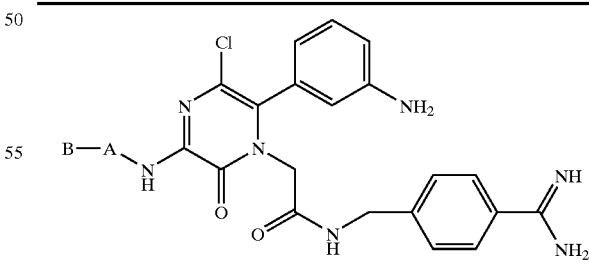

| Ex. No. | B—A | Spectral Characterization Data |
|---|---|---|
| 130 | 1-carboxy-2-propyl | $^1$H NMR (300 MHz, CD$_3$OD) δ 1.26 (d, 3H, J = 7.2 Hz), 2.87–2.95 (m, 1H), 3.55–3.70 (m, 2H), 4.34–4.53 (m, 4H), 7.36–7.80 (m, 8H).; LRMS m/z 512.2 (M$^+$ + H). |

-continued

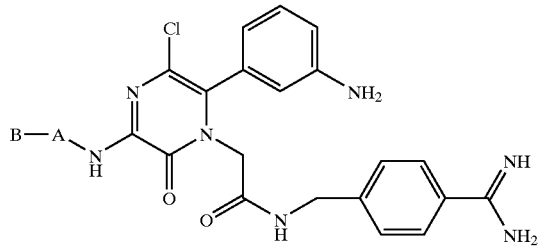

| Ex. No. | B—A | Spectral Characterization Data |
|---|---|---|
| 131 | 2-carboxyethyl | $^1$H NMR (300 MHz, CD$_3$OD) δ 2.87–3.14 (m, 2H), 4.32–4.54 (m, 4H), 5.57 (t, 1H, J = 6.6 Hz), 7.24–7.79 (m, 13H); LRMS m/z 574.2 (M$^+$ + H). |
| 132 | carboxymethyl | $^1$H NMR (300 MHz, CD$_3$OD) δ 2.70 (t, 2H, J = 6.6 Hz), 3.72 (t, 2H, J = 6.6 Hz), 4.38–4.56 (m, 4H), 7.37–7.80 (m, 8H); LRMS m/z 498.2 (M$^+$ + H). |
| 133 | 2-carboxy-1-phenylethyl | $^1$H NMR (300 MHz, CD$_3$OD) δ 4.19 (s, 2H), 4.34–4.59 (m, 4H), 7.42–7.80 (m, 8H); LRMS m/z 484.1 (M$^+$ + H). |
| 134 | (R)-1-carboxyethyl | $^1$H NMR (300 MHz, CD$_3$OD) δ 1.57 (d, 3H, J = 6.0 Hz), 4.32–4.63 (m, 5H), 7.41–7.80 (m, 8H); LRMS m/z 498.4 (M$^+$ + H). |
| 135 | (S)-1-carboxyethyl | $^1$H NMR (300 MHz, CD$_3$OD) δ 1.58 (d, 3H, J = 7.2 Hz), 4.37–4.62 (m, 5H), 7.40–7.80 (m, 8H); LRMS m/z 498.1 (M$^+$ + H). |

Example 136

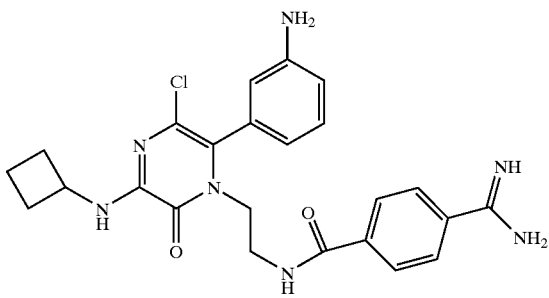

To a solution of 2-{5-chloro-3-(N-cyclobutylamino)-6-(3-nitrophenyl)-2-oxohydropyrazinyl}acetic acid (0.5 g, 13 mmol) in THF (15 L) at 0° C. was added BH$_3$.THF (1.0 M in THF, 4.0 mL, 4.0 mmol) via syringe. The reaction mixture was allowed to warm to room temperature and stirred for 12 hours. The reaction mixture was poured into ice water. The aqueous mixture was extracted with ethyl acetate (2×25 mL). The organic extracts were washed with bicarbonate (1×25 mL) and brine (1×25 mL). The organic layer was dried (NaSO$_4$) and the solvent removed to give a yellow foam (0.39 g), which after chromatography (30%–70% EtOAc/Hexanes) gave 0.24 g of a yellow foam (EX-136A): m/z+1=365.

To a solution of alcohol EX-136A (0.19 g, 0.5 mmol) in dichloromethane (10 mL) at 0° C. was added triethylamine (0.087 mL, 0.6 mmol) and methanesulfonyl chloride (0.04 mL, 0.55 mmol). The reaction was stirred at room temperature for 1 h and then diluted with water and dichloromethane. The layers were separated and the organic layer washed with brine (1×20 mL) and dried (Na$_2$SO$_4$). The solvent was removed to give a yellow oil EX-136B, which was taken on to the next step without purification: m/z+1= 443.

To a solution of mesylate EX-136B (021 g, 0.47 mmol) in DMF/water (5 mL/5 drops) at room temperature was added sodium azide. After 12 h, the reaction was diluted with ether and water. The layers were separated, and the organic layer washed with brine (1×10 mL) and dried (Na$_2$SO$_4$). The solvent was removed to give a yellow oil EX-136C, which was taken on to the next step without purification: m/z+1= 390.

To a solution of azide EX-136C (1.10 g, 2.8 mmol) in THF/H$_2$O (20 mL/10 drops) was added Ph$_3$P at room temperature. The reaction was stirred overnight and then diluted with water and dichloromethane. The layers were separated and the organic layer washed with bicarbonate (1×25 mL) and brine (1×25 mL). The organic extract was dried (Na$_2$SO$_4$), and the solvent removed to give an orange oil, which after column chromatography (5% MeOH in dichloromethane) gave the desired product EX-136D as a yellow oil (0.95 g): m/z+1=364.

To a solution of acid, 4-(N-benzyloxycarbonylamidino) benzoic acid, (0.45 g, 1.2 mmol) in DMF (20 mL) was added EDC (0.37 g, 1.9 mmol) and HOBt (0.26 g, 1.9 mmol) at room temperature. After 15 min, the amine EX-136D (0.45 g, 1.2 mmol) in DMF/triethylamine (10 mL/0.67 mL, 4.8 mmoL) was added via canula. The reaction was stirred overnight at room termperature. The reaction was diluted with water and ether. The layers were separated, and the organic layer washed with bicarbonate (1×25 mL) and brine (1×25 mL). The organic extract was dried (Na$_2$SO$_4$), and the solvent removed to give an oil, which after chromatography (70% ethyl acetate in hexanes) gave the product as a yellow oil EX-136E (0.67 g): m/z+1=644.

To a solution of EX-136E (0.67 g, 1.0 mmol) in ethanol (30 mL) was added HCl (2.0 M solution in ether, 2 mL) and 10% Pd/C (0.2 g). The reaction was placed on a Parr apparatus and shaken at 40 psi for 2 hours. The reaction mixture was filtered through a pad of celite, and the solvent removed to give an oil (0.48 g). To a solution of the oil in ether was added 2.0 M HCl in ether to give a precipitate. The precipitate was filtered to give a gummy residue, which was dissolved in water and lyophilized to give the product as an HCl salt (0.45 g): m/z+1=480.

Example 137

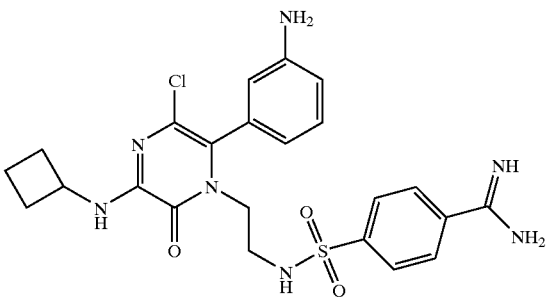

To a solution of amine EX-136D (0.42 g, 1.1 mmol) in dichloromethane at room temperature was added TEA (0.31 mL, 2.2 mmol) and 4-cyanobenzenesulfonyl chloride (0.23 g, 1.1 mmoL.). After stirring at room temperature, the reaction was diluted with dichloromethane and bicarbonate. The layers were separated, and the organic layer was washed with brine. The organic extract was dried ($Na_2SO_4$) and solvent removed to give (0.56 g) of a yellow solid EX-137A: m/z+1=529.

To a solution of EX-137A (0.56 g, 1.0 mmol) in THF (20 mL) at 0° C. was added LiHMDS (1.0 M in THF, 5.3 mL, 5.0 mmol) dropwise. The reaction was allowed to warn to room temperature and stirred for 1 h. The reaction mixture was diluted with water (10 mL) and stirred for 30 min. The crude amidine EX-137B was taken onto the next step without purification: m/z+1=546.

To the crude amidine EX-137B in THF/$H_2O$ (8:2) was added $Na_2CO_3$ (0.37 g, 4.0 mmol) and Cbz-Cl (0.31 mL, 2.2 mmol) at 0° C. The reaction was stirred vigorously for 30 minutes and then poured into a seperatory funnel. The layers were separated, and the aqueous layer was extracted with ethyl acetate (2×25 mL). The organic extracts were combined and washed with brine (1×25 mL) and bicarbonate (1×25 mL). The organic extract was dried ($Na_2SO_4$), and the solvent removed to give a yellow solid EX-137C (0.49 a): m/z+1=1680.

To a solution of EX-137C (0.49 g, 0.72 mmol) in 40 mL of ethanol in a Parr bottle was added 10% Pd/C (0.2 g) and HCl (2.0 M solution in ether, 0.75 mL, 1.44 mmol). The reaction was shaken for 2 hours at 40 psi. The reaction mixture was filtered through celite and washed with methanol. The solvent was removed to give the crude product as an oil. To the oil was added ether and 2.0 M HCl in ether to give a white precipitate that was filtered and washed with ether. The hygroscopic solid was dissolved in water and tyophilized to give the product as a HCl salt (0.37 g): m/z+1=516.

Example 138

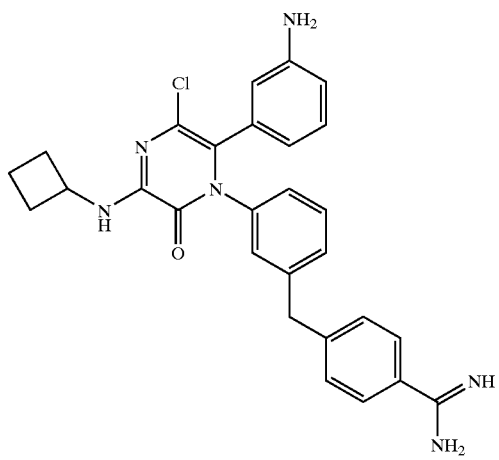

To a stirred solution of 10.0 g of (4-cyanophenyl)boronic acid (68 mmol) in 350 mL of THF was added 14.7 g of 3-nitrobenzyl bromide (68 mmol), 1.0 g of Pd(PPh$_3$)$_4$, and 30 mL of 2N $Na_2CO_3$ aqueous solution. The mixture was stirred at room temperature for overnight. The mixture was concentrated in vacuo, redissolved in ethyl acetate, and washed with brine. The ethyl acetate layer was dried over $MgSO_4$ and concentrated in vacuo. The crude was purified on silica gel with 10% ethyl acetate/hexane to give 12.5 g of the product EX-138A (77%).

5.0 g of the nitro compound EX-138A (21 mmol) was stirred in 150 mL of 10% HCl EtOH/$H_2O$ solution at refluxing temperature for 5 hr. The mixture was cooled to room temperature and concentrated in vacuo. The crude product was purified on silica gel with 30% ethyl acetate/hexane to give 3.2 g of the pure product EX-138B (73%).

To a stirred solution of 2.0 g of the amino compound EX-138B (9.6 mmol), 1.5 g of 3-nitrobenzaldehyde (9.8 mmol), 50 mg of Yb(OTf)$_3$, and 5 g of 4A molecular sieves in 50 mL of $CH_2Cl_2$ was added 1.0 g of TMSCN (10 mmol) dropwise. The mixture was stirred at room temperature overnight. The mixture was concentrated in vacuo and redissolved in ethyl acetate. The ethyl acetate solution was washed with brine, dried over $MgSO_4$, and concentrated in vacuo. The product was purified on silica gel with 10% ethyl acetate/hexane to give 2.8 g of the pure product EX-138C (79%).

To a stirred solution of 2.5 g of the cyano amine EX-138C (6.8 mmol) in 70 mL of 1,2-dichlorobenzene was added 3.5 g of oxalyl chloride (27.5 mmol). The mixture was stirred at 100° C. for overnight. The reaction was allowed to cool to room temperature and concentrated in high vacuum. The product was purified on silica gel with 20% ethyl acetate/hexane to give 1.6 g of the pure product EX-138D (48%).

The solution of 1.5 g of the dichloro pyrazinone EX-138D (3.1 mmol) and 1.1 g of the cyclobutylamine (15.5 mmol) in 30 mL of ethyl acetate was stirred at 70C. for 3 hr. The reaction mixture was concentrated in vacuo and redissolved in ethyl acetate. The ethyl acetate layer was washed with brine, dried over $MgSO_4$, and concentrated in vacuo. The crude product was purified with 25% ethyl acetate/hexane to give 1.57 g of the pure product EX-138E (99%).

1.7 g of the cyano pyrazinone EX-138E (3.3 mmol), 0.4 g of $NH_2OH.HCl$ (5.8 mmol), and 0.9 g of $K_2CO_3$ (6.5 mmol) were stirred in 30 mL of dry ethanol overnight. The reaction mixture was concentrated and redissolved in ethyl acetate. The ethyl acetate solution was washed with brine, dried over $MgSO_4$, and concentrated in vacuo. The crude was purified on silica gel with 30% ethyl acetate/hexane to give 1.1 g of the pure product EX-138F (61%).

0.5 g of the hydroxyamidine compound EX-138F (0.9 mmol), 0.16 g of carbonyl diimidazole (1.0 mmol), and 0.19 g of triethylamine (1.9 mmol) were stirred in refluxing THF (10 mL) for overnight. The mixture was concentrated in vacuo and redissolved in ethyl acetate. The ethyl acetate layer was washed with brine, dried over $MgSO_4$, and concentrated in vacuo. The crude was purified on silica gel with 25% ethyl acetate/hexane to give 0.4 g of the pure product EX-138G (80%).

0.3 g of the carboxylate amidine (0.5 mmol) and 50 mg of Pd/C in 10 mL of ethanol were shaken under 40 PSI $H_2$ for 5 hr. The reaction mixture was filtered to remove Pd/C, and the solution was concentrated in vacuo. The crude was purified on silica gel with 60% ethyl acetate/hexane to afford 0.18 g of the pure product: MS (M+H): 499.14.

Example 139

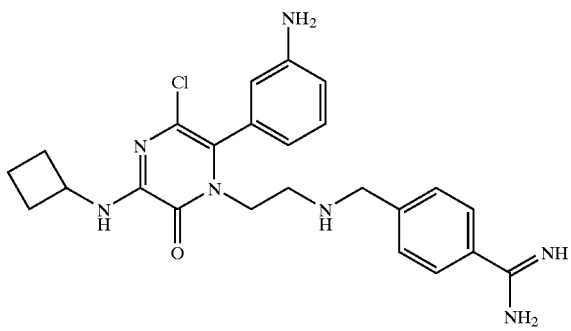

To a solution of EX-136B (0.97 g, 2.0 mmol) in acetonitrile (30 mL) was added NaI (0.12 g, 0.8 mmol), K₂CO₃ (1.21 g, 8.0 mmol) and amine (0.89 g, 2.2 mmol). The reaction was heated at 80° C. for 16 h and the solvent removed to give an oil, which was taken up in ethyl acetate and water. The mixture was poured into a seperatory funnel and the layers separated. The organic layer was washed with brine and dried (Na₂SO₄). The solvent was removed to give an oil, which after chromatography (2% MeOH—10% MeOH in dichloromethane) gave 0.68 g of product EX-139A: m/z+1=629.

To a solution of EX-139A (0.60 g, 0.95 mmol) in DMF (15 mL) at room temperature was added SnCl₂.H₂O. The reaction was stirred at room temperature overnight. The reaction was poured into ice water, 10 M NaOH and dichloromethane. The layers were separated, and the organic layer washed with 10% KF and water. The organic extracts were collected and dried (Na₂SO₄). The solvent was removed to give a foam, which was purified by chromatography (dichloromethane—10% MeOH/dichloromethane) to give the desired product EX-139B (0.21 g): m/z+1=600.

To a round bottom containing EX-139B (0.56 g, 0.93 mmol) was added 30% HBr/AcOH (20 mL). The reaction was stirred at room temperature for 18 hours. The reaction was diluted with ether to give a precipitate, which was filtered and washed with ether. The crude precipitate was purified by RP-HPLC to give the desired product as a TFA salt (0.31 g). The TFA salt was converted to the HCl salt by passing through Biorad AG2-X8 ion exchange resin, followed by lyophilization to give the final product as the HCl salt (0.28 g): m/z+1=466.

Example 140

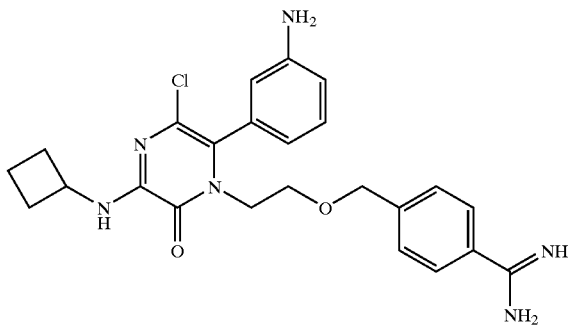

To a stirred solution of NaH (60% dispersion, 0.22 g, 2.75 mmole) in THF (2 mL) was added α-bromo-p-tolunitrile drop wise (0.5 g, 2.55 mmole) in THF (2 ml). Added to the mixture was EX-136A (1.0 g, 2.75 mmole) in THF (1 mL). After stirring at room temperature for 18 hr the reaction was concentrated in vacuo and an aqueous work up performed. The residue was chromatographed by MPLC (1% MeOH/CH₂Cl₂) and triturated with ether to yield EX-140A as an orange solid (405 mg, 30%): HPLC/LRMS>99%, (M+H)⁺ 480; HRMS (EI) calcd for C₂₄H₂₃ClN₅O₄ 480.1439, found 480.1456.

A stirred mixture of EX-140A (405 mg, 0.845 mmoles), potassium carbonate (257 mg, 1.86 mmoles), and hydroxylamine hydrochloride (211 mg, 3.05 mmoles) in water/ethanol (7.4 mL, ratio 1:2.6) was refluxed for 3 hrs, cooled to room temperature, concentrated in vacuo, and an aqueous work up carried out. Residue chromatographed on MPLC (50% ethyl acetate/hexane) giving the product EX-140B as a orange glassy solid (192.4 mg, 44.4%); HPLC/LRMS 98%, (M+H)⁺ 513; HRMS (EI) calcd for C₂₄H₂₆ClN₆O₅ 513.1653, found 513.1698.

To a cooled solution of EX-140B (0.5 g, 0.976 mmole) in THF (25 mL) was added 2.5N NaOH (3.91 mL, 9.77 mmole). Added drop wise then was ethyl chloroformate (0.233 mL, 2.4 mmole) at 0–5° C., and the reaction mixture was allowed to warm to room temperature with stirring for 18 hrs. The aqueous was drawn off, organic dried over sodium sulfate, filtered, and concentrated in vacuo. The residue was triturated with diethyl ether to yield product EX-140C (358 mg, 68%); HPLC/LRMS 94%, (M+H)⁺ 539; HRMS (EI) calcd for C₂₇H₂₄ClN₆O₆ 539.1446, found 539.1468.

To a mixture of EX-140C (100 mg, 0.185 mmole) and iron powder (42 mg, 0.754 mmole) in water/ethanol (18 mL, ratio 50/50) was added a few drops of concentrated hydrochloric acid. The resulting mixture was stirred at 75° C. for 3 hr. The mixture was then filtered through celite, and solvent removed in vacou. The residue was triturated with diethyl ether to yield the product as a white solid in quantitative yield: ¹H NMR (300 MHz, DMF d₇) δ 10.30–9.80 (br m, 3H, H₂N—C=NH), 8.18 (m, 2H), 7.81 (m, 1H), 7.64 (m, 2H), 7.35 (m, 1H), 6.98 (m, 1H), 6.88 (br s, 1H), 6.74 (m, 1H), 5.59 (br s, 2H), 4.69 (br s, 3H), 4.17 (br s, 2H), 3.82 (br s,2H), 2.55–2.35 (m, 4H), 1.91 (br s, 2H); ¹³C NMR (75 MHz, DMF-d₇) δ 167.28, 151.15, 149.99, 148.61, 145.50, 133.46, 129.75, 128.65, 127.95, 127.75, 125.39, 124.96, 118.69, 116.69, 115.32, 74.82, 67.24, 46.31, 45.72, 15.35; HPLC/LRMS 99%, (M+H)⁺ 467; HRMS (EI) calcd for C₁₄H₂₈ClN₆O₂ 467.1962, found 467.1966.

Example 141

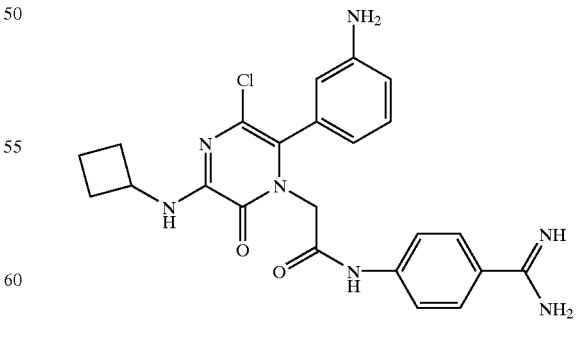

A solution of 2-{5-chloro-3-(N-cyclobutylamino)-6-(3-nitrophenyl)-2-oxohydropyrazinyl}acetic acid (1.0 g, 2.6 mmol) in methylene chloride (20 mL) was treated with 1-hydroxybenzotriazole (432 mg, 3.2 mmol), EDC (613 mg, 3.2 mmol), and 2 (423 mg, 3.2 mmol) and the reaction allowed to stir for 18 hr. Water was then added and extracted 3×with methylene chloride. The organics were washed once with saturated sodium carbonate, once with 1 N hydrochloric acid and once with brine, dried over magnesium sulfate, filtered and concentrated in-vacuo to afford EX-141A (960 mg, 1.9 mmol) as an orange foam.

A solution of EX-141A (500 mg, 1.0 mmol) in ethyl alcohol (20.0 mL) and concentrated hydrochloric acid (5 mL) was treated with tin(II) chloride dihydrate (1.1 g, 5.0 mmol) and heated to 65° C. for 1.5 hrs. The mixture was cooled to room temperature and poured into water (100 mL), 1 N potassium hydroxide was added to make basic, and then extracted 3 times with ethyl acetate. The organic layer was dried over magnesium sulfate, filtered and concentrated in vacuo to afford EX-141B (425 mg, 0.92 mmol) as an orange solid: M+H 463.

A suspension of EX-141B (200 mg, 0.43 mmol) in ethyl alcohol (10 mL) was cooled to 0° C. and hydrogen chloride was bubbled through the solution for 10 nm. The reaction was allowed to warm to room temperature, stirred for 2 hrs, and then concentrated in vacuo. The residue was dissolved in ethyl alcohol (5.0 mL), cooled to 0° C., treated with ammonia (5.0 mL, 2.0 M in ethyl alcohol), warmed to room temperature and stirred for 18 hrs. The reaction mixture was evaporated to dryness, purified by reverse phase HPLC (Waters, delta prep 3000), and lyophilized to give the product (150 mg, 031 mmol): M+H 480.

Example 142

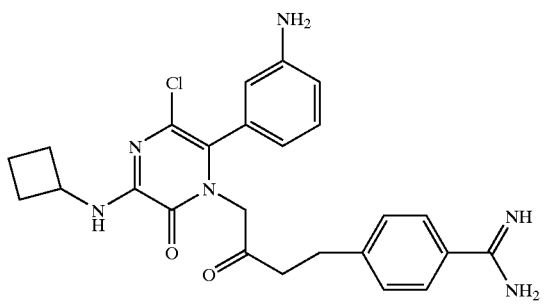

To a solution of 2-{5-chloro-3-(N-cyclobutylamino)-6-(3-aminophenyl)-2-oxohydropyrazinyl}acetic acid (0.5 g, 1.4 mmol.) in THF/H$_2$O (16 mL:4 mL) at room temperature was added Na$_2$CO$_3$ (0.29 g, 3.08 mmol) and Boc$_2$O (0.37 g, 1.7 mmol). After stirring overnight at room temperature the pH of the reaction was adjusted to 4 and then poured into ethyl acetate and water. The layers were separated and the organic layer washed with brine. The organic extract was dried (Na$_2$SO$_4$) and the solvent removed to give an oil EX-142A, which was used without further purification (0.6 g): m/z+1=449.

To a solution of the boc-acid EX-142A (0.6 g, 1.3 mmol) in methanol:benzene (2 mL:8 mL) was added (trimethyl) diazomethane (0.8 mL, 1.7 mmol) at room temperature. After stirring at room temperature, the solvent was removed to give the desired product EX-142B without further purification (0.6 g): m/z+1=463.

To a solution of 4-cyanophenylethyne (0.47 g, 3.5 mmol) in THF (15 mL) at −78° C. was added n-BuLi (2.23 mL, 4.4 mmol). After stirring at −78° C. for 15 min, EX-142B was added in THF (10 mL) at −78° C. via canula. The reaction was allowed to warm to room temperature over 2 hours. The reaction was quenched by addition of ammonium chloride and then diluted with ether. The layers were separated, and the organic layer dried (Na$_2$SO$_4$). The solvent was removed, and the residue purified by chromatography (20% ethyl acetate −40% ethyl acetate/hexanes) to give the desired product EX-142C (0.35 g): m/z+1=558.

To a solution of EX-142C (0.10 g, 0.18 mmol) in THF (15 mL) in a Parr bottle was added 10% Pd/C (0.1 g). The reaction was shaken on a Parr apparatus for 2 hours at 30 psi. The reaction was filtered through celite and washed with ethyl acetate. The solvent was removed to give the product EX-142D as a foam (0.08 g): m/z+1=562.

To a solution of EX-142D (0.33 g, 0.58 mmol) in dioxane (10 mL) was added 4.0 M HCl in dioxane (15 mL). After 2 hours, the solvent was removed, and the residue triturated with ether to give a precipitate EX-142E which was filtered and used in the next step (0.25 g) m/z+1=462.

To a solution of EX-142E (0.25 g, 0.5 mmol) in dry ethanol (15 mL) was bubbled HCl has for 5 minutes at 0° C. The reaction was allowed to warm to room temperature and stirred for 3 hours. The solvent was removed to give a yellow oil EX-142F which was used in the next step (0.29 g): m/z+1=508.

To a solution of EX-142F (0.29 g, 0.5 mmol.) in methanol (5 mL) was added 2.0M NH$_3$ in methanol (15 mL). Ammonia gas was bubbled through the reaction mixture for 5 minutes. After stirring overnight the solvent was removed to give a yellowish residue. The residue was dissolved in water and purified by RP-HPLC to give the compound as a TFA salt (0.17 g): m/z+1=479.

Example 143

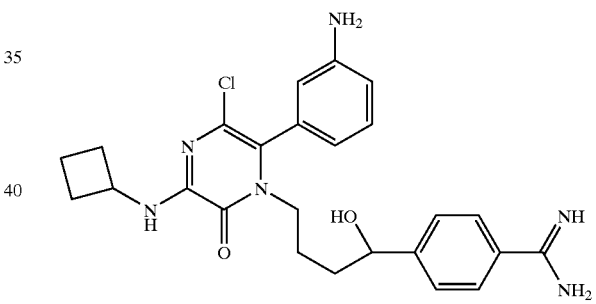

To 4-cyanophenacyl bromide (5.79 g, 25.8 mmol) in 100 ml of toluene was added triphenylphosphine (7.12 g, 27.1 mmol) and the mixture was stirred overnight. The resulting solid was collected by vacuum filtration and washed with ethyl ether to give 12.1 g of an off white solid EX-143A (96% yield): m/z (M+H) 406.

To (4-Cyanophenacyl)triphenylphosphonium bromide (EX-143A) (12.1 g, 24.9 mmol) in 100 ml of methanol was added 20 ml of 10% NaOH (aq) with stirring. The mixture was diluted with 1 L of water, and the solid collected by vacuum filtration. The solid was washed twice with 100 ml of water and dried to give 9.1 g of a yellow solid EX-143B (90% yield): m/z (M+H) 406.

To a solution of alcohol EX-136A (0.1 g, 0.28 mmol) in dichloromethane (10 mL) at room temperature was added 4A molecular sieves and NMO (0.05 g, 0.42 mmol). After 10 min, TPAP (0.05 g, 0.014 mmol) was added and the reaction stirred for 15 minutes. The reaction was diluted with dichloromethane and washed with 10% Na$_2$SO$_3$, brine and 10% CuSO$_4$ aqueous solutions. The organic layer was dried (Na$_2$SO$_4$), and the solvent removed to give a brown solid, which after chromatography (30% ethyl acetate —50% ethyl acetate/hexanes) gave 0.08 g of a yellow solid EX-143C: m/z (M+H) 363.

A mixture of EX-143C (0.712 g, 1.97 mmol) and EX-143B (0.796 g, 1.97 mmol) in 10 ml of benzene was heated at 80° C. for 4 hours. The solvent was removed in vacuo, and the residue was purified by silica gel chromatograph with 30–40% EtOAc/Hex to give 0.69 g of a yellow foam EX-143D (72% yield): m/z (M+H) 490.

To a mixture of EX-143D (0.300 g, 0.61 mmol) in 8 ml of CH₃OH at 0° C. was added sodium borohydride (0.093 g, 2.45 mmol), and the mixture was warmed to room temperature. The reaction was quenched with 1N HCl, extracted with EtOAc and the layers were separated. The organic layer was dried over sodium sulfate, filtered and removed in vacuo to give 0.300 g of an orange foam EX-143E (100% yield): m/z(M+H) 492.

A mixture of EX-143E (0.300 g, 0.61 mmol) and 10% palladium on carbon (0.030 g) in 5 ml of CH₃OH was shaken on the parr apparatus under an atmosphere of H₂, for 7 hours at 20 psi and then 2 hours at 40 psi. Then 0.5 ml of 2 M hydrogen chloride in diethyl ether was added, and the resulting mixture shaken on the parr apparatus for an additional hour under an atmosphere of H₂ at 40 psi. The reaction mixture was filtered, and the filtrate was concentrated in vacuo to give an orange residue. The residue was purified by silica gel chromatography with 3% CH₃OH/CH₂Cl₂ to give 0.064 g of a yellow solid EX-143F (23% yield): m/z (M+H) 464.

To a mixture of EX-143F (0.050 g, 0.108 mmol) in 6 ml of EtOH at 0° C. was bubbled in anhydrous hydrogen chloride as for 10 min. The solution was allowed to come to room temperature and stirred for 2 hours. The solvent was removed in vacuo, and the resulting residue dried under vacuum for 30 min. The residue was dissolved in 5 ml EtOH, and the solution treated with 5 ml of 2M ammonium in EtOH. The solution was stirred overnight. The solvent was removed in vacuo, and the resulting residue was purified by preparative HPLC with 5–30% CH₃CN/H₂O to give 0.030 g of a white solid (38% yield): m/z (M+H) 481.

Example 144

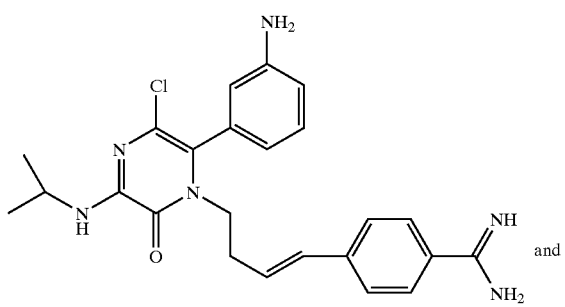

and

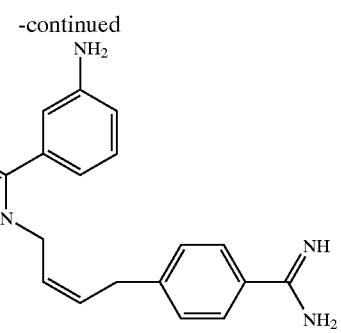

Using the procedure of Example 143 except using 2-{5-chloro-3-isopropylamino-6-(3-nitrophenyl)-2-oxohydropyrazinyl}acetic acid afforded the corresponding alcohol EX-144A as a yellow solid in 38% yield: m/z (M+H) 353.

Using the procedure of EX-143C except using EX-144A afforded the title compound EX-144B as a yellow solid in 32% yield: m/z (M+H) 351.

Using the procedure of EX-143D except using EX-144B afforded the title compound as a yellow foam EX-144C in 77% yield: m/z (M–H) 476.

Using the procedure of EX-143E except using EX-144C afforded the title compound as a yellow foam EX-144D in 46% yield: m/z (M+H) 480.

To a mixture of chlorotrimethylsilane (0.45 ml, 3.54 mmol) and sodium iodide (0.53 g, 3.53 mmol) in 1.4 ml of CH₃CN at 0° C. was added EX-144D (0.282 g, 0.59 mmol) in 1.4 ml of CH₃CN dropwise over 5 min. The mixture was allowed to come to room temperature and monitored by TLC. The reaction was quenched with 10% NaOH and extracted with EtOAc. The organic layer was washed with 5% Na₂S₂O₃ (aq), dried over sodium sulfate and filtered. The solvent was removed in vacuo and the resulting residue was purified by silica gel chromatography with 25–35% EtOAc/Hex to give 0.160 g of a yellow foam EX-144E (59% yield): m/z (M+H) 464.

To EX-144E (0.157 g, 0.339 mmol) in 4 ml of DMF was added tin(II)chloride (0.765 g, 3.39 mmol), and the solution was stirred for 3.5 hours. The reaction was quenched with 10% NaOH and extracted with CH₂Cl₂. The organic layer was washed with 10% KF (aq), dried over sodium sulfate and filtered. The solvent was removed in vacuo, and the resulting residue was purified by silica gel chromatography with 40–50% EtOAc/Hexane to give 0.099 g of a yellow foam EX-144F (67% yield): m/z(M+H) 434.

To EX-144F (0.081 g, 0.187 mmol) in 5 ml of EtOH at 0° C. was bubbled in anhydrous hydrogen chloride gas for 20 min. The solution was warmed to room temperature and stirred for 2 hours. The solvent was removed in vacuo and the resulting residue dried under vacuum for 10 min. The residue was dissolved in 3 ml EtOH and the solution treated with 5 ml of 2 M ammonium in EtOH. The solution was stirred 1 hour, cooled to 0° C. and treated with anhydrous NH₃ gas bubbled in over 20 min. The solution was warmed to room temperature and stirred over two nights. The solvent was removed in vacuo, and the resulting residue was purified by preparative HPLC with 10–70% CH₃CN/H₂O to give 0.063 g of a white solid (38% yield) after lyophilization: m/z (M+H) 451.

Example 145

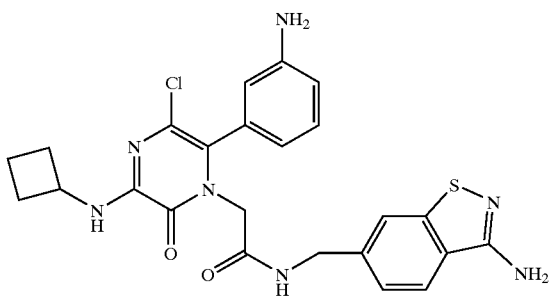

To EX-32E (0.2 g, 0.4 mmol) in DMSO (3 ml) was added Na$_2$S (0.39 g, 0.5 mmol) at room temperature under N$_2$. The mixture was heated to 70° C. overnight, then cooled to −5° C. Aqueous ammonia (1 ml) was added. Aqueous 5% sodium hypochlorite (0.4 ml) was added dropwise during 10 min to the stirred mixture. The mixture was kept stirring for 2 hr. at 0° C. The product was then purified on RF-HPLC to yield 45 mg solid. HRMS calcd for C$_{24}$H$_{24}$ClN$_7$ O$_2$S (M+H): 510.1479. Found: 510.1477. Anal. Calcd for C$_{24}$H$_{24}$ClN$_7$O$_2$ S+2TFA, 2.6H$_2$O: C, 42.85; H, 4.01; N, 12.49. Found: C, 42.45; H, 3.84; N, 12.90.

Example 146

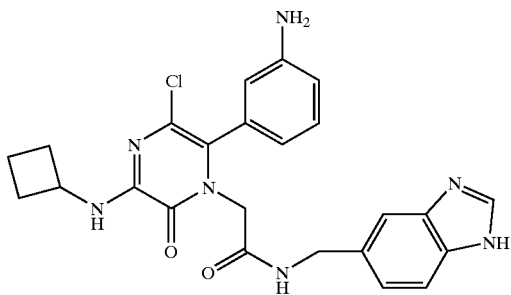

A solution of 5-methylbenzimidazole (2.5 g, 18.9 mmol) in methylene chloride (4 mL) and pyridine (5 mL) was treated with benzyl chloroformate (4.8 g, 28.3 mmol). The mixture was stirred for 18 hrs., and 1N hydrochloric acid (200 mL), and methylene chloride (100 mL) then was added. The layers were separated, and the aqueous extracted 2×with methylene chloride. The organics were combined, washed with brine, dried over magnesium sulfate and concentrated in-vacuo. Purification by column chromatography (silica gel 200–400 mesh) eluting with 15% ethyl acetate/hexanes afforded EX-146A (3.6 g, 13.5 mmol) as an off white solid. $^1$H NMR (CDCl$_3$) 2.47 (d, J=7.0 Hz, 3H), 5.49 (s, 2H), 7.20 (t, J=8.9 Hz, 1H), 7.28–7.66 (m, 5H), 7.83–7.90 (m, 1H), 8.46 (d, J=18.0 Hz, 1H).

A solution of EX-146A (1.0 g, 3.7 mmol) in carbon tetrachloride (30 mL) was treated with N-bromosuccinimide (668 mg, 3.7 mmol) and benzoyl peroxide (20 mg) and heated to reflux for 64 hrs. After cooling to room temperature, water (100 ml) was added and extracted 3 times with ethyl acetate, dried over magnesium sulfate, filtered and concentrated in vacuo. Purification by column chromatography (silica gel 200–400 mesh) eluting with 20% ethyl acetate/hexanes, afforded EX-146B (420 mg, 1.2 mmol) as an off white solid: M+H 344 (100%), M+2H 346 (100%).

A solution of di-tert-butyl iminodicarboxylate (280 mg, 1.3 mmol) in tetrahydrofuran was cooled to 0° C., and treated with sodium hydride (60% dispersion, 60 mg, 1.4 mmol). The mixture was stirred for 30 minutes and then was added EX-146B (410 mg, 1.2 mmol). The mixture was allowed to warmed to room temperature and stirred for 1 hour, at which time water (100 mL) was added, and the reaction mixture extracted 3×with ethyl acetate. The ethyl acetate was dried over magnesium sulfate, filtered, and concentrated in vacuo to afford EX-146C (573 mg, 1.19 mmol): M+H 482.

A solution of EX-146C (573 mg, 1.19 mmol) in methanol (5 mL) was treated with 2 M hydrochloric acid in diethyl ether (5 mL) for 23 hrs. The mixture was diluted with diethyl ether (50 mL), and the resulting precipitate was filtered off and dried in vacuo to afford EX-146D (145 mg, 0.66 mmol), as a tan solid: M+H 148.

A solution of EX-146D (140 mg, 0.64 mmol) in methylene chloride (9 mL) and dimethylformamide (1 mL) was treated with 1-hydroxybenzotriazole (156 mg, 1.2 mmol) for 20 min. Then was added EDC (295 mg, 1.5 mmol), N,N-diisopropylethylamine (298 mg, 23 mmol), and 2-{5-chloro-3-(N-cyclobutylamino)-6-(3-nitrophenyl)-2-oxohydropyrazinyl}acetic acid (290 mg, 0.77 mmol) and the reaction allowed to stir for 18 hr. Water was then added and extracted 3×with ethyl acetate. The organics were then washed 1× with brine, dried over magnesium sulfate, filtered and concentrated in vacuo. Purification by column chromatography (silica gel 200–400 mesh) eluting with 10% methanol/ethyl acetate afforded EX-146E (200 mg, 0.39 mmol) as a yellow solid: M+H 508.

A solution of EX-146E (200 mg, 0.39 mmol) in methanol (10 mL) was treated with 3 N hydrochloric acid in methanol (0.4 mL) and 5% Pd(C) (40 mg). The mixture was hydrogenated at 45 psi hydrogen, on a Parr shaker apparatus for 2.5 hrs. The catalyst was then filtered off and washed extensively with methanol. The filtrate was concentrated in vacuo. The residue was dissolved in ethyl alcohol and triturated with diethyl ether. The solid formed was filtered and extensively washed with diethyl ether to afford the product (130 mg, 0.25 mmol) as an off-white solid: M+H 478.

Example 147

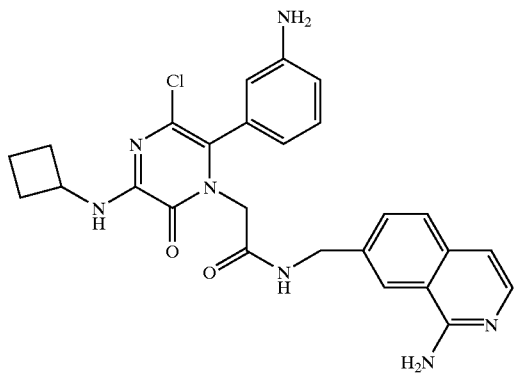

6-methylisoquinoline was prepared by the method of Hendrickson, J. B.; Rodriquez, C. J. Org. Chem. 1983,48, 3344: $^1$H NMR (CDCl$_3$) δ 9.18 (s, 1 H), 8.47 (d, 5.8 Hz, 1 H), 7.86 (d, J=83 Hz, 1 H), 7.58 (bs, 1 H), 7.56 (d, 5.8 Hz, 1 H), 7.43 (dd, J=8.3 Hz, J=1.61 Hz, 1 H), 2.57 (s, 3 H).

6-methylisoquinoline was converted to 1-chloro-6-methylisoquinoline by the method of Rewinkel, J. B. M.; Lucas, H.; van Galen, P. J. M.; Noach, A. B. J.; van Dinther, T. G.; Rood, A. M. M.; Jenneboer, A. J. S. M.; van Boeckel, C. A. A. *Bioorganic and Medicinal Chemistry Letters* 1999, 9, 685: ¹H NMR (CDCl₃) δ 8.16–8.24 (m, 2 H), 7.58 (s, 1 H), 7.46–7.52 (m, 2 H), 2.58 (s, 3 H).

To a solution of 1-chloro-6-methylisoquinoline (3.20 g, 18.1 mmol) in CCl₄ (250 mL) was added NBS (2.59 g, 14.6 mmol) and benzoyl peroxide (500 mg). The resulting mixture was heated at reflux overnight. After this time the solvent was removed and the residue was purified by flash chromatography (SiO₂, 20/1 hexanes-ethyl acetate) to afford 3.0 g (80% yield) of the desired α-bromo compound EX-147A: ¹H NMR (CDCl₃) δ 8.28–8.35 (m, 2 H), 7.83 (s, 1 H), 7.71 (dd, J=8.9 Hz, J=1.2 Hz, 1 H), 7.58 (d, J=5.6 Hz, 1 H), 4.62 (s, 2 H); LRMS (ESI) [M+H]+=256, 258.

To a solution of the α-bromo product EX-147A (2.45 g, 9.56 mmol) in DMF (100 mL) was added potassium phthalimide (1.99 g of 98%, 10.5 mmol) and the reaction was allowed to stir at room temperature for 12 h. The mixture was then concentrated, and the residue was purified by flash column chromatography (SiO₂, 10/1 to 5/1 hexanes-ethyl acetate) to afford 436 mg (14% yield) of the phthalimide alkylation product EX-147B: ¹H NMR (CDCl₃) δ 8.25–8.32 (m, 2 H), 7.85–7.89 (m, 3 H), 7.73–7.77 (m, 3 H), 7.59 (d, J=5.4 Hz, 1 H), 5.05 (s, 2 H); LRMS (ESI) [M+H]+=323.

The phthalimide product EX-147B (436 mg, 1.35 mmol) was dissolved in methanol (25 mL) and treated with hydrazine hydrate (79 µL of 98%, 1.62 mmol). The resulting mixture was heated at reflux for 2 h. At this time the reaction mixture was cooled, and the solid phthaloylhydrazide was filtered. The filtrate was concentrated to afford 268 mg of the desired product EX-147C with a trace of phthaloylhydrazide (the mixture was used in the next step without further purification): ¹H NMR (DMSO-d₆) δ 7.47–8.26 (complex m, 5 H), 3.94 (s, 2 H).

The pyrazinone free acid 2-{5-chloro-3-(N-cyclobutylamino)-6-(3-nitrophenyl)-2-oxohydropyrazinyl}acetic acid was coupled to the aminomethylisoquinoline EX-147C using the standard polymeric carbodiimide coupling procedure. The HOBt adduct EX-147D was formed upon purification by flash chromatography (SiO₂, 80/1 CHCl₃—MeOH): 1H NMR (CDCl3) d 8.37 (d, J=8.4 Hz, 1 H), 8.27–8.33 (m, 2 H), 8.09 (d, J=8.4 Hz, 1 H), 7.73–7.78 (m, 2 H), 7.69 (s, 1 H), 7.63 (t, J=8.1 Hz, 1 H), 7.42–7.56 (complex m, 4 H), 7.37 (d, J=5.4H, 1 H), 6.78 (bt, 1 H), 6.52 (d, J=8.1 Hz, 1 H), J=4.63 (apparent t, J=5.4 Hz, 2 H), 4.48–4.59 (m, 1 H), 4.90 (ABq, J=15.3 Hz, δν=25.6 Hz, 2 H), 2.40–2.53 (m, 2 H), 1.92–2.08 (m, 2 H), 1.72–1.85 (m, 2 H); LRMS (ESI) [M+H]+=652.

To the HOBt adduct EX-147D from Step A (199 mg, 0.31 mmol) in DMF (15 mL) was added ammonium acetate (3.20 g) and the reaction was heated at reflux for 12 h. After this time the reaction was concentrated, and the residue was purified by reverse phase HPLC (Gilson, YMC CombiPrep ODS-A 50×20 mm, Gradient 35% ACN 65% 0.1% TFA to 65% ACN over 10 min) to afford 22.3 mg of the desired aminoisoquinoline EX-147E: LRMS (ESI) [M+H]+=534.

The product EX-147E was hydrogenated to give the product as previously described: LRMS (ESI) [M+H]+=505.

Example 148

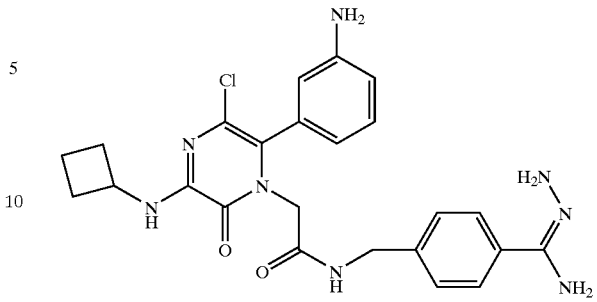

To a solution of 2-{5-chloro-3-(N-cyclobutylamino)-6-(3-nitrophenyl)-2-oxohydropyrazinyl}acetic acid (3.51 g, 93 mmol) in 60 mL of DMF at 0° C. was added HOBt (1.51 g, 11.7 mmol) and EDC (2.15 g, 11.2 mmol). After 30 nin, a solution of 4-cyanobenzylamine (1.20 g, 7.0 mmol) in DMF (20 mL) and TEA (4.8 mL, 35.0 mmol) was added via canula. After stirring at room temperature for 2 hours, the reaction was poured into water and ether. The layers were separated and the aqueous layer extracted with ethyl acetate. The organic extracts were collected and washed with bicarbonate and brine. The organic fraction was dried (MgSO₄) and the solvent removed to give the product as a yellow solid EX-148A (3.40 g): m/z+1=493.

To a solution of EX-148A (1.4 g, 2.8 mmol) in ethanol (30 mL) in a Parr bottle was added 10% Pd/C (0.07 g). The reaction was shaken on a Parr apparatus for 2 hours and then filtered through celite. The solvent was removed to give the product as an off-white solid EX-148B (1.27 g): m/z+1=463.

To a solution of EX-148B (1.22 g, 2.6 mmol) in THF (40 mL) at room temperature was added TEA (0.47 mL, 3.38 mmol), DMAP (0.03 g, 0.26 mmol) and Boc₂O (0.63 g, 2.86 mmol). After stirring overnight the reaction was diluted with ethyl acetate and water. The layers were separated and the organic layer washed with 1N HCl, bicarbonate and brine. The solvent was removed to give an oil which was a mixture EX-148C of mono and diboc products. The crude mixture was used in the next step (1.72 g): m/z+1=563 and m/z+1=663.

To a solution of EX-148C (1.72 g, 3.0 mmol) in pyridine (25 mL) was added TEA (2.42 mL, 17.0 mmol). A stream of H₂S gas was bubbled through the reaction mixture for 15 minutes at room temperature. After stirring at room temperature for 2 days the solvent was removed in vacuo and residue diluted with ethyl acetate. The organic mixture was washed with 1 N HCl and dried (Na₂SO₄). The solvent was removed to give an oil, which after chromatography (30% to 50% ethyl acetate/hexanes) gave the product EX-148D as a foam (0.63 g): m/z+1=597.

To a solution of EX-148D (0.32 g, 0.46 mmol) in acetone at room temperature was added methyl iodide (1.0 mL, 16.1 mmol). After stirring the reaction mixture for 2 days the solvent was removed in vacuo to give an orange solid EX-148E (0.42 g): m/z+1=711.

To a solution of EX-148E (0.42 g, 0.50 mmol) in methanol (10 mL) was added 0.017 mL of hydrazine at room temperature. After stirring the reaction mixture for 2 days in the dark the solvent was removed in vacuo to give an oily residue. The residue was triturated with ether to give a yellow solid EX-148F, which was used in the next step (0.41 g): m/z+1=695.

To a suspension of EX-148F (0.41 g, 0.50 mmol) in dichloromethane (10 mL) at room temperature was added TFA (10 mL). After 2 hours the solvent was removed in vacuo and the residue triturated with ether to give the crude product. The crude product was dissolved in water and purified by RP-HPLC to give the final product as a TFA salt (0.31 g): m/z+1=495.

Example 149

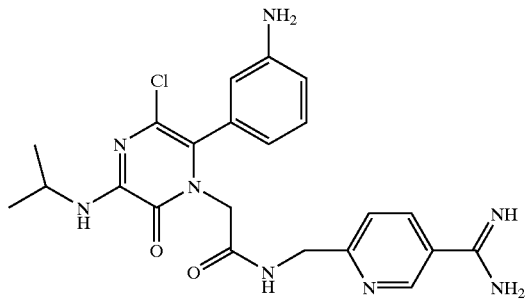

2-{5-chloro-3-(N-isopropylamino)-6-(3-nitrophenyl)-2-oxohydropyrazinyl}acetic acid (230 mg, 0.628 mmole) and 5-(N-benzyloxycarbonylamidino)pyrid-2-ylmethylamine (223.8 mg, 0.628 mmole) were coupled by standard resin coupling conditions described herein. The crude product resulting from coupling was then triturated with diethyl ether, filtered, and dried under vacuum. The cake was then stirred in a mixture of ethyl acetate/acetonitrile/ethanol and purged with nitrogen. A catalytic amount of palladium black was added with excess ammonium formate, and then stirred under ambient pressure by means of a hydrogen balloon at room temperature for 18 hrs. The reaction was filtered through celite and the filtrate concentrated in vacuo. The residue was stirred in 3N HCl Dioxane, diluted with diethyl ether, and filtered. The cake was dried in a vacuum desicator to give the product as a tan solid (76.3 mg, 22%): HPLC/LRMS>91%, (M+H)$^+$ 469; HRMS (EI) calcd for $C_{22}H_{26}ClN_8O_2$ 469.1867, found 469.1882.

Example 150

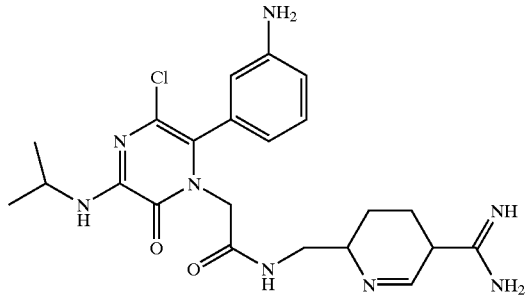

The product of Example 149 was stirred in methanol with a catalytic amount of palladium black and excess ammonium formate, and then reduced under ambient pressure with hydrogen balloon after 3 hrs. The reaction was filtered through celite and concentrated in vacuo. The residue was chromatographed with HPLC (5% acetonitrile to 65% acetonitrile/water/0.1%TFA), and the product isolated as a white solid (11.7 mg, 4%): HPLC/LRMS>99%, (M+H)$^+$ 473; HRMS (EI) calcd for $C_{22}H_{30}ClN_8O$, 473.2180, found 473.2173.

Example 151

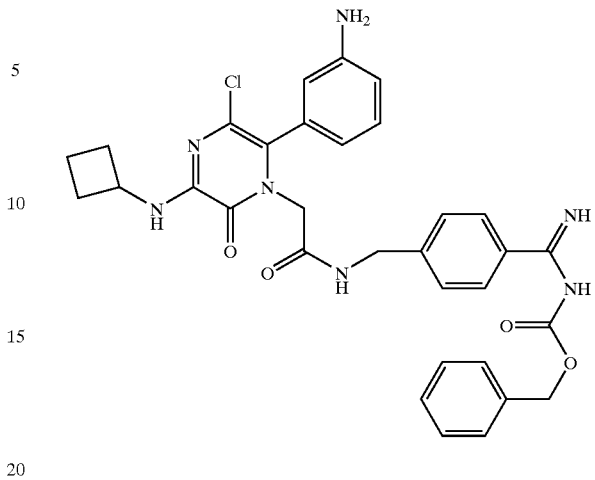

2-{5-chloro-3-(N-cyclobutylamino)-6-(3-(tert-butoxycarbonylamino)phenyl)-2-oxohydropyrazinyl}acetic acid and 4-(benzyloxycarbonylamidino)benzylamine hydrochloride were coupled under standard resin conditions as described herein. The residue was chromatographed by HPLC (5% acetonitrile to 65% acetonitrile/water/0.1% TFA), and then converted to the hydrochloride salt to yield the title compound as an off white solid (218 mg, 11%): $^1$H NMR (300 MHz, DMF-d$_7$) δ 11.28(br s, 1H), 10.99 (br s, 1H), 10.16–9.98 (br m, 2H), 9.09 (m, 2H), 8.26 (m, 2H), 8.03 (m, 1H), 7.89 (1H), 7.92 (m, 1H), 7.75–7.50 (m, 8H), 5.63 (s, 2H), 4.96 (m, 2H), 4.73 (m, 2H), 4.52 (br m, 1H), 2.51–2.36 (m, 4H), 1.96–1.86 (m, 2H): HPLC/LRMS 89%, (M+H)$^+$ 614; HRMS (EI) calcd for $C_{32}H_{33}ClN_7O_4$ 614.2283, found 614.2301.

Example 152

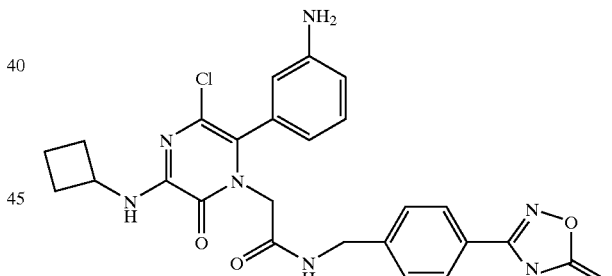

To a stirred solution of 4-Di-tert-butoxycarbonylaminomethyl-N-hydroxy-benzamidine (Synthetic Communication, 28(23), 4419–4429 (1998)) (10.99 g, 30.1 mmole) in THF (350 mL) was added 2.5N NaOH (120.44 mL, 301.1 mmoles) and cooled to 0–5° C. on an Ice-bath. Ethyl chloroformate (7.20 mL, 75.3 mmole) was added dropwise, allowed to warm to room temperature, and stirred 18 hrs. The aqueous was drawn off, and the organic concentrated in vacuo. The residue was taken up in diethyl ether repeatedly and dried on vacuum pump to give the product EX-152A as a white solid (8.25 g, 70%): $^1$H NMR (300 MHz, Acetone-d$_6$) δ 7.91 (d, J=8.4 Hz, 2H), 7.32 (d, J=8.1 Hz, 2H), 4.81 (s, 2H), 1.47 (s, 18H); HPLC/LRMS>91%, (M+Na)$^+$ 414; HRMS (EI) calcd for $C_{19}H_{26}N_3O_6$ 392.1822, found 392.1855.

EX-152A (0.72 g, 1.8 mmole) was stirred in 3N HCl-MeOH (6 mL, 18 mmole) at room temperature for 5 hrs. The reaction mixture was diluted with diethyl ether, filtered, and dried cake in vacuum dessicator to give the product EX-152B as a white solid in quantitative yield: $^1$H NMR (300 MHz, DMSO-$d_6$) δ 13.40 (br s, 1H), 8.83 (br s, 2H), 7.91 (d, J=8.4 Hz, 2H), 7.71 (d, J=8.4 Hz, 2H), 4.08 (s, 2H); $^{13}$C NMR (75 MHz, DMSO-$d_6$) δ 160.61, 157.87, 139.0, 130.42, 126.99, 123.88, 42.32; HPLC>99%; HRMS (EI) calcd for C9H10N3O2 192.0773, found 192.0736.

2-{5-chloro-3-(N-cyclobutylamino)-6-(3-(tert-butoxycarbonylamino)phenyl)-2-oxohydropyrazinyl}acetic acid and EX-152B were coupled under standard resin conditions as described herein. The residue was chromatographed by HPLC (5% acetonitrile to 65% acetonitrile/water/0.1 TFA), and converted to the hydrochloride salt to yield the product as an off white solid (114 mg, 13%): $^1$H NMR (300 MHz, DMF-$d_7$) _13.40 (br s,1H), 8.89 (m, 1H), 8.13 (m, 2H), 8.04 (m, 1H), 7.95 (m, 1H), 7.78 (m, 2H), 7.60 (m, 1H), 7.53 (m. 2H), 4.85–4.67 (m, 3H), 4.56 (m,2H), 2.51–2.39 (m, 4H), 1.97–1.92 (m,2H); $^{13}$C NMR (75 MHz, DMF-$d_7$) _166.85, 162.78, 160.63, 158.17, 151.25, 148.99, 144.20, 134.30, 134.02, 130.76, 130.59, 128.30, 126.85, 126.20, 125.61, 124.59, 122.81, 122.76, 48.84, 46.36, 42.67, 30.65, 15.33; HPLC/LRMS>99%, (M+H)$^+$ 522; HRMS (EI) calcd for $C_{25}H_{25}ClN_7O_4$ 522.1657, found 522.1671.

Example 153

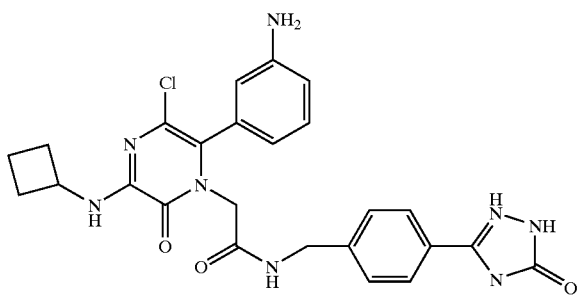

To a solution of the product of Example 90 (0.6 g, 1.0 mmol) in THF:H$_2$O (161 mL:4 mL) was added Na$_2$CO$_3$ (0.28 g, 3.0 mmol) and Boc$_2$O (0.71 g, 3.0 mmol) at 0° C. After stirring for 3 hours the reaction was diluted with ethyl acetate and water. The layers were separated and the organic layer washed with brine and dried (Na$_2$SO$_4$). The solvent was removed in vacuo to give a crude solid, which after chromatography (30%–50% ethyl acetate/hexanes) gave the desired product EX-153A (0.71 g): m/z+1=752.

To a solution of EX-153A (0.71 g, 0.94 mmol) in methanol (15 mL) was added hydrazine (3 mL, 3.0 mmol) at room temperature. After stirring, overnight, the solvent was removed to give a yellow oil, which after chromatography (dichloromethane—10% methanol/dichloromethane), gave the product EX-153B as a foam (0.26 g): m/z+1=621.

To a solution of EX-153B (0.26 g, 0.41 mmol) in dichloromethane (5 mL) at room temperature was added TFA (5 mL). After 1 hour, the solvent was removed in vacuo to give an oil. The oil was triturated with ether to give a solid which was filtered. The hygroscopic solid was redissolved in water and lyophilized to give the product as a TFA salt (0.23 g): m/z+1=521.

Example 154

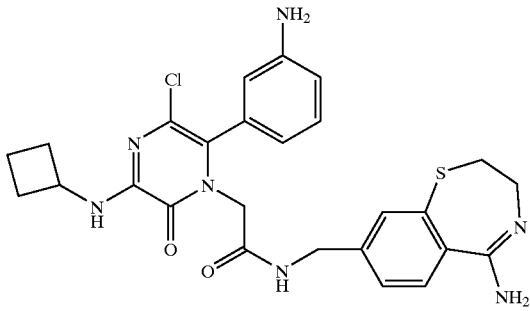

2-Fluoro4-methylbenzonitile was prepared from 4-bromo-3-fluorotoluene by the methods outlines and referenced in Maligres, P. E.; Waters, M. S.; Fleitz, F.; Askin, D. Tetrahedron Lett. 1999,40,8193: $^1$H NMR (CDCl$_3$) δ 7.50 (m, 1 H), 7.05 (m, 2 H), 2.43 (s, 3 H).

α-Bromo-3-fluoro-4-tolunitrile was prepared by the standard procedure outlined earlier for the unsubstituted 4-amidinobenzylamine derivative in Example 44: $^1$H NMR (CDCl$_3$) δ 7.56–7.61 (m, 1 H), 7.45–7.48 (m, 1 H), 7.23–7.30 (m, 1 H), 4.43 (s, 2 H).

α-N,N-Di-(tert-butoxycarbonyl)amino-3-fluoro-4-tolunitrile (EX-154A) was also prepared by the standard procedure outlined earlier for the unsubstituted 4-amidinobenzylamine derivative in Example 44: $^1$H NMR (CDCl$_3$) δ 7.00.7.60 (complex m, 3 H), 4.79 (s, 2 H), 1.46 (s, 18 H).

To the fluoronitrile product EX-154A (10.0 g, 28.8 mmol) in n-butanol (500 mL) was added 2-aminoethanethiol hydrochloride (3.68 g of 98%,31.7 mmol), followed by KOH (4.04 g of 88%, 63.4 mmol). The resulting mixture was heated to 100° C. for 1 h. At this time, LCMS indicated reaction was complete. The solvent was evaporated, and the residue was dried at high vacuum to afford 9.0 g of the crude desired mono-Boc product EX-154B: $^1$H NMR (DMSO-$d_6$) δ 7.05–7.75 (complex m, 3 H), 4.15 (m, 2 H), 2.69–2.78 (complex m, 4 H), 1.37 (s, 9 H); LRMS (ESI) [M+H]$^+$=308.

EX-154B was converted to the Z-protected material EX-154C as described for the parent 4-amidinobenzylamine derivative in Example 44: $^1$H NMR (CDCl$_3$) δ 7.24–7.40 (m, 8 H), 5.10 (s, 2 H), 4.70 (s, 2 H), 3.42–3.56 (m, 2 H), 2.70–2.88 (m, 2 H), 1.42–1.50 (m, 9 H); LRMS (ESI) [M−Boc+Na]$^+$=464.

EX-154C was converted to the free amine hydrochloride EX-154D as described for the parent 4-amidinobenzylamine derivative in Example 44: $^1$H NMR (DMSO-$d_6$) δ 7.23–7.49 (m, 8 H), 4.99 (s, 2 H), 4.06–4.19 (m, 2 H), 3.18–3.32 (m, 2 H), 2.71–2.80 (m, 2 H); LRMS (ESI) [M+H]$^+$=342 for free base.

The product was prepared from 2-{5-chloro-3-(N-cyclobutylamino)-6-(3-nitrophenyl)-2-oxohydropyrazinyl}acetic acid and the aminomethylbenzothiazepine EX-154D by the standard protocol reported earlier: LRMS (ESI) [M+H]$^+$=538.

Example 155

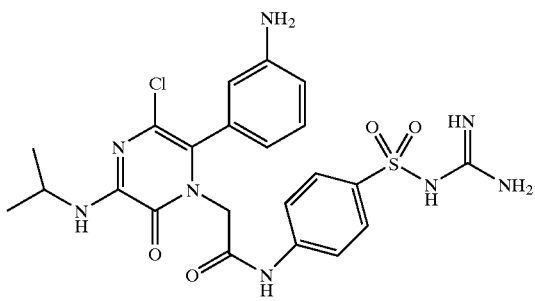

To a solution of 2-{5-chloro-3-(N-isopropylamino)-6-(3-nitrophenyl)-2-oxohydropyrazinyl}acetic acid (0.4 g, 1.1 mmol) in benzene (10 mL) was added TEA (0.15 mL) at room temperature. After 30 min, pivaloyl chloride (0.13 mL, 1.1 mmol) was added at 0° C. and the reaction stirred for 1 hour. In a separate round bottom containing 4-aminophenylsulfonylguanidine (0.23 g, 1.1 mmol) was added pyridine (20 mL) and the mixed anhydride from above. The reaction was heated to 80° C. for 1 h and then allowed to cool. The solvent was removed in vacuo to give a brown foam EX-155A which was used without purification in the next step: m/z+1=563.

To a solution of crude EX-155A (0.6 g, 1.11 mmol) in ethanol (20 mL) was added 2 M HCl in ether (2 mL) and 10% Pd/C (0.5 g) at room temperature. The reaction was shaken on a Parr apparatus at 40 psi for 1 hour. The reaction mixture was filtered and the solvent removed in vacuo to give an oil. The crude product was basified with 2.5 M NaOH and extracted with ethyl acetate. The organic layer was dried ($Na_2SO_4$) and the solvent removed to give a solid, which was taken up in 1 N HCl and lypholized to give the product as an HCl salt (0.24 g): m/z+1=533.

Example 156

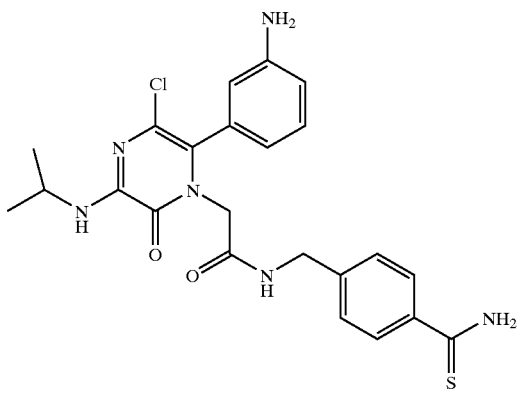

To a solution of 2-{5-chloro-3-(N-isopropylamino)-6-(3-nitrophenyl)-2-oxohydropyrazinyl}acetic acid (0.76 g, 2.1 mmol) was added HOBt (0.34 g, 2.5 mmol) and EDC (0.49 g, 2.5 mmol). After 20 minutes, the amine hydrochloride (0.27 g, 1.6 mmol) and TEA (1.11 mL, 9.0 mmol) were added to the reaction mixture. The reaction mixture was stirred for 3 hours and then diluted with water and ether. The organic layer was washed with 1 N NaOH and brine. The organic extract was dried ($Na_2SO_4$) and the solvent removed to give an orange foam EX-156A (0.75 g): m/z+1=493.

To a solution of EX-156A (0.75 g, 1.7 mmol) in THF:ethanol (20 mL:20 mL) was added 10% Pd/C (0.25 g). The reaction was shaken on a Parr apparatus at 40 psi for 3 hours. The reaction was filtered through a pad of celite, and the solvent removed to give a foam EX-156B (0.68 g): m/z+1=421.

To a solution of EX-156B (0.68 g, 1.6 mmol) in pyridine (20 mL) was added TEA (3 mL). Hydrogen sulfide gas was bubbled through the solution for 5 minutes and then stirred for 24 hours at room temperature. The reaction was diluted with water and ethyl acetate. The layers were separated, and the organic layer washed with brine. The organic extract was dried ($Na_2SO_4$), and the solvent removed to give an oil (containing some pyridine). The oil was purified by RP-HPLC to give the product as a TFA salt (0.35 g): m/z+1=455.

Example 157

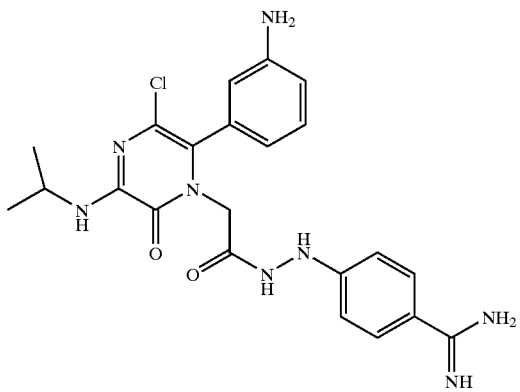

To a solution of 2-{5-chloro-3-(N-isopropylamino)-6-(3-aminophenyl)-2-oxohydropyrazinyl}acetic acid (0.5 g, 1.5 mmol) in DMF (20 mL) was added EDC (0.46 g, 2.4 mmol), TEA (0.69 mL, 4.9 mmol) and HOBt (0.32 g, 2.4 mmol) at 0° C. After 15 minutes 4-cyanophenylhydrazine hydrochloride (0.25 g, 1.5 mmol.) was added. The reaction was allowed to warm to room temperature and stirred for 2 hours. The reaction was diluted with ether and water. The layers were separated, and the organic layer washed with bicarbonate and brine. The organic extracts were dried ($Na_2S\ O_4$), and the solvent was removed in vacuo to give a solid, which after chromatography (ethyl acetate) gave the desired product EX-157A (0.32 g): m/z+1=452.

HCl gas was bubbled into a solution of EX-157A (0.32 g, 0.71 mmol) in dry ethanol (10 mL) for 10 min. After stirring overnight at room temperature, the solvent was removed in vacuo to give the crude product EX-157B as a yellow oil (0.35 g): m/z+1=498.

Ammonia gas was bubbled into a solution of EX-157B (0.35 g, 0.70 mmol) in methanol (10 mL) for 5 min. After stirring for 2 hours at room temperature, the solvent was removed in vacuo to give a solid. The solid was taken up in water and purified by RP-HPLC to give the desired product (0.145 g): m/z+1=469.

Example 158

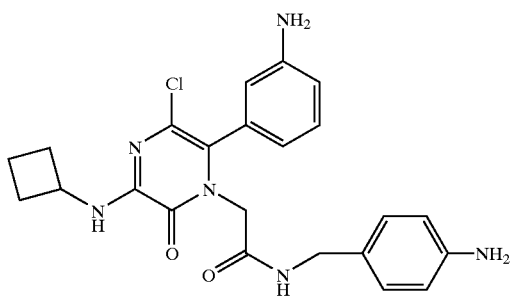

2-{5-chloro-3-(N-cyclobutylamino)-6-(3-(tert-butoxycarbonylamino)phenyl)-2-oxohydropyrazinyl}acetic acid and 4-(benzyloxycarbonylamino)benzylamine hydrochloride were coupled under standard resin conditions as described in Example 147 to give the product: m/z+1=454.

Example 159

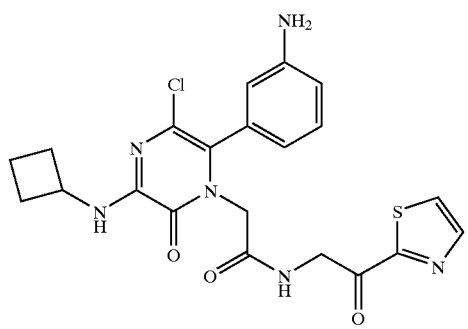

2-{5-chloro-3-(N-cyclobutylamino)-6-(3-(tert-butoxycarbonylamino)phenyl)-2-oxohydropyrazinyl}acetic acid and 2-oxo-2-thiazolylethylamine hydrochloride were coupled under standard conditions as described herein to give the product: m/z+1=503.

Example 160

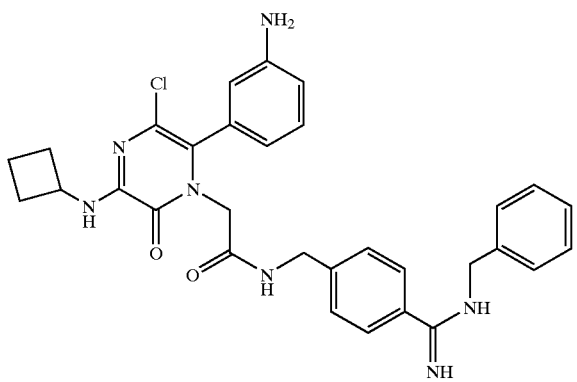

To a mixture of the product of Example 90 (0.020 g, 0.034 mmol) and benzylamine (0.037 g, 0.34 mmol) was added 1 ml of $CH_3OH$, and the resulting mixture was heated at 65° C. for 15 hours. The crude reaction mixture was purified by preparative HPLC with 10–70% $CH_3CN/H_2O$ (0.05% TFA) to give 0.011 g of a white solid after lyophilization (40% yield): m/z(M+H) 570.

Example 161

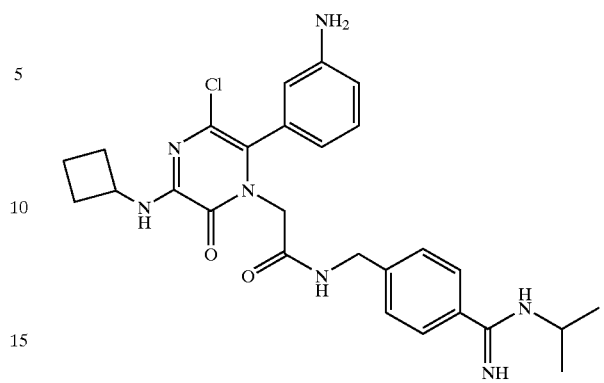

Prepared according to the procedure of Example 160 except using isopropylamine and heating for 40 hours afforded the product as a white solid (61% yield): m/z (M+H) 522.

Example 162

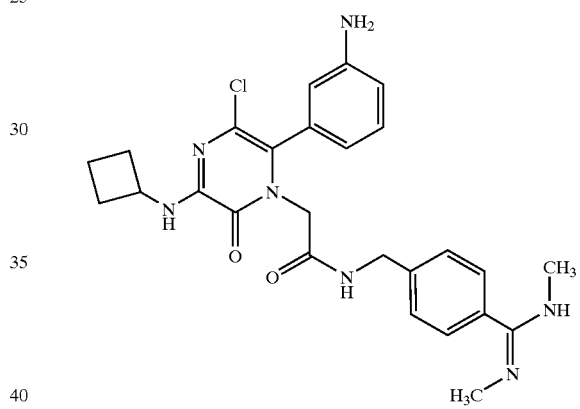

Prepared according to the procedure of Example 160 except using 2 M methylamine in methanol afforded the product as a white solid (71% yield): ml, (M+H) 508.

Example 163

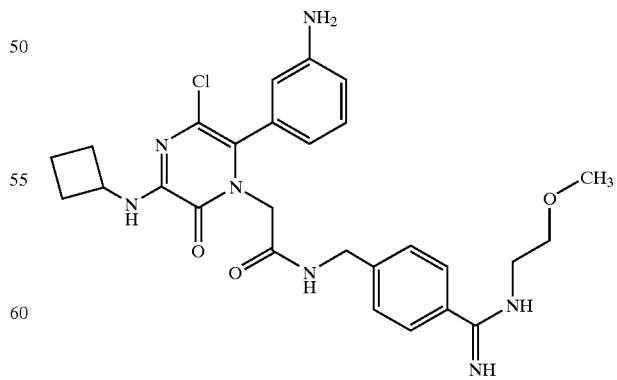

Prepared according to the procedure of Example 160 except using 2-methoxyethylamine afforded the product as a white solid (35% yield): m/z (M+H) 538.

Example 164

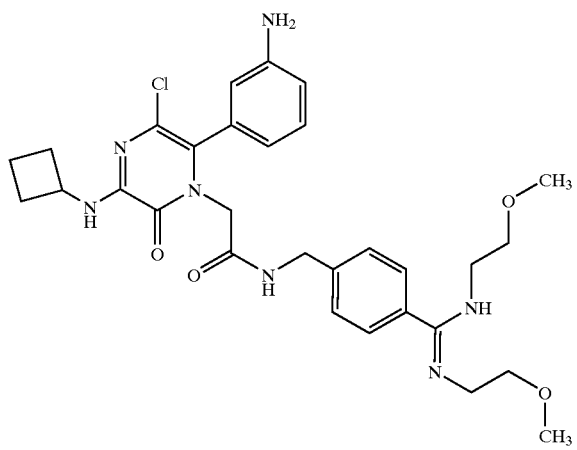

Prepared according to the procedure of example Example 160 except using 2-methoxyethylamine afforded the product as a white solid (18% yield): m/z (M+H) 596.

Example 165

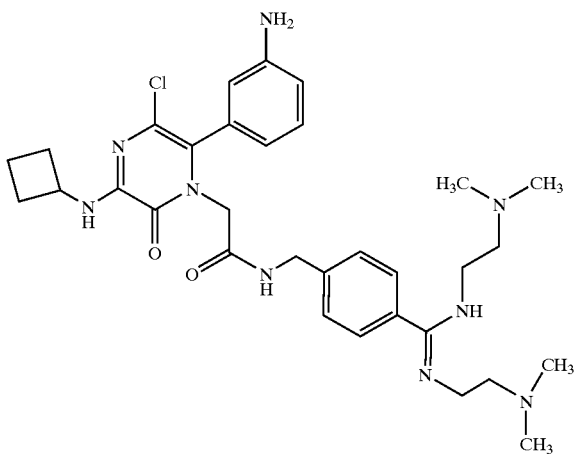

Prepared according to the procedure of example Example 160 except N,N-dimethylethylenediamine afforded the product as an off-white solid (24% yield): m/z (M+H) 622.

Example 166

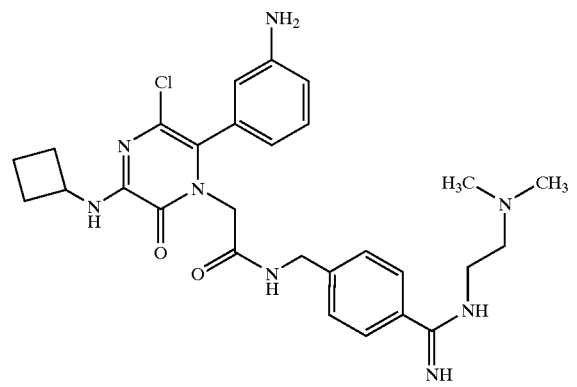

Prepared according to the procedure of example PHA-427798 except except N,N-dimethylethylenediamine afforded the product as an off-white solid (13% yield): m/z (M+H) 551.

Using the examples and methods described herein previously, the following examples having a amidinoaralkyl or amidinoheteroaralkyl type $Y^0$ group could be prepared:

- 6-[3-aminophenyl]-5-chloro-3-[N-ethyl-N-methylhydrazino]-N-[[4-aminoiminomethylphenyl]methyl]-2-oxo-1(2H)-pyrazineacetamide;
- 6-[3-aminophenyl]-5-chloro-3-[N,N-diethylhydrazino]-N-[[4-aminoiminomethylphenyl]methyl]-2-oxo-1(2H)-pyrazineacetamide;
- 6-[3-amino-5-carboxyphenyl]-5-chloro-N-[[4-aminoiminomethylphenyl]methyl]-3-[N,N-dimethylhydrazino]-2-oxo-1(2H)-pyrazineacetamide;
- 6-[3-amino-5-carboxyphenyl]-5-chloro-3-[N-ethyl-N-methylhydrazino]-N-[[4-aminoiminomethylphenyl]methyl]-2-oxo-1 (2H)-pyrazineacetamide;
- 6-[3-amino-5-carboxyphenyl]-5-chloro-3-[N,N-diethylhydrazino]-N-[[4-aminoiminomethylphenyl]methyl]-2-oxo-1(2H)-pyrazineacetamide;
- 6-[3,5-diaminophenyl]-5-chloro-N-[[4-aminoiminomethylphenyl]methyl]-3-[N,N-dimethylhydrazino]-2-oxo-1(2H)-pyrazineacetamide;
- 6-[3,5-diaminophenyl]-5-chloro-3-[N-ethyl-N-methylhydrazino]-N-[[4-aminoiminomethylphenyl]methyl]-2-oxo-1(2H)-pyrazineacetamide;
- 6-[3,5-diaminophenyl]-5-chloro-3-[N,N-diethylhydrazino]-N-[[4-aminoiminomethylphenyl]methyl]-2-oxo-1 (2H)-pyrazineacetamide;
- 6-[3-amino-5-(N-benzylamidocarbonyl)phenyl]-5-chloro-N-[[4-aminoiminomethylphenyl]methyl]-3-[N,N-dimethylhydrazino]-2-oxo-1(2H)-pyrazineacetamide;
- 6-[3-amino-5-(N-benzylamidocarbonyl)phenyl]-5-chloro-3-[N-ethyl-N-methylhydrazino]-N-[[4-aminoiminomethylphenyl]methyl]-2-oxo-1(2H)-pyrazineacetamide;
- 6-[3-amino-5-(N-benzylamidocarbonyl)phenyl]-5-chloro-3-[N,N-diethylhydrazino]-N-[[4-aminoiminomethylphenyl]methyl]-2-oxo-1(2H)-pyrazineacetamide.

Using the examples and methods described herein previously, the following further examples having a amidinoaralkyl or amidinoheteroaralkyl type $Y^0$ group could be prepared of the formula:

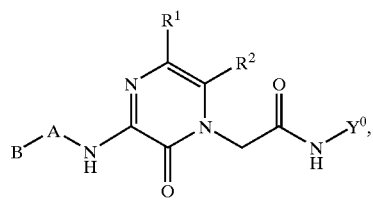

wherein;
- $R^2$ is 3-amidocarbonyl-5-aminophenyl, B is 3-chlorophenyl, A is $CH_2CH_2$, $Y^0$ is 4-amidinobenzyl, and $R^1$ is chloro;
- $R^2$ is 3-amino-5-(N-benzylamidocarbonyl)phenyl, B is 3-chlorophenyl, A is $CH_2CH_2$, $Y^0$ is 4-amidinobenzyl, and $R^1$ is chloro;
- $R^2$ is 3-amino-5-(N-(2-chlorobenzyl)amidocarbonyl)phenyl, B is 3-chlorophenyl, A is $CH_2CH_2$, $Y^0$ is 4-amidinobenzyl, and $R^1$ is chloro;
- $R^2$ is 3-amino-5-(N-(2-chlorobenzyl)amidosulfonyl)phenyl, B is 3-chlorophenyl, A is $CH_2CH_2$, $Y^0$ is 4-amidinobenzyl, and $R^1$ is chloro;
- $R^2$ is 3-amino-5-(N-(2-trifluoromethylbenzyl)amidocarbonyl)phenyl, B is 3-chlorophenyl, A is $CH_2CH_2$, $Y^0$ is 4-amidinobenzyl, and $R^1$ is chloro;

$R^2$ is 3,5-diaminophenyl, B is 3-chlorophenyl, A is $CH_2CH_2$, $Y^0$ is 4-amidinobenzyl, and $R^1$ is chloro;

$R^2$ is 3-amino-5-carboxyphenyl, B is 3-chlorophenyl, A is $CH_2CH_2$, $Y^0$ is 4-amidinobenzyl, and $R^1$ is chloro;

$R^2$ is 3-amidocarbonyl-5-aminophenyl, B is 3-chlorophenyl, A is $CH_2CH_2$, $Y^0$ is 4-amidinobenzyl, and $R^1$ is hydrido;

$R^2$ is 3-amino-5-(N-benzylamidocarbonyl)phenyl, B is 3-chlorophenyl, A is $CH_2CH_2$, $Y^0$ is 4-amidinobenzyl, and $R^1$ is hydrido;

$R^2$ is 3-amino-5-(N-(2-chlorobenzyl)amidocarbonyl)phenyl, B is 3-chlorophenyl, A is $CH_2CH_2$, $Y^0$ is 4-amidinobenzyl, and $R^1$ is hydrido;

$R^2$ is 3-amino-5-(N-(2-chlorobenzyl)amidosulfonyl)phenyl, B is 3-chlorophenyl, A is $CH_2CH_2$, $Y^0$ is 4-amidinobenzyl, and $R^1$ is hydrido;

$R^2$ is 3-amino-5-(N-(2-trifluoromethylbenzyl)amidocarbonyl)-phenyl, B is 3-chlorophenyl, A is $CH_2CH_2$, $Y^0$ is 4-amidinobenzyl, and $R^1$ is hydrido;

$R^2$ is 3,5-diaminophenyl, B is 3-chlorophenyl, A is $CH_2CH_2$, $Y^0$ is 4-amidinobenzyl, and $R^1$ is hydrido;

$R^2$ is 3-amino-5-carboxyphenyl, B is 3-chlorophenyl, A is $CH_2CH_2$, $Y^0$ is 4-amidinobenzyl, and $R^1$ is hydrido;

$R^2$ is 3-thienyl, B is 3-chlorophenyl, A is $CH_2CH_2$, $Y^0$ is 4-amidinobenzyl, and $R^1$ is chloro;

$R^2$ is 3-amino-5-benzylphenyl, B is 3-chlorophenyl, A is $CH_2CH_2$, $Y^0$ is 4-amidinobenzyl, and $R^1$ is chloro;

$R^2$ is 3-amino-5-(2-phenylethyl)phenyl, B is phenyl, A is $CH_2$, $Y^0$ is 4-amidinobenzyl, and $R^1$ is chloro;

$R^2$ is 3-amino-5-benzylaminophenyl, B is 3-chlorophenyl, A is $CH_2CH_2$, $Y^0$ is 4-amidinobenzyl, and $R^1$ is chloro;

$R^2$ is 3-amino-5-(2-phenylethylamino)phenyl, B is 2-imidazoyl, A is $CH_2CH_2CH_2$, $Y^0$ is 4-amidinobenzyl, and $R^1$ is chloro;

$R^2$ is 3-amino-5-benzyloxyphenyl, B is phenyl, A is $CH_2CH_2$, $Y^0$ is 4-amidinobenzyl, and $R^1$ is chloro;

$R^2$ is 3-amino-5-(2-phenylethoxy)phenyl, B is phenyl, A is $CH_2CH_2$, $Y^0$ is 4-amidinobenzyl, and $R^1$ is chloro;

$R^2$ is 3-amino-5-(4-trifluoromethylbenzylamino)phenyl, B is 3-aminophenyl, A is C(O)NH, $Y^0$ is 4-amidinobenzyl, and $R^1$ is hydrido;

$R^2$ is 3-amino-5-(4-trifluoromethylbenzyloxy)phenyl, B is 3-amidinophenyl, A is $CH_2$, $Y^0$ is 4-amidinobenzyl, and $R^1$ is chloro;

$R^2$ is 3-amino-5-benzylphenyl, B is phenyl, A is $CH_2CH_2$, $Y^0$ is 4-amidinobenzyl, and $R^1$ is chloro;

$R^2$ is 3-amino-5-(2-phenylethyl)phenyl, B is phenyl, A is $CH_2CH_2$, $Y^0$ is 4-amidinobenzyl, and $R^1$ is chloro;

$R^2$ is 3-amino-5-benzylaminophenyl, B is phenyl, A is $CH_2CH_2$, $Y^0$ is 4-amidinobenzyl, and $R^1$ is chloro;

$R^2$ is 3-amino-5-(2-phenylethylamino)phenyl, B is 4-aminophenyl, A is $CH_2$, $Y^0$ is 4-amidinobenzyl, and $R^1$ is chloro;

$R^2$ is 3-amino-5-benzyloxyphenyl, B is phenyl, A is $CH_2CH_2$, $Y^0$ is 4-amidinobenzyl, and $R^1$ is hydrido;

$R^2$ is 3-amino-5-(4-trifluoromethylbenzylamino)phenyl, B is phenyl, A is $CH_2$, $Y^0$ is 4-amidinobenzyl, and $R^1$ is chloro;

$R^2$ is 3-amino-5-(2-phenylethoxy)phenyl, B is 4-pyridyl, A is $CH_2CH_2$, $Y^0$ is 4-amidinobenzyl, and $R^1$ is chloro;

$R^2$ is 3-amino-5-(4-trifluoromethylbenzyloxy)phenyl, B is 3-pyridyl, A is $CH_2CH_2$, $Y^0$ is 4-amidinobenzyl, and $R^1$ is chloro;

$R^2$ is 3-amino-5-benzylphenyl, B is 4-pyridyl, A is $CH_2CH_2$, $Y^0$ is 4-amidinobenzyl, and $R^1$ is chloro;

$R^2$ is 3-amino-5-(2-phenylethyl)phenyl, B is phenyl, A is $CH_2CH_2$, $Y^0$ is 4-amidinobenzyl, and $R^1$ is hydrido;

$R^2$ is 3-amino-5-benzylaminophenyl, B is 3-chlorophenyl, A is $CH_2CH_2$, $Y^0$ is 4-amidinobenzyl, and $R^1$ is fluoro;

$R^2$ is 3-amino-5-(2-phenylethylamino)phenyl, B is 3-chlorophenyl, A is $CH_2CH_2$, $Y^0$ is 4-amidinobenzyl, and $R^1$ is chloro;

$R^2$ is 3-amino-5-(2-phenylethoxy)phenyl, B is 3-chlorophenyl, A is $CH_2CH_2$, $Y^0$ is 4-amidinobenzyl, and $R^1$ is chloro;

$R^2$ is 3-amino-5-(4-trifluoromethylbenzylamino)phenyl, B is 3-chlorophenyl, A is $CH_2CH_2$, $Y^0$ is 4-amidinobenzyl, and $R^1$ is chloro;

$R^2$ is 3-amino-5-(4-trifluoromethylbenzyloxy)phenyl, B is 3-chlorophenyl, A is $CH_2CH_2$, $Y^0$ is 4-amidinobenzyl, and $R^1$ is chloro;

$R^2$ is 3-aminophenyl, B is 2-propyl, A is a bond, $Y^0$ is 4-amidino-3-fluorobenzyl, and $R^1$ is chloro;

$R^2$ is 3-aminophenyl, B is 2-propyl, A is a bond, $Y^0$ is 4-amidino-3-fluorobenzyl, and $R^1$ is hydrido;

$R^2$ is 3,5-diaminophenyl, B is 2,2,2-trifluoroethyl, A is a bond, $Y^0$ is 4-amidinobenzyl, and $R^1$ is chloro;

$R^2$ is 3,5-diaminophenyl, B is (S)-2-butyl, A is a bond, $Y^0$ is 4-amidinobenzyl, and $R^1$ is chloro;

$R^2$ is 3,5-diaminophenyl, B is isopropyl, A is a bond, $Y^0$ is 4-amidinobenzyl, and $R^1$ is chloro;

$R^2$ is 3,5-diaminophenyl, B is isopropyl, A is a bond, $Y^0$ is 4-amidino-2-fluorobenzylbenzyl, and $R^1$ is chloro;

$R^2$ is 3,5-diaminophenyl, B is ethyl, A is a bond, $Y^0$ is 4-amidinobenzyl, and $R^1$ is chloro;

$R^2$ is 3,5-diaminophenyl, B is ethyl, A is a bond, $Y^0$ is 4-amidino-2-fluorobenzyl, and $R^1$ is chloro;

$R^2$ is 3-amino-5-carboxyphenyl, B is 2,2,2-trifluoroethyl, A is a bond, $Y^0$ is 4-amidinobenzyl, and $R^1$ is chloro;

$R^2$ is 3-amino-5-carboxyphenyl, B is (S)-2-butyl, A is a bond, $Y^0$ is 4-amidinobenzyl, and $R^1$ is chloro;

$R^2$ is 3-amino-5-carboxyphenyl, B is isopropyl, A is a bond, $Y^0$ is 4-amidino-2-fluorobenzylbenzyl, and $R^1$ is chloro;

$R^2$ is 3-amino-5-carboxyphenyl, B is ethyl, A is a bond, $Y^0$ is 4-amidinobenzyl, and $R^1$ is chloro;

$R^2$ is 3-amino-5-carboxyphenyl, B is ethyl, A is a bond, $Y^0$ is 4-amidino-2-fluorobenzyl, and $R^1$ is chloro;

$R^2$ is 3-amino-5-(N-benzylamidocarbonyl)phenyl, B is 2,2,2-trifluoroethyl, A is a bond, $Y^0$ is 4-amidinobenzyl, and $R^1$ is chloro;

$R^2$ is 3-amino-5-(N-benzylamidocarbonyl)phenyl, B is (S)-2-butyl, A is a bond, $Y^0$ is 4-amidinobenzyl, and $R^1$ is chloro;

$R^2$ is 3-amino-5-(N-benzylamidocarbonyl)phenyl, B is isopropyl, A is a bond, $Y^0$ is 4-amidino-2-fluorobenzylbenzyl, and $R^1$ is chloro;

$R^2$ is 3-amino-5-(N-benzylamidocarbonyl)phenyl, B is ethyl, A is a bond, $Y^0$ is 4-amidinobenzyl, and $R^1$ is chloro;

$R^2$ is 3-amino-5-(N-benzylamidocarbonyl)phenyl, B is ethyl, A is a bond, $Y^0$ is 4-amidino-2-fluorobenzyl, and $R^1$ is chloro;

$R^2$ is 3-amino-5-benzylphenyl, B is 2,2,2-trifluoroethyl, A is a bond, $Y^0$ is 4-amidinobenzyl, and $R^1$ is chloro;

R² is 3-amino-5-benzylphenyl, B is (S)-2-butyl, A is a bond, Y⁰ is 4-amidinobenzyl, and R¹ is chloro;

R² is 3-amino-5-benzylphenyl, B is isopropyl, A is a bond, Y⁰ is 4-amidinobenzyl, and R¹ is chloro;

R² is 3-amino-5-benzylphenyl, B is isopropyl, A is a bond, Y⁰ is 4-amidino-2-fluorobenzylbenzyl, and R¹ is chloro;

R² is 3-amino-5-benzylphenyl, B is ethyl, A is a bond, Y⁰ is 4-amidinobenzyl, and R¹ is chloro;

R² is 3-amino-5-benzylphenyl, B is ethyl, A is a bond, Y⁰ is 4-amidino-2-fluorobenzyl, and R¹ is chloro;

R² is 3-amino-5-(2-phenylethyl)phenyl, B is 2,2,2-trifluoroethyl, A is a bond, Y⁰ is 4-amidinobenzyl, and R¹ is chloro;

R² is 3-amino-5-(2-phenylethyl)phenyl, B is (S)-2-butyl, A is a bond, Y⁰ is 4-amidinobenzyl, and R¹ is chloro;

R² is 3-amino-5-(2-phenylethyl)phenyl, B is isopropyl, A is a bond, Y⁰ is 4-amidinobenzyl, and R¹ is chloro;

R² is 3-amino-5-(2-phenylethyl)phenyl, B is isopropyl, A is a bond, Y⁰ is 4-amidino-2-fluorobenzylbenzyl, and R¹ is chloro;

R² is 3-amino-5-(2-phenylethyl)phenyl, B is ethyl, A is a bond, Y⁰ is 4-amidinobenzyl, and R¹ is chloro;

R² is 3-amino-5-(2-phenylethyl)phenyl, B is ethyl, A is a bond, Y⁰ is 4-amidino-2-fluorobenzyl, and R¹ is chloro;

R² is 3-amino-5-benzylaminophenyl, B is 2,2,2-trifluoroethyl, A is a bond, Y⁰ is 4-amidinobenzyl, and R¹ is chloro;

R² is 3-amino-5-benzylaminophenyl, B is (S)-2-butyl, A is a bond, Y⁰ is 4-amidinobenzyl, and R¹ is chloro;

R² is 3-amino-5-benzylaminophenyl, B is isopropyl, A is a bond, Y⁰ is 4-amidinobenzyl, and R¹ is chloro;

R² is 3-amino-5-benzylaminophenyl, B is isopropyl, A is a bond, Y⁰ is 4-amidino-2-fluorobenzylbenzyl, and R¹ is chloro;

R² is 3-amino-5-benzylaminophenyl, B is ethyl, A is a bond, Y⁰ is 4-amidinobenzyl, and R¹ is chloro;

R² is 3-amino-5-benzylaminophenyl, B is ethyl, A is a bond, Y⁰ is 4-amidino-2-fluorobenzyl, and R¹ is chloro;

R² is 3-amino-5-(2-phenylethylamino)phenyl, B is 2,2,2-trifluoroethyl, A is a bond, Y⁰ is 4-amidinobenzyl, and R¹ is chloro;

R² is 3-amino-5-(2-phenylethylamino)phenyl, B is (S)-2-butyl, A is a bond, Y⁰ is 4-amidinobenzyl, and R¹ is chloro;

R² is 3-amino-5-(2-phenylethylamino)phenyl, B is isopropyl, A is a bond, Y⁰ is 4-amidinobenzyl, and R¹ is chloro;

R² is 3-amino-5-(2-phenylethylamino)phenyl, B is isopropyl, A is a bond, Y⁰ is 4-amidino-2-fluorobenzylbenzyl, and R¹ is chloro;

R² is 3-amino-5-(2-phenylethylamino)phenyl, B is ethyl, A is a bond, Y⁰ is 4-amidinobenzyl, and R¹ is chloro;

R² is 3-amino-5-(2-phenylethylamino)phenyl, B is ethyl, A is a bond, Y⁰ is 4-amidino-2-fluorobenzyl, and R¹ is chloro;

R² is 3-amino-5-benzyloxyphenyl, B is 2,2,2-trifluoroethyl, A is a bond, Y⁰ is 4-amidinobenzyl, and R¹ is chloro;

R² is 3-amino-5-benzyloxyphenyl, B is (S)-2-butyl, A is a bond, Y⁰ is 4-amidinobenzyl, and R¹ is chloro;

R² is 3-amino-5-benzyloxyphenyl, B is isopropyl, A is a bond, Y⁰ is 4-amidinobenzyl, and R¹ is chloro;

R² is 3-amino-5-benzyloxyphenyl, B is isopropyl, A is a bond, Y⁰ is 4-amidino-2-fluorobenzylbenzyl, and R¹ is chloro;

R² is 3-amino-5-benzyloxyphenyl, B is ethyl, A is a bond, Y⁰ is 4-amidinobenzyl, and R¹ is chloro;

R² is 3-amino-5-benzyloxyphenyl, B is ethyl, A is a bond, Y⁰ is 4-amidino-2-fluorobenzyl, and R¹ is chloro;

R² is 3-amino-5-(2-phenylethoxy)phenyl, B is 2,2,2-trifluoroethyl, A is a bond, Y⁰ is 4-amidinobenzyl, and R¹ is chloro;

R² is 3-amino-5-(2-phenylethoxy)phenyl, B is (S)-2-butyl, A is a bond, Y⁰ is 4-amidinobenzyl, and R¹ is chloro;

R² is 3-amino-5-(2-phenylethoxy)phenyl, B is isopropyl, A is a bond, Y⁰ is 4-amidinobenzyl, and R¹ is chloro;

R² is 3-amino-5-(2-phenylethoxy)phenyl, B is isopropyl, A is a bond, Y⁰ is 4-amidino-2-fluorobenzylbenzyl, and R¹ is chloro;

R² is 3-amino-5-(2-phenylethoxy)phenyl, B is ethyl, A is a bond, Y⁰ is 4-amidinobenzyl, and R¹ is chloro;

R² is 3-amino-5-(2-phenylethoxy)phenyl, B is ethyl, A is a bond, Y⁰ is 4-amidino-2-fluorobenzyl, and R¹ is chloro;

R² is 3-amino-5-(4-trifluoromethylbenzylamino)phenyl, B is 2,2,2-trifluoroethyl, A is a bond, Y⁰ is 4-amidinobenzyl, and R¹ is chloro;

R² is 3-amino-5-(4-trifluoromethylbenzylamino)phenyl, B is (S)-2-butyl, A is a bond, Y⁰ is 4-amidinobenzyl, and R¹ is chloro;

R² is 3-amino-5-(4-trifluoromethylbenzylamino)phenyl, B is isopropyl, A is a bond, Y⁰ is 4-amidinobenzyl, and R¹ is chloro;

R² is 3-amino-5-(4-trifluoromethylbenzylamino)phenyl, B is isopropyl, A is a bond, Y⁰ is 4-amidino-2-fluorobenzylbenzyl, and R¹ is chloro;

R² is 3-amino-5-(4-trifluoromethylbenzylamino)phenyl, B is ethyl, A is a bond, Y⁰ is 4-amidinobenzyl, and R¹ is chloro;

R² is 3-amino-5-(4-trifluoromethylbenzylamino)phenyl, B is ethyl, A is a bond, Y⁰ is 4-amidino-2-fluorobenzyl, and R¹ is chloro;

R² is 3-amino-5-(4-trifluoromethylbenzyloxy)phenyl, B is 2.2,2-trifluoroethyl, A is a bond, Y⁰ is 4-amidinobenzyl, and R¹ is chloro;

R² is 3-amino-5-(4-trifluoromethylbenzyloxy)phenyl, B is (S)-2-butyl, A is a bond, Y⁰ is 4-amidinobenzyl, and R¹ is chloro;

R² is 3-amino-5-(4-trifluoromethylbenzyloxy)phenyl, B is isopropyl, A is a bond, Y⁰ is 4-amidinobenzyl, and R¹ is chloro;

R² is 3-amino-5-(4-trifluoromethylbenzyloxy)phenyl, B is isopropyl, A is a bond, Y⁰ is 4-amidino-2-fluorobenzylbenzyl, and R¹ is chloro;

R² is 3-amino-5-(4-trifluoromethylbenzyloxy)phenyl, B is ethyl, A is a bond, Y⁰ is 4-amidinobenzyl, and R¹ is chloro;

R² is 3-amino-5-(4-trifluoromethylbenzyloxy)phenyl, B is ethyl, A is a bond, Y⁰ is 4-amidino-2-fluorobenzyl, and R¹ is chloro;

R² is 3,5-diaminophenyl, B is cyclopropyl, A is a bond, Y⁰ is 4-amidinobenzyl, and R¹ is chloro;

R² is 3,5-diaminophenyl, B is cyclobutyl, A is a bond, Y⁰ is 4-amidino-2-fluorobenzyl, and R¹ is chloro;

R² is 3,5-diaminophenyl, B is cyclopropyl, A is a bond, Y⁰ is 4-amidino-2-fluorobenzyl, and R¹ is chloro;

R² is 3,5-diaminophenyl, B is cyclobutyl, A is a bond, Y⁰ is 4-amidinobenzyl, and R¹ is hydrido;

R² is 3,5-diaminophenyl, B is cyclobutyl, A is a bond, Y⁰ is 4-amidino-3-fluorobenzyl, and R¹ is chloro;

R² is 3,5-diaminophenyl, B is cyclopentyl, A is a bond, Y⁰ is 4-amidinobenzyl, and R¹ is chloro;

R² is 3-carboxy-5-aminophenyl, B is cyclopropyl, A is a bond, Y⁰ is 4-amidinobenzyl, and R¹ is chloro;

R² is 3-carboxy-5-aminophenyl, B is cyclobutyl, A is a bond, Y⁰ is 4-amidino-2-fluorobenzyl, and R¹ is chloro;

R² is 3-carboxy-5-aminophenyl, B is cyclopropyl, A is a bond, Y⁰ is 4-amidino-2-fluorobenzyl, and R¹ is chloro;

R² is 3-carboxy-5-aminophenyl, B is cyclobutyl, A is a bond, Y⁰ is 4-amidinobenzyl, and R¹ is hydrido;

R² is 3-carboxy-5-aminophenyl, B is cyclobutyl, A is a bond, Y⁰ is 4-amidino-3-fluorobenzyl, and R¹ is chloro;

R² is 3-carboxy-5-aminophenyl, B is cyclopentyl, A is a bond, Y⁰ is 4-amidinobenzyl, and R¹ is chloro;

R² is 3-amino-5-(N-benzylamidocarbonyl)phenyl, B is cyclopropyl, A is a bond, Y⁰ is 4-amidinobenzyl, and R¹ is chloro;

R² is 3-amino-5-(N-benzylamidocarbonyl)phenyl, B is cyclobutyl, A is a bond, Y⁰ is 4-amidino-2-fluorobenzyl, and R¹ is chloro;

R² is 3-amino-5-(N-benzylamidocarbonyl)phenyl, B is cyclobutyl, A is a bond, Y⁰ is 4-amidinobenzyl, and R¹ is chloro;

R² is 3-amino-5-(N-benzylamidocarbonyl)phenyl, B is cyclopropyl, A is a bond, Y⁰ is 4-amidino-2-fluorobenzyl, and R¹ is chloro;

R² is 3-amino-5-(N-benzylamidocarbonyl)phenyl, B is cyclobutyl, A is a bond, Y⁰ is 4-amidinobenzyl, and R¹ is hydrido;

R² is 3-amino-5-(N-benzylamidocarbonyl)phenyl, B is cyclobutyl, A is a bond, Y⁰ is 4-amidino-3-fluorobenzyl, and R¹ is chloro;

R² is 3-amino-5-(N-benzylamidocarbonyl)phenyl, B is cyclopentyl, A is a bond, Y⁰ is 4-amidinobenzyl, and R¹ is chloro;

R² is 3-amino-5-(N-(2-chlorobenzyl)amidosulfonyl)phenyl, B is cyclopropyl, A is a bond, Y⁰ is 4-amidinobenzyl, and R¹ is chloro;

R² is 3-amino-5-(N-(2-chlorobenzyl)amidosulfonyl)phenyl, B is cyclobutyl, A is a bond, Y⁰ is 4-amidino-2-fluorobenzyl, and R¹ is chloro;

R² is 3-amino-5-(N-(2-chlorobenzyl)amidosulfonyl)phenyl, B is cyclobutyl, A is a bond, Y⁰ is 4-amidinobenzyl, and R¹ is chloro;

R² is 3-amino-5-(N-(2-chlorobenzyl)amidosulfonyl)phenyl, B is cyclopropyl, A is a bond, Y⁰ is 4-amidino-2-fluorobenzyl, and R¹ is chloro;

R² is 3-amino-5-(N-(2-chlorobenzyl)amidosulfonyl)phenyl, B is cyclobutyl, A is a bond, Y⁰ is 4-amidinobenzyl, and R¹ is hydrido;

R² is 3-amino-5-(N-(2-chlorobenzyl)amidosulfonyl)phenyl, B is cyclobutyl, A is a bond, Y⁰ is 4-amidino-3-fluorobenzyl, and R¹ is chloro;

R² is 3-amino-5-(N-(2-chlorobenzyl)amidosulfonyl)phenyl, B is cyclopentyl, A is a bond, Y⁰ is 4-amidinobenzyl, and R¹ is chloro;

R² is 3-amino-5-(N-(2-trifluoromethylbenzyl)amidocarbonyl)-phenyl, B is cyclopropyl, A is a bond, Y⁰ is 4-amidinobenzyl, and R¹ is chloro;

R² is 3-amino-5-(N-(2-trifluoromethylbenzyl)amidocarbonyl)-phenyl, B is cyclobutyl, A is a bond, Y⁰ is 4-amidino-2-fluorobenzyl, and R¹ is chloro;

R² is 3-amino-5-(N-(2-trifluoromethylbenzyl)amidocarbonyl)-phenyl, B is cyclobutyl, A is a bond, Y⁰ is 4-amidinobenzyl, and R¹ is chloro;

R² is 3-amino-5-(N-(2-trifluoromethylbenzyl)amidocarbonyl)-phenyl, B is cyclopropyl, A is a bond, Y⁰ is 4-amidino-2-fluorobenzyl, and R¹ is chloro;

R² is 3-amino-5-(N-(2-trifluoromethylbenzyl)amidocarbonyl)-phenyl, B is cyclobutyl, A is a bond, Y⁰ is 4-amidinobenzyl, and R¹ is hydrido;

R² is 3-amino-5-(N-(2-trifluoromethylbenzyl)amidocarbonyl)-phenyl, B is cyclobutyl, A is a bond, Y⁰ is 4-amidino-3-fluorobenzyl, and R¹ is chloro;

R² is 3-amino-5-(N-(2-trifluoromethylbenzyl)amidocarbonyl)-phenyl, B is, cyclopentyl, A is a bond, Y⁰ is 4-amidinobenzyl, and R¹ is chloro;

R² is 3-amino-5-benzylphenyl, B is cyclopropyl, A is a bond, Y⁰ is 4-amidinobenzyl, and R¹ is chloro;

R² is 3-amino-5-benzylphenyl, B is cyclobutyl, A is a bond, Y⁰ is 4-amidino-2-fluorobenzyl, and R¹ is chloro;

R² is 3-amino-5-benzylphenyl, B is cyclobutyl, A is a bond, Y⁰ is 4-amidinobenzyl, and R¹ is chloro;

R² is 3-amino-5-benzylphenyl, B is cyclopropyl, A is a bond, Y⁰ is 4-amidino-2-fluorobenzyl, and R¹ is chloro;

R² is 3-amino-5-benzylphenyl, B is cyclobutyl, A is a bond, Y⁰ is 4-amidinobenzyl, and R¹ is hydrido;

R² is 3-amino-5-benzylphenyl, B is cyclobutyl, A is a bond, Y⁰ is 4-amidino-3-fluorobenzyl, and R¹ is chloro;

R² is 3-amino-5-benzylphenyl, B is cyclopentyl, A is a bond, Y⁰ is 4-amidinobenzyl, and R¹ is chloro;

R² is 3-amino-5-(2-phenylethyl)phenyl, B is cyclopropyl, A is a bond, Y⁰ is 4-amidinobenzyl, and R¹ is chloro;

R² is 3-amino-5-(2-phenylethyl)phenyl, B is cyclobutyl, A is a bond, Y⁰ is 4-amidino-2-fluorobenzyl, and R¹ is chloro;

R² is 3-amino-5-(2-phenylethyl)phenyl, B is cyclobutyl, A is a bond, Y⁰ is 4-amidinobenzyl, and R¹ is chloro;

R² is 3-amino-5-(2-phenylethyl)phenyl, B is cyclopropyl, A is a bond, Y⁰ is 4-amidino-2-fluorobenzyl, and R¹ is chloro;

R² is 3-amino-5-(2-phenylethyl)phenyl, B is cyclobutyl, A is a bond, Y⁰ is 4-amidinobenzyl, and R¹ is hydrido;

R² is 3-amino-5-(2-phenylethyl)phenyl, B is cyclobutyl, A is a bond, Y⁰ is 4-amidino-3-fluorobenzyl, and R¹ is chloro;

R² is 3-amino-5-(2-phenylethyl)phenyl, B is cyclopentyl, A is a bond, Y⁰ is 4-amidinobenzyl, and R¹ is chloro;

R² is 3-amino-5-benzylaminophenyl, B is cyclopropyl, A is a bond, Y⁰ is 4-amidinobenzyl, and R¹ is chloro;

R² is 3-amino-5-benzylaminophenyl, B is cyclobutyl, A is a bond, Y⁰ is 4-amidino-2-fluorobenzyl, and R¹ is chloro;

R² is 3-amino-5-benzylaminophenyl, B is cyclobutyl, A is a bond, Y⁰ is 4-amidinobenzyl, and R¹ is chloro;

R² is 3-amino-5-benzylaminophenyl, B is cyclopropyl, A is a bond, Y⁰ is 4-amidino-2-fluorobenzyl, and R¹ is chloro;

R² is 3-amino-5-benzylaminophenyl, B is cyclobutyl, A is a bond, Y⁰ is 4-amidinobenzyl, and R¹ is hydrido;

R² is 3-amino-5-benzylaminophenyl, B is cyclobutyl, A is a bond, Y⁰ is 4-amidino-3-fluorobenzyl, and R¹ is chloro;

$R^2$ is 3-amino-5-benzylaminophenyl, B is cyclopentyl, A is a bond, $Y^0$ is 4-amidinobenzyl, and $R^1$ is chloro;

$R^2$ is 3-amino-5-(2-phenylethylamino)phenyl, B is cyclopropyl, A is a bond, $Y^0$ is 4-amidinobenzyl, and $R^1$ is chloro;

$R^2$ is 3-amino-5-(2-phenylethylamino)phenyl, B is cyclobutyl, A is a bond, $Y^0$ is 4-amidino-2-fluorobenzyl, and $R^1$ is chloro;

$R^2$ is 3-amino-5-(2-phenylethylamino)phenyl, B is cyclobutyl, A is a bond, $Y^0$ is 4-amidinobenzyl, and $R^1$ is chloro;

$R^2$ is 3-amino-5-(2-phenylethylamino)phenyl, B is cyclopropyl, A is a bond, $Y^0$ is 4-amidino-2-fluorobenzyl, and $R^1$ is chloro;

$R^2$ is 3-amino-5-(2-phenylethylamino)phenyl, B is cyclobutyl, A is a bond, $Y^0$ is 4-amidinobenzyl, and $R^1$ is hydrido;

$R^2$ is 3-amino-5-(2-phenylethylamino)phenyl, B is cyclobutyl, A is a bond, $Y^0$ is 4-amidino-3-fluorobenzyl, and $R^1$ is chloro;

$R^2$ is 3-amino-5-(2-phenylethylamino)phenyl, B is cyclopentyl, A is a bond, $Y^0$ is 4-amidinobenzyl, and $R^1$ is chloro;

$R^2$ is 3-amino-5-benzyloxyphenyl, B is cyclopropyl, A is a bond, $Y^0$ is 4-amidinobenzyl, and $R^1$ is chloro;

$R^2$ is 3-amino-5-benzyloxyphenyl, B is cyclobutyl, A is a bond, $Y^0$ is 4-amidino-2-fluorobenzyl, and $R^1$ is chloro;

$R^2$ is 3-amino-5-benzyloxyphenyl, B is cyclobutyl, A is a bond, $Y^0$ is 4-amidinobenzyl, and $R^1$ is chloro;

$R^2$ is 3-amino-5-benzyloxyphenyl, B is cyclopropyl, A is a bond, $Y^0$ is 4-amidino-2-fluorobenzyl, and $R^1$ is chloro;

$R^2$ is 3-amino-5-benzyloxyphenyl, B is cyclobutyl, A is a bond, $Y^0$ is 4-amidinobenzyl, and $R^1$ is hydrido;

$R^2$ is 3-amino-5-benzyloxyphenyl, B is cyclobutyl, A is a bond, $Y^0$ is 4-amidino-3-fluorobenzyl, and $R^1$ is chloro;

$R^2$ is 3-amino-5-benzyloxyphenyl, B is cyclopentyl, A is a bond, $Y^0$ is 4-amidinobenzyl, and $R^1$ is chloro;

$R^2$ is 3-amino-5-(2-phenylethoxy)phenyl, B is cyclopropyl, A is a bond, $Y^0$ is 4-amidinobenzyl, and $R^1$ is chloro;

$R^2$ is 3-amino-5-(2-phenylethoxy)phenyl, B is cyclobutyl, A is a bond, $Y^0$ is 4-amidino-2-fluorobenzyl, and $R^1$ is chloro;

$R^2$ is 3-amino-5-(2-phenylethoxy)phenyl, B is cyclobutyl, A is a bond, $Y^0$ is 4-amidinobenzyl, and $R^1$ is chloro;

$R^2$ 3-amino-5-(2-phenylethoxy)phenyl, B is cyclopropyl, A is a bond, $Y^0$ is 4-amidino-2-fluorobenzyl, and $R^1$ is chloro;

$R^2$ is 3-amino-5-(2-phenylethoxy)phenyl, B is cyclobutyl, A is a bond, $Y^0$ is 4-amidinobenzyl, and $R^1$ is hydrido;

$R^2$ is 3-amino-5-(2-phenylethoxy)phenyl, B is cyclobutyl, A is a bond, $Y^0$ is 4-amidino-3-fluorobenzyl, and $R^1$ is chloro;

$R^2$ is 3-amino-5-(2-phenylethoxy)phenyl, B is cyclopentyl, A is a bond, $Y^0$ is 4-amidinobenzyl, and $R^1$ is chloro;

$R^2$ is 3-amino-5-(4-trifluoromethylbenzylamino)phenyl, B is cyclopropyl, A is a bond, $Y^0$ is 4-amidinobenzyl, and $R^1$ is chloro;

$R^2$ is 3-amino-5-(4-trifluoromethylbenzylamino)phenyl, B is cyclobutyl, A is a bond, $Y^0$ is 4-amidino-2-fluorobenzyl, and $R^1$ is chloro;

$R^2$ is 3-amino-5-(4-trifluoromethylbenzylamino)phenyl, B is cyclobutyl, A is a bond, $Y^0$ is 4-amidinobenzyl, and $R^1$ is chloro;

$R^2$ is 3-amino-5-(4-trifluoromethylbenzylamino)phenyl, B is cyclopropyl, A is a bond, $Y^0$ is 4-amidino-2-fluorobenzyl, and $R^1$ is chloro;

$R^2$ is 3-amino-5-(4-trifluoromethylbenzylamino)phenyl, B is cyclobutyl, A is a bond, $Y^0$ is 4-amidinobenzyl, and $R^1$ is hydrido;

$R^2$ is 3-amino-5-(4-trifluoromethylbenzylamino)phenyl, B is cyclobutyl, A is a bond, $Y^0$ is 4-amidino-3-fluorobenzyl, and $R^1$ is chloro;

$R^2$ is 3-amino-5-(4-trifluoromethylbenzylamino)phenyl, B is cyclopentyl, A is a bond, $Y^0$ is 4-amidinobenzyl, and $R^1$ is chloro;

$R^2$ is 3-amino-5-(4-trifluoromethylbenzyloxy)phenyl, B is cyclopropyl, A is a bond, $Y^0$ is 4-amidinobenzyl, and $R^1$ is chloro;

$R^2$ is 3-amino-5-(4-trifluoromethylbenzyloxy)phenyl, B is cyclobutyl, A is a bond, $Y^0$ is 4-amidino-2-fluorobenzyl, and $R^1$ is chloro;

$R^2$ is 3-amino-5-(4-trifluoromethylbenzyloxy)phenyl, B is cyclobutyl, A is a bond, $Y^0$ is 4-amidinobenzyl, and $R^1$ is chloro;

$R^2$ is 3-amino-5-(4-trifluoromethylbenzyloxy)phenyl, B is cyclopropyl, A is a bond, $Y^0$ is 4-amidino-2-fluorobenzyl, and $R^1$ is chloro;

$R^2$ is 3-amino-5-(4-trifluoromethylbenzyloxy)phenyl, B is cyclobutyl, A is a bond, $Y^0$ is 4-amidinobenzyl, and $R^1$ is hydrido;

$R^2$ is 3-amino-5-(4-trifluoromethylbenzyloxy)phenyl, B is cyclobutyl, A is a bond, $Y^0$ is 4-amidino-3-fluorobenzyl, and $R^1$ is chloro;

$R^2$ is 3-amino-5-(4-trifluoromethylbenzyloxy)phenyl, B is cyclopentyl, A is a bond, $Y^0$ is 4-amidinobenzyl, and $R^1$ is chloro.

Using the examples and methods described herein previously, the following additional examples having a guanidinoalkyl type $Y^{AT}$ group could be prepared of the formula:

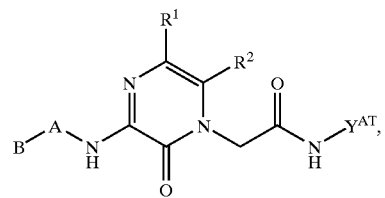

wherein;

$R^2$ is phenyl, B is phenyl, A is $CH_2CH_2$, $Y^{AT}$ is 5-guanidino-1-oxo-1-(2-thiazolyl)-2-pentyl, and $R^1$ is hydrido;

$R^2$ is 3,5-diaminophenyl, B is phenyl, A is $CH_2CH_2$, $Y^{AT}$ is 5-guanidino-1-oxo-1-(2-thiazolyl)-2-pentyl, and $R^1$ is chloro;

$R^2$ is 3-carboxy-5-aminophenyl, B is phenyl, A is $CH_2CH_2$, $Y^{AT}$ is 5-guanidino-1-oxo-1-(2-thiazolyl)-2-pentyl, and $R^1$ is chloro;

$R^2$ is 3,5-diaminophenyl, B is isopropyl, A is a bond, $Y^{AT}$ is 5-guanidino-1-oxo-1-(2-thiazolyl)-2-pentyl, and $R^1$ is chloro;

$R^2$ is 3-carboxy-5-aminophenyl, B is isopropyl, A is a bond, $Y^{AT}$ is 5-guanidino-1-oxo-1-(2-thiazolyl)-2-pentyl, and $R^1$ is chloro;

R² is 3,5-diaminophenyl, B is cyclobutyl, A is a bond, $Y^{AT}$ is 5-guanidino-1-oxo-1-(2-thiazolyl)-2-pentyl, and R¹ is chloro;

R² is 3-carboxy-5-aminophenyl, B is cyclobutyl, A is a bond, $Y^{AT}$ is 5-guanidino-1-oxo-1-(2-thiazolyl)-2-pentyl, and R¹ is chloro.

Assays for Biological Activity

TF-VIIa Assay

In this assay 100 nM recombinant soluble tissue factor and 2 nM recombinant human factor VIIa are added to a 96 well assay plate containing 0.4 mM of the substrate, N-Methylsulfonyl-D-phe-gly-arg-p-nitroaniline and either inhibitor or buffer (5 mM CaCl₂, 50 mM Tris-HCl, pH 8.0, 100 mm NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of TF-VIIa activity is calculated from $OD_{405\ nm}$ value from the experimental and control sample.

Xa Assay

Human factor Xa (0.3 nM) and 0.15 mM N-α-Benzyloxycarbonyl-D-arginyl-L-glycyl-L-arginine-p-nitroaniline-dihydrochloride (S-2765) are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of Xa activity is calculated from $OD_{405}$ nm value from the experimental and control sample.

Thrombin Assay

Human thrombin (0.28 nM) and 0.06 mM H-D-Phenylalanyl-L-pipecolyl-L-arginine-p-nitroaniline dihydrochloride are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of thrombin activity is calculated from $OD_{405\ nm}$ value from the experimental and control sample.

Trypsin Assay

Trypsin (5 ug/ml; type IX from porcine pancreas) and 0.375 mM N-α-Benzoyl-L-arginine-p-nitroanilide (L-BAPNA) are added to a 96-well assay plate containing either inhibitor or buffer (50 mM Tris-HCl, pH 8.0, 100 mM NaCl, 0.1% BSA). The reactions, in a final volume of 100 ul are measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of trypsin activity is calculated from $OD_{405\ nm}$ value from the experimental and control sample.

Recombinant soluble TF, consisting of amino acids 1–219 of the mature protein sequence was expressed in *E. coli* and purified using a Mono Q Sepharose FPLC. Recombinant human VIIa was purchased from American Diagnostica, Greenwich Conn. and chromogenic substrate N-Methylsulfonyl-D-phe-gly-arg-p-nitroaniline was prepared by American Peptide Company, Inc., Sunnyvale, Calif. Factor Xa was obtained from Enzyme Research Laboratories, South Bend Ind., thrombin from Calbiochem, La Jolla, Calif., and trypsin and L-BAPNA from Sigma, St. Louis Mo. The chromogenic substrates S-2765 and S-2238 were purchased from Chromogenix, Sweden.

Using bioassay procedures described herein, the biological activity of the compounds of Examples 1 through Example 109 and Tables 1 through Table 7 are summarized in Table 8 and Table 9.

TABLE 8

Inhibitory Activity of Pyrazinones toward TF-VIIA, Thrombin II, Factor Xa, and Trypsin II.

I

General Structure

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
|---|---|---|---|---|
| 1 | 1 | 1 | >100 | 0.2 |
| 2 | 5 | 0.4 | >100 | 1 |
| 3 | 0.2 | <0.04 | 1 | 0.4 |
| 4 | 0.3 | 0.1 | 3 | 0.5 |

TABLE 8-continued

Inhibitory Activity of Pyrazinones toward TF-VIIA, Thrombin II, Factor Xa, and Trypsin II.

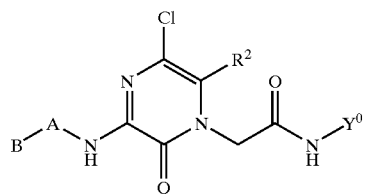

General Structure

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
|---|---|---|---|---|
| 5 | 7 | 1 | 4 | 1 |
| 6 | 0.1 | <0.04 | 1 | 0.4 |
| 7 | 0.2 | 0.1 | 3 | 0.4 |
| 8 | 3 | 0.2 | 1 | 0.4 |
| 9 | >30 | 30 | >0 | >30 |
| 10 | >30 | >0 | >0 | >30 |
| 11 | 91 | <0.1 | >100 | 1 |
| 12 | >100 | 7 | >100 | 1 |
| 13 | >100 | 48 | >100 | 14 |
| 14 | >100 | 29 | >100 | 0.3 |
| 15 | >100 | >100 | >100 | 1 |
| 16 | >100 | 13 | >100 | 1 |
| 17 | 0.71 | 15.32 | 41% | 0.24 |
| 18 | 47% | 20% | 0 | 1.13 |
| 19 | 0.8 | 0.22 | 22% @ 30 | 0.27 |
| 20 | 41% @ 30 | 4 | 6% @ 30 | 7 |
| 21 | 8% @ 30 | 26.8 | 21% @ 30 | 2 |
| 22 | 0% @ 30 | 47% @ 30 | 13% @ 30 | 1.7 |
| 23 | 1.7 | 17 | 38% @ 30 | 0.32 |
| 24 | 0% @ 30 | 46% @ 30 | 22% @ 30 | 1.3 |
| 25 | 7% | 3% | 4% | 9% |
| 26 | 1% | 4% | 5% | 3% |
| 27 | 12.5 | >30 | >30 | 16 |
| 28 | 3 | >30 | >30 | 0.23 |
| 29 | pending | pending | pending | pending |
| 30 | pending | pending | pending | pending |
| 31 | 22% | 4% | 4% | 20% |
| 32 | 12 | 0 | 0 | 0 |
| 33 | 4% | 30 | 0 | 3.6 |
| 34 | 20% | 0.59 | 0 | 1.3 |
| 35 | 29% | 5% | 10% | 2.88 |
| 36 | 5% | 31% | 0 | 30% |
| 37 | 1.8 | 1.9 | 0 | 0.3 |
| 38 | 0.9 | 0.58 | 22% | 0.4 |
| 39 | 1.7 | 0.26 | 0 | 0.28 |
| 40 | 0.06 | 0 | 0 | 0.1 |
| 41 | 0.02 | 8 | 0 | 0.1 |
| 42 | 0.5 | 17% | 0 | 0.53 |
| 43 | 0.25 | 43% | 0 | 0.15 |
| 44 | 2.1 | 40% | 4% | 0.54 |
| 45 | 0.89 | 13 | 9% | 0.25 |
| 46 | 0.98 | 18.7 | 10% | 0.23 |
| 47 | 0.66 | 1.14 | 10.6 | 0.20 |
| 48 | 0.57 | 6.4 | 20% | 0.38 |
| 49 | 0.57 | 6.4 | 28.9 | 0.19 |
| 50 | 0.50 | 14.2 | 39% | 0.24 |
| 51 | 0.65 | 2.14 | 9.68 | 0.17 |
| 52 | 0.59 | 7.0 | 24.0 | 0.15 |
| 53 | 0.30 | 11.1 | 7% | 0.15 |
| 54 | 11.3 | 0% | 0% | 0% |
| 55 | 0.15 | 0.12 | 0% | 0.18 |
| 56 | 16.7 | 3.13 | 0% | 0.738 |
| 57 | 1.4 | 0.15 | 0% | 0.22 |
| 58 | 0% | 1% | 1% | 4% |
| 59 | 0% | 0% | 2% | 7% |
| 60 | 0.901 | <0.04 | 5.65 | 0.192 |
| 61 | 1% | 0% | 0% | 10% |
| 62 | 5.6 | 4% | 10% | 2.2 |

TABLE 8-continued

Inhibitory Activity of Pyrazinones toward TF-VIIA, Thrombin II, Factor Xa, and Trypsin II.

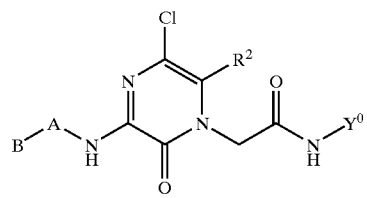

General Structure

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
|---|---|---|---|---|
| 63 | 28% | 6% | 0 | 7 |
| 64 | 0.78 | 2 | 19% | 0.07 |
| 65 | 0.36 | 2.8 | 12% | 0.3 |
| 66 | 0.34 | 40% | 0 | 0.28 |
| 67 | 0.20 | 4.25 | 0 | 0.14 |
| 68 | 32% | 0% | 6% | 4.8 |
| 69 | 0.06 | 2.6 | 2.6 | 0.07 |
| 73 | 0.03 | 4.4 | 0 | 0.1 |
| 74 | 3.25 | 1.78 | 13% | 0.15 |
| 75 | 0.21 | 2 | 9% | 0.04 |
| 76 | 0.12 | 0 | 0 | 0.28 |
| 77 | 2.52 | 0.98 | >30 | 1.13 |
| 78 | 0.43 | 0.3 | 16% @ 30 | 0.23 |
| 79 | 4.14 | 0.3 | 30% @ 30 | 0.15 |
| 80 | 1.29 | 4.55 | 29% @ 30 | 0.16 |
| 81 | 1 | 0.89 | 33% @ 30 | 0.22 |
| 82 | 20 | 4.67 | 32% @ 30 | 0.17 |
| 83 | 0.75 | 0.84 | >30 | 0.36 |
| 84 | 3.03 | 0.5 | >30 | 0.2 |
| 85 | 0.88 | 0.92 | 42% @ 30 | 0.19 |
| 86 | 0.07 | 0.9 | 26% @ 30 | 78% @ 1 |
| 87 | 0.07 | 1.5 | >30 | 0.26 |
| 88 | 0.1 | 15 | >30 | 0.27 |
| 89 | 5% @ 30 | 3% @ 30 | 5% @ 30 | 9% @ 30 |
| 90 | 0.02 | 8 | 16% @ 30 | 0.1 |
| 91 | 0.07 | 0.4 | 7 | 0.5 |
| 92 | 0.053 | 17.7 | 18% @ 30 | 0.25 |
| 93 | 0.07 | 15.4 | >30 | 0.16 |
| 94 | 0.04 | 48% @ 30 | >30 | 0.24 |
| 95 | 0.6 | 0.58 | >30 | 0.21 |
| 96 | 0.26 | 6.39 | >30 | 0.12 |
| 97 | 0.04 | 29% @ 30 | >30 | 0.24 |
| 98 | 0.09 | 20% @ 30 | 10% @ 30 | 0.07 |
| 99 | 6% @ 30 | 0% @ 30 | 8% @ 30 | 7% @ 30 |
| 100 | 1.6 | 0.1 | >30 | 62% @ 1 |
| 101 | 0.6 | 0.1 | >30 | 83% @ 1 |
| 102 | 1.2 | 1 | 43% @ 30 | 0.39 |
| 103 | 0.3 | 1.3 | 11% @ 30 | 0.45 |
| 104 | 1.2 | 19 | >30 | 0.7 |
| 105 | 0 | 17% | 5% | 0.49 |
| 106 | 1.11 | 28.8 | 30% | 0.25 |
| 107 | 0.57 | 48% | 35% | 0.24 |
| 108 | 4.13 | 16% | 20% | 0.5 |
| 109 | 6.17 | 46% | 10% | 0.22 |
| 110 | 0.05 | 20% | 15% | 0.37 |
| 111 | 0.12 | >30 | >30 | 0.28 |
| 112 | 0.27 | 13 | 35 | 0.032 |
| 113 | 6.19 | 0.88 | 14 | 0.025 |
| 114 | 0.38 | 4.3 | 6.5 | 0.024 |
| 115 | 0.55 | 7.5 | 10% | 0.04 |
| 116 | 1.2 | 27% | 12% | 0.19 |
| 117 | 0.033 | 21% | 18% | 0.022 |
| 118 | 0.052 | 3% | 52.31 | 0.06 |
| 119 | 0.01 | 45% | 26% | 0.019 |
| 120 | 0.1 | 47% at 100 μM | 43% at 100 μM | 0.022 |
| 121 | 0.0095 | 44% at 83 μM | 23% at 83 μM | 0.017 |
| 122 | | | | |
| 123 | 0.02 | 1% | 2% | 0.09 |

TABLE 8-continued

Inhibitory Activity of Pyrazinones toward TF-VIIA, Thrombin II, Factor Xa, and Trypsin II.

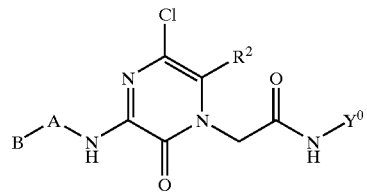

General Structure

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
|---|---|---|---|---|
| 124 | 0.016 | 4.68 | 17% | 0.027 |
| 125 | 0.038 | 32% at 100 µM | 36% at 100 µM | 0.029 |
| 126 | 0.02 | 2% | 10% | 0.06 |
| 127 | 0.031 | 23% | 27% | 0.03 |
| 128-1 | 0.022 | 69 at 100 µM | 25% at 100 µM | 0.04 |
| 128-2 | 0.0256 | 60.2 at 100 µM | 41% at 100 µM | 0.056 |
| 128-3 | 0.0082 | 12.5 at 100 µM | 40% at 100 µM | 0.033 |
| 128-4 | 0.0107 | 24 at 100 µM | 42% at 100 µM | 0.051 |
| 128-5 | 0.0847 | 54.5 at 100 µM | 43% at 100 µM | 0.09 |
| 128-6 | 0.3323 | 40% at 100 µM | 29% at 100 µM | 0.481 |
| 128-7 | 0.242 | 43% at 100 µM | 40% at 100 µM | 0.229 |
| 128-8 | 0.067 | 75.2 at 100 µM | 44% at 100 µM | 0.104 |
| 128-9 | 0.007 | 45% at 100 µM | 36% at 100 µM | 0.041 |
| 128-10 | 0.009 | 73 at 100 µM | 72 at 100 µM | 0.051 |
| 128-11 | 0.0114 | 46% at 100 µM | 35% at 100 µM | 0.054 |
| 128-12 | 0.011 | 47% at 100 µM | 33% at 100 µM | 0.062 |
| 128-13 | 0.0491 | 36% at 100 µM | 26% at 100 µM | 0.181 |
| 128-14 | 0.0074 | 35.4 at 100 µM | 24% at 100 µM | 0.036 |
| 128-15 | 0.0066 | 13.3 at 100 µM | 32% at 100 µM | 0.036 |
| 128-16 | 0.007 | 10.2 at 100 µM | 36% at 100 µM | 0.037 |
| 128-17 | 0.0109 | 20.2 at 100 µM | 41% at 100 µM | 0.05 |
| 128-18 | 0.0185 | 21% at 100 µM | 16% at 100 µM | 0.094 |
| 128-19 | 0.0261 | 37% at 100 µM | 18% at 100 µM | 0.133 |
| 128-20 | 0.033 | 72 at 100 µM | 39% at 100 µM | 0.081 |
| 128-21 | 0.037 | 71 at 100 µM | 45 at 100 µM | 0.116 |
| 128-22 | 0.052 | 61 at 100 µM | 49 at 100 µM | 0.155 |
| 128-23 | 0.0337 | 48 at 100 µM | 44 at 100 µM | 0.078 |
| 128-24 | 0.0187 | 60.6 at 100 µM | 44 at 100 µM | 0.06 |
| 129 | 0.058 at 100 µM | 17 at 100 µM | 22% at 100 µM | 0.051 at 100 µM |
| 130 | 0.18 at 100 µM | 72 at 100 µM | 24% at 100 µM | 0.044 at 100 µM |
| 131 | 0.14 at 100 µM | 55 at 100 µM | 21% at 100 µM | 0.048 at 100 µM |
| 132 | 0.21 at 100 µM | 42% at 100 µM | 27% at 100 µM | 0.065 at 100 µM |
| 133 | 0.09 at 100 µM | 9 at 100 µM | 22% at 100 µM | 0.033 at 100 µM |
| 134 | 0.051 | 100 | 34 | 0.033 |
| 135 | 6.4 | 16 at 100 µM | 6% at 100 µM | 1.6 |
| 136 | 10.7 | >30 at 100 µM | 15% at 100 µM | 2.53 |
| 137 | 30 | 4% at 100 µM | 4% at 100 µM | 9.1 |
| 138 | 8% | 39% at 100 µM | 28% at 100 µM | 0.7 |
| 139 | 4.71 | 35.81 at 100 µM | 41% at 100 µM | 0.73 |
| 140 | 13.33 | 47.36 at 100 µM | 24% at 100 µM | 1.17 |
| 141 | 2% | 11% at 100 µM | 13% at 100 µM | 2% |
| 142 | 0.2 | 4.6 at 100 µM | 17 at 100 µM | 0.125 |
| 143 | 43.21 | 54.45 at 100 µM  12 | 30% at 100 µM | 2.63 |
| 144 | 6.4 | 16 at 100 µM | 6% at 100 µM | 1.6 |
| 145 | 26.8 | >30 | 3% | 34% |
| 146 | 30 | >30 | 5% | 21.6 |
| 147 | 5% | >30 | >30 | >30 |
| 148 | 7.03 | 4% @ 100 uM | 8% @ 100 uM | 33% |
| 149 | 1.9 | 17% | 2% | 0.64 |
| 150 | 0.36 | 25 | 4% | 0.28 |
| 151 | 0.23 | 29% | 17% | 0.38 |
| 152 | 28% | >30 | >30 | 15% |
| 153 | 12% | >30 | 8% | 8% |
| 154 | 7% | 2% | 6% | 7% |
| 155 | 1% | 2% | 11% | 4% |
| 156 | 27% | 5% | 7% | 21% |
| 157 | 0.7 | 35 | 64 | 0.09 |
| 158 | 10% | 6% | >30 | >30 |

TABLE 8-continued

Inhibitory Activity of Pyrazinones toward TF-VIIA, Thrombin II, Factor Xa, and Trypsin II.

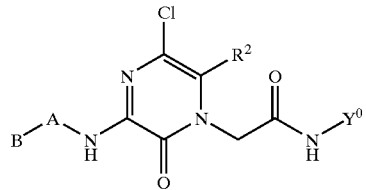

General Structure

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
| --- | --- | --- | --- | --- |
| 159 | 5% | 2% | 9% | 13% |
| 160 | 18 | 9% | 7% | 27.6 |
| 161 | 88.4 | 7% | 7% | 90 |
| 162 | 35% | 2% | 2% | 36% |
| 163 | 40 | 4% | 4% | 59 |
| 164 | 24% | 5% | 2% | 15% |
| 165 | 63 | 5% | 4% | 83 |
| 166 | 63 | 5% | 2% | 81 |
| 1471-1 | 8.17 | 2.57 | 10% | 0.79 |
| 1471-2 | 3.62 | 86% @ .04 | 10% | 0 |
| 1471-3 | 13.59 | 6.31 | 0 | 1.29 |
| 1471-4 | 29.4 | 18.3 | 0 | 3.1 |
| 1471-5 | 8.69 | 0.09 | 12% | 1.79 |
| 1471-6 | 2.85 | 63% @ .04 | 14% | 0.68 |
| 1471-7 | 4.28 | 0.06 | 4% | 0.87 |
| 1471-8 | 3.86 | 70% @ .04 | 27% | 0.65 |
| 1471-9 | 0.77 | 7.63 | 29% | 0.24 |
| 1471-10 | 0.6 | 69% @ .04 | 45% | 0.18 |
| 1471-11 | 1.69 | 12.03 | 9% | 0.93 |
| 1471-12 | 7.97 | 37% @ 30 | 9% | 0.93 |
| 1471-13 | 1.47 | 0.33 | 0% | 0.53 |
| 1471-14 | 0.18 | 62% @ .04 | 23 | 0.05 |
| 1471-15 | 0.63 | 0.16 | 10% | 0.24 |
| 1471-16 | 0.82 | 0.1 | 23% | 0.28 |
| 1471-17 | 11.01 | 3.76 | 16 | 0.24 |
| 1471-18 | 11.21 | 0.15 | 26% | 0.8 |
| 1471-19 | 33% | 16.86 | 26% | 1.6 |
| 1471-20 | 42% | 9.46 | 34% | 0.57 |
| 1471-21 | 8.18 | 0.08 | 30 | 0.24 |
| 1471-22 | 14.56 | 0.32 | 28% | 0.5 |
| 1471-23 | 8.88 | 0.2 | 36% | 0.28 |
| 1471-24 | 10.05 | 0.05 | 23 | 0.27 |
| 1471-25 | 2.45 | 24.47 | 31% | 0.36 |
| 1471-27 | 4.19 | 40% | 16% | 0.59 |
| 1471-28 | 7.22 | 26.99 | 8% | 0.39 |
| 1471-29 | 2.18 | 0.67 | 21% | 0.47 |
| 1471-30 | 0.83 | 0.13 | 41% | 0.08 |
| 1471-31 | 1.98 | 0.72 | 17% | 0.47 |
| 1471-32 | 1.19 | 0.17 | 25% | 0.23 |
| 1471-33 | 31% | 34% | 22% | 0.36 |
| 1471-34 | 17.47 | 0.74 | 24% | 0.25 |
| 1471-35 | 37% | 40% | 22% | 0.27 |
| 1471-36 | 11% | 15% | 6% | 0.74 |
| 1471-37 | 39% | 6.02 | 7% | 0.43 |
| 1471-38 | 24.38 | 3.92 | 18% | 0.34 |
| 1471-39 | 23.45 | 4.06 | 11% | 0.29 |
| 1471-40 | 40% | 4.03 | 11% | 0.47 |
| 1471-41 | 18.33 | 25.8 | 34% | 0.33 |
| 1471-42 | 10.45 | 0.55 | 15% | 0.45 |
| 1471-43 | 25.26 | 34% | 18% | 0.44 |
| 1471-44 | 34% | 25% | 13% | 0.53 |
| 1471-45 | 13.22 | 1.19 | 24% | 0.27 |
| 1471-46 | 13.02 | 1.76 | 21% | 0.37 |
| 1471-47 | 12.59 | 2.24 | 22% | 0.41 |
| 1471-48 | 15.7 | 0.92 | 17% | 0.42 |
| 1471-57 | 4.73 | 0.9 | 11% | 0.67 |
| 1471-58 | 12.44 | 76% @ .04 | 0% | 4.03 |
| 1471-59 | 7.52 | 1.95 | 0% | 1.03 |

TABLE 8-continued

Inhibitory Activity of Pyrazinones toward TF-VIIA, Thrombin II, Factor Xa, and Trypsin II.

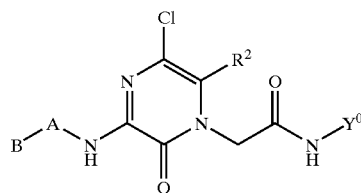

General Structure

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
| --- | --- | --- | --- | --- |
| 1471-60 | 13.01 | 2.97 | 0% | 1.52 |
| 1471-61 | 5 | 0.04 | 0% | 1.2 |
| 1471-62 | 4% | 24% | 0% | >30 |
| 1471-63 | 3.45 | 56% @ .04 | 2% | 0.84 |
| 1471-64 | 3.02 | 78% @ .04 | 2% | 0.61 |
| 1471-67 | 12% | 27% | 16% | 0.82 |
| 1471-70 | 10% | 33% | 12% | 1.01 |
| 1471-71 | 6% | 24% | 0% | 2.58 |
| 1471-72 | 15% | 12.2 | 22% | 0.72 |
| 1507-01 | 6.3 | 18.9 | 16% | 0.9 |
| 1507-02 | 9.4 | 36% | 9% | 1.1 |
| 1507-03 | 3.6 | 21 | 21% | 0.8 |
| 1507-04 | 29.5 | 9.5% | >30 | 9% @ 1 |
| 1507-05 | 4.7 | 22 | 10% | |
| 1507-06 | 20 | 0.5 | >30 | 8% @ 1 |
| 1507-07 | 25% | 27 | >30 | 7% @ 1 |
| 1507-08 | 7% | 10% | 1% | |
| 1507-09 | 22.6 | 0.97 | 13% | 0.7 |
| 1507-10 | 24% | 39.5% | >30 | 7% @ 1 |
| 1507-11 | 3 | <0.04 | >30 | 27% @ 1 |
| 1507-12 | 6.7 | 0.6 | >30 | 12% @ 1 |
| 1507-13 | 26.7 | 6% | >30 | 8% @ 1 |
| 1507-15 | 12 | 25% | >30 | 11% @ 1 |
| 1507-16 | 5.8 | 21.3 | 18% | 1 |
| 1507-17 | 27.4 | 0.9 | 16% | 2.8 |
| 1507-18 | 10.6 | 10.6 | >30 | 6% @ 1 |
| 1507-19 | 12.9 | 45% | 4% | |
| 1507-20 | 20.9 | 10.5% | >30 | 11% @ 1 |
| 1507-21 | 0.4 | 4.6 | 23% | 0.36 |
| 1507-22 | 45% | 1.5% | >30 | 8% @ 1 |
| 1507-23 | 28.9 | 11% | >30 | 11% @ 1 |
| 1507-24 | 0% | 7.5% | 15% | 25% @ 30 |
| 1507-25 | 1.6 | 22.4 | >30 | 60% @ 1 |
| 1507-26 | 20.5 | 11.5% | >30 | 11% @ 1 |
| 1507-28 | 38% | 1.5 | >30 | 1% @ 1 |
| 1507-29 | 5.8 | 27% | 4% | |
| 1507-30 | 13.4 | 18.5 | >30 | 0% @ 1 |
| 1507-31 | 3.7 | 21.5% | >30 | 2% @ 1 |
| 1507-32 | 21.3 | 16.5% | >30 | 0% @ 1 |
| 1507-33 | 28.4 | 8.5% | >30 | 2% @ 1 |
| 1507-34 | 8.5 | 20% | >30 | 0% @ 1 |
| 1507-35 | 19.9 | 15.9 | 28% | 0.49 |
| 1507-36 | 13.8 | 18% | 0% | |
| 1507-38 | 16 | 34.5% | >30 | 0% @ 1 |
| 1507-40 | 5.7 | 30 | 11% | |
| 1507-41 | 48% | 10.5% | 17% | 13.9 |
| 1507-42 | 11.6 | 23.5% | >30 | 0% @ 1 |
| 1507-43 | 4.1 | 7.1 | 21% | 0.97 |
| 1507-44 | 6 | 0.5 | 9% | |
| 1507-45 | 7.3 | 1 | >30 | 0% @ 1 |
| 1507-46 | 4.3 | 36% | 8% | |
| 1507-47 | 17.6 | 37% | 19% | 1.6 |
| 1507-48 | 18.3 | 14% | >30 | 11% @ 1 |
| 1512-01 | 18 | 18% | 4% | |
| 1512-02 | 19.2 | 19% | 3% | |
| 1512-04 | 10.8 | 17% | 8% | |
| 1512-05 | 16.7 | 1.7 | 10% | |
| 1512-06 | 12.6 | 23.6 | 4% | |

TABLE 8-continued
Inhibitory Activity of Pyrazinones toward TF-VIIA, Thrombin II, Factor Xa, and Trypsin II.
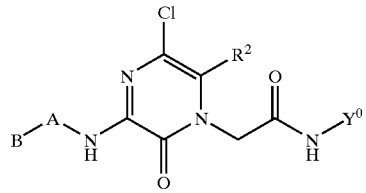
General Structure
| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
| --- | --- | --- | --- | --- |
| 1512-07 | 3.6 | 30 | 4% | |
| 1512-11 | 30 | 22% | 5% | |
| 1512-12 | 11.3 | 10.5 | 5% | |
| 1512-14 | 3.2 | 27.9 | 7% | |
| 1512-15 | 20.9 | 23% | 6% | |
| 1512-16 | 6.5 | 34% | 10% | |
| 1512-17 | 39% | 6% | 4% | |
| 1512-19 | 14.3 | 17% | 3% | |
| 1512-20 | 11.2 | 9% | 8% | |
| 1512-23 | 14.6 | 34% | 6% | |
| 1512-26 | 26.9 | 7% | 5% | |
| 1512-27 | 16.5 | 13% | 3% | |
| 1512-29 | 47% | 8% | 4% | |
| 1512-31 | 43% | 9% | 14% | |
| 1512-32 | 21.9 | 10% | 5% | |
| 1512-35 | 22.5 | 23% | 4% | |
| 1512-36 | 3.8 | 48% | 9% | |
| 1512-39 | 6 | 47% | 4% | |
| 1512-40 | 40% | 9% | 3% | |
| 1512-41 | 30 | 4.4 | 4% | |
| 1512-42 | 25 | 15% | 1% | |
| 1512-43 | 11 | 27% | 9% | |
| 1512-44 | 43% | 20% | 6% | |
| 1512-45 | 27% | 16% | 11% | |
| 1512-46 | 11.7 | 27.2 | 10% | |
| 1512-47 | 3.5 | 0.3 | 13% | |
| 1515-01 | 7 | 25% | >30 | 2.3 |
| 1515-02 | 3.8 | 26% | >30 | 1.5 |
| 1515-03 | 1.9 | 40% | >30 | 2.9 |
| 1515-04 | 5.2 | 43% | >30 | 2.8 |
| 1515-05 | 4 | 9.8 | >30 | 0.9 |
| 1515-06 | 1.7 | 6.2 | >30 | 1.1 |
| 1515-07 | 14.2 | 3.8 | >30 | 1.2 |
| 1515-08 | 11% | 9% | >30 | 2 |
| 1515-09 | 4.1 | 44% | >30 | 1.1 |
| 1515-10 | 5.7 | 38% | >30 | 1.1 |
| 1515-11 | 4.3 | 44% | >30 | 1.9 |
| 1515-12 | 6.3 | 9% | >30 | 8.2 |
| 1515-13 | 1.4 | 37% | >30 | 1.3 |
| 1515-14 | 2.9 | 7% | >30 | 4 |
| 1515-15 | 2.6 | 1% | >30 | 11.7 |
| 1515-16 | 8.8 | 3% | >30 | 17.3 |
| 1515-17 | 4.4 | 43% | >30 | 3.2 |
| 1515-18 | 0.6 | 4.4 | >30 | 1.1 |
| 1515-19 | 24.2 | 9.4 | >30 | 8.4 |
| 1515-20 | 32% | 36% | >30 | 1.2 |
| 1515-22 | 4.2 | 25% | >30 | 2.7 |
| 1515-23 | 6.2 | 18% | >30 | 8.5 |
| 1515-24 | 1.6 | 22% | >30 | 6.7 |
| 1515-25 | 2.9 | 3.5 | >30 | 1.4 |
| 1515-26 | 1.6 | 3.3 | >30 | 1.3 |
| 1515-27 | 1.1 | 2 | >30 | 2 |
| 1515-28 | 3 | 2.1 | >30 | 2.4 |
| 1515-29 | 5.2 | 1 | >30 | 2.2 |
| 1515-30 | 1.2 | 0.4 | >30 | 1.2 |
| 1515-31 | 8.1 | 0.1 | >30 | 1.2 |
| 1515-32 | 25% | 6.3 | >30 | 1.4 |
| 1515-33 | 2.3 | 1.1 | >30 | 1 |

TABLE 8-continued
Inhibitory Activity of Pyrazinones toward TF-VIIA, Thrombin II, Factor Xa, and Trypsin II.
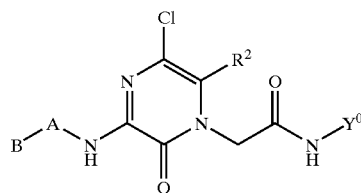
General Structure
| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
|---|---|---|---|---|
| 1515-34 | 4.4 | 2.4 | >30 | 1.3 |
| 1515-35 | 1.8 | 1.2 | >30 | 1.1 |
| 1515-36 | 2.7 | 8.6 | >30 | 5.4 |
| 1515-37 | 3.6 | 4 | >30 | 1.6 |
| 1515-38 | 1.8 | 2.5 | >30 | 1.4 |
| 1515-39 | 1.6 | 1.7 | >30 | 2.3 |
| 1515-40 | 4.4 | 1.7 | >30 | 2.4 |
| 1515-41 | 2.6 | 0.4 | >30 | 1 |
| 1515-42 | 1.8 | 0.5 | >30 | 1.4 |
| 1515-43 | 6.8 | 0.1 | >30 | 1.1 |
| 1515-44 | 30% | 7.7 | >30 | 1.4 |
| 1515-45 | 2.9 | 1 | >30 | 1.2 |
| 1515-46 | 4.8 | 2 | >30 | 1.3 |
| 1515-47 | 3.1 | 1.6 | >30 | 1.8 |
| 1515-48 | 4.1 | 6.2 | >30 | 4.1 |
| 1517-01 | 1.2 | 1.8 | 0 | 0.38 |
| 1517-03 | 9 | 36% | 0 | 2 |
| 1517-04 | 5.7 | 14.5 | 0 | 4.5 |
| 1517-05 | 4.6 | 29.8 | 0 | 1.2 |
| 1517-06 | 2.5 | 11.9 | 0 | 1.6 |
| 1517-07 | 0.4 | 1.1 | 0 | 0.32 |
| 1517-08 | 43% | 30% | 0 | 3.8 |
| 1517-09 | 2.6 | 30% | 0 | 1.5 |
| 1517-10 | 2 | 38% | 0 | 2.1 |
| 1517-11 | 3 | 22% | 0 | 1.9 |
| 1517-12 | 0.8 | 18.1 | 0 | 2.1 |
| 1517-13 | 0.6 | 0.1 | 0 | 0.28 |
| 1517-14 | 30% | 20% | 0 | 8.4 |
| 1517-15 | 3.1 | 5.3 | 0 | 1.5 |
| 1517-16 | 3.4 | 26.1 | 0 | 5.1 |
| 1517-17 | 1.8 | 4.1 | 0 | 0.85 |
| 1517-18 | 1.3 | 1 | 0 | 0.98 |
| 1517-19 | 0.9 | 0.1 | 0 | 0.4 |
| 1517-20 | 22% | 25% | 0 | 7.3 |
| 1517-23 | 2.3 | 4.3 | 0 | 1.4 |
| 1517-24 | 1.8 | 1 | 0 | 0.84 |
| 1517-25 | 1.4 | 16.5 | 0 | 0.72 |
| 1517-26 | 1.8 | 2.1 | 0 | 0.32 |
| 1517-29 | 0.9 | 1.2 | 0 | 0.3 |
| 1517-31 | 9.1 | 19.9 | 0 | 0.69 |
| 1517-33 | 0.4 | 5.2 | 0 | 0.21 |
| 1517-35 | 33% | 9% | 0 | 23.6 |
| 1517-36 | 3 | 28.1 | 0 | 0.61 |
| 1517-37 | 0.4 | 3.7 | 0 | 0.28 |
| 1517-38 | 0.7 | 8.7 | 0 | 0.33 |
| 1517-39 | 0.7 | 20.4 | 0 | 0.43 |
| 1517-40 | 1.2 | 6.4 | 0 | 0.37 |
| 1517-41 | 2.2 | 16.6 | 0 | 0.59 |
| 1517-43 | 25% | 4% | 0 | 43% |
| 1517-44 | 0.2 | 4 | 0 | 0.22 |
| 1517-46 | 0.4 | 11.3 | 0 | 0.36 |
| 1517-47 | 9.8 | 5.2 | 0 | 0.65 |
| 1517-48 | 1.2 | 2.4 | 0 | 0.29 |
| 1522-02 | 0.5 | 20 | >30 | 0.2 |
| 1522-05 | 0.6 | 10 | >30 | 0.2 |
| 1522-06 | 5.5 | 20 | >30 | 0.3 |
| 1522-07 | 0.47 | 1 | >30 | 0.15 |
| 1522-08 | 0.27 | 1 | >30 | 0.1 |

TABLE 8-continued
Inhibitory Activity of Pyrazinones toward TF-VIIA, Thrombin II, Factor Xa, and Trypsin II.
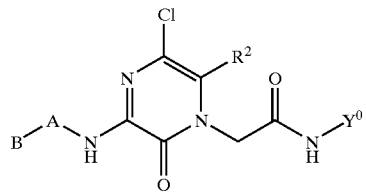
General Structure
| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
| --- | --- | --- | --- | --- |
| 1522-09 | 0.2 | 3 | >30 | 0.2 |
| 1522-11 | 0.43 | 1 | >30 | 0.2 |
| 1522-12 | 0.81 | 8 | >30 | 0.3 |
| 1522-13 | 0.75 | 8 | >30 | 0.2 |
| 1522-14 | 0.84 | 8 | >30 | 0.2 |
| 1522-15 | 0.54 | 4 | >30 | 0.2 |
| 1522-17 | 0.62 | 1 | >30 | 0.35 |
| 1522-18 | 1.7 | 20 | >30 | 0.2 |
| 1522-19 | 13 | >30 | >30 | 0.3 |
| 1522-20 | 5 | >30 | >30 | 0.2 |
| 1522-21 | 0.72 | 3 | >30 | 0.2 |
| 1522-23 | 2.2 | 20 | >30 | 0.3 |
| 1522-27 | 6.3 | 20 | >30 | 0.35 |
| 1522-28 | >30 | >30 | >30 | 2 |
| 1522-31 | 6.4 | 8 | >30 | 0.35 |
| 1522-33 | 0.88 | 10 | >30 | 0.2 |
| 1522-34 | 0.5 | 8 | >30 | 0.2 |
| 1522-35 | 4 | 10 | >30 | 0.35 |
| 1522-36 | 1 | 10 | >30 | 0.3 |
| 1522-37 | 2 | 0.08 | >30 | 0.3 |
| 1522-38 | 1 | 0.1 | >30 | 0.3 |
| 1522-40 | 0.5 | 0.8 | >30 | 0.2 |
| 1522-41 | 0.5 | 10 | >30 | 0.2 |
| 1522-42 | 1 | 2 | >30 | 0.15 |
| 1522-43 | 0.8 | 20 | >30 | 0.3 |
| 1522-44 | 0.8 | 10 | >30 | 0.2 |
| 1522-46 | 1 | 10 | >30 | 0.2 |
| 1522-47 | 3 | 15 | >30 | 2 |
| 1526-01 | 0.02 | 13.13 | >30 | 0.15 |
| 1526-03 | 0.06 | 17.3 | >30 | 0.15 |
| 1526-04 | 0.03 | 18.08 | >30 | 0.16 |
| 1526-05 | 0.1 | 15 | >30 | 0.19 |
| 1526-06 | 0.17 | 12.04 | >30 | 0.21 |
| 1526-07 | 0.08 | 20.91 | >30 | 0.19 |
| 1526-09 | 0.03 | 11.23 | >30 | 0.14 |
| 1526-11 | 0.05 | 3.21 | >30 | 0.15 |
| 1526-12 | 0.04 | 28.41 | >30 | 0.2 |
| 1526-13 | 0.06 | 22.42 | >30 | 0.2 |
| 1526-14 | 0.04 | 7.63 | >30 | 0.14 |
| 1526-15 | 0.06 | 6.88 | >30 | 0.15 |
| 1526-16 | 0.04 | 5.6 | >30 | 0.13 |
| 1526-17 | 0.08 | 2.21 | >30 | 0.17 |
| 1526-19 | 0.04 | 16.97 | >30 | 0.15 |
| 1526-21 | 0.05 | 20.03 | >30 | 0.18 |
| 1526-23 | 0.03 | 9.45 | >30 | 0.15 |
| 1526-24 | 0.04 | 11.06 | >30 | 0.17 |
| 1526-25 | 0.14 | 40% | >30 | 0.19 |
| 1526-26 | 0.06 | 14.27 | >30 | 0.16 |
| 1526-29 | 0.12 | 50% | >30 | 0.22 |
| 1526-30 | 0.08 | 21.42 | >30 | 0.2 |
| 1526-33 | 0.26 | 29% | >30 | 0.24 |
| 1526-40 | 0.1 | 17.85 | >30 | 0.22 |
| 1526-41 | 0.07 | 24.04 | >30 | 0.16 |
| 1543-03 | 0.64 | 26% | 34% | 0.06 |
| 1543-05 | 0.06 | 27% | 14% | 0.07 |
| 1543-07 | 0.21 | 24.56 | 19% | 0.09 |
| 1543-09 | 0.69 | 14% | 12% | 0.18 |
| 1543-11 | 0.07 | 16.56 | 24% | 0.04 |

TABLE 8-continued

Inhibitory Activity of Pyrazinones toward TF-VIIA, Thrombin II, Factor Xa, and Trypsin II.

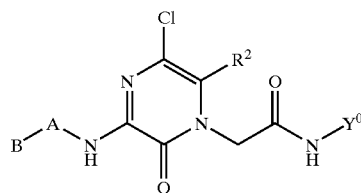

General Structure

| Ex. No. | IC50 or % Inhibition TF-VIIa (30 υM) | IC50 or % Inhibition Thrombin II (30 υM) | IC50 or % Inhibition Factor Xa (30 υM) | IC50 or % Inhibition Trpysin II (30 υM) |
|---|---|---|---|---|
| 1543-13 | 0.09 | 41% | 12% | 0.06 |
| 1543-15 | 0.95 | 45% | 41% | 0.14 |
| 1543-19 | 0.22 | 37% | 11% | 0.08 |
| 1543-21 | 0.29 | 17.12 | 27% | 0.06 |
| 1543-25 | 0.28 | 8.12 | 26% | 0.05 |
| 1543-27 | 0.38 | 24.6 | 27% | 0.06 |
| 1543-31 | 0.04 | 24.26 | 8% | 0.06 |
| 1543-33 | 0.03 | 19.34 | 14% | 0.05 |
| 1543-34 | 0.08 | 17.32 | 20% | 0.06 |
| 1543-35 | 0.07 | 23.61 | 8% | 0.07 |
| 1543-36 | 0.08 | 12.57 | 15% | 0.05 |
| 1543-37 | 1.23 | 16% | 16% | 0.12 |
| 1543-38 | 0.09 | 18.26 | 14% | 0.06 |
| 1543-39 | 0.04 | 12.77 | 14% | 0.05 |
| 1543-40 | 0.04 | 11.45 | 10% | 0.04 |
| 1543-41 | 3% | 0% | 9% | 6% |
| 1543-45 | 1% | 0% | 5% | 8% |
| 1543-46 | 22% | 0% | 11% | 18% |

TABLE 9

Inhibitory Activity of Pyrazinones toward Factor Xa, TF-VIIA, Thrombin II, and Trypsin II.

| Example Number | % Inhibition TF-VIIa (100 υM) | % Inhibition Thrombin II (100 υM) | % Inhibition Factor Xa (100 υM) | % Inhibition Trpysin II (100 υM) |
|---|---|---|---|---|
| E-0001 | 0 | 0 | 1 | 0 |
| E-0002 | 0 | 0 | 0 | 0 |
| E-0003 | 0 | 10 | 0 | 0 |
| E-0004 | 0 | 6 | 0 | 0 |
| E-0005 | 0 | 0 | 0 | 0 |
| E-0006 | 2 | 0 | 0 | 1 |
| E-0007 | 0 | 0 | 0 | 0 |
| E-0008 | 0 | −0.2 | 0 | 0 |
| E-0009 | 0 | 8 | 1 | 1 |
| E-0010 | 0 | 5 | 0 | 0 |
| E-0011 | 0 | 0 | 0 | 0 |
| E-0012 | 0 | 0 | 0 | 0 |
| E-0013 | 0 | 2 | 0 | 1 |
| E-0014 | 0 | 6 | 0 | 0 |
| E-0015 | 0 | 3 | 0 | 3 |
| E-0016 | 0 | 10 | 0 | 4 |
| E-0017 | 0 | 10 | 0 | 1 |
| E-0018 | 1 | 10 | 0 | 4 |
| E-0019 | 0 | 9 | 0 | 2 |
| E-0020 | 0 | 13 | 1 | 4 |
| E-0021 | 0 | 9 | 1 | 5 |
| E-0022 | 0 | 12 | 0 | 2 |
| E-0023 | 0 | 5 | 0 | 1 |
| E-0024 | 0 | 0 | 0 | 1 |
| E-0025 | 0 | 13 | 0 | 3 |
| E-0026 | 0 | 13 | 0 | 3 |
| E-0027 | 0 | 10 | 0 | 2 |
| E-0028 | 0 | 8 | 0 | 3 |
| E-0029 | 0 | 8 | 0 | 2 |
| E-0030 | 0 | 8 | 0 | 4 |
| E-0031 | 0 | 4 | 0 | 1 |
| E-0032 | 0 | 6 | 0 | 3 |
| E-0033 | 0 | 6 | 0 | 5 |
| E-0034 | 0 | 7 | 6 | 3 |
| E-0035 | 4 | 12 | 0 | 2 |
| E-0036 | 0 | 1 | 0 | 0 |
| E-0037 | 0 | 5 | 0 | 2 |
| E-0038 | 0 | 9 | 0 | 3 |
| E-0039 | 0 | 9 | 1 | 2 |
| E-0040 | 0 | 7 | 0 | 4 |
| E-0041 | 0 | 8 | 0 | 2 |
| E-0042 | 0 | 8 | 0 | 5 |
| E-0043 | 0 | 12 | 0 | 3 |
| E-0044 | 0 | 9 | 0 | 2 |
| E-0045 | 0 | 7 | 0 | 4 |
| E-0046 | 0 | 7 | 0 | 4 |
| E-0047 | 0 | 9 | 0 | 2 |
| E-0048 | 0 | 1 | 0 | 0 |
| E-0049 | 2 | 0 | 0 | 0 |
| E-0050 | 0 | 0 | 0 | 0 |

TABLE 9-continued

Inhibitory Activity of Pyrazinones toward Factor Xa, TF-VIIA, Thrombin II, and Trypsin II.

| Example Number | % Inhibition TF-VIIa (100 υM) | % Inhibition Thrombin II (100 υM) | % Inhibition Factor Xa (100 υM) | % Inhibition Trpysin II (100 υM) |
|---|---|---|---|---|
| E-0051 | 0 | 0 | 0 | 0 |
| E-0052 | 0 | 0 | 0 | 0 |
| E-0053 | 0 | 0 | 0 | 0 |
| E-0054 | 0 | 0 | 0 | 0 |
| E-0055 | 0 | 0 | 0 | 0 |
| E-0056 | 0 | 0 | 0 | 0 |
| E-0057 | 0 | 0 | 6 | 0 |
| E-0058 | 0 | 0 | 0 | 0 |
| E-0059 | 0 | 0 | 0 | 0 |
| E-0060 | 0 | 0 | 0 | 0 |
| E-0061 | 0 | 0 | 0 | 0 |
| E-0062 | 0 | 0 | 0 | 0 |
| E-0063 | 0 | 0 | 0 | 0 |
| E-0064 | 0 | 0 | 0 | 0 |
| E-0065 | 0 | 0 | 0 | 0 |
| E-0066 | 0 | −0.2 | 0 | 0 |
| E-0067 | 0 | 1 | 0 | 0 |
| E-0068 | 0 | 3 | 0 | 0 |
| E-0069 | 0 | 0 | 0 | 0 |
| E-0070 | 0 | 0 | 0 | 0 |
| E-0071 | 0 | 0 | 0 | 0 |
| E-0072 | 0 | 0 | 0 | 0 |
| E-0073 | 0 | 0 | 2 | 6 |
| E-0074 | 0 | 0 | 0 | 8 |
| E-0075 | 0 | 0 | 0 | 7 |
| E-0076 | 0 | 0 | 1 | 10 |
| E-0077 | 0 | 0 | 3 | 7 |
| E-0078 | 0 | 3 | 1 | 10 |
| E-0079 | 0 | 0 | 4 | 11 |
| E-0080 | 1 | 0 | 4 | 5 |
| E-0081 | 0 | 24 | 5 | 8 |
| E-0082 | 4 | 0 | 4 | 3 |
| E-0083 | 2 | 53 | 3 | 6 |
| E-0084 | 0 | 0 | 0 | 8 |
| E-0085 | 0 | 5 | 0 | 9 |
| E-0086 | 0 | 0 | 4 | 11 |
| E-0087 | 0 | 0 | 0 | 10 |
| E-0088 | 0 | 0 | 3 | 9 |
| E-0089 | 3 | 0 | 4 | 8 |
| E-0090 | 0 | 0 | 2 | 11 |
| E-0091 | 1 | 0 | 4 | 8 |
| E-0092 | 1 | 0 | 3 | 9 |
| E-0093 | 0 | 14 | 0 | 10 |
| E-0094 | 2 | 0 | 2 | 7 |
| E-0095 | 2 | 0 | 4 | 9 |
| E-0096 | 0 | 5 | 0 | 10 |
| E-0097 | 0 | 0 | 3 | 11 |
| E-0098 | 0 | 0 | 2 | 8 |
| E-0099 | 0 | 0 | 1 | 10 |
| E-0100 | 7 | 0 | 6 | 12 |
| E-0101 | 11 | 2 | 10 | 11 |
| E-0102 | 0.4 | 0 | 3 | 13 |
| E-0103 | 2 | 0 | 3 | 11 |
| E-0104 | 3 | 0 | 5 | 9 |
| E-0105 | 0 | 0 | 3 | 12 |
| E-0106 | 5 | 0 | 3 | 9 |
| E-0107 | 4 | 0 | 6 | 12 |
| E-0108 | 0 | 0 | 4 | 12 |
| E-0109 | 2 | 0 | 3 | 12 |
| E-0110 | 0 | 0 | 3 | 14 |
| E-0111 | 4 | 0 | 1 | 14 |
| E-0112 | 11 | 0 | 1 | 13 |
| E-0113 | 14 | 0 | 3 | 11 |
| E-0114 | 10 | 0 | 3 | 14 |
| E-0115 | 15 | 0 | 3 | 11 |
| E-0116 | 13 | 0 | 4 | 10 |
| E-0117 | 9 | 0 | 1 | 9 |
| E-0118 | 12 | 0 | 3 | 9 |
| E-0119 | 13 | 0 | 5 | 10 |
| E-0120 | 8 | 0 | 1 | 9 |
| E-0121 | 0 | 8 | 0.1 | 0 |
| E-0122 | 0 | 8 | 0.1 | 0 |
| E-0123 | 0 | 6 | 0.1 | 1 |
| E-0124 | 0 | 6 | 0.1 | 0 |
| E-0125 | 0 | 4 | 0.1 | 0 |
| E-0126 | 0 | 4 | 0.1 | 0 |
| E-0127 | 0 | 5 | 0.1 | 0 |
| E-0128 | 0 | 7 | 0.1 | 0 |
| E-0129 | 0 | 5 | 0.1 | 0 |
| E-0130 | 0 | 2 | 0.1 | 0 |
| E-0131 | 0 | 0 | 0.1 | 1 |
| E-0132 | 0 | 0 | 0.1 | 0 |
| E-0133 | 0 | 5 | 0.1 | 0 |
| E-0134 | 0 | 5 | 0.1 | 1 |
| E-0135 | 0 | 3 | 0.1 | 2 |
| E-0136 | 0 | 3 | 0.1 | 1 |
| E-0137 | 2 | 3 | 0.1 | 0 |
| E-0138 | 1 | 4 | 0.1 | 3 |
| E-0139 | 0 | 4 | 0.1 | 3 |
| E-0140 | 0 | 4 | 0.1 | 2 |
| E-0141 | 0 | 4 | 0.1 | 2 |
| E-0142 | 1 | 5 | 0.1 | 3 |
| E-0143 | 1 | 2 | 0.1 | 1 |
| E-0144 | 0 | 0 | 0.1 | 1 |
| E-0145 | 0 | 5 | 0.1 | 0 |
| E-0146 | 0 | 8 | 0.1 | 0 |
| E-0147 | 0 | 3 | 0.1 | 1 |
| E-0148 | 0 | 5 | 0.1 | 3 |
| E-0149 | 0 | 4 | 0.1 | 0 |
| E-0150 | 0 | 6 | 0.1 | 2 |
| E-0151 | 0 | 6 | 0.1 | 3 |
| E-0152 | 0 | 6 | 0.1 | 4 |
| E-0153 | 0 | 3 | 0.1 | 1 |
| E-0154 | 0 | 5 | 0.1 | 3 |
| E-0155 | 2 | 6 | 0.1 | 4 |
| E-0156 | 0 | −0.4 | 0.1 | 1 |
| E-0157 | 0 | 5 | 0.1 | 0 |
| E-0158 | 0 | 3 | 0.1 | 6 |
| E-0159 | 0 | 4 | 0.1 | 1 |
| E-0160 | 0 | 6 | 0.1 | 2 |
| E-0161 | 0 | 6 | 0.1 | 1 |
| E-0162 | 0 | 7 | 0.1 | 4 |
| E-0163 | 0 | 5 | 0.1 | 0 |
| E-0164 | 0 | 5 | 0.1 | 0 |
| E-0165 | 0 | 7 | 0.1 | 0 |
| E-0166 | 0 | 6 | 0.1 | 1 |
| E-0167 | 0 | 4 | 0.1 | 1 |
| E-0168 | 7 | 5 | 0.1 | 0 |
| E-0169 | 0 | 2 | 0.1 | 1 |
| E-0170 | 0 | 7 | 0.1 | 0 |
| E-0171 | 0 | 9 | 0.1 | 2 |
| E-0172 | 0 | 6 | 0.1 | 0 |
| E-0173 | 0 | 5 | 0.1 | 1 |
| E-0174 | 0 | 5 | 0.1 | 1 |
| E-0175 | 0 | 6 | 0.1 | 2 |
| E-0176 | 0 | 7 | 0.1 | 0 |
| E-0177 | 0 | 6 | 0.1 | 0 |
| E-0178 | 0 | 3 | 0.1 | 2 |
| E-0179 | 0 | 10 | 0.1 | 0 |
| E-0180 | 0 | 3 | 0.1 | 0 |
| E-0181 | 0 | 5 | 0.1 | 3 |
| E-0182 | 0 | 5 | 0.1 | 0 |
| E-0183 | 0 | 5 | 0.1 | 2 |
| E-0184 | 0 | 2 | 0.1 | 0 |
| E-0185 | 0 | 3 | 0.1 | 2 |
| E-0186 | 0 | 5 | 0.1 | 0 |
| E-0187 | 0 | 8 | 0.1 | 1 |
| E-0188 | 0 | 2 | 0.1 | 8 |
| E-0189 | 0 | 6 | 0.1 | 1 |
| E-0190 | 0 | 4 | 0.1 | 3 |
| E-0191 | 0 | 6 | 0.1 | 0 |
| E-0192 | 0 | 0 | 0.1 | 0 |

TABLE 9-continued

Inhibitory Activity of Pyrazinones toward Factor Xa,
TF-VIIA, Thrombin II, and Trypsin II.

| Example Number | % Inhibition TF-VIIa (100 υM) | % Inhibition Thrombin II (100 υM) | % Inhibition Factor Xa (100 υM) | % Inhibition Trpysin II (100 υM) |
|---|---|---|---|---|
| E-0193 | 0 | 5 | 0.1 | 0 |
| E-0194 | 0 | 14 | 0.2 | 0 |
| E-0195 | 0 | 1 | 0.1 | 0 |
| E-0196 | 0 | 1 | 0.1 | 0 |
| E-0197 | 0 | 3 | 0.1 | 1 |
| E-0198 | 0 | 0 | 0.1 | 3 |
| E-0199 | 0 | 1 | 0.1 | 2 |
| E-0200 | 0 | 33 | 0.2 | 2 |
| E-0201 | 0 | 1 | 0.1 | 1 |
| E-0202 | 0 | 1 | 0.1 | 1 |
| E-0203 | 0 | 5 | 0.1 | 2 |
| E-0204 | 0 | 1 | 0.1 | 1 |
| E-0205 | 0 | 1 | 0.1 | 2 |
| E-0206 | 0 | 2 | 0.1 | 1 |
| E-0207 | 0 | 2 | 0.1 | 1 |
| E-0208 | 0 | 4 | 0.1 | 1 |
| E-0209 | 1 | 3 | 0.1 | 3 |
| E-0210 | 0 | 6 | 0.1 | 2 |

What is claimed is:

1. A compound of the Formula:

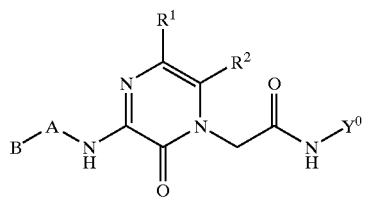

or a pharmaceutically acceptable salt thereof, wherein;

B is a C3–C7 cycloalkyl, wherein (a) each ring carbon is optionally substituted with $R^{33}$, (b) a ring carbon, other than the ring carbon at the point of attachment, is optionally substituted with oxo provided that no more than one ring carbon is substituted by oxo at the same time, (c) a ring carbon in a first alpha position relative to the ring carbon at the point of attachment is optionally substituted by $R^9$, (d) a ring carbon in a second alpha position relative to the ring carbon at the point of attachment is optionally substituted by $R^{13}$, (e) a ring carbon, if present, in a first beta position relative to the ring carbon at the point of attachment and in an alpha position relative to the ring atom optionally substituted by $R^9$, is optionally substituted by $R^{10}$, (f) a ring carbon, if present, in a second beta position relative to the ring carbon at the point of attachment and in an alpha position relative to the ring atom optionally substituted by $R^{13}$, is optionally substituted by $R^{12}$, (g) a ring carbon, if present, in a first gamma position relative to the ring carbon at the point of attachment and in an alpha position relative to the ring atom optionally substituted by $R^{10}$, is optionally substituted by $R^{11}$, and (h) a ring carbon, if present, in a second gamma position relative to the carbon at the point of attachment and in an alpha position relative to the ring atom optionally substituted by $R^{12}$, is optionally substituted by $R^{33}$;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

$R^{33}$ and $R^{34}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, and cyano;

A is a bond or $(CH(R^{15}))_{pa}$—$(W^7)_{rr}$ wherein rr is 0 or 1, pa is an integer selected from 0 through 3, and $W^7$ is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

$R^1$ is selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^0$—Q;

$Z^0$ is selected from the group consisting of a bond, $CH_2$, $CH_2CH_2$, $W^0$—$(CH(R^{42}))_p$ wherein p is 0 or 1 and $W^0$ is selected from the group consisting of O, S and $N(R^{41})$;

$R^{41}$ and $R^{42}$ are independently hydrido or alkyl;

Q is phenyl or a heteroaryl of 5 or 6 ring members, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$Y^0$ is phenyl or a heteroaryl of 5 or 6 ring members, having the formula

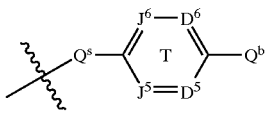

wherein $J^5$, $J^6$, $D^5$, $D^6$ and the ring carbon atoms to which they are attached define a phenyl or 5- or 6-membered heteroaryl ring, T, wherein one of $J^5$ and $J^6$ is absent when T is a 5-membered heteroaryl ring, $J^5$ is optionally substituted by $R^{17}$ when $J^5$ is a carbon atom, $J^6$ is optionally substituted by $R^{18}$ when $J^6$ is a carbon atom, $D^5$ is optionally substituted by $R^{16}$ when $D^5$ is a carbon atom and $D^6$ is optionally substituted by $R^{19}$ when $D^6$ is a carbon atom;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$Q^b$ is selected from the group consisting of $NR^{20}R^{21}$, hydrido, and $C(NR^{25})NR^{23}R^{24}$, with the proviso that no more than one of $R^{20}$ and $R^{21}$ is hydroxy and with the further proviso that no more than one of $R^{23}$ an $R^{24}$ is hydroxy;

$R^{20}$, $R^{21}$, $R^{23}$, $R^{24}$, and $R^{25}$ are independently selected from the group consisting of hydrido, alkyl, and hydroxy; and $Q^s$ is selected from the group consisting of a bond, $CH_2$, and $CH_2CH_2$.

2. The compound of claim 1 or a pharmaceutically acceptable salt thereof, wherein;

B is selected from the group consisting of cyclopropyl, cyclobutyl, cyclopentyl, cyclohexyl, bicyclo[3.1.0]hexan-6-yl, and cycloheptyl, wherein (a) each ring carbon is optionally substituted with $R^{33}$, (b) a ring carbon in a first alpha position relative to the ring carbon at the point of attachment is optionally substituted by $R^9$, (c) a ring carbon in a second alpha position relative to the ring carbon at the point of attachment is optionally substituted by $R^{13}$ (d) a ring carbon, if present, in a first beta position relative to the ring carbon at the point of attachment and in an alpha position relative to the ring atom optionally substituted by $R^9$, is optionally substitued by $R^{10}$, and (e) a ring carbon, if present, in a second beta position relative to the ring carbon at the point of attachment and in an alpha position relative to the ring atom optionally substituted by $R^{13}$, is optionally substituted by $R^{12}$;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N, N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl)amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, fluoro, chloro, bromo, cyano, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzloxy, 4-bromobenzylamino, 5-bromopyrid-2-ylmethylamino, 4-butoxyphenamino, 3-chlorobenzyl, 4-chiorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy;

$R^{33}$ is selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, and cyano;

A is selected from the group consisting of a bond, NH, $N(CH_3)$, $N(O_3)$, $CH_2$, $CH_3CH$, $CF_3CH$, NHC(O), $N(CH_3)C(O)$, C(O)NH, $C(O)N(CH_3)$, $CH_2CH_2$, $CH_2CH_2CH_2$, $CH_3CHCH_2$, and $CF_3CHCH_2$;

$R^1$ is selected from the group consisting of hydrido, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;

$R^2$ is $Z^0$—Q;

$Z^0$ is selected from the group consisting of a bond, $CH_2$, $CH_2CH_2$, O, S, NH, $N(CH_3)$, $OCH_2$, $SCH_2$, $N(H)CH_2$, and $N(CH_3)CH_2$;

Q is selected from the group consisting of phenyl and 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl heteroaryl rings, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$Y^0$ is selected from the group consisting of:

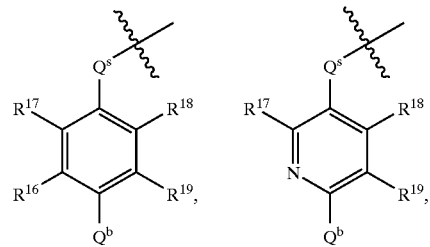

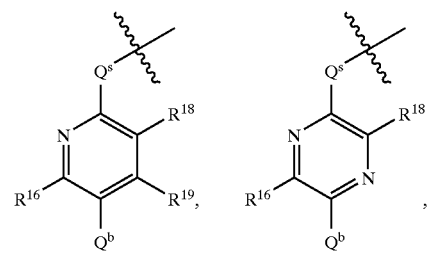

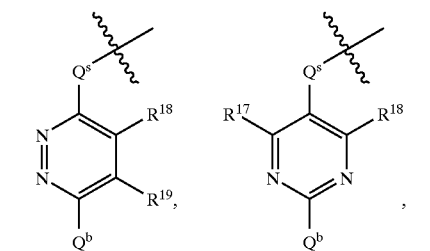

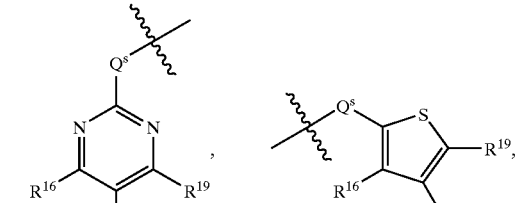

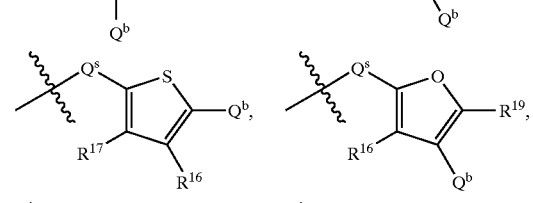

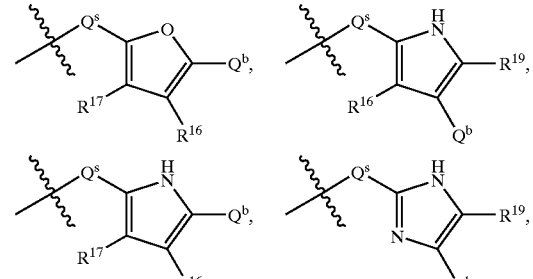

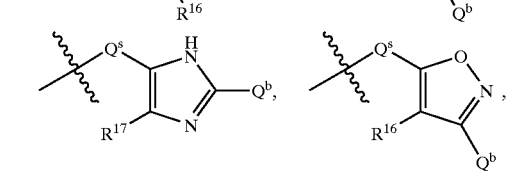

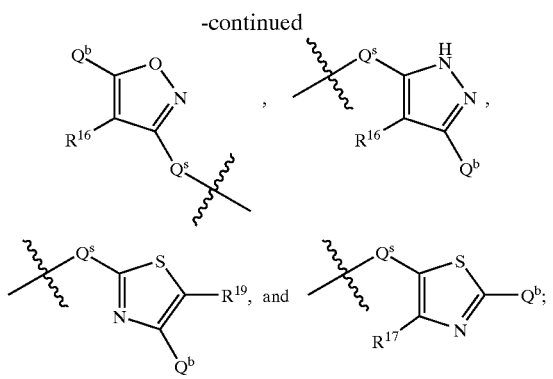

R[16], R[17], R[18], and R[19] are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano;

$Q^b$ is $C(NR^{25})NR^{23}R^{24}$ or hydrido, with the proviso that no more than one of R[23] and R[24] is hydroxy;

R[23], R[24], and R[25] are independently selected from the group consisting of hydrido, methyl, ethyl, and hydroxy; and $Q^s$ is selected from the group consisting of a bond, $CH_2$ and $CH_2CH_2$.

3. The compound of claim 2 or a pharmaceutically acceptable salt thereof, wherein;

B is selected from the group consisting of cyclopropyl, cyclobutyl cyclopentyl, cyclohexyl, cycloheptyl, 2-(2R)-bicyclo[2.2.1]-heptyl, and bicyclo[3.1.0]hexan-6-yl;

A is selected from the group consisting of a bond, $CH_2$, NHC(O), $CH_2CH_2$, and $CH_2CH_2$ $CH_2$;

R[1] is selected from the group consisting of hydrido, hydroxy, amino, amidino, hydroxyamino, aminomethyl, methylamino, cyano, methyl, trifluoromethyl, methoxy, hydroxymethyl, methoxyamino, methylthio, trifluoromethoxy, fluoro, and chloro;

R[2] is $Z^0$—Q;

$Z^0$ is selected from the group consisting of a bond, $CH_2$, O, S, NH, $N(CH_3)$, $OCH_2$, and $SCH_2$;

Q is selected from the group consisting of 3-amidocarbonyl-5-aminophenyl, 3-amino-5-(N-benzylamidocarbonyl)phenyl, 3-amino-5-benzylphenyl, 3-amino-5-(2-phenylethyl)phenyl, 3-amino-5-benzylaminophenyl, 3-amino-5-(2-phenylethylamino)phenyl, 3-amino-5-benzyloxyphenyl, 3-amino-5-(2-phenylethoxy)phenyl, 3-amino-5-(N-(2-chlorobenzyl)amidocarbonyl)phenyl, -amino-5-(N-(3-fluorobenzyl)amidocarbonyl)phenyl, 3-amino-5-(N-(2-trifluoromethylbenzyl)amidocarbonyl)phenyl, 3-amino-5-(N-(1-phenylethyl)amidocarbonyl)phenyl, 3-amino-5-(N-(1-methyl-1-phenylethyl)amidocarbonyl)phenyl, 3-amino-5-(N-benzylamidosulfonyl)phenyl, 3-amino-5-(N-(2-chlorobenzyl)amidosulfonyl)phenyl, 3-amino-5-(N-ethylamidocarbonyl)phenyl, -amino-5-(N-isopropylamidocarbonyl)phenyl, 3-amino-5-(N-propylamidocarbonyl)phenyl, 3-amino-5-(N-isobutylamidocarbonyl)phenyl, 3-amino-5-(N-(2-butyl)amidocarbonyl)phenyl, 3-amino-5-(N-cyclobutylamidocarbonyl)phenyl, 3-amino-5-(N-cyclopentylamidocarbonyl)phenyl, 3-amino-5-(N-cyclohexylamidocarbonyl)phenyl, 5-amino-2-fluorophenyl, 3-amino-5-hydroxymethylphenyl, 5-amino-3-methoxycarbonylphenyl, 3-amidinophenyl, 3-amino-2-methylphenyl, 5-amino-2-methylthiophenyl, 3-aminophenyl, 3-amino-5-(4-trifluoromethylbenzylamino)phenyl, 3-amino-5-(4-trifluoromethylbenzyloxy)phenyl, 3-carboxyphenyl, 3-carboxy-5-hydroxyphenyl, 3-amino-5-carboxyphenyl, 3-chlorophenyl, 2-chlorophenyl, 3-cyanophenyl, 3,5-diaminophenyl, 3-dimethylaminophenyl, 2-fluorophenyl, 3-fluorophenyl, 2-hydroxyphenyl, 3-hydroxyphenyl, 3-methanesulfonylaminophenyl, 2-methoxyphenyl, 3-methoxyphenyl, 3-methoxyaminophenyl, 3-methoxycarbonylphenyl, 2-methylaminophenyl, 3-methylaminophenyl, 2-methylphenyl, 3-methylphenyl, 4-methylphenyl, phenyl, 3-trifluoroacetamidophenyl, 3-trifluoromethylphenyl, 2-trifluoromethylphenyl, 5-amino-2-thienyl, 5-amino-3-thienyl, 3-bromo-2-thienyl, 3-pyridyl, 4-pyridyl, 2-thienyl, and 3-thienyl;

$Y^0$ is selected from the group consisting of;

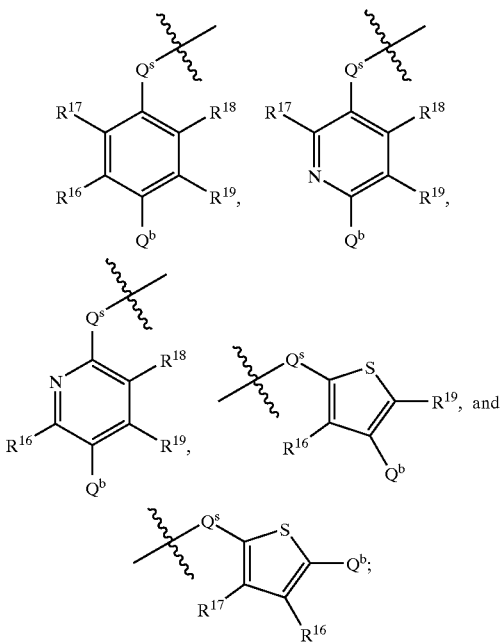

R[16] and R[19] are independently selected from the group consisting of hydrido, amidino, amino, aminomethyl, methoxy, methylamino, hydroxy, hydroxyethyl, fluoro, chloro, and cyano;

R[17] and R[18] are independently selected from the group consisting of hydrido, fluoro, chloro, hydroxy, hydroxymethyl, amino, carboxy, and cyano;

$Q^b$ is $C(NR^{25})NR^{23}R^{24}$ or hydrido;

$R^{23}$, $R^{24}$, and $R^{25}$ are independently hydrido or methyl; and $Q^s$ is $CH_2$.

4. The compound of claim 1, or a pharmaceutically acceptable salt thereof, wherein;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

$R^{33}$ and $R^{34}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, and cyano;

A is a bond or $(CH(R^{15}))_{pa}$—$(W^7)_{rr}$ wherein rr is 0 or 1, pa is an integer selected from 0 through 3, and $W^7$ is $N(R^7)$;

$R^7$ is hydrido or alkyl;

$R^{15}$ is selected from the group consisting of hydrido, halo, alkyl, and haloalkyl;

$R^2$ is $Z^0$—Q;

$Z^0$ is a bond;

$Q^b$ is selected from the group consisting of $NR^{20}R^{21}$, hydrido, and $C(NR^{25})NR^{23}R^{24}$;

$R^{20}$, $R^{21}$, $R^{23}$, $R^{24}$, and $R^{25}$ are independently hydrido or alkyl; and $Q^s$ is $CH_2$.

5. The compound of claim 4 or a pharmaceutically acceptable salt thereof, wherein;

B is selected from the group consisting of cyclopropyl, cyclobutyl, cyclopentyl, cyclohexyl, cycloheptyl, 2-(2R)-bicyclo[2.2.1]-heptyl, and bicyclo[3.1.0]hexan-6-yl, wherein (a) each ring carbon is optionally substituted with $R^{33}$, (b) a ring carbon in a first alpha position relative to the ring carbon at the point of attachment is optionally substituted by $R^9$, (c) a ring carbon in a second alpha position relative to the ring carbon at the point of attachment is optionally substituted by $R^{13}$, (d) a ring carbon, if present, in a firs beta position relative to the ring carbon at the point of attachment and in an alpha position relative to the ring atom optionally substituted by $R^9$, is optionally substituted by $R^{10}$, and (e) a ring carbon, if present, in second beta position relative to the ring carbon at the point of attachment and in an alpha position relative to the ring atom optionally substituted by $R^{13}$, is optionally substituted by $R^{12}$;

$R^9$, $R^{11}$, and $R^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrido, amidino, amidocarbonyl, N-methylamidocarbonyl, N-benzylamidocarbonyl, N-(2-chlorobenzyl)amidocarbonyl, N-(3-fluorobenzyl)amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, methoxyamino, amidosulfonyl, N-methylamidosulfonyl, N,N-dimethylamidosulfonyl, methanesulfonamido, methoxycarbonyl, fluoro, chloro, bromo, and cyano;

$R^{33}$ is selected from the group consisting of hydrido, amidino, guanidino, methyl, ethyl, methoxy, ethoxy, hydroxy, carboxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, and cyano;

A is selected from the group consisting of a bond, NH, $N(CH_3)$, $CH_2$, $CH_3CH$, $CH_2CH_2$, and $CH_2CH_2 CH_2$;

$R^1$ is selected from the group consisting of hydrido, hydroxy, hydroxymethyl, amino, aminomethyl, methylamino, cyano, methyl, trifluoromethyl, methoxy, methylthio, trifluoromethoxy, fluoro, and chloro;

$R^2$ is selected from the group consisting of phenyl and 2-thienyl, 2-furyl, 2-pyrrolyl, 2-imidazolyl, 2-thiazolyl, 3-isoxazolyl, 2-pyridyl, and 3-pyridyl heteroaryl rings, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

Y⁰ is selected from the group consisting of:

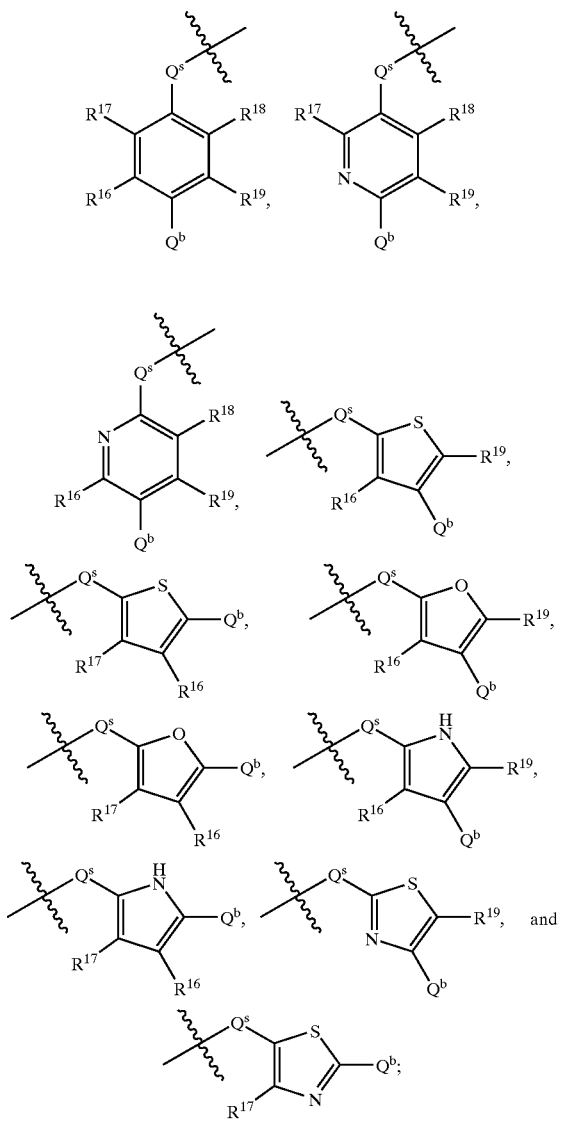

R¹⁶, R¹⁷, R¹⁸, and R¹⁹ are independently selected from the group consisting of hydrido, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, hydroxymethyl, carboxy, and cyano;

$Q^b$ is $NR^{20} R^{21}$ or $C(NR^{25})NR^{23} R^{24}$;

$R^{20}$, $R^{21}$, $R^{23}$, $R^{24}$, and $R^{25}$ are independently selected from the group consisting of hydrido, methyl, and ethyl; and $Q^s$ is $CH_2$.

6. The compound of claim 5 or a pharmaceutically acceptable salt thereof, wherein;

B is selected from the group consisting of cyclopropyl, cyclobutyl, cyclopentyl, cyclohexyl, and 2-(2R)-bicyclo[2.2.1]-heptyl, A is selected from the group consisting of a bond, $CH_2$, $CH_2CH_2$ and $CH_2CH_2 CH_2$;

R¹ is selected from the group consisting of hydrido, hydroxy, hydroxymethyl, amino, aminomethyl, cyano, methyl, trifluoromethyl, and fluoro;

R² is selected from the group consisting of 3-amidocarbonyl-5-aminophenyl, 3-amino-5-(N-benzylamidocarbonyl)phenyl, 3-amino-5-(N-(2-chlorobenzyl)amidocarbonyl)phenyl, 3-amino-5-(N-(3-fluorobenzyl)amidocarbonyl)phenyl, 3-amino-5-(N-(2-trifluoromethyl benzyl)amidocarbonyl)phenyl, 3-amino-5-(N-(1-phenylethyl)amidocarbonyl)phenyl, 3-amino-5-(N-(1-methyl-1-phenylethyl)amidocarbonyl)phenyl, 3-amino-5-(N-benzylamidosulfonyl)phenyl, 3-amino-5-(N-(2-chlorobenzyl)amidosulfonyl)phenyl, 3-amino-5-(N-ethylamidocarbonyl)phenyl, 3-amino-5-(N-isopropylamidocarbonyl)phenyl, 3-amino-5-(N-propylamidocarbonyl)phenyl, 3-amino-5-(N-isobutylamidocarbonyl phenyl, 3-amino-5-(N-(2-butyl)amidocarbonyl)phenyl, 3-amino-5-(N-cyclobutylamidocarbonyl)phenyl, 3-amino-5-(N-cyclopentylamidlocarbonyl)phenyl, 3-amino-5-(N-cyclohexylamidocarbonyl)phenyl, 5-amino-2-fluorophenyl, 3 amino-5-hydroxymethylphenyl, 5-amino-3-methoxycarbonylphenyl, 3-amidinophenyl, 3-amino-2-methylphenyl, 5-amino-2-methylthiophenyl, 3-aminophenyl, 3-carboxyphenyl, 3-carboxy-5-aminophenyl, 3-carboxy-5-hydroxyphenyl, 3-carboxymethyl-5-aminophenyl, 3-carboxymethyl-5-hydroxyphenyl, 3-carboxymethylphenyl, 3-chlorophenyl, 2-chlorophenyl, 3-cyanophenyl, 3,5-diaminophenyl, 3-dimethylaminophenyl, 2-fluorophenyl, 3-fluorophenyl, 2,5-difluorophenyl, 2-hydroxyphenyl, 3-hydroxyphenyl, 3-methanesulfonylaminophenyl, 2-methoxyphenyl, 3-methoxyphenyl, 3-methoxyaminophenyl, 3-methoxycarbonylphenyl, 2-methylaminophenyl, 3-methylaminophenyl, 2-methylphenyl, 3-methylphenyl, 4-methylphenyl, phenyl, 3-trifluoroacetamidophenyl, 3-trifluoromethylphenyl, 2-trifluoromethylphenyl, 5-amino-2-thienyl, 5-amino-3-thienyl, 3-bromo-2-thienyl, 3-pyridyl, 4-pyridyl, 2-thienyl, and 3-thienyl;

Y⁰ is selected from the group consisting of:

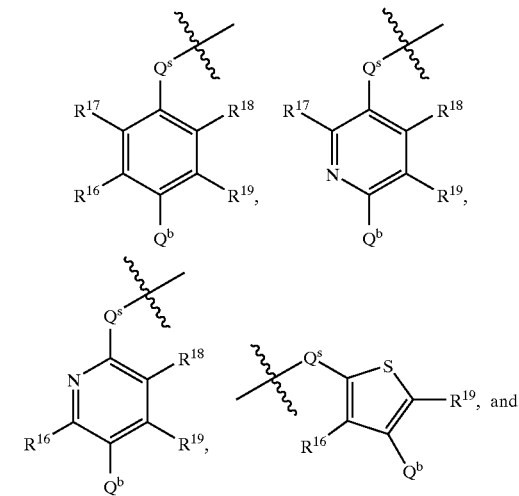

-continued

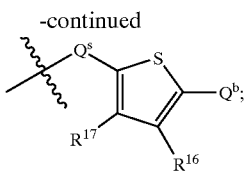

R$^{16}$ and R$^{19}$ are independently selected from the group consisting of hydrido, amidino, amino, aminomethyl, methoxy, methylamino, hydroxy, hydroxy methyl, fluoro, chloro, and cyano;

R$^{17}$ and R$^{18}$ are independently selected from the group consisting of hydrido, fluoro, chloro, hydroxy, hydroxymethyl, amino, carboxy, and cyano;

Q$^b$ is C(NR$^{25}$)NR$^{23}$R$^{24}$;

R$^{23}$, R$^{24}$, and R$^{25}$ are independently hydrido or methyl; and

Q$^s$ is CH$_2$.

7. The compound of claim 6 or a pharmaceutically acceptable salt thereof, wherein;

B is selected from the group consisting of cyclopropyl, cyclobutyl, cyclopentyl, cyclohexyl, and 2-(2R)-bicyclo[2.2.1]-heptyl;

R$^2$ is selected from the group consisting of 3-amidocarbonyl-5-aminophenyl, 3-amino-5-(N-benzylamidocarbonyl)phenyl, 3-amino-5-(N-(2-chlorobenzyl)amidocarbonyl)phenyl, 3-amino-5-(N-(3-fluorobenzyl)amidocarbonyl)phenyl, 3-amino-5-(N-(2-trifluoromethylbenzyl)amidocarbonyl)phenyl, 3-amino-5-(N-(1-phenylethyl)amidocarbonyl)phenyl, 3-amino-5-(N-(1-methyl-1-phenylethyl)amidocarbonyl)phenyl, 3-amino-5-(N-benzylamidosulfonyl)phenyl, 3-amino-5-(N-(2-chlorobenzyl)amidosulfonyl)phenyl, 3-amino-5-(N-ethylamidocarbonyl)phenyl, 3-amino-5-(N-isopropylamidocarbonyl)phenyl, 3-amino-5-(N-propylamidocarbonyl)phenyl, 3-amino-5-(N-isobutylamidocarbonyl)phenyl, 3-amino-5-(N-(2-butyl)amidocarbonyl)phenyl, 3-amino-5-(N-cyclobutylamidocarbonyl)phenyl, 3-amino-5-(N-cyclopentylamidocarbonyl)phenyl, 3-amino-5-(N-cyclohexylamidocarbonyl)phenyl, 3-aminophenyl, 3-carboxy-5-aminophenyl, 3-chlorophenyl, 3,5-diaminophenyl, 3-dimethylaminophenyl, 3-hydroxyphenyl, 3-methanesulfonylaminophenyl, 3-methylaminophenyl, 2-methylphenyl, 3-methylphenyl, phenyl, 3-trifluoroacetamidophenyl, 3-bromo-2-thienyl, 2-thienyl, and 3-thienyl; and Y$^0$ is selected from the group consisting of 5-amidino-2-thienylmethyl, 4-amidinobenzyl, 2-fluoro-4-amidinobenzyl, and 3-fluoro-4-amdinobenzyl.

8. The compound of claim 1 where said compound, or a pharmaceutically acceptable salt thereof, is selected from the group consisting of:

R$^2$ is 3-aminophenyl, B is cyclopropyl, A is a bond, Y$^0$ is 4-amidinobenzyl, and R$^1$ is chloro;

R$^2$ is 3-aminophenyl, B is cyclobutyl, A is a bond, Y$^0$ is 4-amidino-2-fluorobenzyl, and R$^1$ is chloro;

R$^2$ is 3-aminophenyl, B is cyclobutyl, A is a bond, Y$^0$ is 4-amidinobenzyl, and R$^1$ is chloro;

R$^2$ is 3-aminophenyl, B is cyclopropyl, A is a bond, Y$^0$ is 4-amidino-2-fluorobenzyl, and R$^1$ is chloro;

R$^2$ is 3-aminophenyl, B is cyclobutyl, A is a bond, Y$^0$ is 4-amidinobenzyl, and R$^1$ is hydrido;

R$^2$ is 3-aminophenyl, B is cyclobutyl, A is a bond, Y$^0$ is 4-amidino-3-fluorobenzyl, and R$^1$ is chloro;

R$^2$ is 3-aminophenyl, B is cyclopentyl, A is a bond, Y$^0$ is 4-amidinobenzyl, and R$^1$ is chloro;

R$^2$ is 5-amino-2-thienyl, B is cyclobutyl, A is a bond, Y$^0$ is 4-amidinobenzyl, and R$^1$ is chloro;

R$^2$ is 3-aminophenyl, B is cyclopropyl, A is CH$_2$, Y$^0$ is 4-amidinobenzyl, and R$^1$ is chloro;

R$^2$ is 3-aminophenyl, B is 2-(2R)-bicyclo[2.2.1]-heptyl, A is a bond, Y$^0$ is 4-amidinobenzyl, and R$^1$ is chloro;

R$^2$ is 3-aminophenyl, B is cyclopentyl, A is a bond, Y$^0$ is 4-amidino-2-fluorobenzyl, and R$^1$ is chloro;

R$^2$ is 3-aminophenyl, B is cyclohexyl, A is CH$_2$CH$_2$, Y$^0$ is 4-amidinobenzyl, and R$^1$ is hydrido;

R$^2$ is 2-hydroxyphenyl, B is cyctobutyl, A is a bond, Y$^0$ is 4-amidinobenzyl, and R$^1$ is chloro;

R$^2$ is phenyl, B is cyclobutyl, A is a bond, Y$^0$ is 4-amidinobenzyl, and R$^1$ is chloro;

R$^2$ is 3-thienyl, B is cyclobutyl, A is a bond, Y$^0$ is 4-amidinobenzyl and R$^1$ is hydrido;

R$^2$ is 3-amino-5-carbomethoxyphenyl, B is cyclobutyl, A is a bond, Y$^0$ is 4-amidinobenzyl, and R$^1$ is hydrido;

R$^2$ is 3-amino-5-carboxyphenyl, B is cyclobutyl, A is a bond, Y$^0$ is 4-amidinobenzyl, and R$^1$ is hydrido;

R$^2$ is 3,5-diaminophenyl, B is cyclobutyl, A is a bond, Y$^0$ is 4-amidinobenzyl, and R$^1$ is hydrido;

R$^2$ is 2-amino-6-carboxy-4-pyridyl, B is cyclobutyl, A is a bond, Y$^0$ is 4-amidinobenzyl, and R$^1$ is hydrido;

R$^2$ is 3-amino-5-carbomethoxyphenyl, B is cyclobutyl, A is a bond, Y$^0$ is 4-amidinobenzyl, and R$^1$ is chloro;

R$^2$ is 3-amino-5-carboxyphenyl, B is cyclobutyl, A is a bond, Y$^0$ is 4-amidinobenzyl, and R$^1$ is chloro;

R$^2$ is 2,6-dichlorophenyl, B is cyclobutyl, A is a bond, Y$^0$ is 4-amidinobenzyl, and R$^1$ is chloro;

R$^2$ is 3,5-diaminophenyl, B is cyclopropyl, A is a bond, Y$^0$ is 4-amidinobenzyl, and R$^1$ is chloro;

R$^2$ is 3,5-diaminophenyl, B is cyclobutyl, A is a bond, Y$^0$ is 4-amidino-2-fluorobenzyl, and R$^1$ is chloro;

R$^2$ is 3,5-diaminophenyl, B is cyclopropyl, A is a bond, Y$^0$ is 4-amidino-2-fluorobenzyl, and R$^1$ is chloro;

R$^2$ is 3,5-diaminophenyl, B is cyclobutyl, A is a bond, Y$^0$ is 4-amidinobenzyl, and R$^1$ is hydrido;

R$^2$ is 3,5-diaminophenyl, B is cyclobutyl, A is a bond, Y$^0$ is 4-amidino-3-fluorobenzyl, and R$^1$ is chloro;

R$^2$ is 3,5-diaminophenyl, B is cyclopentyl, A is a bond, Y$^0$ is 4-amidinobenzyl, and R$^1$ is chloro;

R$^2$ is 3-carboxy-5-aminophenyl, B is cyclopropyl, A is a bond, Y$^0$ is 4-amidinobenzyl, and R$^1$ is chloro;

R$^2$ is 3-carboxy-5-aminophenyl, B is cyclobutyl, A is a bond, Y$^0$ is 4-amidino-2-fluorobenzyl, and R$^1$ is chloro;

R$^2$ is 3-carboxy-5-aminophenyl, B is cyclopropyl, A is a bond, Y$^0$ is 4-amidino-2-fluorobenzyl, and R$^1$ is chloro;

R$^2$ is 3-carboxy-5-aminophenyl, B is cyclobutyl, A is a bond, Y$^0$ is 4-amidinobenzyl, and R$^1$ is hydrido;

R$^2$ is 3-carboxy-5-aminophenyl, B is cyclobutyl, A is a bond, Y$^0$ is 4-amidino-3-fluorobenzyl, and R$^1$ is chloro;

R$^2$ is 3-carboxy-5-aminophenyl, B is cyctopentyl, A is a bond, Y$^0$ is 4-amidinobenzyl, and R$^1$ is chloro;

R$^2$ is 3-amino-5-(N-benzylamidocarbonyl)phenyl, B is cyclopropyl, A is a bond, Y$^0$ is 4-amidinobenzyl, and R$^1$ is chloro;

R$^2$ is 3-amino-5-(N-benzylamidocarbonyl)phenyl, B is cyclobutyl, A is a bond, Y$^0$ is 4-amidino-2-fluorobenzyl, and R$^1$ is chloro;

R² is 3-amino-5-(N-benzylamidocarbonyl)phenyl, B is cyclobutyl, A is a bond, Y⁰ is 4-amidinobenzyl, and R¹ is chloro;

R² is 3-amino-5-(N-benzylamidocarbonyl)phenyl, B is cyclopropyl, A is a bond, Y⁰ is 4-amidino-2-fluorobenzyl, and R¹ is chloro;

R² is 3-amino-5-(N-benzylamidocarbonyl)phenyl, B is cyclobutyl, A is a bond, Y⁰ is 4-amidinobenzyl, and R¹ is hydrido;

R² is 3-amino-5-(N-benzylamidocarbonyl)phenyl, B is cyclobutyl, A is a bond, Y⁰ is 4-amidino-3-fluorobenzyl, and R¹ is chloro;

R² is 3-amino-5-(N-benzylamidocarbonyl)phenyl, B is cyclopentyl A is a bond, Y⁰ is 4-amidinobenzyl, and R¹ is chloro;

R² is 3-amino-5-(N-(2-chlorobenzyl)amidosulfonyl)phenyl, B is cyclopropyl, A is a bond, Y⁰ is 4-amidinobenzyl, and R¹ is chloro;

R² is 3-amino-5-(N-(2-chlorobenzyl)amidosulfonyl)phenyl, B is cyclobutyl, A is a bond. Y⁰ is 4-amidino-2-fluorobenzyl, and R¹ is chloro;

R² is 3-amino-5-(N-(2-chlorobenzyl)amidosulfonyl)phenyl, B is cyclobutyl, A is a bond, Y⁰ is 4-amidinobenzyl, and R¹ is chloro;

R² is 3-amino-5-(N-(2-chlorobenzyl)amidosulfonyl)phenyl, B is cyclopropyl, A is a bond, Y⁰ is 4-amidino-2-fluorobenzyl, and R¹ is chloro;

R² is 3-amino-5-(N-(2-chlorobenzyl)amidosulfonyl)phenyl, B is cyclobutyl, A is a bond, Y⁰ is 4-amidinobenzyl, and R¹ is hydrido;

R² is 3-amino-5-(N-(2-chlorobenzyl)amidosulfonyl)phenyl, B is cyclobutyl, A is a bond, Y⁰ is 4-amidino-3-fluorobenzyl, and R¹ is chloro;

R² is 3-amino-5-(N-(2-chlorobenzyl)amidosulfonyl)phenyl, B is cyclopentyl, A is a bond, Y⁰ is 4-amidinobenzyl, and R¹ is chloro;

R² is 3-amino-5-(N-(2-trifluoromethylbenzyl)amidocarbonyl)-phenyl, B is cyclopropyl, A is a bond, Y⁰ is 4-amidinobenzyl, and R¹ is chloro;

R² is 3-amino-5-(N-(2-trifluoromethylbenzyl)amidocarbonyl)-phenyl, B is cyclobutyl, A is a bond, Y⁰ is 4-amidino-2-fluorobenzyl, and R¹ is chloro;

R² is 3-amino-5-(N-(2-trifluoromethylbenzyl)amidocarbonyl)-phenyl, B is cyclobutyl, A is a bond, Y⁰ is 4-amidinobenzyl, and R¹ is chloro;

R² is 3-amino-5-(N-(2-trifluoromethylbenzyl)amidocarbonyl)-phenyl, B is cyclopropyl, A is a bond, Y⁰ is 4-amidino-2-fluorobenzyl, and R¹ is chloro;

R² is 3-amino-5-(N-(2-trifluoromethylbenzyl)amidocarbonyl)-phenyl, B is cyclobutyl, A is a bond, Y⁰ is 4-amidinobenzyl, and R¹ is hydrido;

R² is 3-amino-5-(N-(2-trifluoromethylbenzyl)amidocarbonyl)-phenyl, B is cyclobutyl, A is a bond, Y⁰ is 4-amidino-3-fluorobenzyl, and R¹ is chloro; and R² is 3-amino-5-(N-(2-trifluoromethylbenzyl)amidocarbonyl)-phenyl, B is cyclopentyl, A is a bond, Y⁰ is 4-amidinobenzyl, and R¹ is chloro.

9. The compound of claim 1, or a pharmaceutically acceptable salt thereof, wherein;

R⁹, R¹¹, and R¹³ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

R¹⁰ and R¹² are independently selected from the group consisting of hydrido, amidino, guanidino, aryl, aralkyl, cycloalkyl, cycloalkylalkyl, heteroaryl, heterocyclyl, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroaralkylamino, heterocyclylamino, heterocyclylalkylamino, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, and aminoalkyl;

R³³ and R³⁴ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, and cyano;

A is a bond or $(CH(R^{15}))_{pa}$—$(W^7)_{rr}$ wherein rr is 0 or 1, pa is an integer selected from 0 through 3, and W⁷ is N(R⁷);

R⁷ is hydrido or alkyl;

R¹⁵ is selected from the group consisting of hydrido, halo, alkyl, and haloalkyl;

R² is Z⁰—Q;

Z⁰ is a bond;

$Q^b$ is selected from the group consisting of NR²⁰R²¹, hydrido, and C(NR²⁵)NR²³R²⁴;

R²⁰, R²¹, R²³, R²⁴, and R²⁵ are independently hydrido or alkyl; and $Q^s$ is CH₂.

10. The compound of claim 9 or a pharmaceutically acceptable salt thereof, wherein;

B is selected from the group consisting of cyclopropyl, cyclobutyl cyclopentyl, cyclohexyl, cycloheptyl, 2-(2R)-bicyclo[2.2.1]-heptyl, and bicyclo[3.1.0]hexan-6-yl, wherein (a) each ring carbon is optionally substituted with R³³, (b) a ring carbon in a first alpha position relative to the ring carbon at the point of attachment is optionally substituted by R⁹, (c) a ring carbon in a second alpha position relative to the ring carbon at the point of attachment and is optionally substituted by R¹³, (d) a ring carbon, if present, in a first beta position relative to the ring atom optionally substituted by R⁹, is optionally substituted by R¹⁰, and (e) a ring carbon, if present, in a second beta position relative to the ring carbon at the point of attachment and in an alpha position relative to the ring atom optionally substituted by R¹³, is optionally substituted by R¹²;

R⁹, R¹¹, and R¹³ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

R¹⁰ and R¹² are independently selected from the group consisting of hydrido, amidino, guanidino, hydroxy, hydroxymethyl, 1-hydroxyethyl, 2-hydroxyethyl, amino, aminomethyl, N-methylamino, dimethylamino, methoxyamino, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy;

$R^{33}$ is selected from the group consisting of hydrido, amidino, guanidino, methyl, ethyl, methoxy, ethoxy, hydroxy, carboxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, and cyano;

A is selected from the group consisting of a bond, NH, N(CH$_3$), CH$_2$, CH$_3$CH, CH$_2$CH$_2$, and CH$_2$CH$_2$CH$_2$;

$R^1$ is selected from the group consisting of hydrido, hydroxy, hydroxymethyl, amino, aminomethyl, methylamino, cyano, methyl, trifluoromethyl, methoxy, methylthio, trifluoromethoxy, fluoro, and chloro;

$R^2$ is selected from the group consisting of phenyl and 2-thienyl, 2-furyl, 2-pyrrolyl, 2-imidazolyl, 2-thiazolyl, 3-isoxazolyl, 2-pyridyl, and 3-pyridyl heteroaryl rings wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$Y^0$ is selected from the group consisting of:

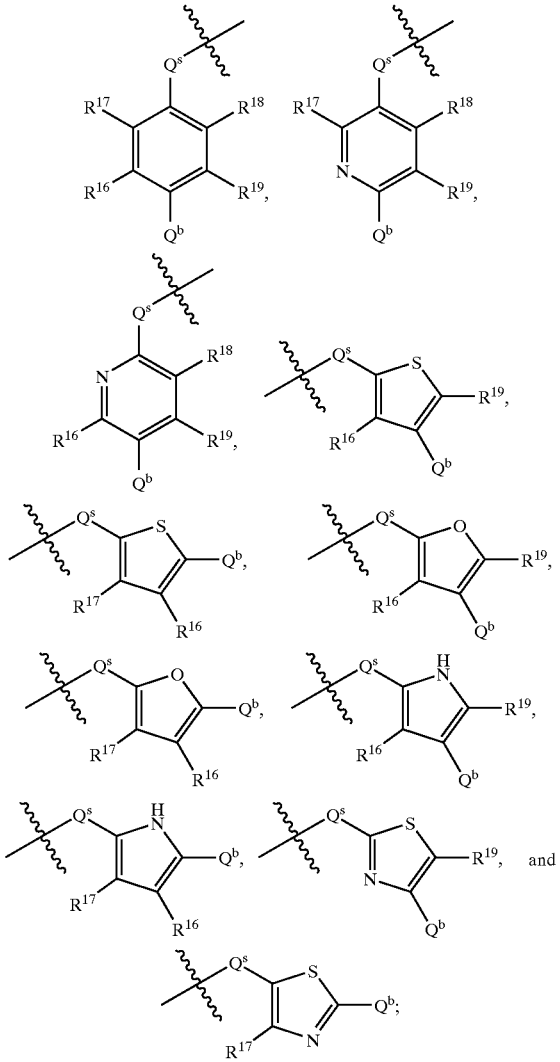

$R^{16}$, $R^{17}$, $R^{18}$, and $R^{19}$ are independently selected from the group consisting of hydrido, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, hydroxymethyl, carboxy, and cyano;

$Q^b$ is $NR^{20} R^{21}$ or $C(NR^{25})NR^{23} R^{24}$;

$R^{20}$, $R^{21}$, $R^{23}$, $R^{24}$, and $R^{25}$ are independently selected from the group consisting of hydrido, methyl, and ethyl; and $Q^s$ is $CH_2$.

11. The compound of claim 10 or a pharmaceutically acceptable salt thereof, wherein;

B is selected from the group consisting of cyclopropyl, cyclobutyl cyclopentyl, cyclohexyl, and 2-(2R)-bicyclo [2.2.1]-heptyl;

A is selected from the group consisting of a bond, $CH_2$, $CH_2CH_2$ and $CH_2CH_2 CH_2$;

$R^1$ is selected from the group consisting of hydrido, hydroxy, hydroxymethyl, amino, aminomethyl, cyano, methyl, trifluoromethyl, and fluoro;

$R^2$ is selected from the group consisting of 3-amino-5-benzylphenyl, 3-amino-5-(2-phenylethyl)phenyl, 3-amino-5-benzylaminophenyl, 3-amino-5-(2-phenylethylamino)phenyl, 3-amino-5-benzytoxyphenyl, 3-amino-5-(2-phenylethoxy)phenyl, 3-amino-5-(4-trifluoromethylbenzylamino)phenyl, and 3-amino-5-(4-trifluoromethylbenzyloxy)phenyl;

$Y^0$ is selected from the group consisting of:

$R^{16}$ and $R^{19}$ are independently selected from the group consisting of hydrido, amidino, amino, aminomethyl, methoxy, methylamino, hydroxy, hydroxymethyl, fluoro, chloro, and cyano;

$R^{17}$ and $R^{18}$ are independently selected from the group consisting of hydrido, fluoro, chloro, hydroxy, hydroxymethyl, amino, carboxy, and cyano;

$Q^b$ is $C(NR^{25})NR^{23} R^{24}$;

$R^{23}$, $R^{24}$, and $R^{25}$ are independently hydrido or methyl; and $Q^s$ is $CH_2$.

12. The compound of claim 11 or a pharmaceutically acceptable salt thereof, wherein;

B is selected from the group consisting of cyclopropyl, cyclobutyl cyclopentyl, cyclohexyl, and 2-(2R)-bicyclo [2.2.1]-heptyl; and $Y^0$ is selected from the group consisting of 5-amidino-2-thienylmethyl, 4-amidinobenzyl, 2-fluoro-4-amidinobenzyl, and 3-fluoro-4-amdinobenzyl.

13. The compound of claim 1 where said compound, or a pharmaceutically acceptable salt thereof, is selected from the group consisting of:

$R^2$ is 3-amino-5-benzylphenyl, B is cyclopropyl, A is a bond, $Y^0$ is 4-amidinobenzyl, and $R^1$ is chloro;

$R^2$ is 3-amino-5-benzylphenyl, B is cyclobutyl, A is a bond, $Y^0$ is amidino-2-fluorobenzyl, and $R^1$ is chloro;

$R^2$ is 3-amino-5-benzylphenyl, B is cyclobutyl, A is a bond, $Y^0$ is amidinobenzyl, and $R^1$ is chloro;

$R^2$ is 3-amino-5-benzylphenyl, B is cyclopropyl, A is a bond, $Y^0$ is 4-amidino-2-fluorobenzyl, and $R^1$ is chloro;

$R^2$ is 3-amino-5-benzylphenyl, B is cyclobutyl, A is a bond, $Y^0$ is -amidinobenzyl, and $R^1$ is hydrido;

$R^2$ is 3-amino-5-benzylphenyl, B is cyclobutyl, A is a bond, $Y^0$ is -amidino-3-fluorobenzyl, and $R^1$ is chloro;

$R^2$ is 3-amino-5-benzylphenyl, B is cyclopentyl, A is a bond, $Y^0$ is 4-amidinobenzyl, and $R^1$ is chloro;

$R^2$ is 3-amino-5-(2-phenylethyl)phenyl, B is cyclopropyl, A is a bond, $Y^0$ is 4-amidinobenzyl, and $R^1$ is chloro;

$R^2$ is 3-amino-5-(2-phenylethyl)phenyl, B is cyclobutyl, A is a bond, $Y^0$ is 4-amidino-2-fluorobenzyl, and $R^1$ is chloro;

$R^2$ is 3-amino-5-(2-phenylethyl)phenyl, B is cyclobutyl, A is a bond, $Y^0$ is 4-amidinobenzyl, and $R^1$ is chloro;

$R^2$ is 3-amino-5-(2-phenylethyl)phenyl, B is cyclopropyl, A is a bond, $Y^0$ is 4-amidino-2-fluorobenzyl, and $R^1$ is chloro;

$R^2$ is 3-amino-5-(2-phenylethyl)phenyl, B is cyclobutyl, A is a bond, $Y^0$ is 4-amidinobenzyl, and $R^1$ is hydrido;

$R^2$ is 3-amino-5-(2-phenylethyl)phenyl, B is cyclobutyl, A is a bond, $Y^0$ is 4-amidino-3-fluorobenzyl, and $R^1$ is chloro;

$R^2$ is 3-amino-5-(2-phenylethyl)phenyl, B is cyclopentyl, A is a bond, $Y^0$ is 4-amidinobenzyl, and $R^1$ is chloro;

$R^2$ is 3-amino-5-benzylaminophenyl, B is cyclopropyl, A is a bond $Y^0$ is 4-amidinobenzyl, and $R^1$ is chloro;

$R^2$ is 3-amino-5-benzylaminophenyl, B is cyclobutyl, A is a bond, is $Y^0$ is 4-amidino-2-fluorobenzyl, and $R^1$ is chloro;

$R^2$ is 3-amino-5-benzylaminophenyl, B is cyclobutyl, A is a bond, $Y^0$ is 4-amidinobenzyl, and $R^1$ is chloro;

$R^2$ is 3-amino-5-benzylaminophenyl, B is cyclopropyl, A is a bond $Y^0$ is 4-amidino-2-fluorobenzyl, and $R^1$ is chloro;

$R^2$ is 3-amino-5-benzylaminophenyl, B is cyclobutyl, A $Y^0$ is a bond, is 4-amidinobenzyl, and $R^1$ is hydrido;

$R^2$ is 3-amino-5-benzylaminophenyl, B is cyclobutyl, A is a bond, $Y^0$ is 4-amidino-3-fluorobenzyl, and $R^1$ is chloro;

$R^2$ is 3-amino-5-benzylaminophenyl, B is cyclopentyl, A is a bond, $Y^0$ is 4-amidinobenzyl, and $R^1$ is chloro;

$R^2$ is 3-amino-5-(2-phenylethylamino)phenyl, B is cyclopropyl, A is a bond, $Y^0$ is 4-amidinobenzyl, and $R^1$ is chloro;

$R^2$ is 3-amino-5-(2-phenylethylamino)phenyl, B is cyclobutyl, A is a bond, $Y^0$ is 4-amidino-2-fluorobenzyl, and $R^1$ is chloro;

$R^2$ is 3-amino-5-(2-phenylethylamino)phenyl, B is cyclobutyl, A is a bond, $Y^0$ is 4-amidinobenzyl and $R^1$ is chloro;

R² is 3-amino-5-(2-phenylethylamino)phenyl, B is cyclopropyl, A i a bond, Y⁰ is 4-amidino-2-fluorobenzyl, and R¹ is chloro;

R² is 3-amino-5-(2-phenylethylamino)phenyl, B is cyclobutyl, A is a bond, Y⁰ is 4-amidinobenzyl, and R¹ is hydrido;

R² is 3-amino-5-(2-phenylethylamino)phenyl, B is cyclobutyl, A is bond, Y⁰ is 4-amidino-3-fluorobenzyl, and R¹ is chloro;

R² is 3-amino-5-(2-phenylethylamino)phenyl, B is cyclopentyl, A is a bond, Y⁰ is 4-amidinobenzyl, and R¹ is chloro;

R² is 3-amino-5-benzyloxyphenyl, B is cyclopropyl, A is a bond, Y⁰ is 4-amidinobenzyl, and R¹ is chloro;

R² is 3-amino-5-benzyloxyphenyl, B is cyclobutyl, A is a bond, Y⁰ is 4-amidino-2-fluorobenzyl, and R¹ is chloro;

R² is 3-amino-5-benzyloxyphenyl, B is cyclobutyl, A is a bond, Y⁰ is 4-amidinobenzyl, and R¹ is chloro;

R² is 3-amino-5-benzyloxyphenyl, B is cyclopropyl, A is a bond, Y⁰ is 4-amidino-2-fluorobenzyl, and R¹ is chloro;

R² is 3-amino-5-benzyloxyphenyl, B is cyclobutyl, A is a bond, Y⁰ is 4-amidinobenzyl, and R¹ is hydrido;

R² is 3-amino-5-benzyloxyphenyl, B is cyclobutyl, A is a bond, Y⁰ is 4-amidino-3-fluorobenzyl, and R¹ is chloro;

R² is 3-amino-5-benzyloxyphenyl, B is cyclopentyl, A is a bond, Y⁰ is 4-amidinobenzyl, and R¹ is chloro;

R² is 3-amino-5-(2-phenylethoxy)phenyl, B is cyclopropyl, A is a bond, Y⁰ is 4-amidinobenzyl, and R¹ is chloro;

R² is 3-amino-5-(2-phenylethoxy)phenyl, B is cyclobutyl, A is a bond, Y⁰ is 4-amidino-2-fluorobenzyl, and R¹ is chloro;

R² is 3-amino-5-(2-phenylethoxy)phenyl, B is cyclobutyl, A is a bond, Y⁰ is 4-amidinobenzyl, and R¹ is chloro;

R² is 3-amino-5-(2-phenylethoxy)phenyl, B is cyclopropyl, A is a bond, Y⁰ is 4-amidino-2-fluorobenzyl, and R¹ is chloro;

R² is 3-amino-5-(2-phenylethoxy)phenyl, B is cyclobutyl, A is a bond, Y⁰ is 4-amidinobenzyl, and R¹ is hydrido;

R² is 3-amino-5-(2-phenylethoxy)phenyl, B is cyclobutyl, A is a bond, Y⁰ is 4-amidino-3-fluorobenzyl, and R¹ is chloro;

R² is 3-amino-5-(2-phenylethoxy)phenyl, B is cyclopentyl, A is a bond, Y⁰ is 4-amidinobenzyl, and R¹ is chloro;

R² is 3-amino-5-(4-trifluoromethylbenzylamino)phenyl, B is cyclopropyl, A is a bond, Y⁰ is 4-amidinobenzyl, and R¹ is chloro;

R² is 3-amino-5-(4-trifluoromethylbenzylamino)phenyl, B is cyclobutyl, A is a bond, Y⁰ is 4-amidino-2-fluorobenzyl, and R¹ is chloro;

R² is 3-amino-5-(4-trifluoromethylbenzylamino)phenyl, B is cyclobutyl, A is a bond, Y⁰ is 4-amidinobenzyl, and R¹ is chloro;

R² is 3-amino-5-(4-trifluoromethylbenzylamino)phenyl, B is cyclopropyl, A is a bond, Y⁰ is 4-amidino-2-fluorobenzyl, and R¹ is chloro;

R² is 3-amino-5-(4-trifluoromethylbenzylamino)phenyl, B is cyclobutyl, A is a bond, Y⁰ is 4-amidinobenzyl, and R¹ is hydrido;

R² is 3-amino-5-(4-trifluoromethylbenzylamino)phenyl, B is cyclobutyl, A is a bond, Y⁰ is 4-amidino-3-fluorobenzyl, and R¹ is chloro;

R² is 3-amino-5-(4-trifluoromethylbenzylamino)phenyl, B is cyclopentyl, A is a bond, Y⁰ is 4-amidinobenzyl, and R¹ is chloro;

R² is 3-amino-5-(4-trifluoromethylbenzyloxy)phenyl, B is cyclopropyl, A is a bond, Y⁰ is 4-amidinobenzyl, and R¹ is chloro;

R² is 3-amino-5-(4-trifluoromethylbenzyloxy)phenyl, B is cyclobutyl, A is a bond, Y⁰ is 4-amidino-2-fluorobenzyl, and R¹ is chloro;

R² is 3-amino-5-(4-trifluoromethylbenzyloxy)phenyl, B is cyclobutyl, A is a bond, Y⁰ is 4-amidinobenzyl, and R¹ is chloro;

R² is 3-amino-5-(4-trifluoromethylbenzyloxy)phenyl, B is cyclopropyl, A is a bond, Y⁰ is 4-amidino-2-fluorobenzyl, and R¹ is chloro;

R² is 3-amino-5-(4-trifluoromethylbenzyloxy)phenyl, B is cyclobutyl, A is a bond, Y⁰ is 4-amidinobenzyl, and R¹ is hydrido;

R² is 3-amino-5-(4-trifluoromethylbenzyloxy)phenyl, B is cyclobutyl, A is a bond, Y⁰ is 4-amidino-3-fluorobenzyl, and R¹ is chloro; and R² is 3-amino-5-(4-trifluoromethylbenzyloxy)phenyl, B is cyclopentyl, A is a bond, Y⁰ is 4-amidinobenzyl, and R¹ is chloro.

14. The compound of claim 1 wherein Y⁰ is amidinoaralkyl or amidinoheteroaralkyl.

15. The compound of claim 14 wherein A is a bond and R¹ is hydrido or halo.

16. The compound of claim 15 wherein B is C3–C7 cycloalkyl.

17. The compound of claim 16 wherein R² is

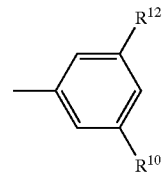

and R¹⁰ and R¹² are as defined in claim 1.

18. The compound of claim 17 wherein one of R¹⁰ and R¹² is amino and the other is selected from the group consisting of amino, carboxy, methoxycarbonyl, N-benzylamidocarbonyl, N-(2-chlorobenzyl)amidosulfonyl, N-(2-trifluoromethylbenzyl)amidocarbonyl, benzyl, 2-phenylethyl, benzylamino, 2-phenylethylamino, benzyloxy, 2-phenylethoxy, 4-trifluoromethylbenzylamino, or 4-trifluoromethylbenzoyloxy.

19. The compound of claim 14 wherein R² is

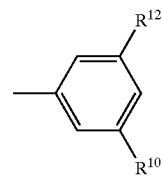

and R¹⁰ and R¹² are as defined in claim 1.

20. The compound of claim 19 wherein one of R¹⁰ and R¹² is amino and the other is selected from the group consisting of amino, carboxy, methoxycarbonyl, N-benzylamidocarbonyl, N-(2-chlorobenzyl)amidosulfonyl, N-(2-trifluoromethylbenzyl)amidocarbonyl, benzyl, 2-phenylethyl, benzylamino, 2-phenylethylamino, benzyloxy, 2-phenylethoxy, 4-trifluoromethylbenzylamino, or 4-trifluoromethylbenzoyloxy.

21. The compound of claim 1 of the formula:

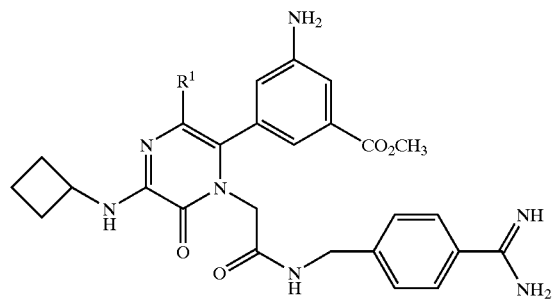

wherein $R^1$ is hydrido or chloro.

22. The compound of claim 1 of the formula:

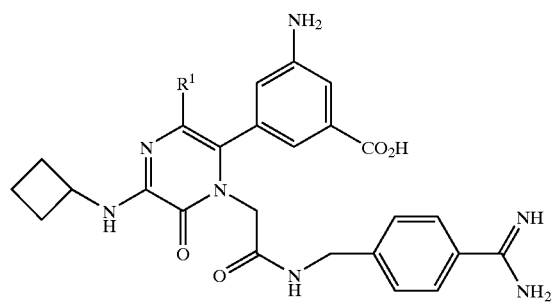

wherein $R^1$ is hydrido or chloro.

23. The compound of claim 1 of the formula:

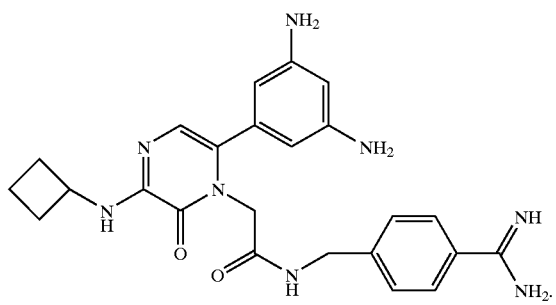

24. The compound of claim 1 of the formula:

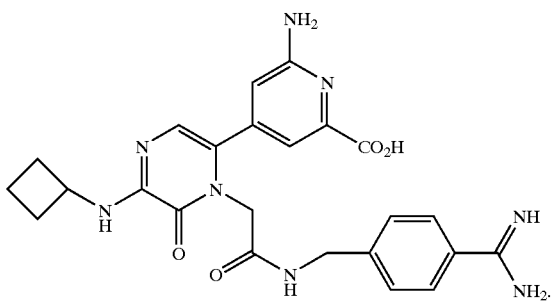

25. The compound of claim 1 of the formula:

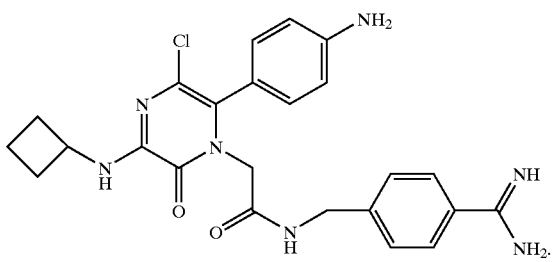

26. The compound of claim 1 of the formula:

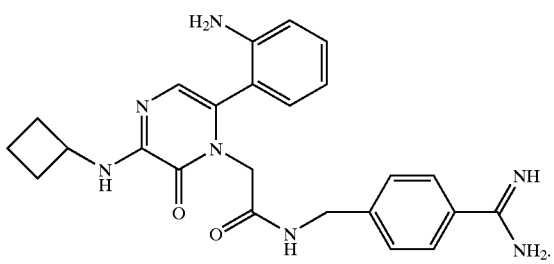

27. The compound of claim 1 of the formula:

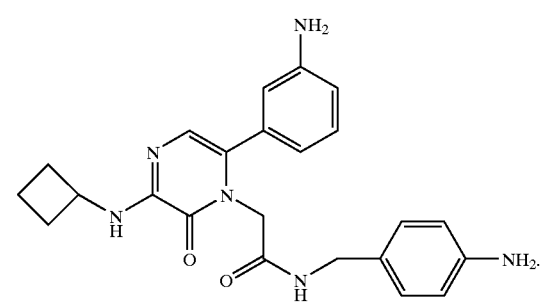

* * * * *